US012767688B2

(12) United States Patent
Janssen et al.

(10) Patent No.: US 12,767,688 B2
(45) Date of Patent: Oct. 20, 2026

(54) COMPOUNDS FOR REGULATING TRAINED IMMUNITY, AND THEIR METHODS OF USE

(71) Applicants: Trained Therapeutix Discovery, Inc., Dallas, TX (US); Icahn School of Medicine at Mount Sinai, New York, NY (US)

(72) Inventors: Henricus Marie Janssen, Eindhoven (NL); Freek Johannes Maria Hoeben, Liessel (NL); Bas Van Genabeek, Sint-Michielsgestel (NL); Serge Hendrikus Mathijs Sontjens, Eindhoven (NL); Willem J. M. Mulder, New York, NY (US)

(73) Assignees: Trained Therapeutix Discovery, Inc., Dallas, TX (US); Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 18/510,323

(22) Filed: Nov. 15, 2023

(65) Prior Publication Data

US 2024/0190921 A1 Jun. 13, 2024

Related U.S. Application Data

(62) Division of application No. 17/698,971, filed on Mar. 18, 2022, now Pat. No. 11,859,021.

(Continued)

(51) Int. Cl.
*C07K 9/00* (2006.01)
*A61K 9/51* (2006.01)
(Continued)

(52) U.S. Cl.
CPC ............ *C07K 9/001* (2013.01); *A61K 9/5123* (2013.01); *A61K 9/5169* (2013.01);
(Continued)

(58) Field of Classification Search
CPC .... A61K 9/5123; A61K 9/5169; C07K 9/001; B82Y 5/00
See application file for complete search history.

(56) References Cited

U.S. PATENT DOCUMENTS 4,406,890 A 9/1983 Tarcsay et al.
4,640,911 A 2/1987 Baschang
(Continued)

FOREIGN PATENT DOCUMENTS

CN 101096386 1/2008
CN 101888780 11/2010
(Continued)

OTHER PUBLICATIONS

Gura et. al., Science, 1997, 278: 1041-1042.*
(Continued)

*Primary Examiner* — Kortney L. Klinkel
(74) *Attorney, Agent, or Firm* — Fish & Richardson P.C.

(57) ABSTRACT

Provided herein are compounds of Formula (I), as well as compositions comprising a compound of Formula (I) and uses thereof.

(Continued)

(I)

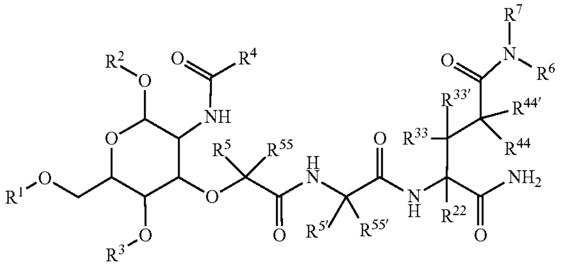

41 Claims, 5 Drawing Sheets

Specification includes a Sequence Listing.

Related U.S. Application Data

(60) Provisional application No. 63/163,428, filed on Mar. 19, 2021.

(51) Int. Cl.

| | |
|---|---|
| ***A61K 47/54*** | (2017.01) |
| ***A61K 47/69*** | (2017.01) |
| ***A61P 35/00*** | (2006.01) |
| ***B82Y 5/00*** | (2011.01) |
| ***C07K 5/02*** | (2006.01) |
| ***C07K 5/062*** | (2006.01) |
| ***C07K 16/28*** | (2006.01) |

(52) U.S. Cl.

CPC .......... *A61K 9/5192* (2013.01); *A61K 47/542* (2017.08); *A61K 47/543* (2017.08); *A61K 47/544* (2017.08); *A61K 47/554* (2017.08); *A61K 47/6917* (2017.08); *A61P 35/00* (2018.01); *C07K 5/0215* (2013.01); *C07K 5/06026* (2013.01); *C07K 16/2818* (2013.01); *B82Y 5/00* (2013.01)

(56) References Cited

U.S. PATENT DOCUMENTS

| | | | |
|---|---|---|---|
| 5,349,060 | A | 9/1994 | Kao et al. |
| 5,540,931 | A | 7/1996 | Hewitt et al. |
| 5,543,158 | A | 8/1996 | Gref et al. |
| 5,552,157 | A | 9/1996 | Yaai et al. |
| 5,565,213 | A | 10/1996 | Nakamori et al. |
| 5,567,434 | A | 10/1996 | Szoka, Jr. |
| 5,665,772 | A | 9/1997 | Cottens et al. |
| 5,738,868 | A | 4/1998 | Shinkarenko |
| 5,741,516 | A | 4/1998 | Webb et al. |
| 5,795,587 | A | 8/1998 | Gao et al. |
| 5,985,890 | A | 11/1999 | Cottens et al. |
| 6,200,985 | B1 | 3/2001 | Cottens et al. |
| 6,440,990 | B1 | 8/2002 | Cottens et al. |
| 7,488,802 | B2 | 2/2009 | Collins et al. |
| 7,943,743 | B2 | 5/2011 | Korman et al. |
| 8,008,449 | B2 | 8/2011 | Korman et al. |
| 8,168,757 | B2 | 5/2012 | Finnefrock et al. |
| 8,217,149 | B2 | 7/2012 | Irving et al. |
| 8,563,603 | B2 | 10/2013 | Chavez |
| 8,865,644 | B2 | 10/2014 | Cho |
| 9,408,829 | B2 | 8/2016 | Lutqens et al. |
| 10,485,884 | B2 | 11/2019 | Sahin et al. |
| 10,525,152 | B2 | 1/2020 | Sigalov |
| 11,859,021 | B2 | 1/2024 | Janssen et al. |
| 12,377,054 | B2 | 8/2025 | Mulder et al. |
| 2002/0086049 | A1 | 7/2002 | Bolton et al. |
| 2005/0182243 | A1 | 8/2005 | Sligar et al. |
| 2005/0234234 | A1 | 10/2005 | Gu et al. |
| 2005/0287636 | A1 | 12/2005 | Cho |
| 2006/0002852 | A1 | 1/2006 | Saltzman et al. |
| 2006/0222652 | A1 | 10/2006 | Sebbel et al. |
| 2006/0251677 | A1 | 11/2006 | Bachmann et al. |
| 2008/0145441 | A1 | 6/2008 | Penades et al. |
| 2009/0028910 | A1 | 1/2009 | DeSimone et al. |
| 2009/0226525 | A1 | 9/2009 | de las Rios et al. |
| 2011/0237435 | A1 | 9/2011 | Ryan |
| 2011/0256224 | A1 | 10/2011 | Sigalov |
| 2013/0045161 | A1 | 2/2013 | Sigalov |
| 2013/0252879 | A1 | 9/2013 | Cho |
| 2015/0182461 | A1 | 7/2015 | Kim et al. |
| 2016/0074473 | A1 | 3/2016 | Turner |
| 2016/0317647 | A1 | 11/2016 | Ciaramella et al. |
| 2018/0250419 | A1 | 9/2018 | Schwendeman et al. |
| 2018/0263907 | A1 | 9/2018 | Hefesha et al. |
| 2019/0008918 | A1 | 1/2019 | Upmanyu et al. |
| 2019/0153443 | A1 | 5/2019 | Fitzgerald et al. |
| 2019/0290593 | A1 | 9/2019 | Mulder et al. |
| 2020/0253884 | A1 | 8/2020 | Mulder et al. |
| 2020/0261591 | A1 | 8/2020 | Mulder et al. |
| 2020/0376102 | A1 | 12/2020 | Mulder et al. |
| 2020/0376146 | A1 | 12/2020 | Mulder et al. |
| 2022/0332762 | A1 | 10/2022 | Janssen et al. |
| 2023/0218537 | A1 | 7/2023 | Mulder et al. |
| 2023/0355537 | A1 | 11/2023 | Mulder et al. |
| 2025/0205262 | A1 | 6/2025 | Teunissen et al. |
| 2025/0268839 | A1 | 8/2025 | Mulder et al. |

FOREIGN PATENT DOCUMENTS

| | | | |
|---|---|---|---|
| CN | 101903018 | | 12/2010 |
| CN | 102027019 | | 4/2011 |
| CN | 102178954 | | 9/2011 |
| CN | 102264364 | A | 11/2011 |
| CN | 103118691 | | 5/2013 |
| CN | 103354749 | | 10/2013 |
| CN | 103533934 | | 1/2014 |
| CN | 103589699 | A | 2/2014 |
| CN | 105828834 | | 8/2016 |
| CN | 106714836 | | 5/2017 |
| CN | 106831614 | A | 6/2017 |
| CN | 111971028 | A | 11/2020 |
| EP | 0003833 | | 9/1979 |
| EP | 0021367 | | 1/1981 |
| EP | 0025495 | | 3/1981 |
| EP | 0102319 | | 3/1984 |
| EP | 0163286 | | 12/1985 |
| EP | 0173960 | | 3/1986 |
| EP | 0192609 | | 8/1986 |
| EP | 0192611 | | 8/1986 |
| JP | 55-28933 | | 2/1980 |
| JP | 58-172399 | | 10/1983 |
| JP | 2007532134 | | 11/2007 |
| JP | 2019515926 | A | 6/2019 |
| KR | 10-2198900 | B1 | 1/2021 |
| WO | WO 1993/010148 | | 5/1993 |
| WO | WO 1994/009010 | | 4/1994 |
| WO | WO 1995/010293 | | 4/1995 |
| WO | WO 1995/016691 | | 6/1995 |
| WO | WO 1996/001645 | | 1/1996 |
| WO | WO 1996/009063 | | 3/1996 |
| WO | WO 1996/041807 | | 12/1996 |
| WO | WO 1998/009989 | | 3/1998 |
| WO | WO 2003/042402 | | 5/2003 |
| WO | WO 2006/053430 | | 5/2006 |
| WO | WO 2007/022474 | | 2/2007 |
| WO | WO 2008/156712 | | 12/2008 |
| WO | WO 2009/051837 | | 4/2009 |
| WO | WO 2009/106999 | | 9/2009 |
| WO | WO 2010/036959 | | 4/2010 |
| WO | WO 2010/047839 | | 4/2010 |
| WO | WO 2010/089411 | | 8/2010 |
| WO | WO 2011/066342 | | 6/2011 |
| WO | WO 2011/082400 | | 7/2011 |

(56) References Cited

FOREIGN PATENT DOCUMENTS

| | | | |
|---|---|---|---|
| WO | WO 2011/159877 | | 12/2011 |
| WO | WO 2011/161699 | | 12/2011 |
| WO | WO 2015/079411 | | 6/2015 |
| WO | WO 2016/019333 | | 2/2016 |
| WO | WO 2016/138286 | | 9/2016 |
| WO | WO 2016/154544 | | 9/2016 |
| WO | WO 2016/172146 | | 10/2016 |
| WO | WO 2016/172615 | A1 | 10/2016 |
| WO | WO 2017/011685 | | 1/2017 |
| WO | WO 2017/024312 | | 2/2017 |
| WO | WO 2017/106690 | | 6/2017 |
| WO | WO 2017/190145 | | 11/2017 |
| WO | WO 2017/205536 | A2 | 11/2017 |
| WO | WO 2018/071549 | | 4/2018 |
| WO | WO 2018/187515 | | 10/2018 |
| WO | WO 2019/103998 | | 5/2019 |
| WO | WO 2023/192956 | | 10/2023 |

OTHER PUBLICATIONS

Johnson et. al., British Journal of Cancer, 2001, 84:1424-1431.*

Cecil Textbook of Medicine, 20th Edition, vol. 1, 1996.*

Office Action in Chinese Appln. No. 202410398398.2, mailed on Nov. 26, 2024, 11 pages (with English translation).

Office Action in Colombian Appln. No. NC2023/0013700, mailed on Nov. 5, 2024, 18 pages (with Machine translation).

Sun, "The Synthesis of Novel Carbonylthiourea, Amide, Imidazo-[2, 1-b]-1, 3, 4-thiadiazole Containing Pyrazole Ring," Master's e-Journal, Engineering Science and Technology I, 2009, Issue 2, 7 pages (with English abstract).

International Preliminary Report on Patentability in International Appln. No. PCT/US2023/065166, mailed on Oct. 10, 2024, 10 pages.

Invitation to Pay Additional Fees in International Appln. No. PCT/US2023/065166, mailed on Jul. 14, 2023, 2 pages.

Office Action in Australian Appln. No. 2018370828, mailed on Nov. 8, 2023, 5 pages.

Office Action in Australian Appln. No. 2018370828, mailed on Oct. 4, 2024, 4 pages.

[No Author], "Highlights of Prescribing Information—Rapamune (sirolimus) oral solution; Rapamune (sirolimus) tablets, for oral use," Distributed by Wyeth Pharmaceuticals Inc., Pfizer, revised on Apr. 2017, 56 pages.

[No Author], Rationale of Drug Design, 1st Ed., China Campeering, Chinese Pharmaceutical Science Press, Apr. 1990, pp. 199-200 (Relevance Explained in Chinese Office Action in Chinese Patent Application No. 201880086231.5, dated Nov. 3, 2022).

Adamczyk et al., "Lipase Mediated Hydrolysis of Rapamycin 42-Hemisuccinate Benzyl and Methyl Esters," Tetrahedron Letters, 1994, 35(7);1019-1022.

Ahmed et al., "Immunological memory and protective immunity: understanding their relation," Science, 1996, 272(5258):54-60.

Ahonen et al., "The CD40-TRAF6 axis controls affinity maturation and the generation of long-lived plasma cells," Nat. Immunol., May 2002, 3(5):451-456.

Anders et al., "HTSeq—a Python framework to work with high-throughput sequencing data," Sep. 25, 2014, 31(2):166-169.

Andre et al., "CD40L stabilizes arterial thrombi by a β3 integrin-dependent mechanism," Nature, Mar. 2002, 8(3):247-252.

Arnold et al., "Inflammatory monocytes recruited after skeletal muscle injury switch into antiinflammatory macrophages to support myogenesis," The Journal of Experimental Medicine, 2007, 204(5):1057-1069.

Assanga et al., "Cell growth curves for different cell lines and their relationship with biological activities," Int. J. Biotechnol. Mol. Biol. Res., Aug. 2013, 4(4):60-70.

Auchincloss, "No tolerance for depletion," Nature Medicine, 2004, 10:21-23.

Back et al., "Anti-inflammatory therapies for atherosclerosis," Nature Reviews Cardiology, Feb. 10, 2015, 12:199-211.

Bayle et al., "Rapamycin analogs with differential binding specificity permit orthogonal control of protein activity," Chemistry & Biology, Jan. 2006, 13(1):99-107.

Bekkering et al., "In Vitro Experimental Model of Trained Innate Immunity in Human Primary Monocytes," Clinical and Vaccine Immunology, Dec. 2016, 23(12):926-933.

Benichou et al., "Innate immunity and resistance to tolerogenesis in allotransplantation," Frontiers in Immunology, 2012, 3:73.

Berge et al., "Pharmaceutical Salts," Journal of Pharmaceutical Sciences, Jan. 1977, 66(1):1-19.

Boussiotis et al., "Molecular and Biochemical Aspects of the PD-1 Checkpoint Pathway," New England Journal of Medicine, 2016, 375:1767-1778.

Braza et al., "Inhibiting Inflammation with Myeloid Cell-Specific Nanobiologics Promotes Organ Transplant Acceptance," Immunity, 2018, 49, 819-828.

Bregoli et al., "Nanomedicine applied to translational oncology: A future perspective on cancer treatment," Nanomedicine: Nanotechnology, Biology and Medicine, 2016, 12(1):81-103.

Bricarello et al., "Reconstituted lipoprotein: a versatile class of biologically-inspired nanostructures," ACS Nano, 2011, 5:42-57.

Brignone et al., "A soluble form of lymphocyte activation gene-3 (IMP321) induces activation of a large range of human effector cytotoxic cells," Journal of Immunology, Sep. 15, 2007, 179(6):4202-4211.

Brundish et al., "Synthesis of N-[2-$^3$H] acetyl-D-muramyl-L-alanyl-D-iso-glutaminyl-L-alanyl-2-(1',2'-dipalmitoyl-sn-glycero-3'-phosphoryl) ethylamide of high specific radioactivity," Journal of Labelled Compounds and Radiopharmaceuticals, 1985, 22(1):29-35.

Buffen et al., "Autophagy Controls BCG-Induced Trained Immunity and the Response to Intravesical BCG Therapy for Bladder Cancer," PLoS Pathog., 2014, 10:e1004485, 10 pages.

Burgess et al., "Immunotherapeutic approaches to sarcoma," Current Treatment Options in Oncology, 2015, 16(6):1-4.

cancer.org [online], "Key Statistics for Melanoma Skin Cancer," Jan. 12, 2022, retrieved on Apr. 18, 2022, retrieved from URL<https://www.cancer.org/cancer/melanoma-skin-cancer/about/key-statistics.html>, 2 pages.

CAS Registry No. 1054609-71-0, STN entry date: Sep. 29, 2008, STN Registry, chemical name unassigned, 1 page.

CAS Registry No. 1054657-07-6, STN entry date: Sep. 29, 2008, STN Registry, chemical name: D-Glutamamide, N-[(8ξ)-N-acetyl-β-muramoyl]-L-alanyl-N5-[(1S)-1-methyl-2-(octyloxy)ethyl]-, 1 page.

CAS Registry No. 1135450-63-3, STN entry date: Apr. 16, 2009, STN Registry, chemical name: L-Threonine, N-(N-acetyl-α-muramoyl)-L-valyl-D-α-glutaminy1-L-arginyl-L-prolyl-N6-L-alanyl-L-lysyl-, methyl ester, 1 page.

CAS Registry No. 1135450-66-6, STN entry date: Apr. 16, 2009, STN Registry, chemical name: L-Threonine, N-(N-acetyl-α-muramoyl)-L-valyl-D-α-glutaminyl-L-arginyl-L-prolyl-N6-L-valyl-L-lysyl-, methyl ester, 1 page.

CAS Registry No. 1135450-69-9, STN entry date: Apr. 16, 2009, STN Registry, chemical name: L-Threonine, N-(N-acetyl-α-muramoyl)-L-valyl-D-α-glutaminyl-L-arginyl-L-prolyl-N6-glycyl-L-lysyl-, methyl ester, 1 page.

CAS Registry No. 1135450-72-4, STN entry date: Apr. 16, 2009, STN Registry, chemical name: L-Threonine, N-(N-acetyl-α-muramoyl)-L-alanyl-D-α-glutaminyl-L-arginyl-L-prolyl-N6-glycyl-L-lysyl-, methyl ester, 1 page.

CAS Registry No. 1135450-74-6, STN entry date: Apr. 16, 2009, STN Registry, chemical name: L-Threonine, N-(N-acetyl-α-muramoyl)-L-alanyl-D-α-glutaminyl-L-arginyl-L-prolyl-N6-L-valyl-L-lysyl-, methyl ester, 1 page.

CAS Registry No. 130279-67-3, STN entry date: Nov. 9, 1990, STN Registry, chemical name: L-Lysine, N-[O-2-(acetylamino)-2-deoxy-β-D-glucopyranosyl-(1→4)-O-(N-acetyl-β-muramosyl)-(1→4)-O-2-(acetylamino)-2-deoxy-β-D-glucopyranosyl-(1→4)-α-muramoyl]-L-alanyl-D-α-glutaminyl-N6-(1-oxooctadecyl)-, (1→1')-amide with L-alanyl-D-α-glutaminyl-N6-(1-oxooctadecyl)-L-lysine (9CI), 1 page.

CAS Registry No. 130324-95-7, STN entry date: Nov. 9, 1990, STN Registry, chemical name: L-Lysine, N2-[N2-[N-[O-2-(acetylamino)-2-deoxy-β-D-glucopyranosyl-(1→4)-O-2-(acetylamino)-2-deoxy-

(56) References Cited

OTHER PUBLICATIONS

3-O-[7-(aminocarbonyl)-12-carboxy-1,4-dimethyl-2,5,10,18-tetraoxo-3,6,11,17-tetraazapentatriacont-1-yl]-β-D-glucopyranosyl-(1-→4)-O-2-(acetylamino)-2-deoxy-β-D-glucopyranosyl-(1-→4)-N-acetyl-β-muramoyl]-L-alanyl]-D-α-glutaminyl]-N6-(1-oxooctadecyl)-, [1R-(1R*,4S*,7R*)]—(9CI), 1 page.

CAS Registry No. 171669-22-0, STN entry date: Dec. 22, 1995, chemical name: D-Glutamamide, N-[N-acetyl-1-O-(phenylmethyl)-α-muramoyl]-L-alanyl-N5-[6-oxo-6-(phenylmethoxy)hexyl]—(9CI), 1 page.

CAS Registry No. 727353-41-5, STN entry date: Aug. 16, 2004, STN Registry, chemical name: L-Arginine, N-(N-acetyl-α-muramoyl)-L-2-aminobutanoyl-D-α-glutaminyl-, methyl ester (9CI), 1 page.

CAS Registry No. 739324-45-9, STN entry date: Sep. 3, 2004, STN Registry, chemical name: D-Glutamamide, N-(N-acetylmuramoyl)-L-alanyl-N5-[(7R)-4-hydroxy-4-oxido-10-oxo-7-[(1-oxohexadecyl)oxy]-3,5,9-trioxa-4-phosphapentacos-1-yl]—(9CI), 1 page.

CAS Registry No. 740048-83-3, STN entry date: Sep. 5, 2004, STN Registry, chemical name: L-Arginine, N-[N-acetyl-1,4,6-tris-O-(1-oxopropyl)-β-muramoyl]-L-2-aminobutanoyl-D-α-glutaminyl-, methyl ester (9CI), 1 page.

CAS Registry No. 74817-61-1, STN entry date: Nov. 16, 1984, STN Registry, chemical name: D-Glutamine, N-(N-acetylmuramoyl)-L-alanyl-, butyl ester, 1 page.

CAS Registry No. 760134-41-6, STN entry date: Oct. 10, 2004, STN Registry, chemical name: L-Arginine, N-(N-acetyl-1,4,6-tri-O-acetyl-α-muramoyl)-L-2-aminobutanoyl-D-α-glutaminyl-, methyl ester (9CI), 1 page.

CAS Registry No. 768320-98-5, STN entry date: Oct. 24, 2004, STN Registry, chemical name: L-Arginine, N-(N-acetyl-β-muramoyl)-L-2-aminobutanoyl-D-α-glutaminyl-, methyl ester (9CI), 1 page.

CAS Registry No. 776255-37-9, STN entry date: Nov. 8, 2004, STN Registry, chemical name: L-Arginine, N-(N-acetyl-1,4,6-tri-O-acetyl-β-muramoyl)-L-2-aminobutanoyl-D-α-glutaminyl-, methyl ester (9CI), 1 page.

CAS Registry No. 777018-44-7, STN entry date: Nov. 8, 2004, STN Registry, chemical name: L-Arginine, N-[N-acetyl-1,4,6-tris-O-(1-oxopropyl)-α-muramoyl]-L-2-aminobutanoyl-D-α-glutaminyl-, methyl ester, (9CI), 1 page.

CAS Registry No. 78113-36-7, STN entry date: Nov. 16, 1984, STN Registry, chemical name: L-Lysine, N-(N-acetylmuramoyl)-L-alanyl-D-α-glutaminyl-N6-(1-oxooctadecyl)-, 1 page.

cdc.gov [online], "Heart Disease Facts," Mar. 2017, retrieved on Mar. 24, 2022, retrieved from URL<https://www.cdc.gov/heartdisease/facts.htm#:~:text=Heart%20Disease%20in%20the%20United%20States&text=One%20person%20dies%20every%2036,United%20States%20from%20cardiovascular%20disease.&text=About%20659%2C000%20people%20in%20the,1%20in%20every%204%20deaths.&text=Heart%20disease%20costs%20the%20United,year%20from%202016%20to%202017>, 4 pages.

Chambenoit et al., "Specific Docking of Apolipoprotein A-I at the Cell Surface Requires a Functional ABCA1 Transporter," The Journal of Biological Chemistry, Mar. 2001, 276(13):9955-9960.

Chatzigeorgiou et al. "Blocking CD40-TRAF6 signaling is a therapeutic target in obesity associated insulin resistance," Proc. Natl. Acad. Sci. U.S.A., Feb. 2014, 18, 2014, 111(7):2685-91.

Cheng et al. "mTOR/HIF1α-Mediated Aerobic Glycolysis as Metabolic Basis for Trained Immunity," Science, Sep. 26, 2014, 345(6204):1-10.

Chinetti-Gbaguidi et al., "Macrophage subsets in atherosclerosis," Nature, Jan. 2015, 12:10-17.

Conde et al., "DC-SIGN+ Macrophages Control the Induction of Transplantation Tolerance," Immunity, Jun. 16, 2015, 42:1143-1158.

Corry et al., "Primarily vascularized allografts of hearts in mice," Transplantation, 1973, 16(4):343-350.

Costello et al., "A Review of the current status and concept of the emerging implications of zinc and zinc transporters in the development of pancreatic cancer," Pancreatic disorders & therapy, Jan. 2013, 19 pages.

Davankov, "International Union of Pure and Applied Chemistry—Analytical Chemistry Division Commission on Separation Methods in Analytical Chemistry (V3)—Analytical Chiral Separation Methods," Pure and Applied Chemistry, 1997, 69(7):1469-1474.

DeMeester et al., "Synthesis of Functionalized N-Acetyl Muramic Acids To Probe Bacterial Cell Wall Recycling and Biosynthesis," J. Am. Chem. Soc., 2018, 140(30):9458-9465.

Demir et al., "Cancer screening of renal transplant patients undergoing long-term immnunosuppressive therapy," Transplantation Proceedings, Jun. 2015, 47(5):1413-1417.

Demirkiran et al., "Conversion From Calcineurin Inhibitor to Mycophenolate Mofetil-Based Immunosuppression Changes the Frequency and Phenotype of $CD4^+$ $FOXP3^+$ Regulatory T Cells," Clinical and Translation Research, Apr. 15, 2009, 87(7):1062-1068.

Ding et al., "Enalapril inhibits tubulointerstitial inflammation and NLRP3 inflammasome expression in BSA-overload nephropathy of rats," Acta Pharmacologica Sinica (2014) 35: 1293-1301.

Dotti, "Blocking PD-1 in cancer immunotherapy," Blood, Aug. 20, 2009, 114(8):1457-1459.

Duarte et al., "Abstract CT099: A phase I study of intralesional *Bacillus calmette-guerin* (BCG) followed by ipilimumab therapy in patients with advanced metastatic melanoma," Cancer Research, 2017, 77(13_Supplement):CT099.

Duivenvoorden et al., "A statin-loaded reconstituted high-density lipoprotein nanoparticle inhibits atherosclerotic plaque inflammation," Jan. 20, 2014, 5(3065):12 pages.

Dutta et al., "Myocardial infarction accelerates atherosclerosis," Nature, Jul. 19, 2012, 487(7407):325-329.

Dzierzbicka et al., "New conjugates of muramyl dipeptide and nor-muramyl dipeptide linked to tuftsin and retro-tuftsin derivatives significantly influence their biological activity," Pharmacological Reports, 2012, 64:217-223.

Dzierzbicka et al., "Synthesis of Conjugates of Muramyl Dipeptide and nor-Muramyl Dipeptide with Retro-Tuftsin (Arg-Pro-Lys-ThrOMe) as Potential Immunostimulants," Polish Journal of Chemistry, 2004, 78:409-416.

Dzierzbicka et al., "Synthesis of new conjugates of MDP and nor-MDP with retro-tuftsin derivatives as potential immunomodulators," Polish Journal of Chemistry, 2008, 82(7):1431-1439.

Endo et al., "Regulation of cytotoxic T lymphocyte triggering by PIR-B on dendritic cells," Proceedings of the National Academy of Sciences of the United States of America, Sep. 23, 2008, 105(38):14515-14520.

Engels et al., "Spectrum of cancer risk among US solid organ transplant recipients," JAMA, 2011, 306(17):1891-1901.

Everett et al., "Rationale and design of the cardiovascular inflammation reduction trial (CIRT): A test of the inflammatory hypothesis of atherthrombosis," Am. Heart J., Aug. 2013, 166(2):199-207.

Extended European Search Report for European Application No. 17790646.8, dated Nov. 25, 2019, 9 pages.

Extended European Search Report for European Application No. 18877470.7, dated Jun. 21, 2023, 7 pages.

Extended European Search Report for European Application No. 18880348.0, dated May 21, 2021, 7 pages.

Extended European Search Report for European Application No. 22155443.9, dated May 20, 2022, 8 pages.

Fantus et al., "The Ups and Downs of TORKinibs in Transplantation," Transplantation, Aug. 2015, 99(8):e117-e118.

Farber et al., "Immunological memory: lessons from the past and a look to the future," Nature Reviews Immunology, 2016, 16(2):124-128.

Fesnak et al., "Engineered T cells: the promise and challenges of cancer immunotherapy," Nature Reviews Cancer, 2016, 16(9):566-581.

Fourcade et al., "Upregulation of Tim-3 and PD-1 expression is associated with tumor antigen¬ specific $CD8^+$ T cell dysfunction in melanoma patients," Journal of Experimental Medicine, Sep. 27, 2010, 207(10):2175-2186.

(56) References Cited

OTHER PUBLICATIONS

Fujimoto et al., "Synthesis of crosslinked peptidoglycan fragments for investigation of their immunobiological functions," Tetrahedron Letters, 2009, 50(26):3631-3634.
Garcia et al., "Monocytic suppressive cells mediate cardiovascular transplantation tolerance in mice," Jul. 2010, J. Clin. Invest., 120(7):2486-2496.
Gardiner et al., "Multinational Evaluation of Mycophenolic Acid, Tacrolimus, Cyclosporin, Sirolimus, and Everolimus Utilization," Ann. Transplant, Jan. 5, 2016, 21:1-11.
Garrod et al., "Murine Skin Transplantation," Journal of Visualized Experiments, 2008, 2 pages.
Geissmann et al., "Blood Monocytes Consist of Two Principal Subsets with Distinct Migratory Properties," Jul. 2003, 19:71-82.
Gemeiner et al., "Immunomodulating Activity of 1,2-Difattyacyl-3-mercaptoglycerol Adducts," Biological Chemistry Hoppe-Seyler, 1992, 373(11):1085-1094.
GEO Accession No. GSE119370, "Expression data from graft infiltrating macrophages treated with mTORi-HDL nanobiologics," Oct. 31, 2018, 2 pages.
Guidelines for Prevention and Management of Complications Following Kidney Transplantation, Li et al. ed., Peoples Military Medical Press, Jan. 31, 2009, p. 227 (Relevance Explained in Chinese Office Action in Chinese Patent Application No. 201780041257.3, dated Dec. 3, 2020).
Gummert et al. "Newer Immunosuppressive Drugs," J Am Soc Nephrol, Jun. 1999, 10(6):1366-1380.
Hackstein et al., "Rapamycin inhibits IL-4-induced dendritic cell maturation in vitro and dendritic cell mobilization and function in vivo," Immunobiology, Blood, Jun. 1, 2003, 101(11):4457-463.
Han et al., "Structural and functional properties of V156K and A158E mutants of apolipoprotein AI in the lipid-free and lipid-bound states," Journal of Lipid Research., 2005, 46(3):589-596.
Hancock et al., "Costimulatory function and expression of CD40 ligand, CD80, and CD86 in vascularized murine cardiac allograft rejection," Proceedings of the National Academy of Sciences of the United States of America, Nov. 1996, 93:13967-13972.
Haug et al., "A phase I trial of Immunosuppression with anti-ICAM-1 (CD54) Matrix Biology in renal allograft recipients," Transplantation, Apr. 1993, 5594):766-773.
Heinzelmann et al., "Endotoxin and muramyl dipeptide modulate surface receptor expression on human mononuclear cells," Immunopharmacology, 2000, 48:117-128.
Herrera et al., "A Novel Pathway of Alloantigen Presentation by Dendritic Cells," The Journal of Immunology, 2004, 173:4828-4837.
Hiroyuki et al., "Synergistic Effect of Nod1 and Nod2 Agonists with Toll-Like Receptor Agonists on Human Dendritic Cells to Generate Interleukin-12 and Helper Type 1 Cells," American Society for Microbiology Infection and Immunity, Dec. 2005, 73(12):7967-7976.
Hodi et al., "Abstract CT001: Durable, long-term survival in previously treated patients with advanced melanoma (MEL) who received nivolumab (NIVO) monotherapy in a phase I trial," Cancer Research, 2016, 76(Issue 14_Supplement):CT001.
Hotchkiss et al., "Sepsis-induced immunosuppression: from cellular dysfunctions to immunotherapy," Nature Reviews Immunology, 2013, 13(12):862-874.
Huang et al., "Mammalian Septins Are Required for Phagosome Formation," Mol. Biol. Cell, Apr. 2008, 19:1717-1726.
Iknl.nl [online], "The Netherlands Cancer Registry," May 12, 2020, retrieved on Mar. 24, 2022, retrieved from URL<https://iknl.nl/en>, 2 pages.
Imhof et al., "Adhesion mechanisms regulating the migration of monocytes," Nature Reviews Immunology, Jun. 2004, 4(6):432-444.
Inamura et al., "Synthesis of peptidoglycan fragments and evaluation of their biological activity," Organic & Biomolecular Chemistry, 2006, 4(2):232-242.
International Preliminary Report on Patentability in International Application No. PCT/US2017/030444, dated Oct. 30, 2018, 8 pages.
International Preliminary Report on Patentability in International Application No. PCT/US2018/061935, dated May 26, 2020, 25 pages.
International Preliminary Report on Patentability in International Application No. PCT/US2018/061939, dated May 26, 2020, 20 pages.
International Preliminary Report on Patentability in International Appln. No. PCT/US2022/021035, mailed on Sep. 28, 2023, 9 pages.
International Search Report and Written Opinion in International Appln. No. PCT/US2023/065166, mailed on Sep. 29, 2023, 16 pages.
International Search Report and Written Opinion of the International Searching Authority for International Application No. PCT/US2017/030444, dated Sep. 22, 2017, 11 pages.
International Search Report and Written Opinion of the International Searching Authority for International Application No. PCT/US2018/061935, dated Apr. 19, 2019, 31 pages.
International Search Report and Written Opinion of the International Searching Authority for International Application No. PCT/US2018/061939, dated Feb. 22, 2019, 22 pages.
International Search Report and Written Opinion of the International Searching Authority for International Application No. PCT/US2022/021035, dated Jul. 25, 2022, 13 pages.
Invitation to Pay Additional Fees in International Appln. No. PCT/US2022/021035, dated May 19, 2022, 2 pages.
Ishida, "Synthesis and Immunoadjuvant Activity of NAcetyl-6-O-phosphono-muramoyl-l-alanyl-d-isoglutamine Methyl Ester and Its Lipophilic Derivatives," Agricultural and Biological Chemistry, 1989, 53:1057-1063.
Ježek et al., "Synthesis of tetrasaccharide containing glycopeptides related to bacterial cell wall starting from free tetrasaccharide by the pentafluorophenyl ester method," Collection of Czechoslovak Chemical Communications, 1990, 55(5), 1326-1335.
Jonas, "Reconstitution of High-Density Lipoproteins," Methods in Enzymology, 1986, 128:553-582.
Kanehisa et al., "KEGG for integration and interpretation of large-scale molecular data sets," Nucleic Acids Research, 2012, 40:D109-D114.
Kawai et al., "Thromboembolic complications after treatment with monoclonal antibody against CD40 ligand," Nature Medicine, Feb. 2000, 6(2):114.
Khalil et al., "The future of cancer treatment: immunomodulation, CARs and combination immunotherapy," Nature Reviews Clinical Oncology, 2016, 13(5):273-290.
Kidner et al., "Combined intralesional Bacille Calmette-Guerin (BCG) and topical imiquimod for in-transit melanoma," Author Manuscript, J. Immunother., 2012, 35(9):716-20.
Kim et al., "S6K1 Negatively Regulates TAK1 Activity in the Toll-Like Receptor Signaling Pathway," Molecular and Cellular Biology, 2014, 34(3):510-521.
Kim et al., "Single step reconstitution of multifunctional high-density lipoprotein-derived nanomaterials using microfluidics," Author Manuscript, ACS Nano, 2013, 7(11):9975-9983.
Kingwell et al., "HDL-targeted therapies: progress, failures and future," Nature Reviews Drug Discovery, 2014, 13:445-464.
Kirk et al., "Treatment with humanized monoclonal antibody against CD154 prevents acute renal allograft rejection in nonhuman primates," Nature Medicine, Jun. 1999, 5(6):686-693.
Krivorutchenko et al., "Study of the adjuvant activity of new MDP derivatives and purified saponins and their influence on HIV-1 replication in vitro," Vaccine, 1997, 15(12/13):1479-1486.
Kruidenier et al., "A selective jumonji H3K27 demethylase inhibitor modulates the proinflammatory macrophage response," Nature, 2012, 488(7411):404-408.
Kuai et al., "High-Density Lipoproteins: Nature's Multifunctional Nanoparticles," ACS Nano, 2016, 10(3):3015-3041.
Kupel et al., "Long-term risk of pulmonary embolism in solid-organ transplant recipients," Experimental and Clinical Transplantation, Apr. 2015, 13(Suppl 1):223-227.

(56) References Cited

OTHER PUBLICATIONS

Kur'yanov et al., "Synthesis of alkyl β-glycosides of 6-(N-acetylmuramoyl-L-alanyl-D-isoglutaminylamino)hexanoic acid and its 4-aminobutyl ester," Chemistry of Natural Compounds, 1994, 30(3):390-394.
Kuryanov et al., "Synthesis of muramyldipeptide lipophilic derivatives," Bioorganicheskaya Khimiya, 1994, 20(4):439-447 (with English abstract).
Lai et al., "Development of Luciferase Reporter-Based Cell Assays," ASSAY and Drug Development Technologies, 2006, 4(3):307-315.
Lameijer, "Targeting macrophage dynamics to regulate the cardiovascular immune response," University of Amsterdam, Jan. 16, 2018.
Langmead et al., "Fast gapped-read alignment with Bowtie 2," Nat. Methods, 2013, 9(4):357-359.
LaRosa et al., "The Innate Immune System in Allograft Rejection and Tolerance," J Immunol, 2007, 178:7503-7509.
Leeper et al., "High-Density Lipoprotein Nanoparticle Imaging in Atherosclerotic Vascular Disease," JACC: Basic to Translational Science, 2017, 2(1):98-100.
Leman et al., "Molecules That Mimic Apolipoprotein A-I: Potential Agents for Treating Atherosclerosis," J. Med. Chem., 2014, 57:2169-2196.
Lien, "Top 10 things primary care physicians should know about maintenance immunosuppression for transplant recipients," The American Journal of Medicine, 2015, 17 pages.
Linsel-Nitschke et al., "HDL as a target in the treatment of atherosclerotic cardiovascular disease," Nature Reviews Drug Discovery, 2005, 4(3):193-205.
Liu et al., "Innate NK Cells and Macrophages Recognize and Reject Allogeneic Nonself In Vivo via Different Mechanisms," J. Immunol., 2012, 188:2703-2711.
Liu et al., "Insight into the Glucose Metabolism of Immune Cells in Sepsis," Journal of Anesthesia and Perioperative Medicine, 2017, 4(1):38-44.
Liu et al., "Rat $CD8^+$ $FOXP3^+$ T suppressor cells mediate tolerance to allogeneic heart transplants, inducing PIR-B in APC and rendering the graft invulnerable to rejection," Transplant Immunology, Dec. 2004, 13:239-247.
Liu et al., "Solid-phase synthesis of muramyl dipeptide (mdp) derivatives using a multipin method," Bioorganic & Medicinal Chemistry Letters, 2000, 10:1361-1363.
Loo et al., "Development of an Fc-enhanced anti-B7-H3 monoclonal antibody with potent antitumor activity," Clinical Cancer Research, May 21, 2012, 18(14):3834-3845.
Lutgens et al., "Atherosclerosis: Targeting the immune system," ISA meeting, Amsterdam, May 23-26, 2015, 48 pages.
Lutgens et al., "Both early and delayed anti-CD40L antibody treatment induces a stable plaque phenotype," PNAS, 2000, 97(13):7464-7469.
Lutgens et al., "Deficient CD40-TRAF6 signaling in leukocytes prevents atherosclerosis by skewing the immune response toward an antiinflammatory profile," The Journal of Experimental Medicine, 2010, 207:391-404.
Lutgens et al., "Requirement for CD154 in the progression of atherosclerosis," Nature Medicine, Nov. 1999, 5(11):1313-1316.
Ma et al., "Paclitaxel Nano-Delivery Systems: A Comprehensive Review," J Nanomed Nanotechnol., Feb. 18, 2013, 4(2):1000164.
Mach et al., "Reduction of atherosclerosis in mice by inhibition of CD40 signaling," Nature, Jul. 9, 1998, 394:200-203.
Maldonado et al., "Polymeric synthetic nanoparticles for the induction of antigen-specific immunological tolerance," PNAS, 2014, E156-E165.
Martner et al. Fundamentals of Practical Clinical Immunology, 1st Ed., Vinca Press, Jun. 1993, pp. 314-315 (Relevance Explained in Chinese Office Action in Chinese Patent Application No. 201880086231.5, dated Nov. 3, 2022).
Matsumoto et al., "Stimulation of nonspecific resistance to infection induced by 6-O-acyl muramyl dipeptide analogs in mice," Infect. and Immun., 1981, 32(2):748-758.
Maury et al., "Raised Serum Levels of Cachectin/Tumor Necrosis Factor a In Renal Allograft Rejection," J. Exp. Med., 1987, 166:1132-1137.
Medical Immunology, He et al. ed., Henan Science and Technology Press, Jan. 31, 1990, p. 116 (Relevance Explained in Chinese Office Action in Chinese Patent Application No. 201780041257.3, dated Dec. 3, 2020).
Megias et al., "TLR2, TLR4 and Dectin-1 signalling in hematopoietic stem and progenitor cells determines the antifungal phenotype of the macrophages they produce," Microbes and Infection, 2016, 18:354-363.
Meshcheryakova et al., "Evidence for correlation between the intensities of adjuvant effects and NOD2 activation by monomeric, dimeric and lipophylic derivatives of N-acetylglucosaminyl-N-acetylmuramyl peptides," Vaccine, 2007, 25:4515-4520.
Mills et al., "Succinate Dehydrogenase Supports Metabolic Repurposing of Mitochondria to Drive Inflammatory Macrophages," Cell, 2016, 167:457-470.
Mitroulis et al., "Modulation of Myelopoiesis Progenitors is an Integral Component of Trained Immunity," Cell, Jan. 2018, 172:147-161.
Miyake et al., "Critical role of macrophages in the marginal zone in the suppression of immune responses to apoptotic cell-associated antigens," J. Clin. Invest., Aug. 2007, 117(8):2268-2278.
Modern Diagnosis and Therapy of Arteriosclerotic Diseases, Wei et al. ed., Jindun Publishing House, May 30, 2015, p. 598 (Relevance Explained in Chinese Office Action in Chinese Patent Application No. 201780041257.3, dated Dec. 3, 2020).
Mohammadi et al., "Specificity of the Transport of Lipid II by FtsW in *Escherichia coli*," The Journal of Biological Chemistry, 2014, 289(21):14707-14718.
Moore et al., "Macrophages in atherosclerosis: a dynamic balance," Oct. 2013, 13(10):709-721.
Moroder et al., "Synthesis of thiol-functionalized N-acetylmuramyl peptide congeners suitable for their conjugation to target molecules," Biological Chemistry Hoppe-Seyler, 1989, 370:365-375.
Moroi et al., "Physico-chemical properties of muroctasin," Arzneimittel-Forschung, 1988, 38(7A):953-959.
Morton et al., "BCG immunotherapy of malignant melanoma: summary of a seven-year experience," Annals of Surgery, 1974, 180:635-643.
Mudge et al., "Creating reference gene annotation for the mouse C57BL6/J genome assembly," Mamm Genome, Jul. 18, 2015, 26:366-378.
Mulder et al., "Therapeutic targeting of trained immunity," Nat. Rev. Drug Discov., 2019, 18(7):553-566.
Naesens et al., "Calcineurin Inhibitor Nephrotoxicity," Clin. J. Am. Soc. Nephrol., 2009, 4:481-508:481-508.
Nahrendorf et al., "The healing myocardium sequentially mobilizes two monocyte subsets with divergent and complementary functions," The Journal of Experimental Medicine, Nov. 26, 2007, 204(12):3037-47.
Nakamura et al., "Rapamycin prolongs cardiac allograft survival in a mouse model by inducing myeloid-derived suppressor cells," American Journal of Transplantation, Sep. 2015, 15(9):2364-77.
Netea et al., "Hypothesis: stimulation of trained immunity as adjunctive immunotherapy in cancer," Journal of Leukocyte Biology, Dec. 2017, 102:1323-1331.
Netea et al., "Innate immune memory: a paradigm shift in understanding host defense," Nature Immunology, 2015, 16(7):675-679.
Netea et al., "Trained immunity: A program of innate immune memory in health and disease," Science, Apr. 2016, 352(6284): aaf1098, 23 pages.
Nicodeme et al., "Suppression of inflammation by a synthetic histone mimic," Nature, 2010, 468(7327):1119-1123.
Oberbarnscheidt et al., "Innate allorecognition," Immunological Reviews, Mar. 2014, 258(1):145-9.
Oberbarnscheidt et al., "Non-self recognition by monocytes initiates allograft rejection," The Journal of Clinical Investigation, Aug. 1, 2014, 124(8):3579-89.
Ochando et al., "Alloantigen-presenting plasmacytoid dendritic cells mediate tolerance to vascularized grafts," Nature Immunology, Jun. 2006, 7(6):652-62.

(56) References Cited

OTHER PUBLICATIONS

Ochando et al., "Innate immune cell collaborations instigate transplant tolerance," American Journal of Transplantation, 2014, 14:2441-2443.
Office Action in Australian Appln. No. 2017257189, dated Feb. 28, 2022, 3 pages.
Office Action in Australian Appln. No. 2017257189, dated Mar. 16, 2021, 6 pages.
Office Action in Australian Appln. No. 2018370237, mailed on Oct. 20, 2023, 6 pages.
Office Action in Canadian Appln. No. 3021645, mailed on Jul. 13, 2023, 5 pages.
Office Action in Chinese Appln. No. 201580085777.5, dated Jan. 19, 2021, 15 pages (with English Translation).
Office Action in Chinese Appln. No. 201580085777.5, dated Jul. 3, 2020, 13 pages (with English Translation).
Office Action in Chinese Appln. No. 201780041257.3, dated Apr. 15, 2022, 31 pages (with English Translation).
Office Action in Chinese Appln. No. 201780041257.3, dated Dec. 3, 2020, 26 pages (with English Translation).
Office Action in Chinese Appln. No. 201780041257.3, dated Oct. 18, 2021, 34 pages (with English Translation).
Office Action in Chinese Appln. No. 201880086231.5, dated Jan. 28, 2022, 23 pages (with English Translation).
Office Action in Chinese Appln. No. 201880086231.5, dated May 29, 2023, 21 pages (with English Translation).
Office Action in Chinese Appln. No. 201880086231.5, dated Nov. 3, 2022, 24 pages (with English Translation).
Office Action in Chinese Appln. No. 201880087082.4, dated Apr. 13, 2022, 17 pages (with English Translation).
Office Action in Chinese Appln. No. 201880087082.4, dated Jan. 12, 2023, 9 pages (with English Translation).
Office Action in Chinese Appln. No. 201880087082.4, dated Jun. 14, 2023, 10 pages (with English translation).
Office Action in European Appln. No. 22155443.9, mailed on Aug. 28, 2023, 6 pages.
Office Action in Japanese Appln. No. 2018-556339, dated Feb. 1, 2022, 6 pages (with English Translation).
Office Action in Japanese Appln. No. 2018-556339, dated Nov. 22, 2022, 6 pages (with English Translation).
Office Action in Japanese Appln. No. 2020-545063, dated Nov. 15, 2022, 9 pages (with English Translation).
Office Action in Japanese Appln. No. 2020-545063, mailed on Jul. 3, 2023, 6 pages (with English translation).
Office Action in Japanese Appln. No. 2020-545065, dated Nov. 22, 2022, 7 pages (with English Translation).
Office Action in U.S. Appl. No. 18/121,527, mailed on Oct. 6, 2023, 10 pages.
Organ Transplantation, Yuyuan Liu ed., Human Science and Technology Press, Oct. 31, 2009, p. 52 (Relevance Explained in Chinese Office Action in Chinese Patent Application No. 201780041257.3, dated Dec. 3, 2020).
Pahl et al., "Macrophages inhibit human osteosarcoma cell growth after activation with the bacterial cell wall derivative liposomal muramyl tripeptide in combination with interferon-γ," J Exp Clin Cancer Res. 2014; 33:27, 13 pages.
Paolicelli et al., "Surface-modified PLGA-based Nanoparticles that can Efficiently Associate and Deliver Virus like Particles," Nanomedicine, Aug. 24, 2010, 5(6):843-853.
Pardoll et al., "The blockade of immune checkpoints in cancer immunotherapy," Nature Reviews Cancer, 2012, 12(4):252-264.
Pardoll, "Immunology beats cancer: a blueprint for successful translation," Nat. Immunol., 2012, 13(12):1129-1132.
Pérez-Medina et al., "In vivo PET imaging of HDL in multiple atherosclerosis models," JACC: Cardiovascular Imaging, Aug. 2016, 9(8):950-61.
Pérez-Medina et al., "Nanoreporter PET predicts the efficacy of anti-cancer nanotherapy," Nature Communications, 2016, 7:11838.
Pérez-Medina et al., "PET imaging of tumor-associated macrophages with $^{89}$Zr-labeled high-density lipoprotein nanoparticles," Journal of Nuclear Medicine, Aug. 2015, 56(8):1272-7.
Potteaux et al., "Suppressed monocyte recruitment drives macrophage removal from atherosclerotic plaques of Apoe$^{-/-}$ mice during disease regression," The Journal of Clinical Investigation, May 2, 2011, 121(5):2025-36.
Priem et al., "Trained Immunity-Promoting Nanobiologic Therapy Suppresses Tumor Growth and Potentiates Checkpoint Inhibition," Cell 2020, 183:786-801.
Pritchard, "Sourcing a chemical succession for cyclosporin from parasites and human pathogens," Drug Discovery Today, May 2005, 10(10):688-691.
PubChem [Online], "SID 40944914," Dec. 5, 2007, [Retrieved on Aug. 9, 2022], retrieved from URL<https://pubchem.ncbi.nlm.nih.gov/substance/40944914>, 5 pages.
Pullen et al., "CD40-tumor necrosis factor receptor-associated factor (TRAP) interactions: regulation of CD40 signaling through multiple TRAP binding sites and TRAP hetero-oligomerization," Biochemistry, 1998, 37:11836-11845.
Ramos-Cabrer et al., "The effect of loading nascent HDL with gadolinium phospholipids in the structural stability of the particles," Proceedings of the International Society for Magnetic Resonance in Medicine, 2014, 22(2014), 1 page.
Ridker et al., "Interleukin-1β inhibition and the prevention of recurrent cardiovascular events: rationale and design of the Canakinumab Anti-inflammatory Thrombosis Outcomes Study (CANTOS)," American Heart Journal, Oct. 1, 2011, 162(4):597-605.
Ritchie et al., "limma powers differential expression analyses for RNA-sequencing and microarray studies," Nucleic Acids Research, Apr. 20, 2015, 43(7):e47-, 13 pages.
Robbins et al., "Local proliferation dominates lesional macrophage accumulation in atherosclerosis," Nature Medicine, Sep. 2013, 19(9):1166-1172, 15 pages.
Saeed et al., "Epigenetic programming of monocyte-to-macrophage differentiation and trained innate immunity," Science, 2014, 345(6204):1251086.
Sakuishi et al., "Targeting Tim-3 and PD-1 pathways to reverse T cell exhaustion and restore anti-tumor immunity," Journal of Experimental Medicine, Sep. 27, 2010, 207(10):2187-2194.
Sanchez-Gaytan et al., "HDL-mimetic PLGA nanoparticle to target atherosclerosis plaque macrophages," Author Manuscript, Bioconjug. Chem., 2015, 26(3):443-451.
Sanchez-Gaytan et al., "Real-Time Monitoring of Nanoparticle Formation via FRET Imaging," Author Manuscript, Angewandte Chemie International Edition, 2017, 56(11):2923-2926.
Schönbeck et al., "CD40 signaling and plaque instability," Circulation Research, Dec. 7, 2001, 89(12):1092-103.
Schönbeck et al., "Inhibition of CD40 signaling limits evolution of established atherosclerosis in mice," Proceedings of the National Academy of Sciences, Jun. 20, 2000, 97(13):7458-7463.
Schwarz et al "Identification of differentially expressed genes induced by transient ischemic stroke," Brain Res Mol Brain Res, 2002; 101(1-2):12-22.
scientificamerican.com [online], "Cancer Immunotherapy: The Cutting Edge Gets Sharper," Oct. 1, 2015, retrieved on Mar. 24, 2022, retrieved from URL<https://www.scientificamerican.com/article/cancer-immunotherapy-the-cutting-edge-gets-sharper/#:~:text=Artificially%20boosting%20the%20body's%20immune,the%20past%20couple%20of%20years>, 5 pages.
Segrest et al., "The Amphipathic α Helix: A Multifunctional Structural Motif in Plasma Apolipoproteins," Advances in Protein Chemistry, 1994, 45:303-369.
Shah et al., "Effects of recombinant apolipoprotein A-$I_{Milano}$ on aortic atherosclerosis in apolipoprotein E-deficient mice," Circulation, Mar. 3, 1998, 97(8):780-5.
Shi et al., "Monocyte recruitment during infection and inflammation," Nature Reviews Immunology, Nov. 2011, 11(11):762-74.
Shimizu et al., "Host CD40 ligand deficiency induces long-term allograft survival and donor-specific tolerance in mouse cardiac transplantation but does not prevent graft arteriosclerosis," The Journal of Immunology, Sep. 15, 2000, 165(6):3506-18.

(56) References Cited

OTHER PUBLICATIONS

Shuchman, "Trading restenosis for thrombosis? New questions about drug-eluting stents," New England Journal of Medicine, Nov. 9, 2006, 355(19):1949-52.
Skajaa et al., "High-density lipoprotein-based contrast agents for multimodal imaging of atherosclerosis," Arteriosclerosis, Thrombosis, and Vascular Biology, 2010, 30(2):169-176.
Skajaa et al., "The biological properties of iron oxide core high-density lipoprotein in experimental atherosclerosis," Biomaterials, 2011, 32:206-213.
Song et al., "Immune Training Unlocks Innate Potential," Cell, Jan. 11, 2018, 172:3-5.
Sporri et al., "Inflammatory mediators are insufficient for full dendritic cell activation and promote expansion of CD4+ T cell populations lacking helper function," Nature immunology, 2005, 6:163-170.
Stone et al., "A prospective natural-history study of coronary atherosclerosis," New England Journal of Medicine, Jan. 20, 2011, 364(3):226-35.
Sun et al., "Interactions of NIPAM nanogels with model lipid multi-bilayers: A neutron reflectivity study," Journal of Colloid and Interface Science, 2018, 536:598-608.
Swirski et al., "Leukocyte behavior in atherosclerosis, myocardial infarction, and heart failure," Science, Jan. 11, 2013, 339(6116):161-6.
Swirski et al., "Ly-6$C^{hi}$ monocytes dominate hypercholesterolemia-associated monocytosis and give rise to macrophages in atheromata," The Journal of Clinical Investigation, Jan. 2, 2007, 117(1):195-205.
Swirski et al., "Monocyte accumulation in mouse atherogenesis is progressive and proportional to extent of disease," Proceedings of the National Academy of Sciences of the United States of America, Jul. 5, 2006, 103(27):10340-10345.
Swirski et al., "Myeloperoxidase-rich Ly-$6C^+$ myeloid cells infiltrate allografts and contribute to an imaging signature of organ rejection in mice," The Journal of Clinical Investigation, Jul. 1, 2010, 120(7):2627-34.
Tang et al., "Immune cell screening of a nanoparticle library improves atherosclerosis therapy," PNAS, Oct. 2016, 113(44):E6731-E6740.
Tang et al., "Inhibiting macrophage proliferation suppresses atherosclerotic plaque inflammation," Science Advances, Apr. 1, 2015, 1(3):e1400223, 10 pages.
Tehranirokh et al., "Microfluidic devices for cell cultivation and proliferation," Biomicrofluidics, 2013, 7:51502.
Tenahrench et al., "The Basic and Clinical of Coliform Cancer," 1st Ed., Shanghai Scientific and Technical Literature Press, Sep. 1999, pp. 252-253 (Relevance Explained in Chinese Office Action in Chinese Patent Application No. 201880086231.5, dated Nov. 3, 2022).
Thomson et al., "Immunoregulatory functions of mTOR inhibition," Nature Reviews Immunology, May 2009, 9(5):324-37.
Transplantatiestichting.nl [online], "Cijfers over donatie en transplantatie," available on or before Mar. 2020, retrieved on Mar. 24, 2022, retrieved from URL<https://www.transplantatiestichting.nl/publicaties-en-naslag/cijfers-over-donatie-en-transplantatie>, 5 pages.
unos.org [online], "Data," Nov. 2002, retrieved on Mar. 24, 2022, retrieved from URL<https://unos.org/data/>, 3 pages.
Valenta et al., "Macrophage PLTP is atheroprotective in LDLr-deficient mice with systemic PLTP deficiency," Journal of Lipid Research, Jan. 1, 2008, 49(1):24-32.
Van den Berg et al., "Blocking CD40-TRAF6 interactions by small-molecule inhibitor 6860766 ameliorates the complications of diet-induced obesity in mice, " International Journal of Obesity, May 2015, 39(5):782-90.
Van der Valk et al., "Prednisolone-containing liposomes accumulate in human atherosclerotic macrophages upon intravenous administration," Author Manuscript, Nanomedicine, 2015, 11:1039-1046.
Vanneman et al., "Combining immunotherapy and targeted therapies in cancer treatment," Nature Reviews Cancer, 2012, 12(4):237-251.
VanNieuwenhze et al., "The total synthesis of lipid I," J. Am. Chem. Soc., 2001, 123:6983-6988.
Vugts et al., "Synthesis of Phosphine and Antibody-Azide Probes for in Vivo Staudinger Ligation in a Pretargeted Imaging and Therapy Approach," Bioconjugate Chem., 2011, 22:2072-2081.
Wang et al., "Glycan sequence-dependent Nod2 activation investigated by using a chemically synthesized bacterial peptidoglycan fragment library," ChemBioChem, 2013, 14:482-488.
Wang et al., "GO-function: deriving biologically relevant functions from statistically significant functions," Briefings in Bioinformatics, Mar. 1, 2012, 13(2):216-27.
Wang et al., "Peptidoglycan microarray as a novel tool to explore protein-ligand recognition," Biopolymers (Pept. Sci.), 2016, 106(4):422-429.
Wang et al., "Synthesis of characteristic *Mycobacterium peptidoglycan* (PGN) fragments utilizing with chemoenzymatic preparation of meso-diaminopimelic acid (DAP), and their modulation of innate immune responses," Organic & Biomolecular Chemistry, 2016, 14:1013-1023.
Wang et al., "Tumor cell-intrinsic PD-1 receptor is a tumor suppressor and mediates resistance to PD-1 blockade therapy," PNAS, Mar. 24, 2020, 117(12):6640-6650.
Wasan et al., "Impact of lipoproteins on the biological activity and disposition of hydrophobic drugs: implications for drug discovery," Nature Review Drug Discovery, 2008, 7:84-99.
Wells et al., "Requirement for T-cell apoptosis in the induction of peripheral transplantation tolerance," Nature Medicine, Nov. 1999, 5(11):1303-7.
Willems et al., "Lipophilic Muramyl Dipeptide-Antigen Conjugates as Immunostimulating Agents," ChemMedChem Communications, 2016, 11:190-198.
Wu et al., "Homeostatic proliferation is a barrier to transplantation tolerance," Nature Medicine, Jan. 2004, 10(1):87-92.
Yan et al., "Indexing TNF-α gene expression using a gene-targeted reporter cell line," BMC Biology, 2009, 7:8.
Yang et al., "Rapamycin-conditioned dendritic cells induced immune tolerance through the regulation of Treg/Th17 cells in mice," Natl. Med. J. China, 2015, 95(30):2469-2473 (with English Abstract).
Yang et al., "Scavenger receptor-BI is a receptor for lipoprotein(a)," Journal of Lipid Research, Sep. 1, 2013, 54(9):2450-7.
Ye et al., "Imaging Macrophage and Hematopoietic Progenitor Proliferation in Atherosclerosis," Circulation Research, 2015, 117(10):835-845.
Zamanian-Daryoush et al., "The Cardioprotective Protein Apoli poprotein A1 Promotes Potent Anti-tumorigenic Effects," Journal of Biological Chemistry, Jul. 19, 2013, 288(29):21237-21252.
Zarzycka et al., "Discovery of small molecule CD40-TRAF6 inhibitors, Journal of Chemical Information and Modeling," Jan. 27, 2015, 55:294-307.
Zecher et al., "An innate response to allogeneic nonself mediated by monocytes," The Journal of Immunology, Dec. 15, 2009, 183(12):7810-6.
Zemlyakov et al., "Synthesis of muramyldipeptide and their isotyped-labeled analogues," Khimiya Prirodnykh Soedinenii, 1990, 2:245-248 (English Translation only).
Zemlyakov et al., "Synthesis of the γ-octadecylamide of N-acetylmuramoyl-L-alanyl-D-isoglutamine," Khimiya Prirodnykh Soedinenii, 1988, 6:892-893 (English Translation only).
Zemlyakov, "Immobilization of synthetic glycopeptides on polymeric supports," Chemistry of Natural Compounds, 1998, 34(1):80-85.
Zhang et al., "A General Framework for Weighted Gene Co-Expression Network Analysis," Statistical Applications in Genetics and Molecular Biology, Aug. 12, 2005, 4(1): 45 pages.
Zhao et al., "Augmenting Drug-Carrier Compatibility Improves Tumour Nanotherapy Efficacy," Nature Communications, Apr. 2016, 7:11221, 11 pages.
Zheng et al., "HDL mimetic CER-001 targets atherosclerotic plaques in patients," Atherosclerosis, 2016, 251:381-388.
Zou et al., "PLGA/liposome hybrid nanoparticles for short-chain ceramide delivery," Pharmaceutical Research, Mar. 2014, 31(3):684-693.

(56) References Cited

OTHER PUBLICATIONS

Office Action in Colombian Appln. No. NC202302783, mailed on Dec. 12, 2024, 14 pages.
Office Action in Japanese Appln. No. 2023-060872, mailed on Jan. 7, 2025, 6 pages (with English translation).
Office Action in Australian Appln. No. 2022204675, dated Aug. 19, 2024, 4 pages.
Office Action in Japanese Appln. No. 2023-060872, mailed on Apr. 16, 2024, 5 pages (with English translation).
Office Action in Japanese Appln. No. 2023-130072, mailed on Sep. 10, 2024, 9 pages (with English translation).
Office Action in Japanese Appln. No. 2023-163975, mailed on Aug. 6, 2024, 4 pages (with English translation).
ec.europa.edu [online], Takeda Oncology, "Mepact product information," Dec. 18, 2023, retrieved from URL<https://ec.europa.eu/health/documents/community-register/2019/20190220143552/anx_143552_en.pdf>, retrieved on Jun. 18, 2025, 1-32 pages.
Office Action in Chilean Appln. No. NC202302783, mailed on May 12, 2025, 28 pages (with Machine translation).
Office Action in Chinese Appln. No. 202410398398.2, mailed on Jun. 28, 2025, 9 pages (with English translation).
Office Action in European Appln. No. 18880348.0, mailed on May 22, 2025, 6 pages.
Office Action in Japanese Appln. No. 2023-163975, mailed on Jun. 10, 2025, 9 pages (with English translation).
Office Action in Japanese Appln. No. 2023-557668, mailed on Jun. 10, 2025, 4 pages (with English translation).
Office Action in Saudi Arabian Appln. No. 523450892, mailed on May 27, 2025, 18 pages (with English translation).
Office Action in Saudi Arabian Appln. No. 523450892, mailed on Jan. 6, 2026, 11 pages (with English translation).
Netea et al., "Trained innate immunity: Concept, nomenclature, and future perspectives," Journal of Allergy Clinical Immunology, Nov. 2024, 154(5):1079-1084.
Extended European Search Report in European Appln. No. 22772322.8, mailed on Feb. 11, 2025, 5 pages.
Ogawa et al., "Muramyl Dipeptide and its Derivatives: Peptide Adjuvant in Immunological Disorders and Cancer Therapy", Curr Bioact Compd, Sep. 2011, 7(3):180-197 (Author Manuscript, 37 pages).
U.S. Appl. No. 18/927,572, filed Oct. 25, 2024, Willem J. M. Mulder.
U.S. Appl. No. 18/806,189, filed Aug. 15, 2024, Willem J. M. Mulder.
U.S. Appl. No. 17/698,971 (U.S. Pat. No. 11,859,021), Mar. 18, 2022 (Jan. 2, 2024), Henricus Marie Janssen.
U.S. Appl. No. 18/850,960, filed Sep. 25, 2024, Abraham J. Teunissen.
U.S. Appl. No. 16/097,013, filed Oct. 26, 2018, Willem J. M. Mulder.
U.S. Appl. No. 18/121,527, filed Mar. 14, 2023, Willem J. M. Mulder.
U.S. Appl. No. 16/862,564, filed Apr. 30, 2020, Willem J. M. Mulder.
U.S. Appl. No. 16/862,570, filed Apr. 30, 2020, Willem J. M. Mulder.
U.S. Appl. No. 17/743,342, filed May 12, 2022, Willem J. M. Mulder.
U.S. Appl. No. 18/076,759, filed Dec. 7, 2022, Willem J. M. Mulder.
U.S. Appl. No. 16/863,333, filed Apr. 30, 2020, Willem J. M. Mulder.
U.S. Appl. No. 16/863,438, filed Apr. 30, 2020, Willem J. M. Mulder.
U.S. Appl. No. 17/698,971, filed Mar. 18, 2022, Henricus Marie Janssen.
Extended European Search Report in European Appln. No. 23782071.7, mailed on Mar. 2, 2026, 10 pages.
Notice of Allowance in Canada Appln. No. 3,082,831, mailed Apr. 23, 2026, 4 pages.
Office Action in Australian Appln. No. 2022239614, mailed on Oct. 14, 2025, 4 pages.
Office Action in Australian Appln. No. 2025200346, mailed on Mar. 12, 2026, 4 pages.
Office Action in Australian Appln. No. 2025201252, mailed on Apr. 16, 2026, 4 pages.
Office Action in Chinese Appln. No. 202410398398.2, mailed on Oct. 20, 2025, 9 pages.
Office Action in Korean Appln. No, 10-2023-7035389, mailed on Apr. 22, 2026, 10 pages.
Ogawa et al., "Muramyl dipeptide and its derivatives: peptide adjuvant in immunological disorders and cancer therapy," Current bioactive compounds, Sep. 1, 2011, 7(3):180-197.
Schrijver et al., "Nanoengineering Apolipoprotein A1-Based Immunotherapeutics," Advances Therapeutics, Jun. 2021, 4(8), 16 pages.
Office Action in Brazilian Appln. No. BR112023018950-0, mailed on Aug. 19, 2026, 4 pages (with English Translation only).
Office Action in Indian Appln. No. 202347068590, mailed on Aug. 13, 2026, 8 pages (with English Translation).

* cited by examiner

SEQUENCE LISTING

```
Sequence total quantity: 346
SEQ ID NO: 1            moltype = AA  length = 22
FEATURE                 Location/Qualifiers
source                  1..22
                        mol_type = protein
                        organism = synthetic construct
SEQUENCE: 1
PVLDLFRELL NELLEZLKQK LK                                            22

SEQ ID NO: 2            moltype = AA  length = 23
FEATURE                 Location/Qualifiers
source                  1..23
                        mol_type = protein
                        organism = synthetic construct
SEQUENCE: 2
GVLDLFRELL NELLEALKQK LKK                                           23

SEQ ID NO: 3            moltype = AA  length = 22
FEATURE                 Location/Qualifiers
source                  1..22
                        mol_type = protein
                        organism = synthetic construct
SEQUENCE: 3
PVLDLFRELL NELLEWLKQK LK                                            22

SEQ ID NO: 4            moltype = AA  length = 22
FEATURE                 Location/Qualifiers
source                  1..22
                        mol_type = protein
                        organism = synthetic construct
SEQUENCE: 4
PVLDLFRELL NELLEALKQK LK                                            22
```

-continued

```
SEQ ID NO: 5            moltype = AA  length = 23
FEATURE                 Location/Qualifiers
source                  1..23
                        mol_type = protein
                        organism = synthetic construct
SEQUENCE: 5
PVLDLFRELL NELLEALKQK LKK                                             23

SEQ ID NO: 6            moltype = AA  length = 22
FEATURE                 Location/Qualifiers
source                  1..22
                        mol_type = protein
                        organism = synthetic construct
SEQUENCE: 6
PVLDLFRELL NEXLEALKQK LK                                              22

SEQ ID NO: 7            moltype = AA  length = 22
FEATURE                 Location/Qualifiers
source                  1..22
                        mol_type = protein
                        organism = synthetic construct
SEQUENCE: 7
PVLDLFKELL NELLEALKQK LK                                              22

SEQ ID NO: 8            moltype = AA  length = 22
FEATURE                 Location/Qualifiers
source                  1..22
                        mol_type = protein
                        organism = synthetic construct
SEQUENCE: 8
PVLDLFRELL NEGLEALKQK LK                                              22

SEQ ID NO: 9            moltype = AA  length = 22
FEATURE                 Location/Qualifiers
source                  1..22
                        mol_type = protein
                        organism = synthetic construct
SEQUENCE: 9
PVLDLFRELG NELLEALKQK LK                                              22

SEQ ID NO: 10           moltype = AA  length = 22
FEATURE                 Location/Qualifiers
source                  1..22
                        mol_type = protein
                        organism = synthetic construct
SEQUENCE: 10
PVLDLFRELL NELLEAZKQK LK                                              22

SEQ ID NO: 11           moltype = AA  length = 22
FEATURE                 Location/Qualifiers
source                  1..22
                        mol_type = protein
                        organism = synthetic construct
SEQUENCE: 11
PVLDLFKELL QELLEALKQK LK                                              22

SEQ ID NO: 12           moltype = AA  length = 22
FEATURE                 Location/Qualifiers
source                  1..22
                        mol_type = protein
                        organism = synthetic construct
SEQUENCE: 12
PVLDLFRELL NELLEAGKQK LK                                              22

SEQ ID NO: 13           moltype = AA  length = 22
FEATURE                 Location/Qualifiers
source                  1..22
                        mol_type = protein
                        organism = synthetic construct
SEQUENCE: 13
GVLDLFRELL NEGLEALKQK LK                                              22

SEQ ID NO: 14           moltype = AA  length = 22
FEATURE                 Location/Qualifiers
source                  1..22
                        mol_type = protein
                        organism = synthetic construct
SEQUENCE: 14
PVLDLFRELL NELLEALXQX LX                                              22
```

-continued

```
SEQ ID NO: 15          moltype = AA  length = 22
FEATURE                Location/Qualifiers
source                 1..22
                       mol_type = protein
                       organism = synthetic construct
SEQUENCE: 15
PVLDLFRELW NELLEALKQK LK                                                22

SEQ ID NO: 16          moltype = AA  length = 22
FEATURE                Location/Qualifiers
source                 1..22
                       mol_type = protein
                       organism = synthetic construct
SEQUENCE: 16
PVLDLLRELL NELLEALKQK LK                                                22

SEQ ID NO: 17          moltype = AA  length = 22
FEATURE                Location/Qualifiers
source                 1..22
                       mol_type = protein
                       organism = synthetic construct
SEQUENCE: 17
PVLELFKELL QELLEALKQK LK                                                22

SEQ ID NO: 18          moltype = AA  length = 22
FEATURE                Location/Qualifiers
source                 1..22
                       mol_type = protein
                       organism = synthetic construct
SEQUENCE: 18
GVLDLFRELL NELLEALKQK LK                                                22

SEQ ID NO: 19          moltype = AA  length = 22
FEATURE                Location/Qualifiers
source                 1..22
                       mol_type = protein
                       organism = synthetic construct
SEQUENCE: 19
PVLDLFRELL NEGLEALKQK LK                                                22

SEQ ID NO: 20          moltype = AA  length = 22
FEATURE                Location/Qualifiers
source                 1..22
                       mol_type = protein
                       organism = synthetic construct
SEQUENCE: 20
PVLDLFREGL NELLEALKQK LK                                                22

SEQ ID NO: 21          moltype = AA  length = 22
FEATURE                Location/Qualifiers
source                 1..22
                       mol_type = protein
                       organism = synthetic construct
SEQUENCE: 21
PVLDLFRELL NELLEALKQK LK                                                22

SEQ ID NO: 22          moltype = AA  length = 22
FEATURE                Location/Qualifiers
source                 1..22
                       mol_type = protein
                       organism = synthetic construct
SEQUENCE: 22
PVLDLFRELL NELLEGLKQK LK                                                22

SEQ ID NO: 23          moltype = AA  length = 22
FEATURE                Location/Qualifiers
source                 1..22
                       mol_type = protein
                       organism = synthetic construct
SEQUENCE: 23
PLLELFKELL QELLEALKQK LK                                                22

SEQ ID NO: 24          moltype = AA  length = 22
FEATURE                Location/Qualifiers
source                 1..22
                       mol_type = protein
                       organism = synthetic construct
SEQUENCE: 24
```

-continued

```
PVLDLFRELL NELLEALQKK LK                                          22

SEQ ID NO: 25          moltype = AA  length = 22
FEATURE                Location/Qualifiers
source                 1..22
                       mol_type = protein
                       organism = synthetic construct
SEQUENCE: 25
PVLDFFRELL NEXLEALKQK LK                                          22

SEQ ID NO: 26          moltype = AA  length = 22
FEATURE                Location/Qualifiers
source                 1..22
                       mol_type = protein
                       organism = synthetic construct
SEQUENCE: 26
PVLDLFRELL NELLELLKQK LK                                          22

SEQ ID NO: 27          moltype = AA  length = 22
FEATURE                Location/Qualifiers
source                 1..22
                       mol_type = protein
                       organism = synthetic construct
SEQUENCE: 27
PVLDLFRELL NELZEALKQK LK                                          22

SEQ ID NO: 28          moltype = AA  length = 22
FEATURE                Location/Qualifiers
source                 1..22
                       mol_type = protein
                       organism = synthetic construct
SEQUENCE: 28
PVLDLFRELL NELWEALKQK LK                                          22

SEQ ID NO: 29          moltype = AA  length = 22
FEATURE                Location/Qualifiers
source                 1..22
                       mol_type = protein
                       organism = synthetic construct
SEQUENCE: 29
AVLDLFRELL NELLEALKQK LK                                          22

SEQ ID NO: 30          moltype = AA  length = 22
FEATURE                Location/Qualifiers
source                 1..22
                       mol_type = protein
                       organism = synthetic construct
SEQUENCE: 30
PVLDLPRELL NELLEALKQK LK                                          22

SEQ ID NO: 31          moltype = AA  length = 22
FEATURE                Location/Qualifiers
source                 1..22
                       mol_type = protein
                       organism = synthetic construct
SEQUENCE: 31
PVLDLFLELL NEXLEALKQK LK                                          22

SEQ ID NO: 32          moltype = AA  length = 22
FEATURE                Location/Qualifiers
source                 1..22
                       mol_type = protein
                       organism = synthetic construct
SEQUENCE: 32
XVLDLFRELL NELLEALKQK LK                                          22

SEQ ID NO: 33          moltype = AA  length = 22
FEATURE                Location/Qualifiers
source                 1..22
                       mol_type = protein
                       organism = synthetic construct
SEQUENCE: 33
PVLDLFREKL NELLEALKQK LK                                          22

SEQ ID NO: 34          moltype = AA  length = 22
FEATURE                Location/Qualifiers
source                 1..22
                       mol_type = protein
                       organism = synthetic construct
```

-continued

```
SEQUENCE: 34
PVLDZFRELL NELLEALKQK LK                                            22

SEQ ID NO: 35          moltype = AA  length = 22
FEATURE                Location/Qualifiers
source                 1..22
                       mol_type = protein
                       organism = synthetic construct
SEQUENCE: 35
PVLDWFRELL NELLEALKQK LK                                            22

SEQ ID NO: 36          moltype = AA  length = 22
FEATURE                Location/Qualifiers
source                 1..22
                       mol_type = protein
                       organism = synthetic construct
SEQUENCE: 36
PLLELLKELL QELLEALKQK LK                                            22

SEQ ID NO: 37          moltype = AA  length = 22
FEATURE                Location/Qualifiers
source                 1..22
                       mol_type = protein
                       organism = synthetic construct
SEQUENCE: 37
PVLDLFREWL NELLEALKQK LK                                            22

SEQ ID NO: 38          moltype = AA  length = 22
FEATURE                Location/Qualifiers
source                 1..22
                       mol_type = protein
                       organism = synthetic construct
SEQUENCE: 38
PVLDLFRELL NEXLEAWKQK LK                                            22

SEQ ID NO: 39          moltype = AA  length = 22
FEATURE                Location/Qualifiers
source                 1..22
                       mol_type = protein
                       organism = synthetic construct
SEQUENCE: 39
PVLDLFRELL EELLKALKKK LK                                            22

SEQ ID NO: 40          moltype = AA  length = 22
FEATURE                Location/Qualifiers
source                 1..22
                       mol_type = protein
                       organism = synthetic construct
SEQUENCE: 40
PVLDLFNELL RELLEALQKK LK                                            22

SEQ ID NO: 41          moltype = AA  length = 22
FEATURE                Location/Qualifiers
source                 1..22
                       mol_type = protein
                       organism = synthetic construct
SEQUENCE: 41
PVLDLWRELL NEXLEALKQK LK                                            22

SEQ ID NO: 42          moltype = AA  length = 22
FEATURE                Location/Qualifiers
source                 1..22
                       mol_type = protein
                       organism = synthetic construct
SEQUENCE: 42
PVLDEFREKL NEXWEALKQK LK                                            22

SEQ ID NO: 43          moltype = AA  length = 22
FEATURE                Location/Qualifiers
source                 1..22
                       mol_type = protein
                       organism = synthetic construct
SEQUENCE: 43
PVLDEFREKL WEXLEALKQK LK                                            22

SEQ ID NO: 44          moltype = AA  length = 22
FEATURE                Location/Qualifiers
source                 1..22
                       mol_type = protein
```

-continued

```
                         organism = synthetic construct
SEQUENCE: 44
PVLDEFREKL NEXLEALKQK LK                                                22

SEQ ID NO: 45            moltype = AA  length = 22
FEATURE                  Location/Qualifiers
source                   1..22
                         mol_type = protein
                         organism = synthetic construct
SEQUENCE: 45
PVLDEFREKL NEXLEALKQK LK                                                22

SEQ ID NO: 46            moltype = AA  length = 22
FEATURE                  Location/Qualifiers
source                   1..22
                         mol_type = protein
                         organism = synthetic construct
SEQUENCE: 46
PVLDLFREKL NEXLEALKQK LK                                                22

SEQ ID NO: 47            moltype = AA  length = 21
FEATURE                  Location/Qualifiers
source                   1..21
                         mol_type = protein
                         organism = synthetic construct
SEQUENCE: 47
VLDLFRELLN EGLEALKQKL K                                                 21

SEQ ID NO: 48            moltype = AA  length = 22
FEATURE                  Location/Qualifiers
source                   1..22
                         mol_type = protein
                         organism = synthetic construct
SEQUENCE: 48
PVLDLFRELL NELLEALKQK LK                                                22

SEQ ID NO: 49            moltype = AA  length = 22
FEATURE                  Location/Qualifiers
source                   1..22
                         mol_type = protein
                         organism = synthetic construct
SEQUENCE: 49
PVLDLFRNLL EKLLEALEQK LK                                                22

SEQ ID NO: 50            moltype = AA  length = 22
FEATURE                  Location/Qualifiers
source                   1..22
                         mol_type = protein
                         organism = synthetic construct
SEQUENCE: 50
PVLDLFRELL WEXLEALKQK LK                                                22

SEQ ID NO: 51            moltype = AA  length = 22
FEATURE                  Location/Qualifiers
source                   1..22
                         mol_type = protein
                         organism = synthetic construct
SEQUENCE: 51
PVLDLFWELL NEXLEALKQK LK                                                22

SEQ ID NO: 52            moltype = AA  length = 22
FEATURE                  Location/Qualifiers
source                   1..22
                         mol_type = protein
                         organism = synthetic construct
SEQUENCE: 52
PVWDEFREKL NEXLEALKQK LK                                                22

SEQ ID NO: 53            moltype = AA  length = 22
FEATURE                  Location/Qualifiers
source                   1..22
                         mol_type = protein
                         organism = synthetic construct
SEQUENCE: 53
VVLDLFRELL NELLEALKQK LK                                                22

SEQ ID NO: 54            moltype = AA  length = 22
FEATURE                  Location/Qualifiers
source                   1..22
```

```
                         mol_type = protein
                         organism = synthetic construct
SEQUENCE: 54
PVLDLFRELL NEWLEALKQK LK                                              22

SEQ ID NO: 55            moltype = AA  length = 19
FEATURE                  Location/Qualifiers
source                   1..19
                         mol_type = protein
                         organism = synthetic construct
SEQUENCE: 55
PLFRELLNEL LEALKQKLK                                                  19

SEQ ID NO: 56            moltype = AA  length = 22
FEATURE                  Location/Qualifiers
source                   1..22
                         mol_type = protein
                         organism = synthetic construct
SEQUENCE: 56
PVLDLFRELL NELLEALKQK KK                                              22

SEQ ID NO: 57            moltype = AA  length = 22
FEATURE                  Location/Qualifiers
source                   1..22
                         mol_type = protein
                         organism = synthetic construct
SEQUENCE: 57
PVLDLFRNLL EELLKALEQK LK                                              22

SEQ ID NO: 58            moltype = AA  length = 21
FEATURE                  Location/Qualifiers
source                   1..21
                         mol_type = protein
                         organism = synthetic construct
SEQUENCE: 58
PVLDEFREKL NEXLEALKQK L                                               21

SEQ ID NO: 59            moltype = AA  length = 22
FEATURE                  Location/Qualifiers
source                   1..22
                         mol_type = protein
                         organism = synthetic construct
SEQUENCE: 59
LVLDLFRELL NELLEALKQK LK                                              22

SEQ ID NO: 60            moltype = AA  length = 19
FEATURE                  Location/Qualifiers
source                   1..19
                         mol_type = protein
                         organism = synthetic construct
SEQUENCE: 60
PVLDLFRELL NELLEALKQ                                                  19

SEQ ID NO: 61            moltype = AA  length = 22
FEATURE                  Location/Qualifiers
source                   1..22
                         mol_type = protein
                         organism = synthetic construct
SEQUENCE: 61
PVLDEFRWKL NEXLEALKQK LK                                              22

SEQ ID NO: 62            moltype = AA  length = 22
FEATURE                  Location/Qualifiers
source                   1..22
                         mol_type = protein
                         organism = synthetic construct
SEQUENCE: 62
PVLDEWREKL NEXLEALKQK LK                                              22

SEQ ID NO: 63            moltype = AA  length = 22
FEATURE                  Location/Qualifiers
source                   1..22
                         mol_type = protein
                         organism = synthetic construct
SEQUENCE: 63
PVLDFFREKL NEXLEALKQK LK                                              22

SEQ ID NO: 64            moltype = AA  length = 22
FEATURE                  Location/Qualifiers
```

-continued

```
source                1..22
                      mol_type = protein
                      organism = synthetic construct
SEQUENCE: 64
PWLDEFREKL NEXLEALKQK LK                                          22

SEQ ID NO: 65         moltype = AA  length = 21
FEATURE               Location/Qualifiers
source                1..21
                      mol_type = protein
                      organism = synthetic construct
SEQUENCE: 65
VLDEFREKLN EXLEALKQKL K                                           21

SEQ ID NO: 66         moltype = AA  length = 22
FEATURE               Location/Qualifiers
source                1..22
                      mol_type = protein
                      organism = synthetic construct
SEQUENCE: 66
PVLDLFRNLL EELLEALQKK LK                                          22

SEQ ID NO: 67         moltype = AA  length = 21
FEATURE               Location/Qualifiers
source                1..21
                      mol_type = protein
                      organism = synthetic construct
SEQUENCE: 67
VLDLFRELLN ELLEALKQKL K                                           21

SEQ ID NO: 68         moltype = AA  length = 22
FEATURE               Location/Qualifiers
source                1..22
                      mol_type = protein
                      organism = synthetic construct
SEQUENCE: 68
PVLDEFRELL KEXLEALKQK LK                                          22

SEQ ID NO: 69         moltype = AA  length = 22
FEATURE               Location/Qualifiers
source                1..22
                      mol_type = protein
                      organism = synthetic construct
SEQUENCE: 69
PVLDEFRKKL NEXLEALKQK LK                                          22

SEQ ID NO: 70         moltype = AA  length = 22
FEATURE               Location/Qualifiers
source                1..22
                      mol_type = protein
                      organism = synthetic construct
SEQUENCE: 70
PVLDEFRELL YEXLEALKQK LK                                          22

SEQ ID NO: 71         moltype = AA  length = 22
FEATURE               Location/Qualifiers
source                1..22
                      mol_type = protein
                      organism = synthetic construct
SEQUENCE: 71
PVLDEFREKL NELXEALKQK LK                                          22

SEQ ID NO: 72         moltype = AA  length = 22
FEATURE               Location/Qualifiers
source                1..22
                      mol_type = protein
                      organism = synthetic construct
SEQUENCE: 72
PVLDLFRELL NEXLWALKQK LK                                          22

SEQ ID NO: 73         moltype = AA  length = 22
FEATURE               Location/Qualifiers
source                1..22
                      mol_type = protein
                      organism = synthetic construct
SEQUENCE: 73
PVLDEFWEKL NEXLEALKQK LK                                          22

SEQ ID NO: 74         moltype = AA  length = 22
```

-continued

```
FEATURE                 Location/Qualifiers
source                  1..22
                        mol_type = protein
                        organism = synthetic construct
SEQUENCE: 74
PVLDKFREKL NEXLEALKQK LK                                              22

SEQ ID NO: 75           moltype = AA  length = 22
FEATURE                 Location/Qualifiers
source                  1..22
                        mol_type = protein
                        organism = synthetic construct
SEQUENCE: 75
PVLDEFREKL NEELEALKQK LK                                              22

SEQ ID NO: 76           moltype = AA  length = 22
FEATURE                 Location/Qualifiers
source                  1..22
                        mol_type = protein
                        organism = synthetic construct
SEQUENCE: 76
PVLDEFRELL FEXLEALKQK LK                                              22

SEQ ID NO: 77           moltype = AA  length = 22
FEATURE                 Location/Qualifiers
source                  1..22
                        mol_type = protein
                        organism = synthetic construct
SEQUENCE: 77
PVLDEFREKL NKXLEALKQK LK                                              22

SEQ ID NO: 78           moltype = AA  length = 22
FEATURE                 Location/Qualifiers
source                  1..22
                        mol_type = protein
                        organism = synthetic construct
SEQUENCE: 78
PVLDEFRDKL NEXLEALKQK LK                                              22

SEQ ID NO: 79           moltype = AA  length = 22
FEATURE                 Location/Qualifiers
source                  1..22
                        mol_type = protein
                        organism = synthetic construct
SEQUENCE: 79
PVLDEFRELL NELLEALKQK LK                                              22

SEQ ID NO: 80           moltype = AA  length = 22
FEATURE                 Location/Qualifiers
source                  1..22
                        mol_type = protein
                        organism = synthetic construct
SEQUENCE: 80
PVLDLFERLL NELLEALQKK LK                                              22

SEQ ID NO: 81           moltype = AA  length = 22
FEATURE                 Location/Qualifiers
source                  1..22
                        mol_type = protein
                        organism = synthetic construct
SEQUENCE: 81
PVLDEFREKL NWXLEALKQK LK                                              22

SEQ ID NO: 82           moltype = AA  length = 20
FEATURE                 Location/Qualifiers
source                  1..20
                        mol_type = protein
                        organism = synthetic construct
SEQUENCE: 82
LDEFREKLNE XLEALKQKLK                                                 20

SEQ ID NO: 83           moltype = AA  length = 22
FEATURE                 Location/Qualifiers
source                  1..22
                        mol_type = protein
                        organism = synthetic construct
SEQUENCE: 83
PVLDEFREKL NEXLEALWQK LK                                              22
```

-continued

```
SEQ ID NO: 84          moltype = AA  length = 22
FEATURE                Location/Qualifiers
source                 1..22
                       mol_type = protein
                       organism = synthetic construct
SEQUENCE: 84
PVLDEFREKL NELLEALKQK LK                                          22

SEQ ID NO: 85          moltype = AA  length = 21
FEATURE                Location/Qualifiers
source                 1..21
                       mol_type = protein
                       organism = synthetic construct
SEQUENCE: 85
PLDLFRELLN ELLEALKQKL K                                           21

SEQ ID NO: 86          moltype = AA  length = 22
FEATURE                Location/Qualifiers
source                 1..22
                       mol_type = protein
                       organism = synthetic construct
SEQUENCE: 86
PVLELFERLL DELLNALQKK LK                                          22

SEQ ID NO: 87          moltype = AA  length = 22
FEATURE                Location/Qualifiers
source                 1..22
                       mol_type = protein
                       organism = synthetic construct
SEQUENCE: 87
PLLELLKELL QELLEALKQK LK                                          22

SEQ ID NO: 88          moltype = AA  length = 22
FEATURE                Location/Qualifiers
source                 1..22
                       mol_type = protein
                       organism = synthetic construct
SEQUENCE: 88
PVLDKFRELL NEXLEALKQK LK                                          22

SEQ ID NO: 89          moltype = AA  length = 22
FEATURE                Location/Qualifiers
source                 1..22
                       mol_type = protein
                       organism = synthetic construct
SEQUENCE: 89
PVLDEFREKL NEXLWALKQK LK                                          22

SEQ ID NO: 90          moltype = AA  length = 19
FEATURE                Location/Qualifiers
source                 1..19
                       mol_type = protein
                       organism = synthetic construct
SEQUENCE: 90
DEFREKLNEX LEALKQKLK                                              19

SEQ ID NO: 91          moltype = AA  length = 22
FEATURE                Location/Qualifiers
source                 1..22
                       mol_type = protein
                       organism = synthetic construct
SEQUENCE: 91
PVLDEFRELL NEXLEALKQK LK                                          22

SEQ ID NO: 92          moltype = AA  length = 22
FEATURE                Location/Qualifiers
source                 1..22
                       mol_type = protein
                       organism = synthetic construct
SEQUENCE: 92
PVLDEFRELY NEXLEALKQK LK                                          22

SEQ ID NO: 93          moltype = AA  length = 22
FEATURE                Location/Qualifiers
source                 1..22
                       mol_type = protein
                       organism = synthetic construct
SEQUENCE: 93
PVLDEFREKL NEXLKALKQK LK                                          22
```

-continued

```
SEQ ID NO: 94          moltype = AA  length = 22
FEATURE                Location/Qualifiers
source                 1..22
                       mol_type = protein
                       organism = synthetic construct
SEQUENCE: 94
PVLDEFREKL NEALEALKQK LK                                          22

SEQ ID NO: 95          moltype = AA  length = 22
FEATURE                Location/Qualifiers
source                 1..22
                       mol_type = protein
                       organism = synthetic construct
SEQUENCE: 95
PVLDLFRELL NLXLEALKQK LK                                          22

SEQ ID NO: 96          moltype = AA  length = 22
FEATURE                Location/Qualifiers
source                 1..22
                       mol_type = protein
                       organism = synthetic construct
SEQUENCE: 96
PVLDLFRELL NEXLEALKQK LK                                          22

SEQ ID NO: 97          moltype = AA  length = 15
FEATURE                Location/Qualifiers
source                 1..15
                       mol_type = protein
                       organism = synthetic construct
SEQUENCE: 97
PVLDLFRELL NELLE                                                  15

SEQ ID NO: 98          moltype = AA  length = 22
FEATURE                Location/Qualifiers
source                 1..22
                       mol_type = protein
                       organism = synthetic construct
SEQUENCE: 98
PVLDLFRELL NEELEALKQK LK                                          22

SEQ ID NO: 99          moltype = AA  length = 22
FEATURE                Location/Qualifiers
source                 1..22
                       mol_type = protein
                       organism = synthetic construct
SEQUENCE: 99
KLKQKLAELL ENLLERFLDL VP                                          22

SEQ ID NO: 100         moltype = AA  length = 22
FEATURE                Location/Qualifiers
source                 1..22
                       mol_type = protein
                       organism = synthetic construct
SEQUENCE: 100
PVLDLFRELL NELLEALKQK LK                                          22

SEQ ID NO: 101         moltype = AA  length = 22
FEATURE                Location/Qualifiers
source                 1..22
                       mol_type = protein
                       organism = synthetic construct
SEQUENCE: 101
PVLDLFRELL NWXLEALKQK LK                                          22

SEQ ID NO: 102         moltype = AA  length = 22
FEATURE                Location/Qualifiers
source                 1..22
                       mol_type = protein
                       organism = synthetic construct
SEQUENCE: 102
PVLDLFRELL NLXLEALKEK LK                                          22

SEQ ID NO: 103         moltype = AA  length = 22
FEATURE                Location/Qualifiers
source                 1..22
                       mol_type = protein
                       organism = synthetic construct
SEQUENCE: 103
```

-continued

```
PVLDEFRELL NEELEALKQK LK                                              22

SEQ ID NO: 104         moltype = AA  length = 15
FEATURE                Location/Qualifiers
source                 1..15
                       mol_type = protein
                       organism = synthetic construct
SEQUENCE: 104
PLLNELLEAL KQKLK                                                      15

SEQ ID NO: 105         moltype = AA  length = 22
FEATURE                Location/Qualifiers
source                 1..22
                       mol_type = protein
                       organism = synthetic construct
SEQUENCE: 105
PAADAFREAA NEAAEAAKQK AK                                              22

SEQ ID NO: 106         moltype = AA  length = 22
FEATURE                Location/Qualifiers
source                 1..22
                       mol_type = protein
                       organism = synthetic construct
SEQUENCE: 106
PVLDLFREKL NEELEALKQK LK                                              22

SEQ ID NO: 107         moltype = AA  length = 22
FEATURE                Location/Qualifiers
source                 1..22
                       mol_type = protein
                       organism = synthetic construct
SEQUENCE: 107
KLKQKLAELL ENLLERFLDL VP                                              22

SEQ ID NO: 108         moltype = AA  length = 22
FEATURE                Location/Qualifiers
source                 1..22
                       mol_type = protein
                       organism = synthetic construct
SEQUENCE: 108
PVLDLFRWLL NEXLEALKQK LK                                              22

SEQ ID NO: 109         moltype = AA  length = 22
FEATURE                Location/Qualifiers
source                 1..22
                       mol_type = protein
                       organism = synthetic construct
SEQUENCE: 109
PVLDEFREKL NERLEALKQK LK                                              22

SEQ ID NO: 110         moltype = AA  length = 22
FEATURE                Location/Qualifiers
source                 1..22
                       mol_type = protein
                       organism = synthetic construct
SEQUENCE: 110
PVLDEFREKL NEXXEALKQK LK                                              22

SEQ ID NO: 111         moltype = AA  length = 22
FEATURE                Location/Qualifiers
source                 1..22
                       mol_type = protein
                       organism = synthetic construct
SEQUENCE: 111
PVLDEFREKL WEXWEALKQK LK                                              22

SEQ ID NO: 112         moltype = AA  length = 22
FEATURE                Location/Qualifiers
source                 1..22
                       mol_type = protein
                       organism = synthetic construct
SEQUENCE: 112
PVLDEFREKL NEXSEALKQK LK                                              22

SEQ ID NO: 113         moltype = AA  length = 22
FEATURE                Location/Qualifiers
source                 1..22
                       mol_type = protein
                       organism = synthetic construct
```

```
SEQUENCE: 113
PVLDEFREKL NEPLEALKQK LK                                          22

SEQ ID NO: 114         moltype = AA  length = 22
FEATURE                Location/Qualifiers
source                 1..22
                       mol_type = protein
                       organism = synthetic construct
SEQUENCE: 114
PVLDEFREKL NEXMEALKQK LK                                          22

SEQ ID NO: 115         moltype = AA  length = 22
FEATURE                Location/Qualifiers
source                 1..22
                       mol_type = protein
                       organism = synthetic construct
SEQUENCE: 115
PKLDEFREKL NEXLEALKQK LK                                          22

SEQ ID NO: 116         moltype = AA  length = 22
FEATURE                Location/Qualifiers
source                 1..22
                       mol_type = protein
                       organism = synthetic construct
SEQUENCE: 116
PHLDEFREKL NEXLEALKQK LK                                          22

SEQ ID NO: 117         moltype = AA  length = 22
FEATURE                Location/Qualifiers
source                 1..22
                       mol_type = protein
                       organism = synthetic construct
SEQUENCE: 117
PELDEFREKL NEXLEALKQK LK                                          22

SEQ ID NO: 118         moltype = AA  length = 22
FEATURE                Location/Qualifiers
source                 1..22
                       mol_type = protein
                       organism = synthetic construct
SEQUENCE: 118
PVLDEFREKL NEXLEALEQK LK                                          22

SEQ ID NO: 119         moltype = AA  length = 22
FEATURE                Location/Qualifiers
source                 1..22
                       mol_type = protein
                       organism = synthetic construct
SEQUENCE: 119
PVLDEFREKL NEELEAXKQK LK                                          22

SEQ ID NO: 120         moltype = AA  length = 22
FEATURE                Location/Qualifiers
source                 1..22
                       mol_type = protein
                       organism = synthetic construct
SEQUENCE: 120
PVLDEFREKL NEELEXLKQK LK                                          22

SEQ ID NO: 121         moltype = AA  length = 22
FEATURE                Location/Qualifiers
source                 1..22
                       mol_type = protein
                       organism = synthetic construct
SEQUENCE: 121
PVLDEFREKL NEELEALWQK LK                                          22

SEQ ID NO: 122         moltype = AA  length = 22
FEATURE                Location/Qualifiers
source                 1..22
                       mol_type = protein
                       organism = synthetic construct
SEQUENCE: 122
PVLDEFREKL NEELEWLKQK LK                                          22

SEQ ID NO: 123         moltype = AA  length = 22
FEATURE                Location/Qualifiers
source                 1..22
                       mol_type = protein
```

-continued

```
                        organism = synthetic construct
SEQUENCE: 123
QVLDLFRELL NELLEALKQK LK                                              22

SEQ ID NO: 124          moltype = AA  length = 22
FEATURE                 Location/Qualifiers
source                  1..22
                        mol_type = protein
                        organism = synthetic construct
SEQUENCE: 124
PVLDLFXELL NELLEALXQX LX                                              22

SEQ ID NO: 125          moltype = AA  length = 22
FEATURE                 Location/Qualifiers
source                  1..22
                        mol_type = protein
                        organism = synthetic construct
SEQUENCE: 125
NVLDLFRELL NELLEALKQK LK                                              22

SEQ ID NO: 126          moltype = AA  length = 22
FEATURE                 Location/Qualifiers
source                  1..22
                        mol_type = protein
                        organism = synthetic construct
SEQUENCE: 126
PVLDLFRELL NELGEALKQK LK                                              22

SEQ ID NO: 127          moltype = AA  length = 22
FEATURE                 Location/Qualifiers
source                  1..22
                        mol_type = protein
                        organism = synthetic construct
SEQUENCE: 127
PVLDLFRELL NELLELLKQK LK                                              22

SEQ ID NO: 128          moltype = AA  length = 22
FEATURE                 Location/Qualifiers
source                  1..22
                        mol_type = protein
                        organism = synthetic construct
SEQUENCE: 128
PVLDLFRELL NELLEFLKQK LK                                              22

SEQ ID NO: 129          moltype = AA  length = 22
FEATURE                 Location/Qualifiers
source                  1..22
                        mol_type = protein
                        organism = synthetic construct
SEQUENCE: 129
PVLELFNDLL RELLEALQKK LK                                              22

SEQ ID NO: 130          moltype = AA  length = 22
FEATURE                 Location/Qualifiers
source                  1..22
                        mol_type = protein
                        organism = synthetic construct
SEQUENCE: 130
PVLELFNDLL RELLEALKQK LK                                              22

SEQ ID NO: 131          moltype = AA  length = 22
FEATURE                 Location/Qualifiers
source                  1..22
                        mol_type = protein
                        organism = synthetic construct
SEQUENCE: 131
PVLELFKELL NELLDALRQK LK                                              22

SEQ ID NO: 132          moltype = AA  length = 22
FEATURE                 Location/Qualifiers
source                  1..22
                        mol_type = protein
                        organism = synthetic construct
SEQUENCE: 132
PVLDLFRELL ENLLEALQKK LK                                              22

SEQ ID NO: 133          moltype = AA  length = 22
FEATURE                 Location/Qualifiers
source                  1..22
```

-continued

```
                         mol_type = protein
                         organism = synthetic construct
SEQUENCE: 133
PVLELFERLL EDLLQALNKK LK                                          22

SEQ ID NO: 134           moltype = AA  length = 22
FEATURE                  Location/Qualifiers
source                   1..22
                         mol_type = protein
                         organism = synthetic construct
SEQUENCE: 134
PVLELFERLL EDLLKALNXK LK                                          22

SEQ ID NO: 135           moltype = AA  length = 22
FEATURE                  Location/Qualifiers
source                   1..22
                         mol_type = protein
                         organism = synthetic construct
SEQUENCE: 135
DVLDLFRELL NELLEALKQK LK                                          22

SEQ ID NO: 136           moltype = AA  length = 22
FEATURE                  Location/Qualifiers
source                   1..22
                         mol_type = protein
                         organism = synthetic construct
SEQUENCE: 136
PALELFKDLL QELLEALKQK LK                                          22

SEQ ID NO: 137           moltype = AA  length = 22
FEATURE                  Location/Qualifiers
source                   1..22
                         mol_type = protein
                         organism = synthetic construct
SEQUENCE: 137
PVLDLFRELL NEGLEAZKQK LK                                          22

SEQ ID NO: 138           moltype = AA  length = 22
FEATURE                  Location/Qualifiers
source                   1..22
                         mol_type = protein
                         organism = synthetic construct
SEQUENCE: 138
PVLDLFRELL NEGLEWLKQK LK                                          22

SEQ ID NO: 139           moltype = AA  length = 22
FEATURE                  Location/Qualifiers
source                   1..22
                         mol_type = protein
                         organism = synthetic construct
SEQUENCE: 139
PVLDLFRELW NEGLEALKQK LK                                          22

SEQ ID NO: 140           moltype = AA  length = 22
FEATURE                  Location/Qualifiers
source                   1..22
                         mol_type = protein
                         organism = synthetic construct
SEQUENCE: 140
PVLDLFRELL NEGLEALXQX LX                                          22

SEQ ID NO: 141           moltype = AA  length = 22
FEATURE                  Location/Qualifiers
source                   1..22
                         mol_type = protein
                         organism = synthetic construct
SEQUENCE: 141
PVLDFFRELL NEGLEALKQK LK                                          22

SEQ ID NO: 142           moltype = AA  length = 22
FEATURE                  Location/Qualifiers
source                   1..22
                         mol_type = protein
                         organism = synthetic construct
SEQUENCE: 142
PVLELFRELL NEGLEALKQK LK                                          22

SEQ ID NO: 143           moltype = AA  length = 22
FEATURE                  Location/Qualifiers
```

```
source                  1..22
                        mol_type = protein
                        organism = synthetic construct
SEQUENCE: 143
PVLDLFRELL NEGLEALKQK LK                                            22

SEQ ID NO: 144          moltype = AA  length = 22
FEATURE                 Location/Qualifiers
source                  1..22
                        mol_type = protein
                        organism = synthetic construct
SEQUENCE: 144
PVLELFENLL ERLLDALQKK LK                                            22

SEQ ID NO: 145          moltype = AA  length = 22
FEATURE                 Location/Qualifiers
source                  1..22
                        mol_type = protein
                        organism = synthetic construct
SEQUENCE: 145
GVLELFENLL ERLLDALQKK LK                                            22

SEQ ID NO: 146          moltype = AA  length = 22
FEATURE                 Location/Qualifiers
source                  1..22
                        mol_type = protein
                        organism = synthetic construct
SEQUENCE: 146
PVLELFENLL ERLLDALQKK LK                                            22

SEQ ID NO: 147          moltype = AA  length = 22
FEATURE                 Location/Qualifiers
source                  1..22
                        mol_type = protein
                        organism = synthetic construct
SEQUENCE: 147
PVLELFENLL ERLFDALQKK LK                                            22

SEQ ID NO: 148          moltype = AA  length = 22
FEATURE                 Location/Qualifiers
source                  1..22
                        mol_type = protein
                        organism = synthetic construct
SEQUENCE: 148
PVLELFENLL ERLGDALQKK LK                                            22

SEQ ID NO: 149          moltype = AA  length = 22
FEATURE                 Location/Qualifiers
source                  1..22
                        mol_type = protein
                        organism = synthetic construct
SEQUENCE: 149
PVLELFENLW ERLLDALQKK LK                                            22

SEQ ID NO: 150          moltype = AA  length = 22
FEATURE                 Location/Qualifiers
source                  1..22
                        mol_type = protein
                        organism = synthetic construct
SEQUENCE: 150
PLLELFENLL ERLLDALQKK LK                                            22

SEQ ID NO: 151          moltype = AA  length = 22
FEATURE                 Location/Qualifiers
source                  1..22
                        mol_type = protein
                        organism = synthetic construct
SEQUENCE: 151
PVLELFENLG ERLLDALQKK LK                                            22

SEQ ID NO: 152          moltype = AA  length = 22
FEATURE                 Location/Qualifiers
source                  1..22
                        mol_type = protein
                        organism = synthetic construct
SEQUENCE: 152
PVFELFENLL ERLLDALQKK LK                                            22

SEQ ID NO: 153          moltype = AA  length = 22
```

```
FEATURE                 Location/Qualifiers
source                  1..22
                        mol_type = protein
                        organism = synthetic construct
SEQUENCE: 153
AVLELFENLL ERLLDALQKK LK                                            22

SEQ ID NO: 154          moltype = AA  length = 22
FEATURE                 Location/Qualifiers
source                  1..22
                        mol_type = protein
                        organism = synthetic construct
SEQUENCE: 154
PVLELFENLL ERGLDALQKK LK                                            22

SEQ ID NO: 155          moltype = AA  length = 22
FEATURE                 Location/Qualifiers
source                  1..22
                        mol_type = protein
                        organism = synthetic construct
SEQUENCE: 155
PVLELFLNLW ERLLDALQKK LK                                            22

SEQ ID NO: 156          moltype = AA  length = 22
FEATURE                 Location/Qualifiers
source                  1..22
                        mol_type = protein
                        organism = synthetic construct
SEQUENCE: 156
PVLELFLNLL ERLLDALQKK LK                                            22

SEQ ID NO: 157          moltype = AA  length = 22
FEATURE                 Location/Qualifiers
source                  1..22
                        mol_type = protein
                        organism = synthetic construct
SEQUENCE: 157
PVLEFFENLL ERLLDALQKK LK                                            22

SEQ ID NO: 158          moltype = AA  length = 22
FEATURE                 Location/Qualifiers
source                  1..22
                        mol_type = protein
                        organism = synthetic construct
SEQUENCE: 158
PVLELFLNLL ERLLDWLQKK LK                                            22

SEQ ID NO: 159          moltype = AA  length = 22
FEATURE                 Location/Qualifiers
source                  1..22
                        mol_type = protein
                        organism = synthetic construct
SEQUENCE: 159
PVLDLFENLL ERLLDALQKK LK                                            22

SEQ ID NO: 160          moltype = AA  length = 22
FEATURE                 Location/Qualifiers
source                  1..22
                        mol_type = protein
                        organism = synthetic construct
SEQUENCE: 160
PVLELFENLL ERLLDWLQKK LK                                            22

SEQ ID NO: 161          moltype = AA  length = 22
FEATURE                 Location/Qualifiers
source                  1..22
                        mol_type = protein
                        organism = synthetic construct
SEQUENCE: 161
PVLELFENLL ERLLEALQKK LK                                            22

SEQ ID NO: 162          moltype = AA  length = 22
FEATURE                 Location/Qualifiers
source                  1..22
                        mol_type = protein
                        organism = synthetic construct
SEQUENCE: 162
PVLELFENWL ERLLDALQKK LK                                            22
```

```
SEQ ID NO: 163          moltype = AA  length = 22
FEATURE                 Location/Qualifiers
source                  1..22
                        mol_type = protein
                        organism = synthetic construct
SEQUENCE: 163
PVLELFENLL ERLWDALQKK LK                                            22

SEQ ID NO: 164          moltype = AA  length = 22
FEATURE                 Location/Qualifiers
source                  1..22
                        mol_type = protein
                        organism = synthetic construct
SEQUENCE: 164
PVLELFENLL ERLLDAWQKK LK                                            22

SEQ ID NO: 165          moltype = AA  length = 22
FEATURE                 Location/Qualifiers
source                  1..22
                        mol_type = protein
                        organism = synthetic construct
SEQUENCE: 165
PVLELFENLL ERLLDLLQKK LK                                            22

SEQ ID NO: 166          moltype = AA  length = 22
FEATURE                 Location/Qualifiers
source                  1..22
                        mol_type = protein
                        organism = synthetic construct
SEQUENCE: 166
PVLELFLNLL EKLLDALQKK LK                                            22

SEQ ID NO: 167          moltype = AA  length = 22
FEATURE                 Location/Qualifiers
source                  1..22
                        mol_type = protein
                        organism = synthetic construct
SEQUENCE: 167
PVLELFENGL ERLLDALQKK LK                                            22

SEQ ID NO: 168          moltype = AA  length = 22
FEATURE                 Location/Qualifiers
source                  1..22
                        mol_type = protein
                        organism = synthetic construct
SEQUENCE: 168
PVLELFEQLL EKLLDALQKK LK                                            22

SEQ ID NO: 169          moltype = AA  length = 22
FEATURE                 Location/Qualifiers
source                  1..22
                        mol_type = protein
                        organism = synthetic construct
SEQUENCE: 169
PVLELFENLL EKLLDALQKK LK                                            22

SEQ ID NO: 170          moltype = AA  length = 22
FEATURE                 Location/Qualifiers
source                  1..22
                        mol_type = protein
                        organism = synthetic construct
SEQUENCE: 170
PVLELFENLL EXLLDALQXX LX                                            22

SEQ ID NO: 171          moltype = AA  length = 22
FEATURE                 Location/Qualifiers
source                  1..22
                        mol_type = protein
                        organism = synthetic construct
SEQUENCE: 171
PVLELFENLL EKLLDLLQKK LK                                            22

SEQ ID NO: 172          moltype = AA  length = 22
FEATURE                 Location/Qualifiers
source                  1..22
                        mol_type = protein
                        organism = synthetic construct
SEQUENCE: 172
PVLELFLNLL ERLGDALQKK LK                                            22
```

```
SEQ ID NO: 173          moltype = AA  length = 22
FEATURE                 Location/Qualifiers
source                  1..22
                        mol_type = protein
                        organism = synthetic construct
SEQUENCE: 173
PVLDLFDNLL DRLLDLLNKK LK                                             22

SEQ ID NO: 174          moltype = AA  length = 22
FEATURE                 Location/Qualifiers
source                  1..22
                        mol_type = protein
                        organism = synthetic construct
SEQUENCE: 174
PVLELFENLL ERLLDALQKK LK                                             22

SEQ ID NO: 175          moltype = AA  length = 22
FEATURE                 Location/Qualifiers
source                  1..22
                        mol_type = protein
                        organism = synthetic construct
SEQUENCE: 175
PVLELFENLL ERLLELLNKK LK                                             22

SEQ ID NO: 176          moltype = AA  length = 22
FEATURE                 Location/Qualifiers
source                  1..22
                        mol_type = protein
                        organism = synthetic construct
SEQUENCE: 176
PVLELWENLL ERLLDALQKK LK                                             22

SEQ ID NO: 177          moltype = AA  length = 22
FEATURE                 Location/Qualifiers
source                  1..22
                        mol_type = protein
                        organism = synthetic construct
SEQUENCE: 177
GVLELFLNLL ERLLDALQKK LK                                             22

SEQ ID NO: 178          moltype = AA  length = 22
FEATURE                 Location/Qualifiers
source                  1..22
                        mol_type = protein
                        organism = synthetic construct
SEQUENCE: 178
PVLELFDNLL EKLLEALQKK LR                                             22

SEQ ID NO: 179          moltype = AA  length = 22
FEATURE                 Location/Qualifiers
source                  1..22
                        mol_type = protein
                        organism = synthetic construct
SEQUENCE: 179
PVLELFDNLL ERLLDALQKK LK                                             22

SEQ ID NO: 180          moltype = AA  length = 22
FEATURE                 Location/Qualifiers
source                  1..22
                        mol_type = protein
                        organism = synthetic construct
SEQUENCE: 180
PVLELFDNLL DKLLDALQKK LR                                             22

SEQ ID NO: 181          moltype = AA  length = 22
FEATURE                 Location/Qualifiers
source                  1..22
                        mol_type = protein
                        organism = synthetic construct
SEQUENCE: 181
PVLELFENLL ERWLDALQKK LK                                             22

SEQ ID NO: 182          moltype = AA  length = 22
FEATURE                 Location/Qualifiers
source                  1..22
                        mol_type = protein
                        organism = synthetic construct
SEQUENCE: 182
```

-continued

```
PVLELFENLL EKLLEALQKK LK                                            22

SEQ ID NO: 183         moltype = AA  length = 22
FEATURE                Location/Qualifiers
source                 1..22
                       mol_type = protein
                       organism = synthetic construct
SEQUENCE: 183
PLLELFENLL EKLLDALQKK LK                                            22

SEQ ID NO: 184         moltype = AA  length = 22
FEATURE                Location/Qualifiers
source                 1..22
                       mol_type = protein
                       organism = synthetic construct
SEQUENCE: 184
PVLELFLNLL ERLLDAWQKK LK                                            22

SEQ ID NO: 185         moltype = AA  length = 22
FEATURE                Location/Qualifiers
source                 1..22
                       mol_type = protein
                       organism = synthetic construct
SEQUENCE: 185
PVLELFENLL ERLLDALQXX LX                                            22

SEQ ID NO: 186         moltype = AA  length = 22
FEATURE                Location/Qualifiers
source                 1..22
                       mol_type = protein
                       organism = synthetic construct
SEQUENCE: 186
PVLELFEQLL ERLLDALQKK LK                                            22

SEQ ID NO: 187         moltype = AA  length = 22
FEATURE                Location/Qualifiers
source                 1..22
                       mol_type = protein
                       organism = synthetic construct
SEQUENCE: 187
PVLELFENLL ERLLDALNKK LK                                            22

SEQ ID NO: 188         moltype = AA  length = 22
FEATURE                Location/Qualifiers
source                 1..22
                       mol_type = protein
                       organism = synthetic construct
SEQUENCE: 188
PVLELFENLL DRLLDALQKK LK                                            22

SEQ ID NO: 189         moltype = AA  length = 22
FEATURE                Location/Qualifiers
source                 1..22
                       mol_type = protein
                       organism = synthetic construct
SEQUENCE: 189
DVLELFENLL ERLLDALQKK LK                                            22

SEQ ID NO: 190         moltype = AA  length = 22
FEATURE                Location/Qualifiers
source                 1..22
                       mol_type = protein
                       organism = synthetic construct
SEQUENCE: 190
PVLEFWDNLL DKLLDALQKK LR                                            22

SEQ ID NO: 191         moltype = AA  length = 18
FEATURE                Location/Qualifiers
source                 1..18
                       mol_type = protein
                       organism = synthetic construct
SEQUENCE: 191
PVLDLLRELL EELKQKLK                                                 18

SEQ ID NO: 192         moltype = AA  length = 18
FEATURE                Location/Qualifiers
source                 1..18
                       mol_type = protein
                       organism = synthetic construct
```

```
SEQUENCE: 192
PVLDLFKELL EELKQKLK                                          18

SEQ ID NO: 193          moltype = AA  length = 18
FEATURE                 Location/Qualifiers
source                  1..18
                        mol_type = protein
                        organism = synthetic construct
SEQUENCE: 193
PVLDLFRELL EELKQKLK                                          18

SEQ ID NO: 194          moltype = AA  length = 18
FEATURE                 Location/Qualifiers
source                  1..18
                        mol_type = protein
                        organism = synthetic construct
SEQUENCE: 194
PVLELFRELL EELKQKLK                                          18

SEQ ID NO: 195          moltype = AA  length = 18
FEATURE                 Location/Qualifiers
source                  1..18
                        mol_type = protein
                        organism = synthetic construct
SEQUENCE: 195
PVLELFKELL EELKQKLK                                          18

SEQ ID NO: 196          moltype = AA  length = 18
FEATURE                 Location/Qualifiers
source                  1..18
                        mol_type = protein
                        organism = synthetic construct
SEQUENCE: 196
PVLDLFRELL EELKNKLK                                          18

SEQ ID NO: 197          moltype = AA  length = 18
FEATURE                 Location/Qualifiers
source                  1..18
                        mol_type = protein
                        organism = synthetic construct
SEQUENCE: 197
PLLDLFRELL EELKQKLK                                          18

SEQ ID NO: 198          moltype = AA  length = 18
FEATURE                 Location/Qualifiers
source                  1..18
                        mol_type = protein
                        organism = synthetic construct
SEQUENCE: 198
GVLDLFRELL EELKQKLK                                          18

SEQ ID NO: 199          moltype = AA  length = 18
FEATURE                 Location/Qualifiers
source                  1..18
                        mol_type = protein
                        organism = synthetic construct
SEQUENCE: 199
PVLDLFRELW EELKQKLK                                          18

SEQ ID NO: 200          moltype = AA  length = 18
FEATURE                 Location/Qualifiers
source                  1..18
                        mol_type = protein
                        organism = synthetic construct
SEQUENCE: 200
NVLDLFRELL EELKQKLK                                          18

SEQ ID NO: 201          moltype = AA  length = 18
FEATURE                 Location/Qualifiers
source                  1..18
                        mol_type = protein
                        organism = synthetic construct
SEQUENCE: 201
PLLDLFKELL EELKQKLK                                          18

SEQ ID NO: 202          moltype = AA  length = 18
FEATURE                 Location/Qualifiers
source                  1..18
                        mol_type = protein
```

```
                        organism = synthetic construct
SEQUENCE: 202
PALELFKDLL EELRQKLR                                                 18

SEQ ID NO: 203          moltype = AA  length = 18
FEATURE                 Location/Qualifiers
source                  1..18
                        mol_type = protein
                        organism = synthetic construct
SEQUENCE: 203
AVLDLFRELL EELKQKLK                                                 18

SEQ ID NO: 204          moltype = AA  length = 18
FEATURE                 Location/Qualifiers
source                  1..18
                        mol_type = protein
                        organism = synthetic construct
SEQUENCE: 204
PVLDFFRELL EELKQKLK                                                 18

SEQ ID NO: 205          moltype = AA  length = 18
FEATURE                 Location/Qualifiers
source                  1..18
                        mol_type = protein
                        organism = synthetic construct
SEQUENCE: 205
PVLDLFREWL EELKQKLK                                                 18

SEQ ID NO: 206          moltype = AA  length = 18
FEATURE                 Location/Qualifiers
source                  1..18
                        mol_type = protein
                        organism = synthetic construct
SEQUENCE: 206
PLLELLKELL EELKQKLK                                                 18

SEQ ID NO: 207          moltype = AA  length = 18
FEATURE                 Location/Qualifiers
source                  1..18
                        mol_type = protein
                        organism = synthetic construct
SEQUENCE: 207
PVLELLKELL EELKQKLK                                                 18

SEQ ID NO: 208          moltype = AA  length = 18
FEATURE                 Location/Qualifiers
source                  1..18
                        mol_type = protein
                        organism = synthetic construct
SEQUENCE: 208
PALELFKDLL EELRQRLK                                                 18

SEQ ID NO: 209          moltype = AA  length = 18
FEATURE                 Location/Qualifiers
source                  1..18
                        mol_type = protein
                        organism = synthetic construct
SEQUENCE: 209
PVLDLFRELL NELLQKLK                                                 18

SEQ ID NO: 210          moltype = AA  length = 18
FEATURE                 Location/Qualifiers
source                  1..18
                        mol_type = protein
                        organism = synthetic construct
SEQUENCE: 210
PVLDLFRELL EELKQKLK                                                 18

SEQ ID NO: 211          moltype = AA  length = 18
FEATURE                 Location/Qualifiers
source                  1..18
                        mol_type = protein
                        organism = synthetic construct
SEQUENCE: 211
PVLDLFRELL EELXQXLX                                                 18

SEQ ID NO: 212          moltype = AA  length = 18
FEATURE                 Location/Qualifiers
source                  1..18
```

```
                        mol_type = protein
                        organism = synthetic construct
SEQUENCE: 212
PVLDLFXELL EELXQXLK                                               18

SEQ ID NO: 213          moltype = AA  length = 18
FEATURE                 Location/Qualifiers
source                  1..18
                        mol_type = protein
                        organism = synthetic construct
SEQUENCE: 213
PALELFKDLL EEFRQRLK                                               18

SEQ ID NO: 214          moltype = AA  length = 18
FEATURE                 Location/Qualifiers
source                  1..18
                        mol_type = protein
                        organism = synthetic construct
SEQUENCE: 214
PVLDLFRELL EELKQKLK                                               18

SEQ ID NO: 215          moltype = AA  length = 18
FEATURE                 Location/Qualifiers
source                  1..18
                        mol_type = protein
                        organism = synthetic construct
SEQUENCE: 215
PVLDLFRELL EEWKQKLK                                               18

SEQ ID NO: 216          moltype = AA  length = 18
FEATURE                 Location/Qualifiers
source                  1..18
                        mol_type = protein
                        organism = synthetic construct
SEQUENCE: 216
PVLELFKELL EELKQKLK                                               18

SEQ ID NO: 217          moltype = AA  length = 18
FEATURE                 Location/Qualifiers
source                  1..18
                        mol_type = protein
                        organism = synthetic construct
SEQUENCE: 217
PVLDLFRELL ELLKQKLK                                               18

SEQ ID NO: 218          moltype = AA  length = 18
FEATURE                 Location/Qualifiers
source                  1..18
                        mol_type = protein
                        organism = synthetic construct
SEQUENCE: 218
PVLDLFRELL NELLQKLK                                               18

SEQ ID NO: 219          moltype = AA  length = 18
FEATURE                 Location/Qualifiers
source                  1..18
                        mol_type = protein
                        organism = synthetic construct
SEQUENCE: 219
PVLDLFRELL NELWQKLK                                               18

SEQ ID NO: 220          moltype = AA  length = 18
FEATURE                 Location/Qualifiers
source                  1..18
                        mol_type = protein
                        organism = synthetic construct
SEQUENCE: 220
PVLDLFRELL EELQKKLK                                               18

SEQ ID NO: 221          moltype = AA  length = 18
FEATURE                 Location/Qualifiers
source                  1..18
                        mol_type = protein
                        organism = synthetic construct
SEQUENCE: 221
DVLDLFRELL EELKQKLK                                               18

SEQ ID NO: 222          moltype = AA  length = 18
FEATURE                 Location/Qualifiers
```

-continued

```
source                 1..18
                       mol_type = protein
                       organism = synthetic construct
SEQUENCE: 222
PVLDAFRELL EALLQLKK                                                  18

SEQ ID NO: 223         moltype = AA  length = 18
FEATURE                Location/Qualifiers
source                 1..18
                       mol_type = protein
                       organism = synthetic construct
SEQUENCE: 223
PVLDAFRELL EALAQLKK                                                  18

SEQ ID NO: 224         moltype = AA  length = 18
FEATURE                Location/Qualifiers
source                 1..18
                       mol_type = protein
                       organism = synthetic construct
SEQUENCE: 224
PVLDLFREGW EELKQKLK                                                  18

SEQ ID NO: 225         moltype = AA  length = 18
FEATURE                Location/Qualifiers
source                 1..18
                       mol_type = protein
                       organism = synthetic construct
SEQUENCE: 225
PVLDAFRELA EALAQLKK                                                  18

SEQ ID NO: 226         moltype = AA  length = 18
FEATURE                Location/Qualifiers
source                 1..18
                       mol_type = protein
                       organism = synthetic construct
SEQUENCE: 226
PVLDAFRELG EALLQLKK                                                  18

SEQ ID NO: 227         moltype = AA  length = 18
FEATURE                Location/Qualifiers
source                 1..18
                       mol_type = protein
                       organism = synthetic construct
SEQUENCE: 227
PVLDLFRELG EELKQKLK                                                  18

SEQ ID NO: 228         moltype = AA  length = 18
FEATURE                Location/Qualifiers
source                 1..18
                       mol_type = protein
                       organism = synthetic construct
SEQUENCE: 228
PVLDLFREGL EELKQKLK                                                  18

SEQ ID NO: 229         moltype = AA  length = 18
FEATURE                Location/Qualifiers
source                 1..18
                       mol_type = protein
                       organism = synthetic construct
SEQUENCE: 229
PVLDLFRELL EEGKQKLK                                                  18

SEQ ID NO: 230         moltype = AA  length = 18
FEATURE                Location/Qualifiers
source                 1..18
                       mol_type = protein
                       organism = synthetic construct
SEQUENCE: 230
PVLELFERLL EDLQKKLK                                                  18

SEQ ID NO: 231         moltype = AA  length = 18
FEATURE                Location/Qualifiers
source                 1..18
                       mol_type = protein
                       organism = synthetic construct
SEQUENCE: 231
PVLDLFRELL EKLEQKLK                                                  18

SEQ ID NO: 232         moltype = AA  length = 18
```

-continued

```
FEATURE                Location/Qualifiers
source                 1..18
                       mol_type = protein
                       organism = synthetic construct
SEQUENCE: 232
PLLELFKELL EELKQKLK                                                18

SEQ ID NO: 233         moltype = AA  length = 18
FEATURE                Location/Qualifiers
source                 1..18
                       mol_type = protein
                       organism = synthetic construct
SEQUENCE: 233
LDDLLQKWAE AFNQLLKK                                                18

SEQ ID NO: 234         moltype = AA  length = 18
FEATURE                Location/Qualifiers
source                 1..18
                       mol_type = protein
                       organism = synthetic construct
SEQUENCE: 234
EWLKAFYEKV LEKLKELF                                                18

SEQ ID NO: 235         moltype = AA  length = 18
FEATURE                Location/Qualifiers
source                 1..18
                       mol_type = protein
                       organism = synthetic construct
SEQUENCE: 235
EWLEAFYKKV LEKLKELF                                                18

SEQ ID NO: 236         moltype = AA  length = 18
FEATURE                Location/Qualifiers
source                 1..18
                       mol_type = protein
                       organism = synthetic construct
SEQUENCE: 236
DWLKAFYDKV AEKLKEAF                                                18

SEQ ID NO: 237         moltype = AA  length = 18
FEATURE                Location/Qualifiers
source                 1..18
                       mol_type = protein
                       organism = synthetic construct
SEQUENCE: 237
DWFKAFYDKV FEKFKEFF                                                18

SEQ ID NO: 238         moltype = AA  length = 18
FEATURE                Location/Qualifiers
source                 1..18
                       mol_type = protein
                       organism = synthetic construct
SEQUENCE: 238
GIKKFLGSIW KFIKAFVG                                                18

SEQ ID NO: 239         moltype = AA  length = 18
FEATURE                Location/Qualifiers
source                 1..18
                       mol_type = protein
                       organism = synthetic construct
SEQUENCE: 239
DWFKAFYDKV AEKFKEAF                                                18

SEQ ID NO: 240         moltype = AA  length = 18
FEATURE                Location/Qualifiers
source                 1..18
                       mol_type = protein
                       organism = synthetic construct
SEQUENCE: 240
DWLKAFYDKV AEKLKEAF                                                18

SEQ ID NO: 241         moltype = AA  length = 18
FEATURE                Location/Qualifiers
source                 1..18
                       mol_type = protein
                       organism = synthetic construct
SEQUENCE: 241
DWLKAFYDKV FEKFKEFF                                                18
```

-continued

```
SEQ ID NO: 242          moltype = AA  length = 18
FEATURE                 Location/Qualifiers
source                  1..18
                        mol_type = protein
                        organism = synthetic construct
SEQUENCE: 242
EWLEAFYKKV LEKLKELP                                                18

SEQ ID NO: 243          moltype = AA  length = 18
FEATURE                 Location/Qualifiers
source                  1..18
                        mol_type = protein
                        organism = synthetic construct
SEQUENCE: 243
DWFKAFYDKF FEKFKEFF                                                18

SEQ ID NO: 244          moltype = AA  length = 18
FEATURE                 Location/Qualifiers
source                  1..18
                        mol_type = protein
                        organism = synthetic construct
SEQUENCE: 244
EWLKAFYEKV LEKLKELF                                                18

SEQ ID NO: 245          moltype = AA  length = 18
FEATURE                 Location/Qualifiers
source                  1..18
                        mol_type = protein
                        organism = synthetic construct
SEQUENCE: 245
EWLKAEYEKV EEKLKELF                                                18

SEQ ID NO: 246          moltype = AA  length = 18
FEATURE                 Location/Qualifiers
source                  1..18
                        mol_type = protein
                        organism = synthetic construct
SEQUENCE: 246
EWLKAEYEKV LEKLKELF                                                18

SEQ ID NO: 247          moltype = AA  length = 18
FEATURE                 Location/Qualifiers
source                  1..18
                        mol_type = protein
                        organism = synthetic construct
SEQUENCE: 247
EWLKAFYKKV LEKLKELF                                                18

SEQ ID NO: 248          moltype = AA  length = 15
FEATURE                 Location/Qualifiers
source                  1..15
                        mol_type = protein
                        organism = synthetic construct
SEQUENCE: 248
PVLDLFRELL EQKLK                                                   15

SEQ ID NO: 249          moltype = AA  length = 16
FEATURE                 Location/Qualifiers
source                  1..16
                        mol_type = protein
                        organism = synthetic construct
SEQUENCE: 249
PVLDLFRELL EELKQK                                                  16

SEQ ID NO: 250          moltype = AA  length = 16
FEATURE                 Location/Qualifiers
source                  1..16
                        mol_type = protein
                        organism = synthetic construct
SEQUENCE: 250
PVLDLFRELL EKLKQK                                                  16

SEQ ID NO: 251          moltype = AA  length = 15
FEATURE                 Location/Qualifiers
source                  1..15
                        mol_type = protein
                        organism = synthetic construct
SEQUENCE: 251
PVLDLFRELL EKLQK                                                   15
```

```
SEQ ID NO: 252          moltype = AA  length = 16
FEATURE                 Location/Qualifiers
source                  1..16
                        mol_type = protein
                        organism = synthetic construct
SEQUENCE: 252
PVLDLFRELL EALKQK                                                    16

SEQ ID NO: 253          moltype = AA  length = 16
FEATURE                 Location/Qualifiers
source                  1..16
                        mol_type = protein
                        organism = synthetic construct
SEQUENCE: 253
PVLDLFENLL ERLKQK                                                    16

SEQ ID NO: 254          moltype = AA  length = 16
FEATURE                 Location/Qualifiers
source                  1..16
                        mol_type = protein
                        organism = synthetic construct
SEQUENCE: 254
PVLDLFRELL NELKQK                                                    16

SEQ ID NO: 255          moltype = AA  length = 18
FEATURE                 Location/Qualifiers
source                  1..18
                        mol_type = protein
                        organism = synthetic construct
SEQUENCE: 255
DWLKAFYDKV AEKLKEAF                                                  18

SEQ ID NO: 256          moltype = AA  length = 18
FEATURE                 Location/Qualifiers
source                  1..18
                        mol_type = protein
                        organism = synthetic construct
SEQUENCE: 256
DWLKAFYDKV AEKLKEAF                                                  18

SEQ ID NO: 257          moltype = AA  length = 18
FEATURE                 Location/Qualifiers
source                  1..18
                        mol_type = protein
                        organism = synthetic construct
SEQUENCE: 257
DWLKAFYDKV AEKLKEAF                                                  18

SEQ ID NO: 258          moltype = AA  length = 18
FEATURE                 Location/Qualifiers
source                  1..18
                        mol_type = protein
                        organism = synthetic construct
SEQUENCE: 258
DWFKAFYDKV AEKLKEAF                                                  18

SEQ ID NO: 259          moltype = AA  length = 18
FEATURE                 Location/Qualifiers
source                  1..18
                        mol_type = protein
                        organism = synthetic construct
SEQUENCE: 259
DWLKAFYDKV AEKFKEAF                                                  18

SEQ ID NO: 260          moltype = AA  length = 18
FEATURE                 Location/Qualifiers
source                  1..18
                        mol_type = protein
                        organism = synthetic construct
SEQUENCE: 260
DWFKAFYDKV AEKFKEAF                                                  18

SEQ ID NO: 261          moltype = AA  length = 18
FEATURE                 Location/Qualifiers
source                  1..18
                        mol_type = protein
                        organism = synthetic construct
SEQUENCE: 261
```

-continued

```
DWLKAFYDKV FEKFKEFF                                                        18

SEQ ID NO: 262          moltype = AA  length = 18
FEATURE                 Location/Qualifiers
source                  1..18
                        mol_type = protein
                        organism = synthetic construct
SEQUENCE: 262
DWLKAFYDKF FEKFKEFF                                                        18

SEQ ID NO: 263          moltype = AA  length = 18
FEATURE                 Location/Qualifiers
source                  1..18
                        mol_type = protein
                        organism = synthetic construct
SEQUENCE: 263
DWFKAFYDKF FEKFKEFF                                                        18

SEQ ID NO: 264          moltype = AA  length = 18
FEATURE                 Location/Qualifiers
source                  1..18
                        mol_type = protein
                        organism = synthetic construct
SEQUENCE: 264
DWLKAFYDKV AEKLKEFF                                                        18

SEQ ID NO: 265          moltype = AA  length = 18
FEATURE                 Location/Qualifiers
source                  1..18
                        mol_type = protein
                        organism = synthetic construct
SEQUENCE: 265
DWLKAFYDKV FEKFKEAF                                                        18

SEQ ID NO: 266          moltype = AA  length = 18
FEATURE                 Location/Qualifiers
source                  1..18
                        mol_type = protein
                        organism = synthetic construct
SEQUENCE: 266
DWLKAFYDKV FEKLKEFF                                                        18

SEQ ID NO: 267          moltype = AA  length = 18
FEATURE                 Location/Qualifiers
source                  1..18
                        mol_type = protein
                        organism = synthetic construct
SEQUENCE: 267
DWLKAFYDKV AEKFKEFF                                                        18

SEQ ID NO: 268          moltype = AA  length = 18
FEATURE                 Location/Qualifiers
source                  1..18
                        mol_type = protein
                        organism = synthetic construct
SEQUENCE: 268
DWLKAFYDKV FEKFKEFF                                                        18

SEQ ID NO: 269          moltype = AA  length = 18
FEATURE                 Location/Qualifiers
source                  1..18
                        mol_type = protein
                        organism = synthetic construct
SEQUENCE: 269
EWLKLFYEKV LEKFKEAF                                                        18

SEQ ID NO: 270          moltype = AA  length = 18
FEATURE                 Location/Qualifiers
source                  1..18
                        mol_type = protein
                        organism = synthetic construct
SEQUENCE: 270
EWLKAFYDKV AEKFKEAF                                                        18

SEQ ID NO: 271          moltype = AA  length = 18
FEATURE                 Location/Qualifiers
source                  1..18
                        mol_type = protein
                        organism = synthetic construct
```

-continued

```
SEQUENCE: 271
EWLKAFYDKV AEKLKEFF                                              18

SEQ ID NO: 272          moltype = AA  length = 18
FEATURE                 Location/Qualifiers
source                  1..18
                        mol_type = protein
                        organism = synthetic construct
SEQUENCE: 272
EWLKAFYDKV FEKFKEAF                                              18

SEQ ID NO: 273          moltype = AA  length = 18
FEATURE                 Location/Qualifiers
source                  1..18
                        mol_type = protein
                        organism = synthetic construct
SEQUENCE: 273
EWLKAFYDKV FEKLKEFF                                              18

SEQ ID NO: 274          moltype = AA  length = 18
FEATURE                 Location/Qualifiers
source                  1..18
                        mol_type = protein
                        organism = synthetic construct
SEQUENCE: 274
EWLKAFYDKV AEKFKEFF                                              18

SEQ ID NO: 275          moltype = AA  length = 18
FEATURE                 Location/Qualifiers
source                  1..18
                        mol_type = protein
                        organism = synthetic construct
SEQUENCE: 275
EWLKAFYDKV FEKFKEFF                                              18

SEQ ID NO: 276          moltype = AA  length = 14
FEATURE                 Location/Qualifiers
source                  1..14
                        mol_type = protein
                        organism = synthetic construct
SEQUENCE: 276
AFYDKVAEKL KEAF                                                  14

SEQ ID NO: 277          moltype = AA  length = 14
FEATURE                 Location/Qualifiers
source                  1..14
                        mol_type = protein
                        organism = synthetic construct
SEQUENCE: 277
AFYDKVAEKF KEAF                                                  14

SEQ ID NO: 278          moltype = AA  length = 14
FEATURE                 Location/Qualifiers
source                  1..14
                        mol_type = protein
                        organism = synthetic construct
SEQUENCE: 278
AFYDKVAEKF KEAF                                                  14

SEQ ID NO: 279          moltype = AA  length = 14
FEATURE                 Location/Qualifiers
source                  1..14
                        mol_type = protein
                        organism = synthetic construct
SEQUENCE: 279
AFYDKFFEKF KEFF                                                  14

SEQ ID NO: 280          moltype = AA  length = 14
FEATURE                 Location/Qualifiers
source                  1..14
                        mol_type = protein
                        organism = synthetic construct
SEQUENCE: 280
AFYDKFFEKF KEFF                                                  14

SEQ ID NO: 281          moltype = AA  length = 14
FEATURE                 Location/Qualifiers
source                  1..14
                        mol_type = protein
```

```
                        organism = synthetic construct
SEQUENCE: 281
AFYDKVAEKF KEAF                                                            14

SEQ ID NO: 282          moltype = AA  length = 14
FEATURE                 Location/Qualifiers
source                  1..14
                        mol_type = protein
                        organism = synthetic construct
SEQUENCE: 282
AFYDKVAEKL KEFF                                                            14

SEQ ID NO: 283          moltype = AA  length = 14
FEATURE                 Location/Qualifiers
source                  1..14
                        mol_type = protein
                        organism = synthetic construct
SEQUENCE: 283
AFYDKVFEKF KEAF                                                            14

SEQ ID NO: 284          moltype = AA  length = 14
FEATURE                 Location/Qualifiers
source                  1..14
                        mol_type = protein
                        organism = synthetic construct
SEQUENCE: 284
AFYDKVFEKL KEFF                                                            14

SEQ ID NO: 285          moltype = AA  length = 14
FEATURE                 Location/Qualifiers
source                  1..14
                        mol_type = protein
                        organism = synthetic construct
SEQUENCE: 285
AFYDKVAEKF KEFF                                                            14

SEQ ID NO: 286          moltype = AA  length = 14
FEATURE                 Location/Qualifiers
source                  1..14
                        mol_type = protein
                        organism = synthetic construct
SEQUENCE: 286
KAFYDKVFEK FKEF                                                            14

SEQ ID NO: 287          moltype = AA  length = 14
FEATURE                 Location/Qualifiers
source                  1..14
                        mol_type = protein
                        organism = synthetic construct
SEQUENCE: 287
LFYEKVLEKF KEAF                                                            14

SEQ ID NO: 288          moltype = AA  length = 14
FEATURE                 Location/Qualifiers
source                  1..14
                        mol_type = protein
                        organism = synthetic construct
SEQUENCE: 288
AFYDKVAEKF KEAF                                                            14

SEQ ID NO: 289          moltype = AA  length = 14
FEATURE                 Location/Qualifiers
source                  1..14
                        mol_type = protein
                        organism = synthetic construct
SEQUENCE: 289
AFYDKVAEKL KEFF                                                            14

SEQ ID NO: 290          moltype = AA  length = 14
FEATURE                 Location/Qualifiers
source                  1..14
                        mol_type = protein
                        organism = synthetic construct
SEQUENCE: 290
AFYDKVFEKF KEAF                                                            14

SEQ ID NO: 291          moltype = AA  length = 14
FEATURE                 Location/Qualifiers
source                  1..14
```

```
                        mol_type = protein
                        organism = synthetic construct
SEQUENCE: 291
AFYDKVFEKL KEFF                                                   14

SEQ ID NO: 292          moltype = AA  length = 14
FEATURE                 Location/Qualifiers
source                  1..14
                        mol_type = protein
                        organism = synthetic construct
SEQUENCE: 292
AFYDKVAEKF KEFF                                                   14

SEQ ID NO: 293          moltype = AA  length = 14
FEATURE                 Location/Qualifiers
source                  1..14
                        mol_type = protein
                        organism = synthetic construct
SEQUENCE: 293
AFYDKVFEKF KEFF                                                   14

SEQ ID NO: 294          moltype = AA  length = 18
FEATURE                 Location/Qualifiers
source                  1..18
                        mol_type = protein
                        organism = synthetic construct
SEQUENCE: 294
DWLKALYDKV AEKLKEAL                                               18

SEQ ID NO: 295          moltype = AA  length = 18
FEATURE                 Location/Qualifiers
source                  1..18
                        mol_type = protein
                        organism = synthetic construct
SEQUENCE: 295
DWFKAFYEKV AEKLKEFF                                               18

SEQ ID NO: 296          moltype = AA  length = 18
FEATURE                 Location/Qualifiers
source                  1..18
                        mol_type = protein
                        organism = synthetic construct
SEQUENCE: 296
DWFKAFYEKF FEKFKEFF                                               18

SEQ ID NO: 297          moltype = AA  length = 18
FEATURE                 Location/Qualifiers
source                  1..18
                        mol_type = protein
                        organism = synthetic construct
SEQUENCE: 297
EWLKALYEKV AEKLKEAL                                               18

SEQ ID NO: 298          moltype = AA  length = 18
FEATURE                 Location/Qualifiers
source                  1..18
                        mol_type = protein
                        organism = synthetic construct
SEQUENCE: 298
EWLKAFYEKV AEKLKEAF                                               18

SEQ ID NO: 299          moltype = AA  length = 18
FEATURE                 Location/Qualifiers
source                  1..18
                        mol_type = protein
                        organism = synthetic construct
SEQUENCE: 299
EWFKAFYEKV AEKLKEFF                                               18

SEQ ID NO: 300          moltype = AA  length = 18
FEATURE                 Location/Qualifiers
source                  1..18
                        mol_type = protein
                        organism = synthetic construct
SEQUENCE: 300
EWLKAFYEKV FEKFKEFF                                               18

SEQ ID NO: 301          moltype = AA  length = 18
FEATURE                 Location/Qualifiers
```

```
source                 1..18
                       mol_type = protein
                       organism = synthetic construct
SEQUENCE: 301
EWLKAFYEKF FEKFKEFF                                             18

SEQ ID NO: 302         moltype = AA  length = 18
FEATURE                Location/Qualifiers
source                 1..18
                       mol_type = protein
                       organism = synthetic construct
SEQUENCE: 302
EWFKAFYEKF FEKFKEFF                                             18

SEQ ID NO: 303         moltype = AA  length = 18
FEATURE                Location/Qualifiers
source                 1..18
                       mol_type = protein
                       organism = synthetic construct
SEQUENCE: 303
DFLKAWYDKV AEKLKEAW                                             18

SEQ ID NO: 304         moltype = AA  length = 18
FEATURE                Location/Qualifiers
source                 1..18
                       mol_type = protein
                       organism = synthetic construct
SEQUENCE: 304
EFLKAWYEKV AEKLKEAW                                             18

SEQ ID NO: 305         moltype = AA  length = 18
FEATURE                Location/Qualifiers
source                 1..18
                       mol_type = protein
                       organism = synthetic construct
SEQUENCE: 305
DFWKAWYDKV AEKLKEWW                                             18

SEQ ID NO: 306         moltype = AA  length = 18
FEATURE                Location/Qualifiers
source                 1..18
                       mol_type = protein
                       organism = synthetic construct
SEQUENCE: 306
EFWKAWYEKV AEKLKEWW                                             18

SEQ ID NO: 307         moltype = AA  length = 18
FEATURE                Location/Qualifiers
source                 1..18
                       mol_type = protein
                       organism = synthetic construct
SEQUENCE: 307
DKLKAFYDKV FEWAKEAF                                             18

SEQ ID NO: 308         moltype = AA  length = 18
FEATURE                Location/Qualifiers
source                 1..18
                       mol_type = protein
                       organism = synthetic construct
SEQUENCE: 308
DKWKAVYDKF AEAFKEFL                                             18

SEQ ID NO: 309         moltype = AA  length = 18
FEATURE                Location/Qualifiers
source                 1..18
                       mol_type = protein
                       organism = synthetic construct
SEQUENCE: 309
EKLKAFYEKV FEWAKEAF                                             18

SEQ ID NO: 310         moltype = AA  length = 18
FEATURE                Location/Qualifiers
source                 1..18
                       mol_type = protein
                       organism = synthetic construct
SEQUENCE: 310
EKWKAVYEKF AEAFKEFL                                             18

SEQ ID NO: 311         moltype = AA  length = 18
```

-continued

```
FEATURE                Location/Qualifiers
source                 1..18
                       mol_type = protein
                       organism = synthetic construct
SEQUENCE: 311
DWLKAFVDKF AEKFKEAY                                                18

SEQ ID NO: 312         moltype = AA  length = 18
FEATURE                Location/Qualifiers
source                 1..18
                       mol_type = protein
                       organism = synthetic construct
SEQUENCE: 312
EKWKAVYEKF AEAFKEFL                                                18

SEQ ID NO: 313         moltype = AA  length = 18
FEATURE                Location/Qualifiers
source                 1..18
                       mol_type = protein
                       organism = synthetic construct
SEQUENCE: 313
DWLKAFVYDK VFKLKEFF                                                18

SEQ ID NO: 314         moltype = AA  length = 18
FEATURE                Location/Qualifiers
source                 1..18
                       mol_type = protein
                       organism = synthetic construct
SEQUENCE: 314
EWLKAFVYEK VFKLKEFF                                                18

SEQ ID NO: 315         moltype = AA  length = 18
FEATURE                Location/Qualifiers
source                 1..18
                       mol_type = protein
                       organism = synthetic construct
SEQUENCE: 315
DWLRAFYDKV AEKLKEAF                                                18

SEQ ID NO: 316         moltype = AA  length = 18
FEATURE                Location/Qualifiers
source                 1..18
                       mol_type = protein
                       organism = synthetic construct
SEQUENCE: 316
EWLRAFYEKV AEKLKEAF                                                18

SEQ ID NO: 317         moltype = AA  length = 18
FEATURE                Location/Qualifiers
source                 1..18
                       mol_type = protein
                       organism = synthetic construct
SEQUENCE: 317
DWLKAFYDRV AEKLKEAF                                                18

SEQ ID NO: 318         moltype = AA  length = 18
FEATURE                Location/Qualifiers
source                 1..18
                       mol_type = protein
                       organism = synthetic construct
SEQUENCE: 318
EWLKAFYERV AEKLKEAF                                                18

SEQ ID NO: 319         moltype = AA  length = 18
FEATURE                Location/Qualifiers
source                 1..18
                       mol_type = protein
                       organism = synthetic construct
SEQUENCE: 319
DWLKAFYDKV AERLKEAF                                                18

SEQ ID NO: 320         moltype = AA  length = 18
FEATURE                Location/Qualifiers
source                 1..18
                       mol_type = protein
                       organism = synthetic construct
SEQUENCE: 320
EWLKAFYEKV AERLKEAF                                                18
```

-continued

```
SEQ ID NO: 321          moltype = AA  length = 18
FEATURE                 Location/Qualifiers
source                  1..18
                        mol_type = protein
                        organism = synthetic construct
SEQUENCE: 321
DWLKAFYDKV AEKLREAF                                                18

SEQ ID NO: 322          moltype = AA  length = 18
FEATURE                 Location/Qualifiers
source                  1..18
                        mol_type = protein
                        organism = synthetic construct
SEQUENCE: 322
EWLKAFYEKV AEKLREAF                                                18

SEQ ID NO: 323          moltype = AA  length = 18
FEATURE                 Location/Qualifiers
source                  1..18
                        mol_type = protein
                        organism = synthetic construct
SEQUENCE: 323
DWLKAFYDRV AERLKEAF                                                18

SEQ ID NO: 324          moltype = AA  length = 18
FEATURE                 Location/Qualifiers
source                  1..18
                        mol_type = protein
                        organism = synthetic construct
SEQUENCE: 324
EWLKAFYERV AERLKEAF                                                18

SEQ ID NO: 325          moltype = AA  length = 18
FEATURE                 Location/Qualifiers
source                  1..18
                        mol_type = protein
                        organism = synthetic construct
SEQUENCE: 325
DWLRAFYDKV AEKLREAF                                                18

SEQ ID NO: 326          moltype = AA  length = 18
FEATURE                 Location/Qualifiers
source                  1..18
                        mol_type = protein
                        organism = synthetic construct
SEQUENCE: 326
EWLRAFYEKV AEKLREAF                                                18

SEQ ID NO: 327          moltype = AA  length = 18
FEATURE                 Location/Qualifiers
source                  1..18
                        mol_type = protein
                        organism = synthetic construct
SEQUENCE: 327
DWLRAFYDRV AEKLKEAF                                                18

SEQ ID NO: 328          moltype = AA  length = 18
FEATURE                 Location/Qualifiers
source                  1..18
                        mol_type = protein
                        organism = synthetic construct
SEQUENCE: 328
EWLRAFYERV AEKLKEAF                                                18

SEQ ID NO: 329          moltype = AA  length = 18
FEATURE                 Location/Qualifiers
source                  1..18
                        mol_type = protein
                        organism = synthetic construct
SEQUENCE: 329
DWLKAFYDKV AERLREAF                                                18

SEQ ID NO: 330          moltype = AA  length = 18
FEATURE                 Location/Qualifiers
source                  1..18
                        mol_type = protein
                        organism = synthetic construct
SEQUENCE: 330
EWLKAFYEKV AERLREAF                                                18
```

```
SEQ ID NO: 331          moltype = AA  length = 18
FEATURE                 Location/Qualifiers
source                  1..18
                        mol_type = protein
                        organism = synthetic construct
SEQUENCE: 331
DWLRAFYDKV AERLKEAF                                                18

SEQ ID NO: 332          moltype = AA  length = 18
FEATURE                 Location/Qualifiers
source                  1..18
                        mol_type = protein
                        organism = synthetic construct
SEQUENCE: 332
EWLRAFYEKV AERLKEAF                                                18

SEQ ID NO: 333          moltype = AA  length = 18
FEATURE                 Location/Qualifiers
source                  1..18
                        mol_type = protein
                        organism = synthetic construct
SEQUENCE: 333
FAEKFKEAVK DYFAKFWD                                                18

SEQ ID NO: 334          moltype = AA  length = 18
FEATURE                 Location/Qualifiers
source                  1..18
                        mol_type = protein
                        organism = synthetic construct
SEQUENCE: 334
DWFKAFYDKV AEKFKEAF                                                18

SEQ ID NO: 335          moltype = AA  length = 18
FEATURE                 Location/Qualifiers
source                  1..18
                        mol_type = protein
                        organism = synthetic construct
SEQUENCE: 335
DWLKAFYDKV AEKLKEAF                                                18

SEQ ID NO: 336          moltype = AA  length = 34
FEATURE                 Location/Qualifiers
source                  1..34
                        mol_type = protein
                        organism = synthetic construct
SEQUENCE: 336
PALEDLRQGL LPVLESFKVF LSALEEYTKK LNTQ                              34

SEQ ID NO: 337          moltype = DNA  length = 23
FEATURE                 Location/Qualifiers
source                  1..23
                        mol_type = other DNA
                        organism = synthetic construct
SEQUENCE: 337
gccagtatgc aagggagctc atg                                          23

SEQ ID NO: 338          moltype = AA  length = 25
FEATURE                 Location/Qualifiers
source                  1..25
                        mol_type = protein
                        organism = synthetic construct
SEQUENCE: 338
GASTAMGATC ANCARGGEGC LCAMG                                        25

SEQ ID NO: 339          moltype = DNA  length = 23
FEATURE                 Location/Qualifiers
source                  1..23
                        mol_type = other DNA
                        organism = synthetic construct
SEQUENCE: 339
gccagtatgc aatggagctc atg                                          23

SEQ ID NO: 340          moltype = AA  length = 25
FEATURE                 Location/Qualifiers
source                  1..25
                        mol_type = protein
                        organism = synthetic construct
SEQUENCE: 340
```

```
GASTAMGATC ANCAMGGEGC LCATG                                         25

SEQ ID NO: 341          moltype = AA  length = 9
FEATURE                 Location/Qualifiers
source                  1..9
                        mol_type = protein
                        organism = synthetic construct
SEQUENCE: 341
ASMTNMELM                                                           9

SEQ ID NO: 342          moltype = AA  length = 18
FEATURE                 Location/Qualifiers
source                  1..18
                        mol_type = protein
                        organism = synthetic construct
SEQUENCE: 342
FWLKAFYDKV AEKLKEAF                                                 18

SEQ ID NO: 343          moltype = AA  length = 18
FEATURE                 Location/Qualifiers
source                  1..18
                        mol_type = protein
                        organism = synthetic construct
SEQUENCE: 343
DFLKAFYDKV AEKLKEAF                                                 18

SEQ ID NO: 344          moltype = AA  length = 18
FEATURE                 Location/Qualifiers
source                  1..18
                        mol_type = protein
                        organism = synthetic construct
SEQUENCE: 344
DWFRAFYDKV AEKFREAF                                                 18

SEQ ID NO: 345          moltype = AA  length = 18
FEATURE                 Location/Qualifiers
source                  1..18
                        mol_type = protein
                        organism = synthetic construct
SEQUENCE: 345
DWFKAFYDRV AERFKEAF                                                 18

SEQ ID NO: 346          moltype = AA  length = 18
FEATURE                 Location/Qualifiers
MOD_RES                 4
                        note = Xaa is L-2,4-diaminobutyric acid
MOD_RES                 9
                        note = Xaa is L-2,4-diaminobutyric acid
MOD_RES                 13
                        note = Xaa is L-2,4-diaminobutyric acid
MOD_RES                 15
                        note = Xaa is L-2,4-diaminobutyric acid
source                  1..18
                        mol_type = protein
                        organism = synthetic construct
SEQUENCE: 346
DWLXAFYDXV AEXLXEAF                                                 18
```

COMPOUNDS FOR REGULATING TRAINED IMMUNITY, AND THEIR METHODS OF USE

CROSS-REFERENCE TO RELATED APPLICATIONS

This application is a divisional and claims priority to pending U.S. patent application Ser. No. 17/698,971, filed Mar. 18, 2022, which claims priority to U.S. Provisional Application No. 63/163,428, filed Mar. 19, 2021, the disclosures of which are hereby incorporated by reference in its entirety for all purposes.

SEQUENCE LISTING

This application contains a Sequence Listing that has been submitted electronically as an XML file named 27527-0195002_SL_ST26.xml. The XML file, created on Nov. 15, 2023, is 306,215 bytes in size. The material in the XML file is hereby incorporated by reference in its entirety.

BACKGROUND

The immune system plays an essential role in the pathophysiology of major diseases such as atherosclerosis, diabetes, and cancer. However, most of the immunotherapy strategies currently being developed focus on either effector molecules, such as cytokines, or T lymphocytes, which are cells from the adaptive immune system. (Mulder et al. *Nat. Rev. Drug Discov.* 2019, 18(7), 553-566; Pardoll et al. *Nat Immunol.,* 2012, 13, 1129-1132). In autoimmune and autoinflammatory diseases, anti-cytokine therapies can successfully neutralize bioactive cytokines, while the most intensely used immunotherapy in cancer patients comprises the application of checkpoint-inhibitor drugs. Though the innate immune system was long believed to lack memory, recent studies show that innate immune cells undergo metabolic and epigenetic rewiring, adjusting their functional programs in a process termed 'trained immunity' which has been implicated in exerting antitumor effects. (Buffen et al., 2014, *PLoS Pathog.* 10, e1004485; Netea et al., J. Leukoc Biol. 2017, 102, 1323-1332).

A range of pattern recognition receptors (PRRs), including TLRs, NOD2, dectin 1 and the inflammasome, can be engaged to promote trained immunity. In addition, in vitro studies have demonstrated that, BCG, and several other PAMPs and DAMPs, including peptidoglycans and β-glucan, can be therapeutically exploited as trained-immunity-promoting agents. However, in vivo therapeutic exploitation of molecules that regulate trained immunity has been hampered by toxicity, immune-related adverse effects and poor bioavailability to target the relevant myeloid cells and their progenitors.

A need exists for therapeutic agents, and compositions thereof that engage the innate immune system, and regulate trained immunity to treat cancer, and other diseases and conditions caused by defective trained immunity.

SUMMARY

In embodiments, provided herein is a compound of formula (I):

(I)

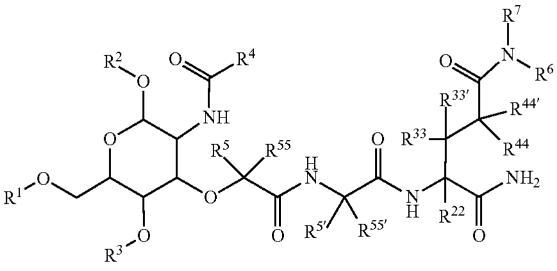

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^{11}$ are each independently —H, or alkyl;

$R^7$ is a $C_{9-30}$ fatty acid chain, —Y—N($R^{11}$)—C(O)—O-alkylene-C(H)($OR^8$)-alkylene-$OR^9$, —C($R^{10}$)(C(O)$NH_2$)-alkylene-N($R^{11}$)—C(O)—$C_{16-30}$ fatty acid chain, —$(CR^{10}R^{10})_2$—O—P(O)(OH)—O-alkylene-C($R^{10}$)($OR^Z$)-alkylene-$OR^{Z'}$, or —Y-triazolyl-L;

$R^Z$ and $R^{Z'}$ are each independently $C_{8-30}$ fatty acid or —C(O)—$C_{16-30}$ fatty acid chain;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^1$—C(O)—W$)_2$, and -alkylene-N-(alkylene-C(O)—W$)_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^{10}$, $R^{22}$, $R^{33}$, $R^{33'}$, $R^{44}$, $R^{44'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)N$R^C R^D$, —NRCC(O)$OR^B$, —OC(O)$R^B$, —C(O)$OR^B$, —C(O)$R^B$, —$CO_2$H, —$NO_2$, —SH, $S(O)_X R^B$ (wherein X is 0, 1, or 2), aryl, arylalkyl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)$OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro;

wherein, when $R^7$ is $C_{9-30}$ fatty acid chain, $R^2$ is —H.

In embodiments, the compound of formula (I) is a compound of formula (IA):

(IA)

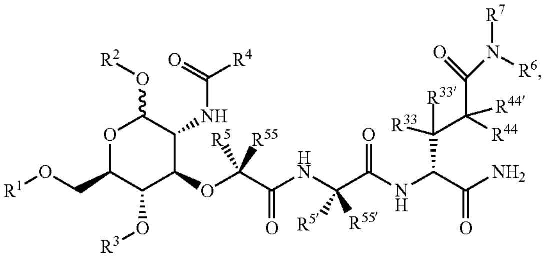

or a pharmaceutically acceptable salt thereof, wherein $R^1$, $R^2$, $R^3$, $R^4$, $R^5$, $R^{55}$, $R^{5'}$, $R^{15'}$, $R^{33}$, $R^{33'}$, $R^{44}$, $R^{44'}$, $R^6$, and $R^7$ are defined herein.

In embodiments, the compound of formula (I) is a compound of formula (IB):

(IB)

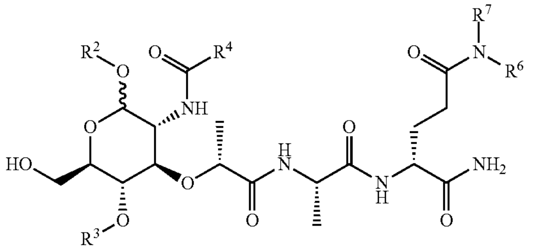

wherein $R^2$, $R^3$, $R^4$, $R^6$, and $R^7$ are defined herein.

In embodiments, the compound of formula (I) is a compound of formula (II):

(II)

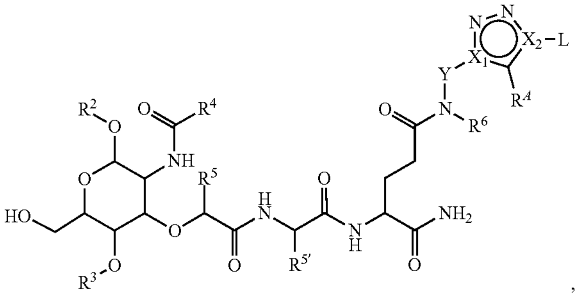

, or a pharmaceutically acceptable salt thereof, wherein $R^2$, $R^3$, $R^4$, $R^5$, $R^{5'}$, $R^6$, Y, $X^1$, $X^2$, $R^A$, L, are defined herein.

In embodiments, the compound of formula (II) is:

(II)

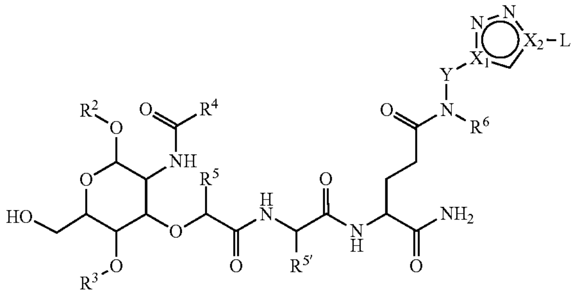

or a pharmaceutically acceptable salt thereof, wherein $R^2$, $R^3$, $R^4$, $R^5$, $R^{5'}$, $R^6$, Y, $X^1$, $X^2$, and L are defined herein.

In embodiments, the compound of formula (I) is a compound of formula (IIA):

(IIA)

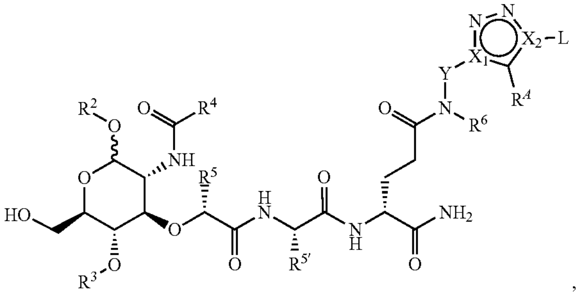

, or a pharmaceutically acceptable salt thereof, wherein $R^2$, $R^3$, $R^4$, $R^5$, $R^{5'}$, $R^6$, Y, $X^1$, $X^2$, L, and $R^A$ are defined herein.

In embodiments, the compound of formula (IIA) is:

(II-A)

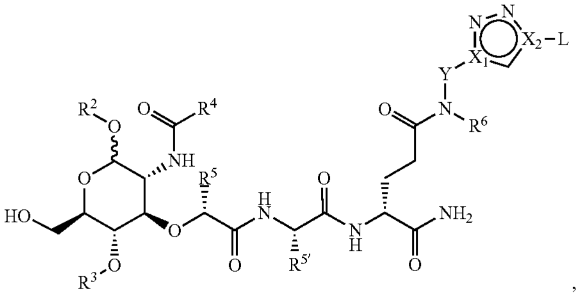

, wherein $R^2$, $R^3$, $R^4$, $R^5$, $R^1$, $R^6$, Y, $X^1$, $X^2$, and L are defined herein.

In embodiments, the present disclosure provides a nanobiologic composition comprising a high-density lipoprotein (HDL)-derived nanoparticle, wherein the nanoparticle comprises a compound of formula (I):

(I)

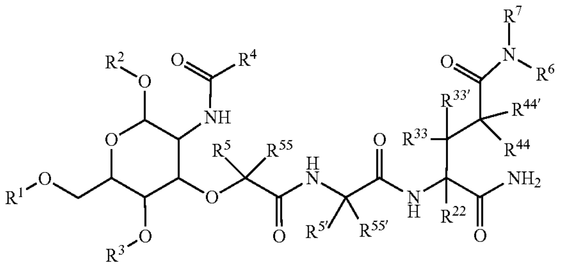

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^{11}$ are each independently —H, or alkyl;

$R^7$ is a fatty acid chain, —Y—N($R^6$)—C(O)—O-alkylene-C(H)($OR^8$)-alkylene-$OR^9$, —Y—N($R^6$)—C(O)—$R^X$, —Y—O—P(O)(OH)—O-alkylene-C(H)($OR^8$)-alkylene-$OR^9$, or —Y— triazolyl-L;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W$)_2$, and -alkylene-N-(alkylene-C(O)—W$)_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^{10}$, $R^{22}$, $R^{33}$, $R^{33'}$, $R^{44}$, $R^{44'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)$NR^CR^D$, —$NR^C$C(O)$OR^B$, —OC(O)$R^B$, —C(O)$OR^B$, —C(O)$R^B$, —$CO_2$H, —$NO_2$, —SH, $S(O)_XR^B$ (wherein X is 0, 1, or 2), aryl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)$OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro.

In embodiments, the present disclosure provides a method for treating a cell-proliferation disorder, or sepsis in a patient in need thereof, comprising administering to the patient a therapeutically effective amount of a compound or nanobiologic composition disclosed herein.

DEFINITIONS

Figure 1:
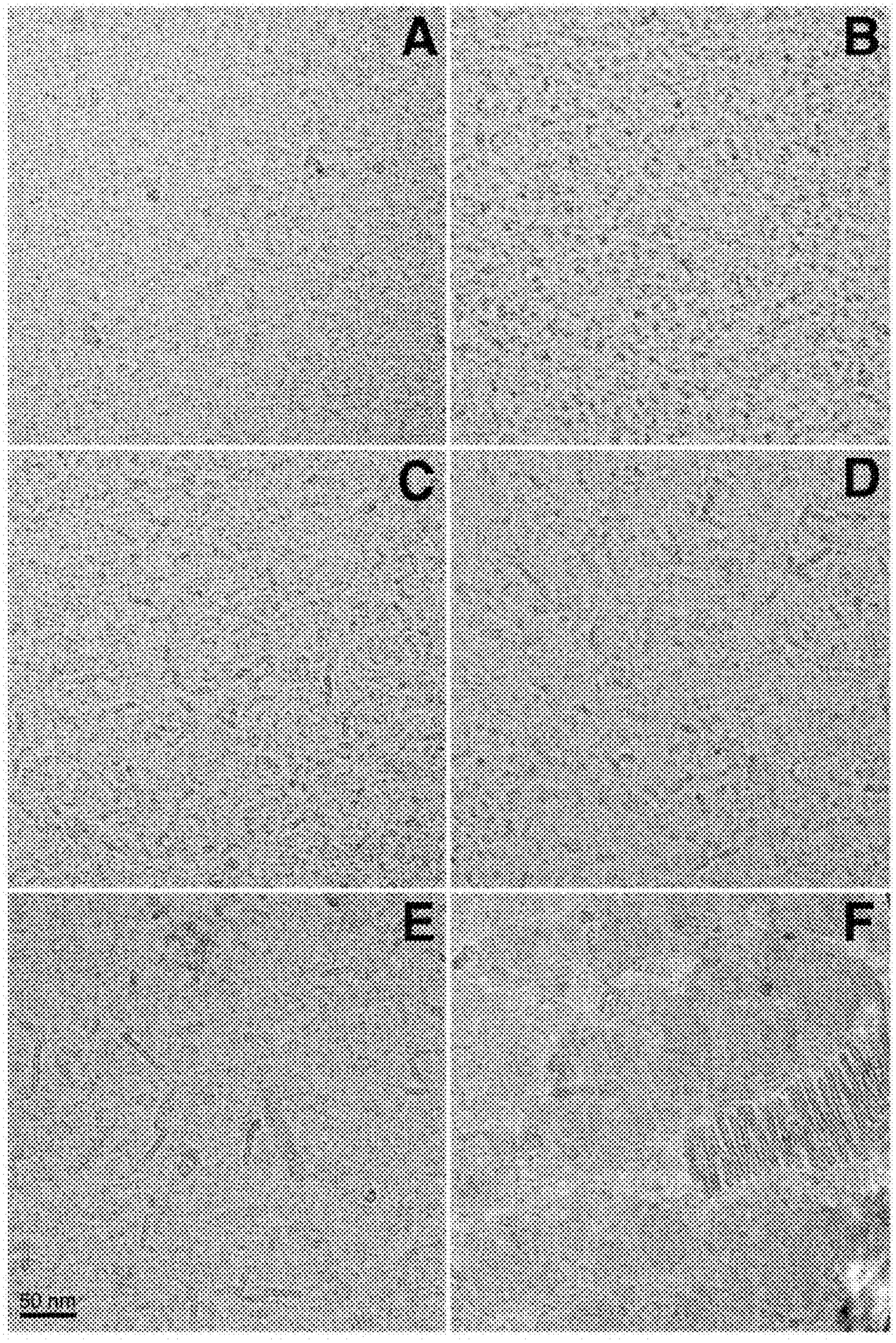
FIG. 1 shows Cryo-TEM pictures for the HDL-derived nanoparticles of entries A to F in Table 8 of Example 24. The 50 nm bar applies to all 6 pictures.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

The term "about" when immediately preceding a numerical value means a range of plus or minus an acceptable degree of variation in the art. In embodiments, the term "about" encompasses 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Salts" include those obtained by reacting a compound functioning as a base, with an inorganic or organic acid to form a salt, or those obtained by reacting a compound functioning as an acid, with an inorganic or organic base to form a salt. "Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, 3-(4-hydroxybenzoyl) benzoic acid, cinnamic, citric, fumaric, glycolic, lactic, maleic, malic, malonic, mandelic, oxalic, picric, pyruvic, salicylic, succinic, methanesulfonic, ethanesulfonic, 2-hydroxyethanesulfonic acid, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, 4-chlorobenzenesulfonic acid, 2-naphthalenesulfonic acid, camphorsulfonic acid, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium, calcium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, PA.

The term "carrier" or "vehicle" as used interchangeably herein encompasses carriers, excipients, adjuvants, and diluents or a combination of any of the foregoing, meaning a material, composition or vehicle, such as a liquid or solid filler, diluent, excipient, solvent or encapsulating material involved in carrying or transporting a pharmaceutical agent from one organ, or portion of the body, to another organ or portion of the body. In addition to the adjuvants, excipients and diluents known to one skilled in the art, the carrier includes nanoparticles of organic and inorganic nature.

For example, in embodiments the present disclosure provides nanoparticle carriers (e.g., HDL-derived nanoparticles) as delivery vehicles for an active agent (e.g., a compound of formula (I), (IA), (IB), (II), (II-1), (II-2), (IIA), (IIA-1), (IIA-2) or Table 1). In embodiments, the agent is encapsulated within the nanoparticle carrier. In other embodiments, the agent is bound to the surface of the nanoparticle carrier. The association of the agent and the nanoparticle carrier may be effected by a variety of means, including noncovalent bonding, and trapping the agent in the interior of the delivery vehicle and the like. In embodiments, the association is sufficiently stable so that agent remains associated with the delivery vehicle until it is delivered to the target site in the treated subject.

The terms "pharmaceutical combination," "therapeutic combination" or "combination" as used herein, refers to a single dosage form comprising at least two therapeutically active agents, or separate dosage forms comprising at least two therapeutically active agents together or separately for use in combination therapy. Administration of a combination therapy includes: administration in the same or different composition(s) and/or combinations, either sequentially, simultaneously, or continuously, through the same or different routes. For example, one therapeutically active agent may be formulated into one dosage form and the other therapeutically active agent may be formulated into a single or different dosage forms. For example, one therapeutically active agent may be formulated into a solid oral dosage form whereas the second therapeutically active agent may be formulated into a solution dosage form for parenteral administration. In embodiments, the combination therapy optionally includes one or more pharmaceutically acceptable carriers or excipients, non-pharmaceutically active compounds, and/or inert substances.

As used herein, the phrase "a disorder characterized by cell proliferation" or "a condition characterized by cell proliferation" include, but are not limited to, cancer, benign and malignant tumors. Examples of cancer and tumors include, but are not limited to, cancers or tumor growth of the bladder, blood vessels, bone, brain, breast, cervix, chest, colon, endometrium, esophagus, eye, head, kidney, liver, lymph nodes, lung, mouth, neck, ovary, pancreas, prostate, rectum, colorectum, skin, stomach, testicles, throat, thyroid, urothelium, and uterus.

The terms "treat", "treating" or "treatment" in reference to a particular disease or disorder includes prevention of the disease or disorder, and/or lessening, improving, ameliorating or abrogating the symptoms and/or pathology of the disease or disorder. Generally the terms as used herein refer to ameliorating, alleviating, lessening, and removing symptoms of a disease or condition. A candidate compound described herein may be in a therapeutically effective amount in a formulation or medicament, which is an amount that can lead to a biological effect, such as apoptosis of certain cells (e.g., cancer cells), reduction of proliferation of certain cells, or lead to ameliorating, alleviating, lessening, or removing symptoms of a disease or condition, for example sepsis. The terms also can refer to reducing or stopping a cell proliferation rate (e.g., slowing or halting tumor growth) or reducing the number of proliferating cancer cells (e.g., removing part or all of a tumor).

The term "patient" or "subject" as used herein, includes all mammals and more particularly includes humans. The methods described herein may be useful for both human therapy and veterinary applications. In one embodiment, the subject is a human.

As used herein, "prevention" or "preventing" refers to a reduction of the risk of acquiring a given disease or disorder. For example, causing at least one of the clinical symptoms of the disease not to develop in a subject that may be exposed to or predisposed to the disease but does not yet experience or display symptoms of the disease.

As used herein, "therapeutically effective amount" means the amount of a compound or a therapeutically active agent that, when administered to a subject for treating a disease or other undesirable medical condition, is sufficient to have a beneficial effect with respect to that disease or condition. The therapeutically effective amount will vary depending on the type of the selected compound or a therapeutically active agent, the disease or condition and its severity, and the age, weight, etc. of the patient to be treated.

By "optional" or "optionally" it is meant that the subsequently described event or circumstance may or may not occur, and that the description includes instances where the event or circumstance occurs and instances in which is does not. For example, "optionally substituted aryl" encompasses both "aryl" and "substituted aryl" as defined below. It will be understood by those skilled in the art, with respect to any group containing one or more substituents, that such groups are not intended to introduce any substitution or substitution patterns that are sterically impractical, synthetically non-feasible and/or inherently-unstable.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

"Alkyl" or "alkyl group" refers to a fully saturated, straight or branched hydrocarbon chain.

In embodiments, an alkyl group contains from one to thirty carbon atoms. In embodiments, an alkyl groups has from one to twelve carbon atoms, and which is attached to the rest of the molecule by a single bond. For example, alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_8$alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted. In embodiments, "alkyl" is a straight-chain hydrocarbon. In embodiments, "alkyl" is a branched hydrocarbon.

"Alkylene" or "alkylene chain" refers to a fully saturated, straight or branched divalent hydrocarbon chain. In embodiments, an alkylene groups has from one to twelve carbon atoms.

Non-limiting examples of $C_1$-$C_{12}$ alkylene include methylene, ethylene, propylene, n-butylene, ethenylene, propenylene, n-butenylene and the like. The alkylene chain is attached to the rest of the molecule through a single bond and to the group through a single bond. The points of attachment of the alkylene chain to the rest of the molecule and to the group can be through one carbon or any two carbons within the chain. Unless stated otherwise specifically in the specification, an alkylene chain can be optionally substituted.

"Alkenyl" or "alkenyl group" refers to a straight or branched hydrocarbon chain. In embodiments, an alkenyl group contains from one to thirty carbon atoms. In embodiments, an alkenyl group contains from two to twelve carbon atoms, and having one or more carbon-carbon double bonds, such as a straight or branched group of 2-8 carbon atoms, referred to herein as $C_2$-$C_8$ alkenyl. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls.

Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkynyl" or "alkynyl group" refers to a straight or branched hydrocarbon chain. In embodiments, an alkynyl group contains from one to thirty carbon atoms. In embodiments, an alkynyl group contains from two to twelve carbon atoms, and having one or more carbon-carbon triple bonds such as a straight or branched group of 2-8 carbon atoms, referred to herein as $C_2$-$C_8$ alkynyl. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Aryl" refers to a hydrocarbon ring system comprising hydrogen, 6 to 18 carbon atoms and at least one aromatic ring, which is attached to the rest molecule by a single bond. For purposes of this invention, the aryl can be a monocyclic, bicyclic, tricyclic, tetracyclic ring system or other multicyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the aryl can be optionally substituted.

"Aralkyl" or "arylalkyl" refers to a group of the formula $-R_b-R_c$ where $R_b$ is an alkylene group as defined above and $R_c$ is one or more aryls as defined above, for example, benzyl, diphenylmethyl and the like. Unless stated otherwise specifically in the specification, an aralkyl group can be optionally substituted.

"Carbocyclyl," "carbocyclic ring" or "carbocycle" refers to a rings structure, wherein the atoms which form the ring are each carbon, and which is attached to the rest of the molecule by a single bond. Carbocyclic rings can comprise from 3 to 20 carbon atoms in the ring. Carbocyclic rings include aryls and cycloalkyl, cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon consisting solely of carbon and hydrogen atoms, which can include fused, spirocyclic, or bridged ring systems, having from three to twenty carbon atoms, and which is attached to the rest of the molecule by a single bond. Monocyclic cycloalkyl include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon consisting solely of carbon and hydrogen atoms, having one or more carbon-carbon double bonds, which can include fused, spirocyclic, or bridged ring systems, having from three to twenty carbon atoms, preferably having from three to ten carbon atoms, and which is attached to the rest of the molecule by a single bond. Monocyclic cycloalkenyl include, for example, cyclopentenyl, cyclohexenyl, cycloheptenyl, cycloctenyl, and the like. Polycyclic cycloalkenyls include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon consisting solely of carbon and hydrogen atoms, having from 3 to 20 carbon atoms and one or more carbon-carbon triple bonds, which can include fused, spirocyclic, or bridged ring systems, and which is attached to the rest of the molecule by a single bond. Monocyclic cycloalkynyls include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered aromatic or non-aromatic ring which consists of 2 to 12 carbon atoms and from one to six heteroatoms selected from the group consisting of nitrogen, oxygen and sulfur. Heterocycles can be aromatic (heteroaryls) or non-aromatic. Unless stated otherwise specifically in the specification, the heterocyclyl can be a monocyclic, bicyclic, tricyclic, tetracyclic ring system or other multicyclic ring system, which can include fused, spirocyclic, or bridged ring systems; and the nitrogen, carbon or sulfur atoms in the heterocyclyl can be optionally oxidized; the nitrogen atom can be optionally quaternized; and the heterocyclyl can be partially or fully saturated. Examples of such heterocyclyls include, but are not limited to, dioxolanyl, thienyl[1,3]dithianyl, decahydroisoquinolyl, biotinyl, dihydrofuranyl, dihydroindolyl, dihydropyranyl, dihydrothienyl, dithiazolyl, homopiperidinyl, pyranyl, pyrazolinyl, thiopyranyl, imidazolinyl, imidazolidinyl, isothiazolidinyl, isoxazolidinyl; morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrrolidin-2-only, pyrazolidinyl, quinuclidinyl, thiazolidinyl, tetrahydrofuryl, tetrahydroisoquinolyl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heteroaryl" refers to a 5- to 20-membered ring system comprising hydrogen atoms, one to thirteen carbon atoms, one to six heteroatoms selected from the group consisting of nitrogen, oxygen and sulfur, and at least one aromatic ring. For purposes of this disclosure, the heteroaryl can be a monocyclic, bicyclic, tricyclic or tetracyclic ring system, which can include fused or bridged ring systems; the heteroaryl may contain one or more non-aromatic rings (e.g., cycloalkyl or heterocyclyl) fused to the aromatic ring. The nitrogen, carbon or sulfur atoms in the heteroaryl can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"Heteroarylalkyl" refers to a group of the formula $-R_b-R_f$ where $R_b$ is an alkylene chain as defined above and $R_f$ is a heteroaryl as defined above. Unless stated otherwise specifically in the specification, a heteroarylalkyl group can be optionally substituted.

The term "substituted" used herein means any of the above groups (i.e., alkyl, alkenyl, alkynyl, aryl, arylalkyl, carbocyclyl, cycloalkyl, cycloalkenyl, cycloalkynyl, heterocyclyl, N-heterocyclyl, heteroaryl, etc) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $NR_gR_h$, $NR_gC(=O)R_h$, $NR_gC(=O)NR_gR_h$, $NR_gC(=O)OR_h$, $NR_gSO_2R_h$, $OC(=O)NR_gR_h$, $OR_g$, $SR_g$, $SOR_g$, $SO_2R_g$, $OSOR_g$, $SO_2OR_g$, $=NSO_2R_g$, and $SO_2NR_gR_h$. "Substituted" also means any of the above groups in which one or more hydrogen atoms are replaced with $C(=O)R_g$, $C(=O)OR_g$, $C(=O)NR_gR_h$, $CH_2SO_2R_g$, $CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, "substituted" means any of the above groups in which two hydrogen atoms are each replaced by a bond to form a fused ring system containing the atoms to which the hydrogens were attached. Moreover, each of the foregoing substituents can also be optionally substituted with one or more of the above substituents.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(+)" in nomenclature, but the skilled artisan will recognize that a structure may denote a chiral center implicitly. In embodiments, an enantiomer or stereoisomer may be provided substantially free of the corresponding enantiomer.

In embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Geometric isomers can also exist in the compounds of the present disclosure. The present disclosure encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the E and Z isomers.

Substituents around a carbon-carbon double bond alternatively can be referred to as "cis" or "trans," where "cis" represents substituents on the same side of the double bond and "trans" represents substituents on opposite sides of the double bond. The arrangements of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein may exist as tautomers and both tautomeric forms are intended to be encompassed by the scope of the present disclosure, even though only one tautomeric structure is depicted.

As used herein, the term "isotopic variant" is meant to include compounds that differ only in the presence of one or more isotopically enriched atoms. Such compounds may be useful as, for example, analytical tools, probes in biological assays, or therapeutic agents. For example, an "isotopic variant" of a compound can contain one or more nonradioactive isotopes, such as for example, deuterium ($^{2}H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^{2}H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

The term "triglyceride" as used herein means an ester derived from glycerol and three fatty acids. The fatty acids may be the same or different. The notation used in this specification to describe a triglyceride is the same as that used below to describe a fatty acid. Fatty acids can attach to the glycerol molecule in any order, e.g., any fatty acid can react with any of the hydroxyl groups of the glycerol molecule for forming an ester linkage. For example. In a non-limiting example, a triglyceride can comprise glycerol with any combination of the following fatty acids: C18:1, C14:1, C16:1, polyunsaturated, and saturated. A triglyceride of C18:1 fatty acid simply means that the fatty acid components of the triglyceride are derived from or based upon a C18:1 fatty acid. That is, a C18:1 triglyceride is an ester of glycerol and three fatty acids of 18 carbon atoms each with each fatty acid having one double bond. Similarly, a C14:1 triglyceride is an ester of glycerol and three fatty acids of 14 carbon atoms each with each fatty acid having one double bond. Likewise, a C16:1 triglyceride is an ester of glycerol and three fatty acids of 16 carbon atoms each with each fatty acid having one double bond. Triglycerides of C18:1 fatty acids in combination with C14:1 and/or C16:1 fatty acids means that: (a) a C18:1 triglyceride is mixed with a C14:1 triglyceride or a C16:1 triglyceride or both; or (b) at least one of the fatty acid components of the triglyceride is derived from or based upon a C18:1 fatty acid, while the other two are derived from or based upon C14:1 fatty acid and/or C16:1 fatty acid.

The term "fatty acid" and like terms mean a carboxylic acid with a long aliphatic tail that is either saturated or unsaturated. The term "long aliphatic tail" and "fatty acid chain" are used interchangeably herein. Fatty acids and fatty acid chains may be esterified to phospholipids and triglycerides. As used herein, the fatty acid chain length includes from C4 to C30 (e.g., C6 to C30), saturated or unsaturated, cis or trans, unsubstituted or substituted, branched or unbranched hydrocarbon chain (e.g., the fatty acid chain length includes from C4 to C30 (e.g., C6 to C30), saturated or unsaturated, cis or trans, unsubstituted or substituted with 1-6 side chains). For example, in embodiments, examples of a fatty acid chain include, but are not limited to, C4, C5, C6, C7, C8, C9, C10, C11, C12, C13, C14, C15, C16, C17, C18, C19, C20, C21, C22, C23, C24, C25, C26, C27, C28, C29, or C30 saturated or unsaturated, cis or trans, unsubstituted or substituted hydrocarbon chain. Unsaturated fatty acids and fatty acid chains have one or more double bonds between carbon atoms. Saturated fatty acids and fatty acid chains do not contain any double bonds. In embodiments, a fatty acid may be described herein by the capital letter "C" for carbon atom, followed by a number describing the number of carbon atoms in the fatty acid, followed by a colon and another number for the number of double bonds in the fatty acid. For example, C16:1 denotes a fatty acid of 16 carbon atoms with one double bond, e.g., palmitoleic acid. The number after the colon in this notation neither designates the placement of the double bond(s) in the fatty acid nor whether the hydrogen atoms bonded to the carbon atoms of the double bond are cis to one another. Other examples of this notation include C18:0 (stearic acid), C18:1 (oleic acid), C18:2 (linoleic acid), C18:3 (a-linolenic acid) and C20:4 (arachidonic acid).

The term "sterols" such as, but not limited to cholesterol, can also be utilized in the methods and compounds described herein. Sterols are animal or vegetable steroids which only contain a hydroxyl group but no other functional groups at C-3. In general, sterols contain 27 to 30 carbon atoms and one double bond in the 5/6 position and occasionally in the 7/8, 8/9 or other positions. Besides these unsaturated species, other sterols are the saturated compounds obtainable by hydrogenation. One example of a suitable animal sterol is cholesterol. Typical examples of suitable phytosterols, which are preferred from the applicational point of view, are ergosterols, campesterols, stigmasterols, brassicasterols and, preferably, sitosterols or sitostanols and, more particularly, β-sitosterols or β-sitostanols. Besides the phytosterols mentioned, their esters are preferably used. The acid component of the ester may go back to carboxylic acids corresponding to formula (CA-I): RI CO—OH (CA-I); in which RI CO is an aliphatic, linear or branched acyl group containing 2 to 30 carbon atoms and O and/or 1, 2 or 3 double bonds. Typical examples are acetic acid, propionic acid, hexanoic acid, butyric acid, valeric acid, caproic acid, caprylic acid, 2-ethyl hexanoic acid, capric acid, cyclopentanepropionic acid, lauric acid, isotridecanoic acid, myristic acid, palmitic acid, palmitoleic acid, stearic acid, isostearic acid, oleic acid, elaidic acid, petroselic acid, linoleic acid, conjugated linoleic acid (CLA), linolenic acid, elaeosteric add, arachic acid, gadoleic acid, behenic acid and erucic acid.

The term "phospholipid" refers to an amphiphilic compound that consists of two hydrophobic fatty acid "tails" and a hydrophilic "head" consisting of a phosphate group. The two components are joined together by a glycerol molecule. The phosphate groups can be modified with simple organic molecules such as choline, ethanolamine or serine. Choline refers to an essential, bioactive nutrient having the chemical formula $R—(CH_2)_2—N(CH_2)_4$. When a phospho-moiety is —R— it is called phosphocholine.

"Lysolipids", as used herein, include (acyl-, single chain) such as in non-limiting embodiments 1-myristoyl-2-hydroxy-sn-glycero-3-phosphocholine (MHPC), 1-palmitoyl- 2-hydroxy-sn-glycero-3-phosphocholine (PHPC) and 1-stearoyl-2-hydroxy-sn-glycero-3-phosphocholine (SHPC).

The term "apolipoprotein A-I" or "apoA-I", and also "apoliprotein A1" or "apoA1", refers to a protein that is encoded by the APOA1 gene in humans.

DETAILED DESCRIPTION

Conventionally, immune systems in vertebrate animals are subdivided into two parts. The first part, innate immunity, provides an initial response to an infection within minutes to hours. Its cellular component comprises natural killer (NK) cells, innate lymphoid cells (ILCs) and phagocytes such as monocytes, macrophages and neutrophils. The innate immune system acts as a rapid first line of defense, triggered through recognition of either pathogens or endogenous danger signals by pattern recognition receptors (PRRs). Upon detecting pathogen-associated molecular patterns (PAMPs), PRRs initiate an innate immune response, which involves activating the subsequent adaptive immune system by antigen presentation, co-stimulation, and cytokine excretion. In addition, PRRs also recognize damage-associated molecular patterns (DAMPs), leading to non-infectious inflammatory responses. The second stage of the response to infection involves the immune system's second part—the adaptive response—in which T and B lymphocytes specifically recognize a pathogen, proliferate and become activated against that pathogen. These cells also build immunological memory of that specific infection. The specificity of the adaptive immune system response is mediated by recombination of the immunoglobulin genes at the lymphocyte level. Immunological memory results in a quicker and quantitatively better immune response (as compared with the primary response alone) against a previously encountered antigen. Though the innate immune system was long believed to lack memory, recent studies show that innate immune cells undergo metabolic and epigenetic rewiring, adjusting their functional programs in a process termed 'trained immunity' that is considered de facto innate immune memory.

Trained Immunity is defined by a secondary long-term hyper-responsiveness, as manifested by increased cytokine excretion caused by metabolic and epigenetic rewiring, to restimulation after a primary insult of myeloid cells and their progenitors and stem cells in the bone marrow, spleen and blood. Trained Immunity (also called innate immune memory) is also defined by a long-term increased responsiveness (e.g. high cytokine production) after restimulation with a secondary stimulus of myeloid innate immune cells, being induced by a primary insult stimulating these cells or their progenitors and stem cells in the bone marrow and spleen, and mediated by epigenetic, metabolic and transcriptional rewiring.

Trained immunity is regulated and maintained through induction of training properties to progenitor cells in the bone marrow, resulting in durable reprogramming that exceeds the myeloid cell lifespan in the bloodstream. Although trained immunity can be induced with a range of 'training agents' in cultured myeloid cells, its systemic induction requires bone marrow progenitor cell engagement.

In one aspect, the present disclosure provides compounds (e.g., of formula (I), (IA), (IB), (II), (II-1), (II-2), (IIA), (IIA-1), (IIA-2) or Table 1) that activate nucleotide-binding oligomerization domain-containing protein 2 (NOD2). The present disclosure also provides nanobiologic compositions comprising a nanoparticle carrier (e.g., HDL-derived nanoparticle) comprising a compound of the present disclosure (e.g., of formula (I), (IA), (IB), (II), (II-1), (II-2), (IIA), (IIA-1), (IIA-2) or Table 1). Nanobiologic compositions of the present disclosure comprising compounds of the present disclosure (e.g., of formula (I), (IA), (IB), (II), (II-1), (II-2), (IIA), (IIA-1), (IIA-2) or Table 1) that activate nucleotide-binding oligomerization domain-containing protein 2 (NOD2) are designed to exhibit bone marrow proclivity. These nanomaterials can be administered (e.g., intravenously) to promote trained immunity. Therapeutically inducing trained immunity may find use, for example, in overcoming immunoparalysis in sepsis and infections, in treating cell proliferation disorders (such as cancer), and augmenting immune responses.

Compounds

In embodiments, the present disclosure provides a compound of formula (I):

(I)

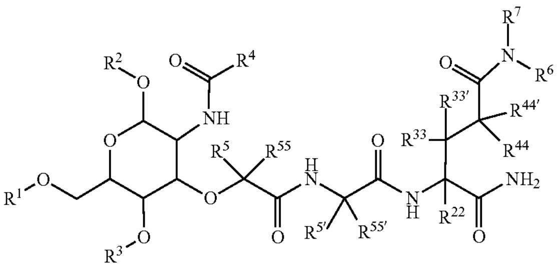

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^{11}$ are each independently —H, or alkyl;

$R^7$ is a fatty acid chain, —Y—N($R^6$)—C(O)—O-alkylene-C(H)(ORs)-alkylene-$OR^9$, —Y—N($R^6$)—C(O)—$R^X$, —Y—O—P(O)(OH)—O-alkylene-C(H)($OR^8$)-alkylene-$OR^9$, or —Y— triazolyl-L;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W$)_2$, and -alkylene-N-(alkylene-C(O)—W$)_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^{22}$, $R^{33}$, $R^{33'}$, $R^{44}$, $R^{44'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)$NR^CR^D$, —NRCC(O)$OR^B$, —OC(O)$R^B$, —C(O)$OR^B$, —C(O)$R^B$, —$CO_2$H, —$NO_2$, —SH, S(O)$_X$$R^B$ (wherein X is 0, 1, or 2), aryl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)O$R^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro.

In embodiments, the present disclosure provides a compound of formula (I):

(I)

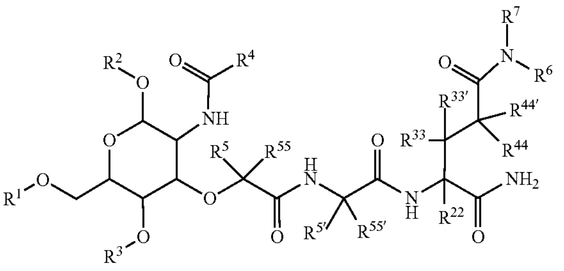

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^1$ are each independently —H, or alkyl;

$R^7$ is a $C_{9-30}$ fatty acid chain, —Y—N($R^{11}$)—C(O)—O-alkylene-C(H)(O$R^8$)-alkylene-O$R^9$, —C($R^{10}$)(C(O)$NH_2$)-alkylene-N($R^{11}$)—C(O)—$C_{16-30}$ fatty acid chain, —($CR^{10}R^{10}$)$_2$—O—P(O)(OH)—O-alkylene-C($R^{10}$)(O$R^Z$)-alkylene-O$R^{Z'}$, or —Y-triazolyl-L;

$R^Z$ and $R^{Z'}$ are each independently $C_{8-30}$ fatty acid chain or —C(O)—$C_{16-30}$ fatty acid chain;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W)$_2$, and -alkylene-N-(alkylene-C(O)—W)$_2$;

W is a fatty acid chain, —O-alkylene-C(H)(O$R^8$)-alkylene-O$R^9$, a phospholipid, or a sterol;

$R^8$ and $R^9$ are each independently $R^X$ or —C(O)—$R^X$;

$R^{10}$, $R^{22}$, $R^{33}$, $R^{33'}$, $R^{44}$, $R^{4'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)N$R^C R^D$, —N$R^C$C(O)O$R^B$, —OC(O)$R^B$, —C(O)O$R^B$, —C(O)$R^B$, —$CO_2$H, —$NO_2$, —SH, S(O)$_X R^B$ (wherein X is 0, 1, or 2), aryl, arylalkyl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)O$R^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro; wherein, when $R^7$ is $C_{9-30}$ fatty acid chain, $R^2$ is —H.

In embodiments of the compound of Formula (I), the compound is of formula (IA):

(IA)

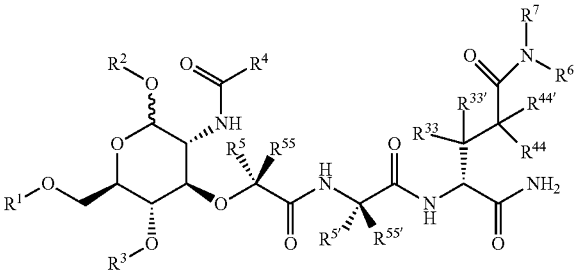

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^1$ are each independently —H, or alkyl;

$R^7$ is a $C_{9-30}$ fatty acid chain, —Y—N($R^{11}$)—C(O)—O-alkylene-C(H)(O$R^8$)-alkylene-O$R^9$, —C($R^0$)(C(O)$NH_2$)-alkylene-N($R^{11}$)—C(O)—$C_{16-30}$ fatty acid chain, —($CR^{10}R^{10}$)$_2$—O—P(O)(OH)—O-alkylene-C($R^{10}$)(O$R^Z$)-alkylene-O$R^{Z'}$, or —Y-triazolyl-L;

$R^Z$ and $R^{Z'}$ are each independently $C_{8-30}$ fatty acid chain or —C(O)—$C_{16-30}$ fatty acid chain;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W)$_2$, and -alkylene-N-(alkylene-C(O)—W)$_2$;

W is a fatty acid chain, —O-alkylene-C(H)(O$R^8$)-alkylene-O$R^9$, a phospholipid, or a sterol;

$R^8$ and $R^9$ are each independently $R^X$ or —C(O)—$R^X$;

$R^{10}$, $R^{22}$, $R^{33}$, $R^{33'}$, $R^{44}$, $R^{4'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)N$R^C R^D$, —NRCC(O)O$R^B$, —OC(O)$R^B$, —C(O)O$R^B$, —C(O)$R^B$, —$CO_2$H, —$NO_2$, —SH, S(O)$_X R^B$ (wherein X is 0, 1, or 2), aryl, arylalkyl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)O$R^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro;

wherein, when $R^7$ is $C_{9\text{-}30}$ fatty acid chain, $R^2$ is —H.

In embodiments, the compound of formula (I) is a compound of formula (IB):

(IB)

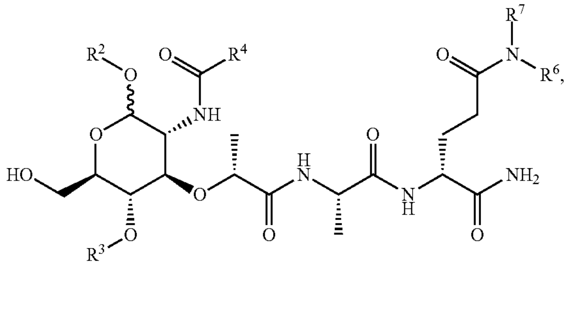

or a pharmaceutically acceptable salt thereof.

In embodiments of the compounds of formula (I), (IA), or (IB), Y is alkylene optionally substituted with —C(O)N($R^C$)($R^D$). In embodiments, Y is —$C_{1\text{-}6}$alkylene. In embodiments, Y is —$CH_2$—. In embodiments, Y is —$CH_2$— or

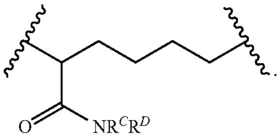

In embodiments, Y is or

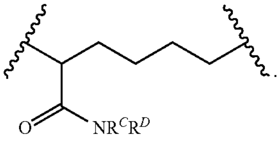

In embodiments, Y is

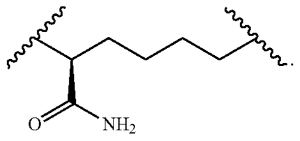 [SMILES: *CCCC[C@H](*)C(N)=O]

In embodiments of the compounds of formula (I), (IA), or (IB), $R^7$ is —Y-triazolyl-L.

In embodiments of the compound of formula (I), (IA), or (IB), $R^7$ comprises a cholesteryl moiety or at least one fatty acid chain comprising at least 17 carbons. In embodiments, $R^7$ comprises a cholesteryl moiety. In embodiments, $R^7$ comprises at least one fatty acid chain comprising at least 17 carbons. In embodiments, $R^7$ comprises at least two fatty acid chain comprising at least 17 carbons. In embodiments, $R^7$ comprises at least two $C_{17}$ fatty acid chains. In embodiments, the $C_{17}$ fatty acid chain is derived from stearic acid or oleic acid. In embodiments, the $C_{17}$ fatty acid chain is derived from stearic acid. In embodiments, the $C_{17}$ fatty acid chain is derived from oleic fatty acid. In embodiments, $R^7$ comprises two $C_{17}$ fatty acid chains derived from stearic acid.

In embodiments of the compound of formula (I), (IA), or (IB), $R^7$ is an alkyl group having at least 16 carbons. In embodiments of the compound of formula (I), (IA), or (IB), $R^7$ is an alkenyl group having at least 16. In embodiments of the compound of formula (I), (IA), or (IB), $R^7$ is an alkyl group having at least 18 carbons. In embodiments of the compound of formula (I), $R^7$ is an alkenyl group having at least 18 carbons.

In embodiments of the compound of formula (I), (IA), or (IB), $R^7$ is $C_{9\text{-}30}$ fatty acid chain. In embodiments of the compound of formula (I), $R^7$ is a —$C_{9\text{-}30}$ alkyl or a $C_{9\text{-}30}$ alkenyl. In embodiments, $R^7$ is a —$C_{9\text{-}30}$ alkyl or a $C_{9\text{-}30}$ alkenyl provided that when $R^7$ is a —$C_{9\text{-}30}$ alkyl then $R^2$ is —H. In embodiments of the compound of formula (I), $R^7$ is a —$C_{9\text{-}30}$ alkyl. In embodiments, $R^7$ is a —$C_{9\text{-}30}$ alkyl and $R^2$ is —H. In embodiments of the compound of formula (I), $R^7$ is a —$C_{9\text{-}30}$ alkenyl. In embodiments, $R^7$ is a —$C_{15\text{-}30}$ alkyl group. In embodiments, $R^7$ is a —$C_{15\text{-}30}$ alkyl group and $R^2$ is —H. In embodiments, $R^7$ is a —$C_{15\text{-}30}$ alkenyl group. In embodiments, $R^7$ is a —$C_{17\text{-}19}$ alkyl. In embodiments, $R^7$ is a —$C_{17\text{-}19}$ alkyl and $R^2$ is —H. In embodiments, $R^7$ is a —$C_{17\text{-}19}$ alkenyl. In embodiments, $R^7$ is a —$C_{18}$ alkyl group. In embodiments, $R^7$ is a —$C_{18}$ alkyl group and $R^2$ is —H. In embodiments, $R^7$ is a —$C_{18}$ alkenyl group.

In embodiments of the compound of formula (I), (IA), or (IB), $R^7$ is:

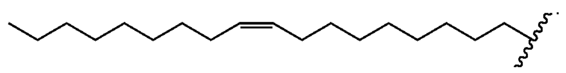 [SMILES: *CCCCCCCC/C=C\CCCCCCCC]

In embodiments of the compound of formula (I), (IA), or (IB), $R^7$ is:

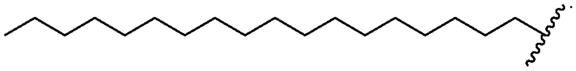 [SMILES: *CCCCCCCCCCCCCCCCCC]

In embodiments of the compound of formula (I), (IA), or (IB), $R^7$ is:

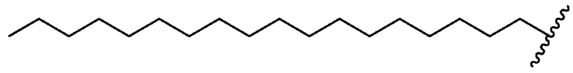 [SMILES: *CCCCCCCCCCCCCCCCCC]

and $R^2$ is —H.

In embodiments of the compound of formula (I), (IA), or (IB), $R^7$ is —Y—N($R^{11}$)—C(O)—O— alkylene-C(H)($OR^8$)-alkylene-$OR^9$.

In embodiments of the compound of formula (I), (IA), or (IB), $R^7$ is —C($R^{10}$)(C(O)$NH_2$)-alkylene-N($R^{11}$)—C(O)—$C_{16\text{-}30}$ fatty acid chain. In embodiments, $R^7$ is —C(H)(C(O)$NH_2$)—$C_5$alkylene-N($R^{11}$)—C(O)—$C_{17\text{-}30}$ fatty acid. In embodiments, $R^7$ is —C(H)(C(O)$NH_2$)-alkylene-N($R^{11}$)—C(O)—$C_{17\text{-}30}$ fatty acid.

In embodiments of the compound of formula (I), (IA), or (IB), $R^7$ is —C($R^{10}$)(C(O)$NH_2$)-alkylene-N($R^{11}$)—C(O)—$C_{16\text{-}30}$ alkyl. In embodiments, $R^7$ is —C($R^{10}$)(C(O)$NH_2$)-alkylene-N($R^{11}$)—C(O)—$C_{17\text{-}30}$ alkyl. In embodiments, $R^7$ is —C(H)(C(O)$NH_2$)-alkylene-N($R^1$)—C(O)—$C_{17\text{-}30}$ alkyl.

In embodiments, $R^7$ is —C(H)(C(O)$NH_2$)—$C_4$alkylene-N($R^{5'}$)—C(O)—$C_{7-30}$alkyl. In embodiments of the compound of formula (I), $R^7$ is —C($R^0$)(C(O)$NH_2$)-alkylene-N($R^{11}$)—C(O)—$C_{16-30}$alkyl and $R^2$ is alkylene-aryl (e.g., benzyl). In embodiments, $R^7$ is —C($R^{10}$)(C(O)$NH_2$)-alkylene-N($R^{11}$)—C(O)—$C_{17-30}$alkyl and $R^2$ is alkylene-aryl (e.g., benzyl). In embodiments, $R^7$ is —C(H)(C(O)$NH_2$)-alkylene-N($R^{11}$)—C(O)—$C_{17-30}$ alkyl and $R^2$ is alkylene-aryl (e.g., benzyl). In embodiments, $R^7$ is —C(H)(C(O)$NH_2$)—$C_4$alkylene-N($R^1$)—C(O)—$C_{17-30}$alkyl and $R^2$ is alkylene-aryl (e.g., benzyl).

In embodiments of the compound of formula (I), (IA), or (IB), $R^7$ is —($CR^{10}R^{10}$)$_2$—O—P(O)(OH)—O-alkylene-C($R^{10}$)($OR^Z$)-alkylene-$OR^{Z'}$. In embodiments of the compound of formula (I), $R^7$ is —$CH_2CH_2$—O—P(O)(OH)—O—$CH_2$—C(H)($OR^Z$)—$CH_2$—$OR^{Z'}$. In embodiments, $R^Z$ and $R^{Z'}$ are each independently $C_{12-20}$alkyl or —C(O)—$C_{16-30}$ fatty acid chain. In embodiments, $R^Z$ and $R^{Z'}$ are each independently $C_{18}$alkyl or —C(O)—$C_{17}$alkyl. In embodiments, $R^Z$ and $R^{Z'}$ are each independently a —C(O)—$C_{16-30}$alkyl. In embodiments, $R^Z$ and $R^{Z'}$ are both a —C(O)—$C_{17}$alkyl.

In embodiments of the compound of formula (I), (IA), or (IB), $R^7$ is —Y—N($R^6$)—C(O)—O— alkylene-C(H)(ORS)-alkylene-$OR^9$. In embodiments, $R^8$ and $R^9$ are each independently $C_{8-30}$alkyl or —C(O)—$C_{8-30}$alkyl. In embodiments, $R^8$ and $R^9$ are each independently $C_{12-20}$alkyl or —C(O)—$C_{11-20}$alkyl. In embodiments, $R^8$ and $R^9$ are each independently $C_{18}$alkyl or —C(O)—$C_{17}$alkyl. In embodiments, $R^8$ and $R^9$ are both —C(O)—$C_{17}$alkyl.

In embodiments of the compounds of formula (I), (IA), or (IB), $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)$NR^CR^D$, —$NR^C$C(O)$OR^B$, —OC(O)$R^B$, —C(O)$OR^B$, —C(O)$R^B$, —$CO_2$H, —$NO_2$, —SH, $S(O)_XR^B$ (wherein X is 0, 1, or 2), aryl, arylalkyl, heteroaryl, heteroarylalkyl, cycloalkyl, heterocycloalkyl.

In embodiments of the compounds of formula (I), (IA), or (IB), $R^A$ is independently selected for each occurrence from the group consisting of halo, alkoxy, haloalkoxy, cyano, hydroxyl, —N($R^C$)($R^D$), —C(O)N($R^C$)($R^D$), —N($R^C$)C(O)$R^B$, —OC(O)$NR^CR^D$, —NRCC(O)$OR^B$, —OC(O)$R^B$, —C(O)$OR^B$, —C(O)$R^B$, —$CO_2$H, —$NO_2$, —SH, $S(O)_XR^B$ (wherein X is 0, 1, or 2), aryl, arylalkyl, heteroaryl, heteroarylalkyl, cycloalkyl, heterocycloalkyl.

In embodiments the compound of formula (I) is a compound of formula (II):

(II)

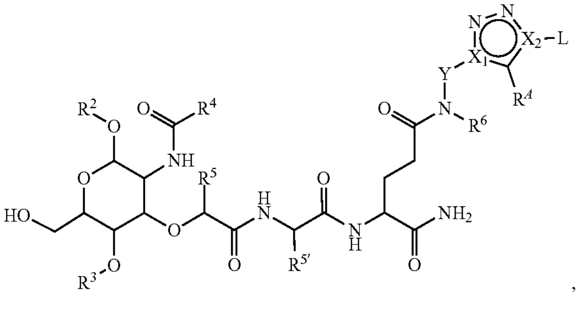

, or a pharmaceutically acceptable salt thereof wherein:

$X_1$ is —N— and $X_2$ is —C—; or $X_1$ is —C— and $X_2$ is —N—;

$R^2$ and $R^3$ are each independently selected from the group consisting of —H, alkyl, aryl, alkylene-aryl, —C(O)-alkyl, and —C(O)-aryl;

$R^4$, $R^5$, and $R^{5'}$ are each alkyl;

$R^6$ and $R^{11}$ are each independently —H, or alkyl;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W)$_2$, and -alkylene-N-(alkylene-C(O)—W)$_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^X$ is a fatty acid chain;

wherein each aforementioned alkyl, alkylene, alkylene-aryl, and aryl is optionally substituted with one or more $R^A$;

$R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)$NR^CR^D$, —NRCC(O)$OR^B$, —OC(O)$R^B$, —C(O)$OR^B$, —C(O)$R^B$, —$CO_2$H, —$NO_2$, —SH, $S(O)_XR^B$(wherein X is 0, 1, or 2), aryl, arylalkyl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)$OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro.

In embodiments, the compound of formula (II) is:

(II)

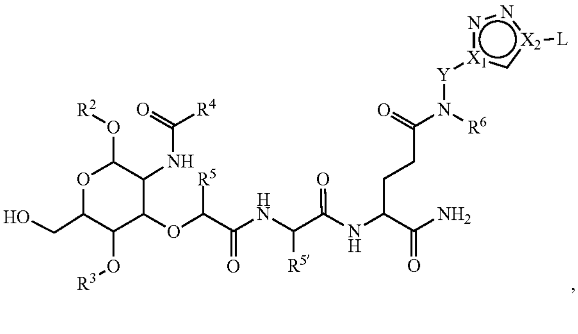

,

In embodiments, the compound of formula (II) is a compound of formula (II-1), or a pharmaceutically acceptable salt thereof (II-1)

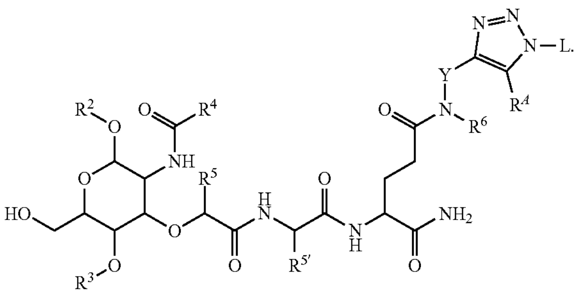

In embodiments, the compound of formula (II-1), is

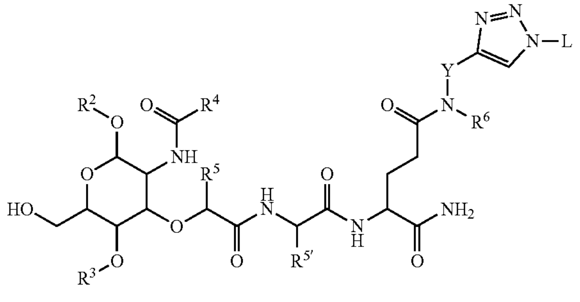

or a pharmaceutically acceptable salt thereof.

In embodiments, the compound of formula (II) is a compound of formula (II-2):

(II-2)

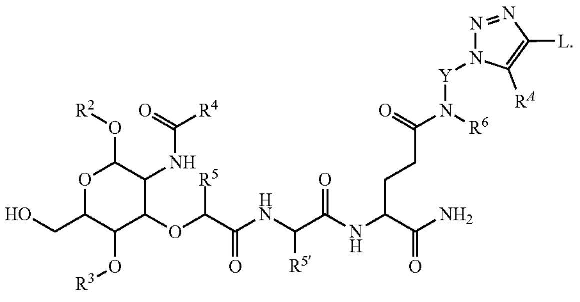

In embodiments, the compound of formula (II-2) is:

(II-2)

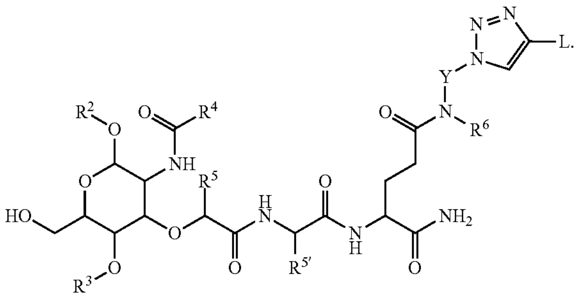

or a pharmaceutically acceptable salt thereof.

In embodiments the compound of formula (I) is a compound of formula (IIA):

(IIA)

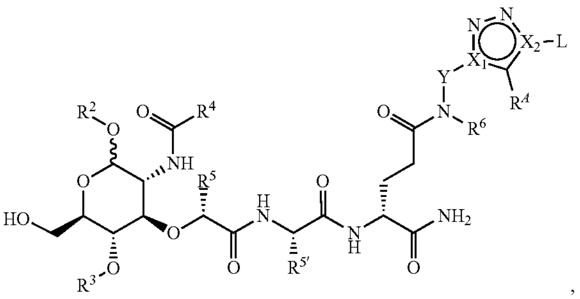

, or a pharmaceutically acceptable salt thereof wherein:

$X_1$ is —N— and $X_2$ is —C—; or $X_1$ is —C— and $X_2$ is —N—

$R^2$ and $R^3$ are each independently selected from the group consisting of —H, alkyl, aryl, alkylene-aryl, —C(O)-alkyl, and —C(O)-aryl;

$R^4$, R, and $R^{5'}$ are each alkyl;

$R^6$ and $R^{11}$ are each independently —H, or alkyl;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—$W)_2$, and -alkylene-N-(alkylene-C(O)—$W)_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^X$ is a fatty acid chain;

wherein each aforementioned alkyl, alkylene, alkylene-aryl, and aryl is optionally substituted with one or more $R^A$;

$R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)N$R^C R^D$, —NRCC(O)$OR^B$, —OC(O)$R^B$, —C(O)$OR^B$, —C(O)$R^B$, —$CO_2H$, —$NO_2$, —SH, $S(O)_X R^B$ (wherein X is 0, 1, or 2), aryl, arylalkyl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)$OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro.

In embodiments, the compound of formula (IIA) is:

(II-A)

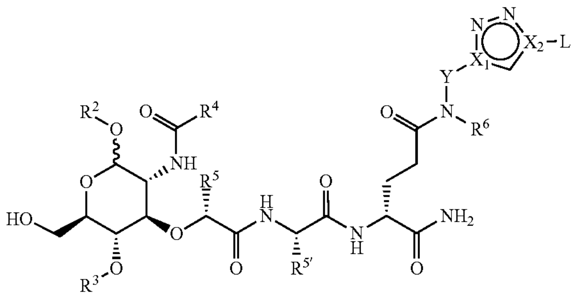

In embodiments the compound of formula (IIA) is a compound of formula (IIA-1), or a pharmaceutically acceptable salt thereof:

(IIA-1)

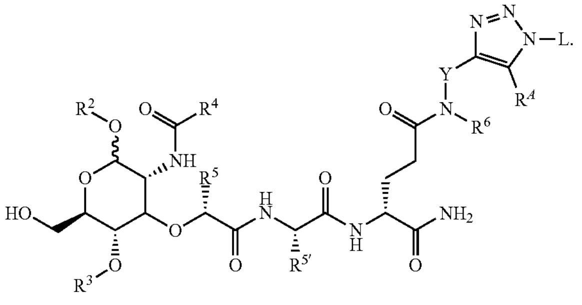

In embodiments, the compound of formula (IIA-1) is:

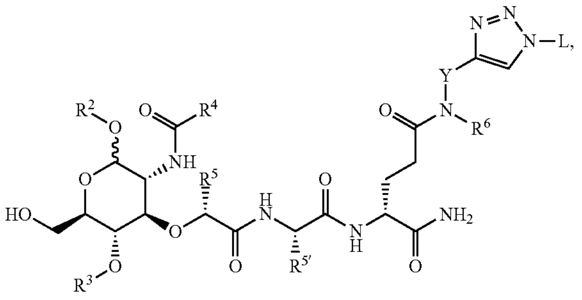

or a pharmaceutically acceptable salt thereof.

In embodiments the compound of formula (IIA) is a compound of formula (IIA-2), or a pharmaceutically acceptable salt thereof:

(IIA-2)

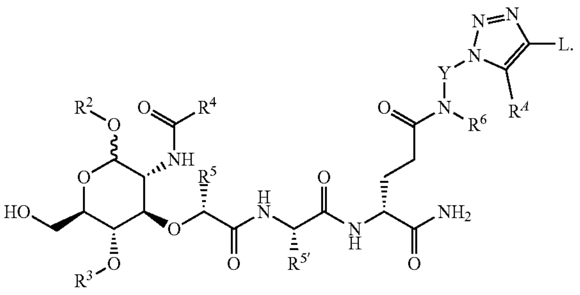

In embodiments, the compound of formula (IIA-2) is:

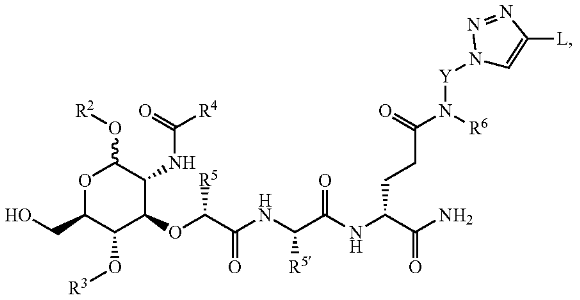

or a pharmaceutically acceptable salt thereof.

In embodiments of the compound of formula (I), (IA), (IB), (II), (II-1), (II-2), (II-A), (IIA-1) or (IIA-2), Y is alkylene. In embodiments of the compound of formula (I), (IA), (IB), (II), (II-1), (II-2), (II-A), (IIA-1) or (IIA-2), Y is $C_{1-6}$alkylene. In embodiments, Y is $C_{1-5}$alkylene. In embodiments, Y is $C_{1-3}$alkylene. In embodiments, Y is alkylene optionally substituted with —C(O)N($R^C$)($R^D$), wherein $R^C$ and $R^D$ are defined herein. In embodiments, Y is —$CH_2$—. In embodiments, Y is

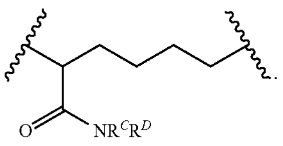

In embodiments, Y is

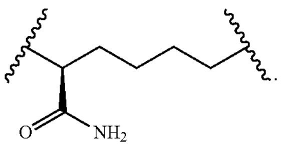

In embodiments of the compound of formula (I), (IA), (IB), (II), (II-1), (II-2), (II-A), (IIA-1) or (IIA-2), $R^A$ is independently selected for each occurrence from the group consisting of hydrogen, halo, alkoxy, haloalkoxy, cyano, hydroxyl, —N($R^C$)($R^D$), —C(O)N($R^C$)($R^D$), —N($R^C$)C(O)$R^B$, —OC(O)N$R^C$$R^D$, —NRCC(O)O$R^B$, —OC(O)$R^B$, —C(O)O$R^B$, —C(O)$R^B$, —$CO_2$H, —$NO_2$, —SH, $S(O)_X R^B$ (wherein X is 0, 1, or 2), aryl, arylalkyl, heteroaryl, heteroarylalkyl, cycloalkyl, heterocycloalkyl, and R.

In embodiments of the compound of formula (I), (IA), (IB), (II), (II-1), (II-2), (II-A), (IIA-1) or (IIA-2), $R^A$ is independently selected for each occurrence from the group consisting of halo, alkoxy, haloalkoxy, cyano, hydroxyl, —N($R^C$)($R^D$), —C(O)N($R^C$)($R^D$), —N($R^C$)C(O)$R^B$, —OC(O)N$R^C$$R^D$, —N$R^C$C(O)O$R^B$, —OC(O)$R^B$, —C(O)O$R^B$, —C(O)$R^B$, —$CO_2$H, —$NO_2$, —SH, $S(O)_xR^B$(wherein X is 0, 1, or 2), aryl, arylalkyl, heteroaryl, heteroarylalkyl, cycloalkyl, heterocycloalkyl, and $R^B$.

In embodiments of the compound of formula (I), (IA), (IB), (II), (II-1), (II-2), (II-A), (IIA-1) or (IIA-2), alkyl, alkylene, alkylene-aryl, and aryl is optionally substituted with one or more $R^A$;

In embodiments of the compound of formula (I), (IA), (IB), (II), (II-1), (II-2), (II-A), (IIA-1) or (IIA-2), $R^C$ and $R^D$ are independently selected for each occurrence from the group consisting of hydrogen, alkyl, haloalkyl —C(O)$R^B$, and —C(O)O$R^B$; or $R^C$ and $R^D$ are taken together with the nitrogen to which they are attached to form a heterocyclic ring optionally substituted with $R^A$.

In embodiments of the compound of formula (I), (IA), (IB), (II), (II-1), (II-2), (II-A), (IIA-1) or (IIA-2), $R^B$ is alkyl, alkenyl, or alkynyl optionally substituted with one or more fluoro.

In embodiments of the compound of formula (I), (IA), (IB), (II), (II-1), (II-2), (II-A), (IIA-1) or (IIA-2), $R^A$ is —H.

In some embodiments of the compound of formula (I), (IA), (IB), (II), (II-1), (II-2), (II-A), (IIA-1) or (IIA-2), $R^2$ is alkyl, aryl, or alkylene-aryl. In embodiments, aryl is optionally substituted with alkyl.

In embodiments of the compound of formula (I), (IA), (IB), (II), (II-1), (II-2), (II-A), (IIA-1) or (IIA-2), $R^2$ and $R^3$ are each independently selected from the group consisting of —H, alkyl, aryl, alkylene-aryl, —C(O)-alkyl, and —C(O)-aryl.

In embodiments of the compound of formula (I), (IA), (IB), (II), (II-1), (II-2), (II-A), (IIA-1) or (IIA-2), $R^2$ is —H or benzyl. In embodiments of the compounds of formula (I), $R^2$ is —H. In embodiments, $R^2$ is benzyl.

In embodiments of the compound of formula (I), (IA), (IB), (II), (II-1), (II-2), (II-A), (IIA-1) or (IIA-2), $R^4$, $R^5$, and $R^{5'}$ are each alkyl.

In embodiments of the compound of formula (I), (IA), (IB), (II), (II-1), (II-2), (II-A), (IIA-1) or (IIA-2), $R^4$ is alkyl. In embodiments, $R^4$ is methyl.

In embodiments of the compound of formula (I), (IA), (IB), (II), (II-1), (II-2), (II-A), (IIA-1) or (IIA-2), $R^3$ is —H. In embodiments $R^6$ is —H. In embodiments, $R^3$ and $R^6$ are both —H.

In embodiments of the compound of formula (I), (IA), (IB), (II), (II-1), (II-2), (II-A), (IIA-1) or (IIA-2), $R^{10}$, $R^{22}$, $R^{33}$, $R^{33'}$, $R^{44}$, $R^{44'}$, $R^{55}$, and $R^{55'}$ are each —H.

In embodiments of the compound of formula (I), (II), (IA), (IB), (II-1), (II-2), (II-A), (IIA-1) or (IIA-2), L comprises a cholesteryl moiety or at least one fatty acid chain comprising at least 13 carbons. In embodiments, L comprises a cholesteryl moiety. In embodiments, L comprises at least one fatty acid chain comprising at least 13 carbons. In embodiments, L comprises at least two fatty acid chains comprising at least 15 carbons. In embodiments, L comprises at least one $C_{17}$ fatty acid chain. In embodiments, L comprises at least two $C_{17}$ fatty acid chains. In embodiments, L comprises at least one fatty acid chains independently selected from a $C_{17}$ alkyl or a $C_{17}$ alkenyl. In embodiments, L comprises at least two fatty acid chains independently selected from a $C_{17}$ alkyl or a $C_{17}$ alkenyl. In embodiments, the $C_{17}$ fatty acid chain is derived from stearic acid or oleic acid. In embodiments, the $C_{17}$ fatty acid chain is derived from stearic acid. In embodiments, the $C_{17}$ fatty acid chain is derived from oleic fatty acid. In embodiments, L comprises two $C_{17}$ fatty acid chains derived from stearic acid.

In embodiments of the compound of formula (I), (IA), (IB), (II), (II-1), (II-2), (II-A), (IIA-1) or (IIA-2), L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W)$_2$, and -alkylene-N-(alkylene-C(O)—W)$_2$.

In embodiments of the compound of formula (I), (IA), (IB), (II), (II-1), (II-2), (II-A), (IIA-1) or (IIA-2), L is selected from the group consisting of $C_{8-30}$ fatty acid chain, —$CH_2$—C(O)—W, —$CH_2$—O—C(O)—W, —$CH_2CH_2$—N—$CH_2CH_2$—C(O)—$NR^{11}$—$CH_2CH_2$—$NR^{11}$—C(O)—W)$_2$, and —$CH_2CH_2$—N—($CH_2CH_2$—C(O)—W)$_2$.

In embodiments of the compound of formula (I), (IA), (IB), (II), (II-1), (II-2), (II-A), (IIA-1) or (IIA-2), L is a $C_{8-30}$ fatty acid chain. In embodiments, L is a $C_{8-30}$alkyl or a $C_{8-30}$alkenyl. In embodiments, L is a $C_{15-20}$alkyl or a $C_{15-20}$alkenyl.

In embodiments of the compound of formula (I), (IA), (IB), (II), (II-1), (II-2), (II-A), (IIA-1) or (IIA-2), L is -alkylene-C(O)—W, -alkylene-O—C(O)—W, -alkylene-N-(alkylene-C(O)—$NR^{11}$-alkylene-$NR^{11}$—C(O)—W)$_2$, or -alkylene-N-(alkylene-C(O)—W)$_2$.

In embodiments of the compound of formula (I), (IA), (IB), (II), (II-1), (II-2), (II-A), (IIA-1) or (IIA-2), L is -alkylene-C(O)—W. In embodiments, L is —$C_{1-6}$alkylene-C(O)—W. In embodiments, L is —$CH_2$—C(O)—W.

In embodiments of the compound of formula (I), (IA), (IB), (II), (II-1), (II-2), (II-A), (IIA-1) or (IIA-2), L is -alkylene-O—C(O)—W. In embodiments, L is —$C_{1-6}$alkylene-O—C(O)—W.

In embodiments, L is —$CH_2$—O—C(O)—W.

In embodiments of the compound of formula (I), (IA), (IB), (II), (II-1), (II-2), (II-A), (IIA-1) or (IIA-2), L is -alkylene-N-(alkylene-C(O)—$NR^{11}$-alkylene-$NR^{11}$—C(O)—W)$_2$. In embodiments, L is —$C_{2-6}$alkylene-N—(—$C_{2-6}$alkylene-C(O)—$NR^1$—$C_{2-6}$alkylene-$NR^{11}$—C(O)—W)$_2$. In embodiments, L is —$CH_2$—$CH_2$—N—($CH_2$—$CH_2$—C(O)—$NR^{11}$—$CH_2$—$CH_2$—$NR^{11}$—C(O)—W)$_2$.

In embodiments of the compound of formula (I), (IA), (IB), (II), (II-1), (II-2), (II-A), (IIA-1) or (IIA-2), L is -alkylene-N-(alkylene-C(O)—W)$_2$. In embodiments, L is —$C_{1-6}$alkylene-N—($C_{1-6}$alkylene-C(O)—W)$_2$. In embodiments, L is —$CH_2$—$CH_2$—N—($CH_2$—$CH_2$—C(O)—W)$_2$.

In embodiments of the compound of formula (I), (IA), (IB), (II), (II-1), (II-2), (II-A), (IIA-1) or (IIA-2), L is a $C_{18}$ fatty acid chain. In embodiments, L is a Cis-alkyl or a $C_{18}$ alkenyl.

In embodiments, L is —$CH_2(CH_2CH_2)_8$—$CH_3$.

In embodiments of the compound of formula (I), (IA), (IB), (II), (II-1), (II-2), (II-A), (IIA-1) or (IIA-2), W is a fatty acid chain, —O-alkylene-C(H)($OR^8$)-alkylene-$OR^9$, a phospholipid, or a sterol.

In embodiments of the compound of formula (I), (IA), (IB), (II), (II-1), (II-2), (II-A), (IIA-1) or (IIA-2), W is a $C_{8-30}$ fatty acid chain. In embodiments, W is a $C_{8-30}$alkyl or a $C_{8-30}$alkenyl. In embodiments, W is a $C_{8-30}$alkyl. In embodiments, W is a $C_{8-30}$alkenyl. In embodiments, W is a $C_{12-18}$ fatty acid chain. In embodiments, W is a $C_{12-18}$alkyl or a $C_{12-18}$alkenyl.

In embodiments, W is a $C_{12-18}$alkyl. In embodiments, W is a $C_{12-18}$alkenyl. In embodiments, W is a Cis fatty acid chain. In embodiments, W is a $C_{17}$ fatty acid chain. In embodiments, W is a $C_{17}$alkyl or a $C_{17}$alkenyl. In embodiments, W is a $C_{17}$alkyl. In embodiments, W is a $C_{17}$alkenyl. In embodiments, W is $—(CH_2CH_2)_8—CH_3$. In embodiments, W is a fatty acid chain comprising at least 15 carbons. In embodiments, W is a fatty acid chain comprising at least 18 carbons. In embodiments, W is a fatty acid chain comprising at least 17 carbons. In embodiments, W is a fatty acid chain comprising at least 18 carbons.

In embodiments of the compounds of formula (I), (IA), (IB), (II), (II-1), (II-2), (II-A), (IIA-1) or (IIA-2), W is:

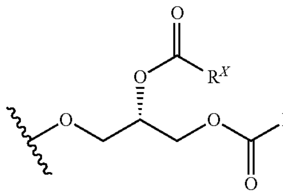

In embodiments, $R^X$ and $R^{X'}$ is each independently a fatty acid chain. In embodiments, $R^X$ and $R^{X'}$ is each independently a fatty acid chain comprising at least 15 carbons. In embodiments, $R^X$ and $R^{X'}$ is each independently a fatty acid chain comprising at least 17 carbons. In some embodiment, $R^X$ and $R^{X'}$ is each independently a $—C_{8-30}$ fatty acid chain. In embodiments, $R^X$ and $R^{X'}$ is each independently a $—C_{8-30}$alkyl or a $—C_{8-30}$alkenyl. In embodiments, $R^X$ and $R^{X'}$ are both a $—C_{8-30}$alkyl. In embodiments, $R^X$ and $R^{X'}$ are both a $—C_{8-30}$alkenyl. In embodiments, $R^X$ and $R^{X'}$ is each independently a $C_{12-18}$fatty acid chain. In embodiments, $R^X$ and $R^{X'}$ is each independently a $—C_{12-18}$alkyl or a $—C_{12-18}$alkenyl. In embodiments, $R^X$ and $R^{X'}$ are a $—C_{12-18}$alkyl. In embodiments, $R^X$ and $R^{X'}$ are a $—C_{12-18}$alkenyl. In embodiments, $R^X$ and $R^{X'}$ is each independently a $C_{17}$fatty acid chain. In embodiments, $R^X$ and $R^{X'}$ are each independently a $C_{17}$alkyl or a $C_{17}$alkenyl. In embodiments, $R^X$ and $R^{X'}$ are a $C_{17}$alkyl. In embodiments, $R^X$ and $R^{X'}$ are a $C_{17}$alkenyl. In embodiments, the $C_{17}$ chains are independently derived from stearic acid or oleic acid. In embodiments, the $C_{17}$ chains are derived from stearic acid. In embodiments, the $C_{17}$ chains are derived from oleic acid. In embodiments, $R^X$ and $R^{X'}$ are both $—(CH_2CH_2)_8—CH_3$.

In embodiments of the compounds of formula (I), (IA), (IB), (II), (II-1), (II-2), (II-A), (IIA-1) or (IIA-2), W is a sterol.

In embodiments of the compounds of formula (I), (IA), (IB), (II), (II-1), (II-2), (II-A), (IIA-1) or (IIA-2), W is cholesterol:

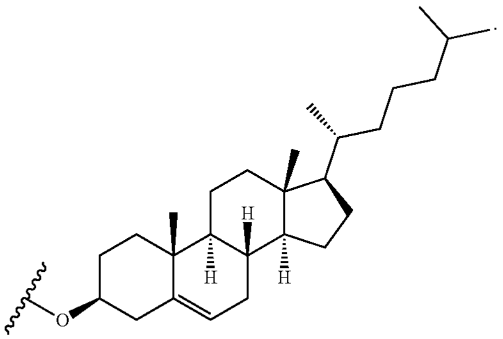

In embodiments of the compound of formula (I), (IA), (IB), (II), (II-1), (II-2), (II-A), (IIA-1) or (IIA-2), W is a phospholipid is selected from the group consisting of: a phosphatidylcholine (PC), a phosphatidylglycerol (PG), a phosphatidylserine (PS), a phosphatidylethanolamine (PE), a phosphatidic acid (PA), and a lysophosphatidylcholine. In embodiments, W is a phosphatidylcholine (PC). In embodiments, W is a phosphatidylglycerol (PG). In embodiments, W is a phosphatidylserine (PS). In embodiments, W is a phosphatidylethanolamine (PE). In embodiments, W is a phosphatidic acid (PA). In embodiments, W is a lysophosphatidylcholine.

In embodiments of the compound of formula (I), (IA), (IB), (II), (II-1), (II-2), (II-A), (IIA-1) or (IIA-2), W is:

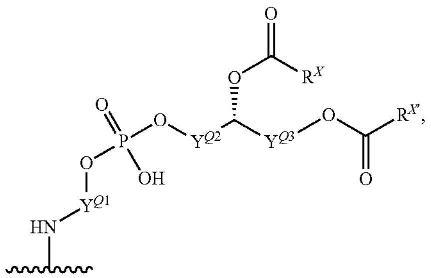

wherein $Y^{Q1}$, $Y^{Q2}$, and $Y^{Q3}$ are each independently alkylene. In embodiments, $Y^{Q1}$ is $C_{2-6}$alkylene, and $Y^{Q2}$, and $Y^{Q3}$ are each independently $—C_{1-3}$alkylene. In embodiments, $R^X$ and $R^{X'}$ are each independently a fatty acid chain having at least 15 carbons, or in particular embodiments $R^X$ and $R^{X'}$ are each independently a fatty acid chain having at least 17 carbons. In embodiments, $R^X$ and $R^{X'}$ are each independently a $C_{8-30}$ fatty acid chain. In embodiments, $R^X$ and $R^{X'}$ are each independently a $C_{8-30}$ alkyl or a $C_{8-30}$ alkenyl. In embodiments, $R^X$ and $R^{X'}$ are each independently a $C_{15-30}$ alkyl or a $C_{15-30}$ alkenyl. In embodiments, $R^X$ and $R^{X'}$ are each independently a $C_{15-20}$ alkyl or a $C_{15-20}$ alkenyl. In embodiments, $R^X$ and $R^{X'}$ are each independently a $C_{17}$alkyl or a $C_{17}$ alkenyl. In embodiments, $R^X$ and $R^{X'}$ are both $—(CH_2CH_2)_8—CH_3$.

In embodiments of the compound of formula (I), (IA), (IB), (II), (II-1), (II-2), (II-A), (IIA-1) or (IIA-2), the W is:

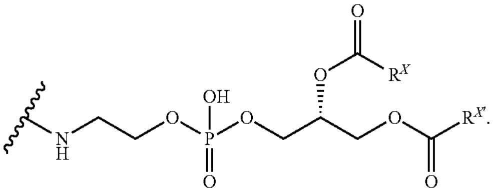

In embodiments of the compound of formula (I), (IA), (IB), (II), (II-1), (II-2), (II-A), (IIA-1) or (IIA-2), the W is:

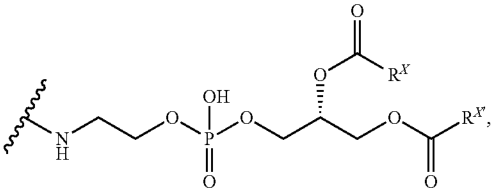

or a pharmaceutically acceptable salt thereof;

wherein $R^X$ and $R^{X'}$ are each independently a $C_{8-30}$ fatty acid chain. In embodiments, the fatty acid is saturated. In embodiments, $R^X$ and $R^{X'}$ are each independently a $C_{8-30}$ alkyl or a $C_{8-30}$ alkenyl. In embodiments, $R^X$ and $R^{X'}$ are each independently a $C_{15-20}$ alkyl or a $C_{15-20}$ alkenyl. In embodiments, $R^X$ and $R^{X'}$ are each independently a $C_{17}$alkyl or a $C_{17}$ alkenyl. In embodiments, $R^X$ and $R^{X'}$ are both —$(CH_2CH_2)_8$—$CH_3$.

In embodiments of the compound of formula (I), (IA), (IB), (II), (II-1), (II-2), (II-A), (IIA-1) or (IIA-2), $R^8$ and $R^9$ are each independently $R^X$ or —C(O)—$R^X$;

In embodiments of the compound of formula (I), (IA), (IB), (II), (II-1), (11-2), (II-A), (IIA-1) or (IIA-2), $R^6$ and $R^{11}$ are each independently —H, or alkyl.

In embodiments, the present disclosure provides a compound selected from the group consisting of:

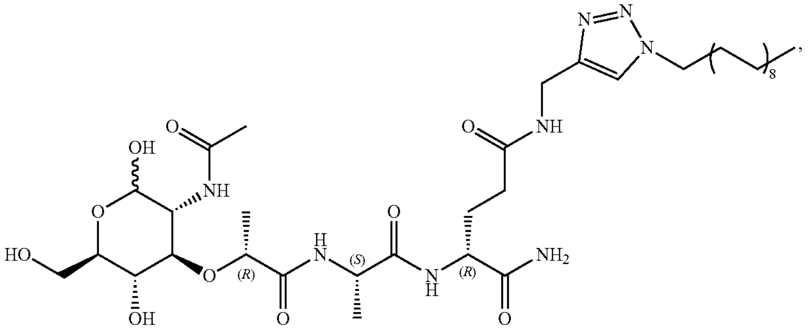

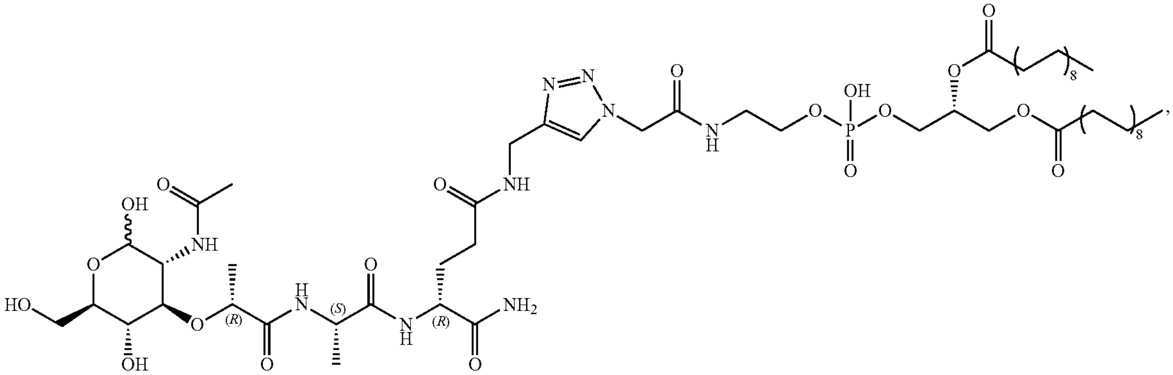

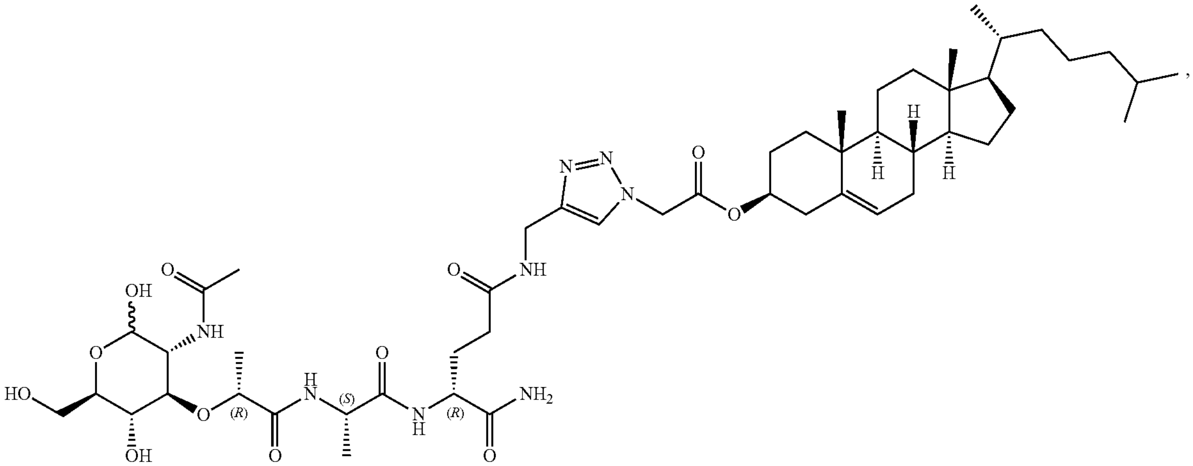

-continued
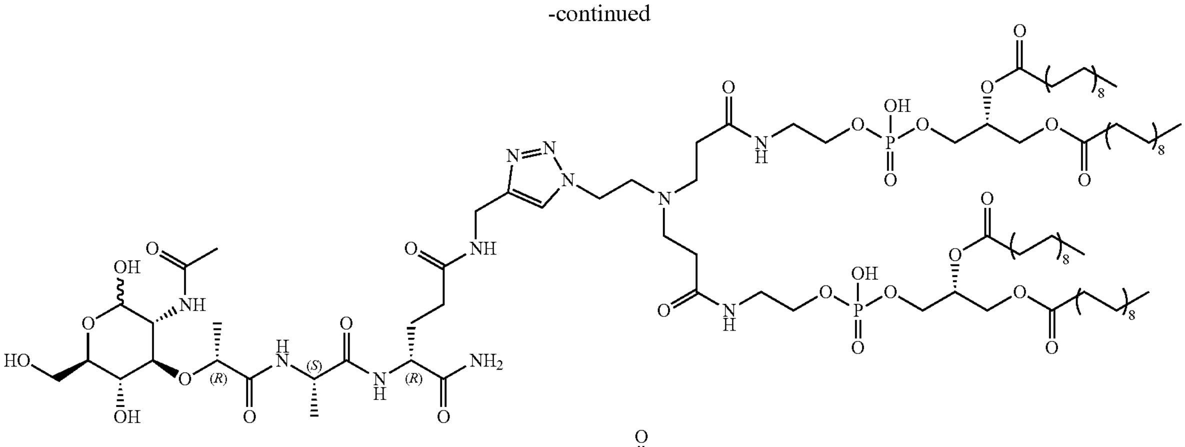
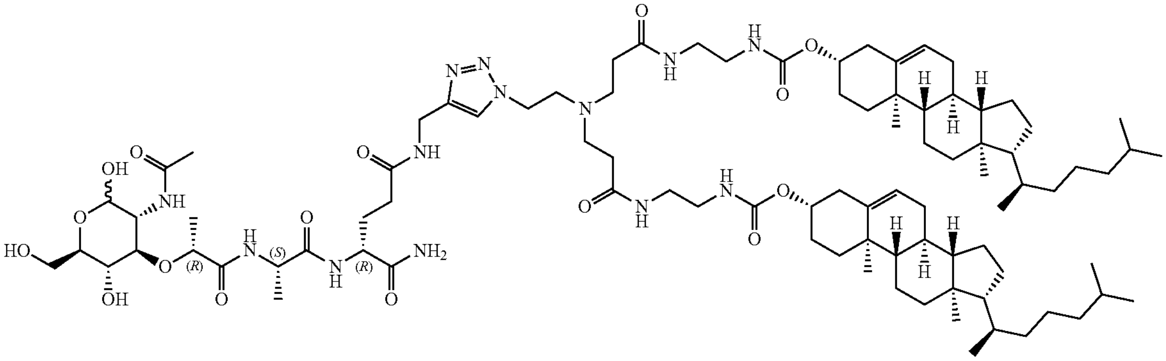
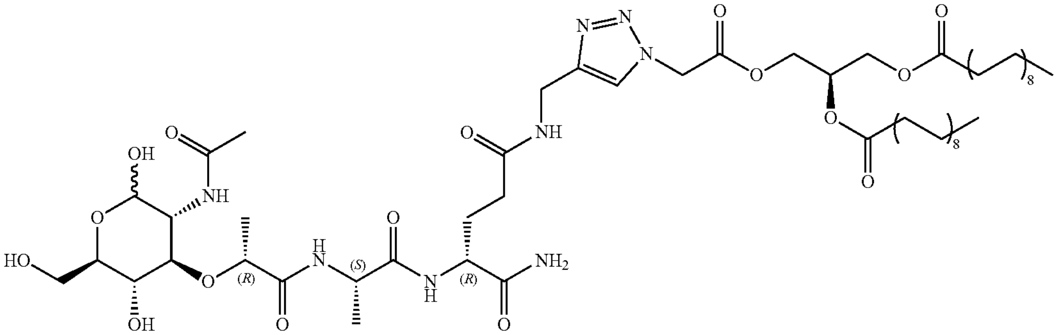
,
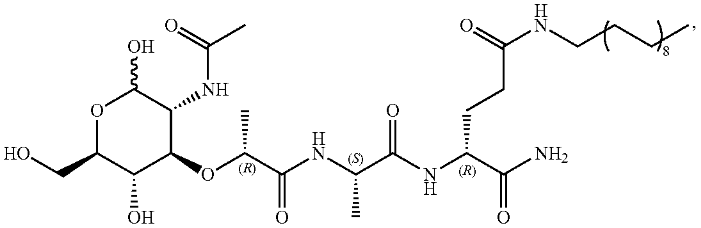
, and
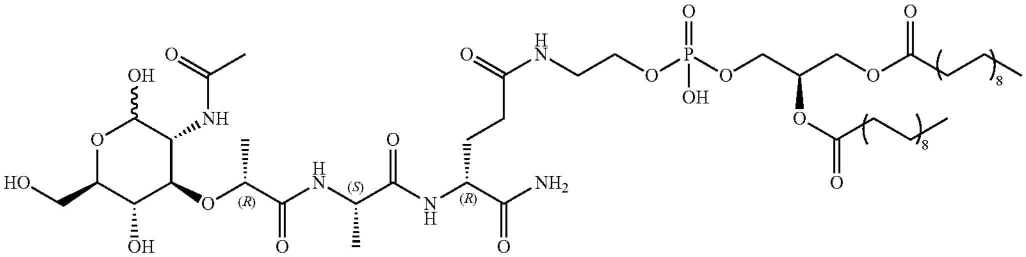
or stereoisomer thereof (e.g., an alpha or beta anomer thereof, or a tautomer thereof).
In embodiments, the present disclosure provides a compound selected from the group consisting of:

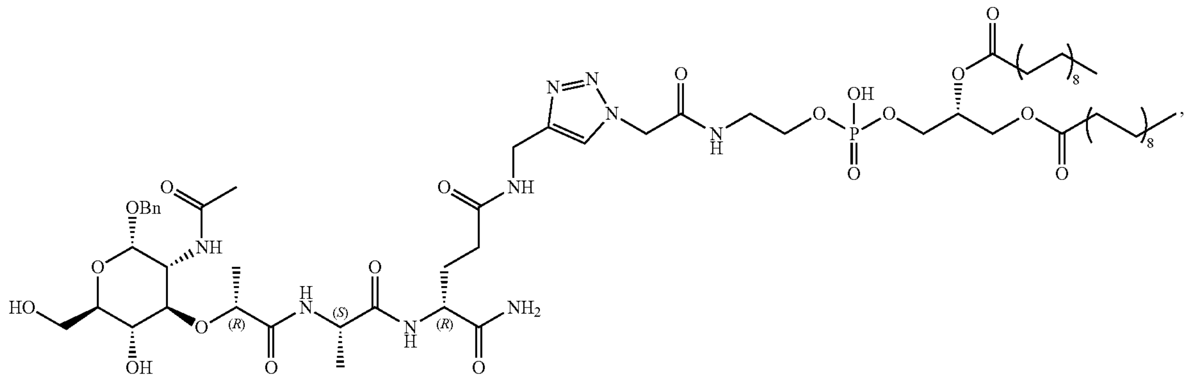
,
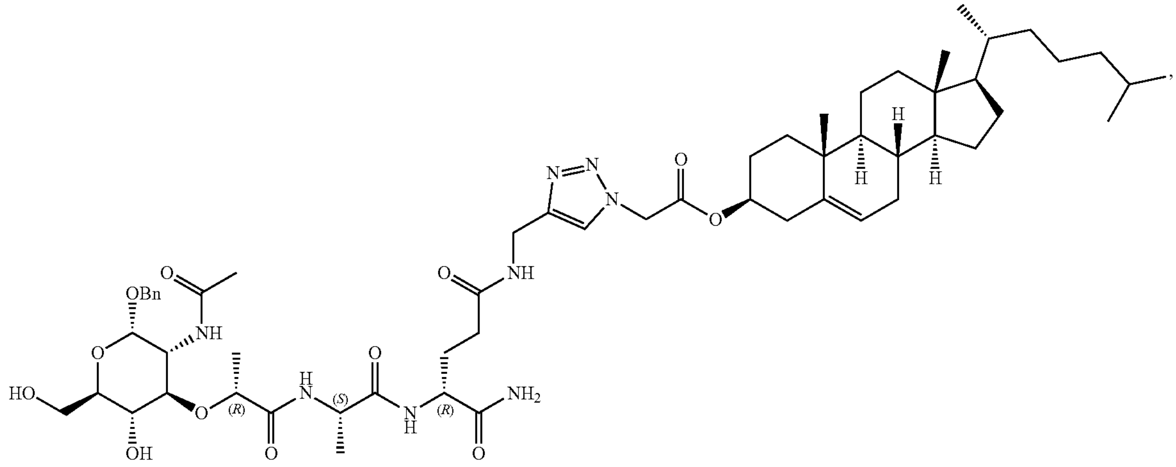
,
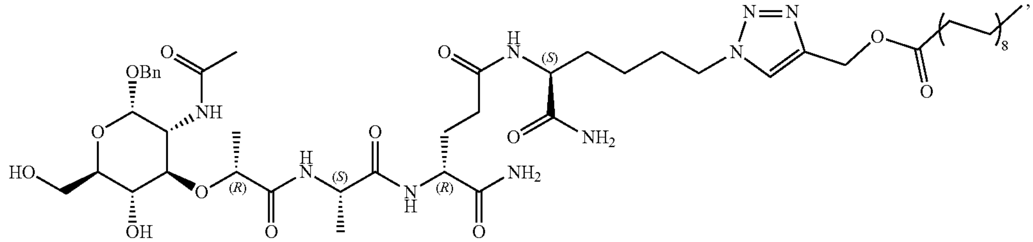
,
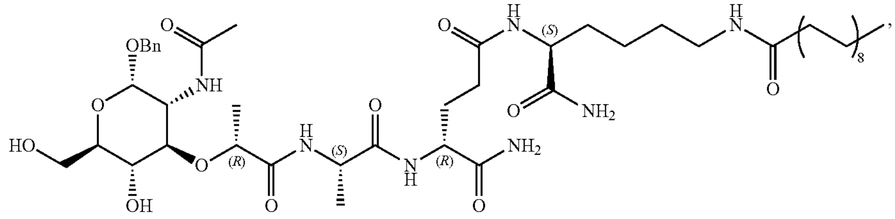
,
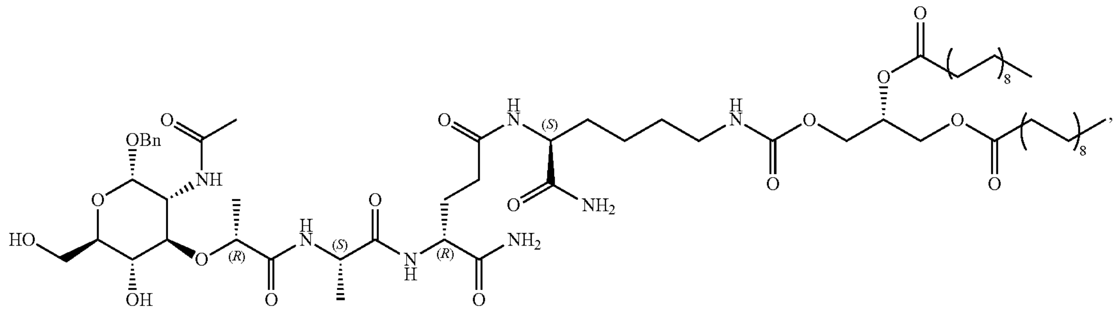
, or a stereoisomer thereof (e.g., an anomer thereof, or mixture of anomers thereof).

In embodiments, the present disclosure provides a compound of formula (I), (IA), (IB), (II), (II-1), (II-2), (IIA), (IIA-1), (IIA-2) or a stereoisomer thereof.

In embodiments, the present disclosure provides a compound of formula (I), (IA), (IB), (II), (II-1), (II-2), (IIA), (IIA-1), (IIA-2) or a diastereomer, or tautomer thereof.

In embodiments, provided herein is one or more compounds selected from Table 1.

In embodiments, provided herein is one or more pharmaceutically acceptable salts of a compound selected from Table 1.

In embodiments, provided herein is one or more compounds of selected from Table 1, or a stereoisomer, or a pharmaceutically acceptable salt thereof.

TABLE 1
| Compounds | | |
|---|---|---|
| No. | | Compound |
| 1 | MDP-C18 [click] | 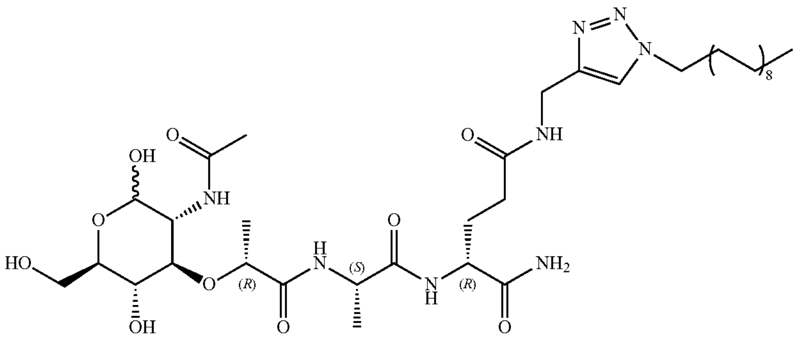 |
| 2 | MDP-DSPE [click] | 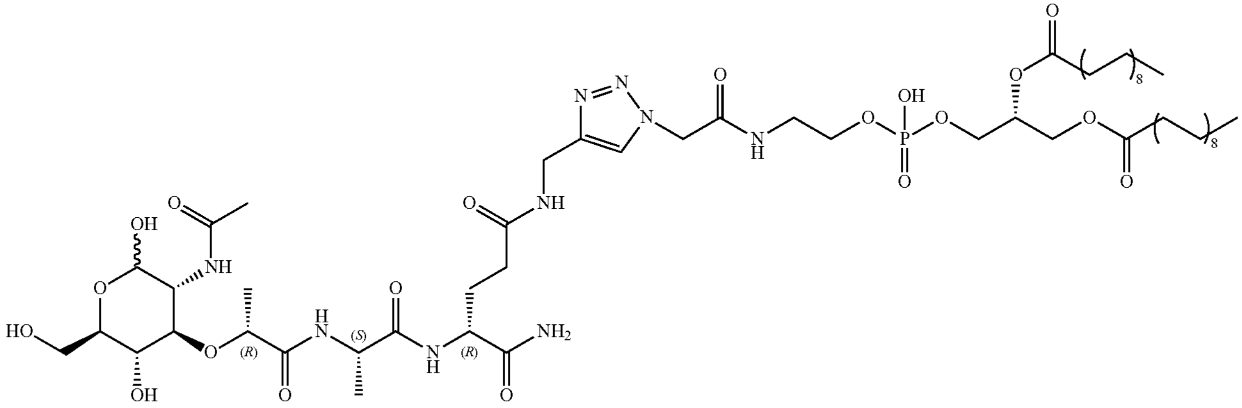 |

TABLE 1-continued
| Compounds | | |
|---|---|---|
| No. | | Compound |
| 3 | MDP-chol [click] | 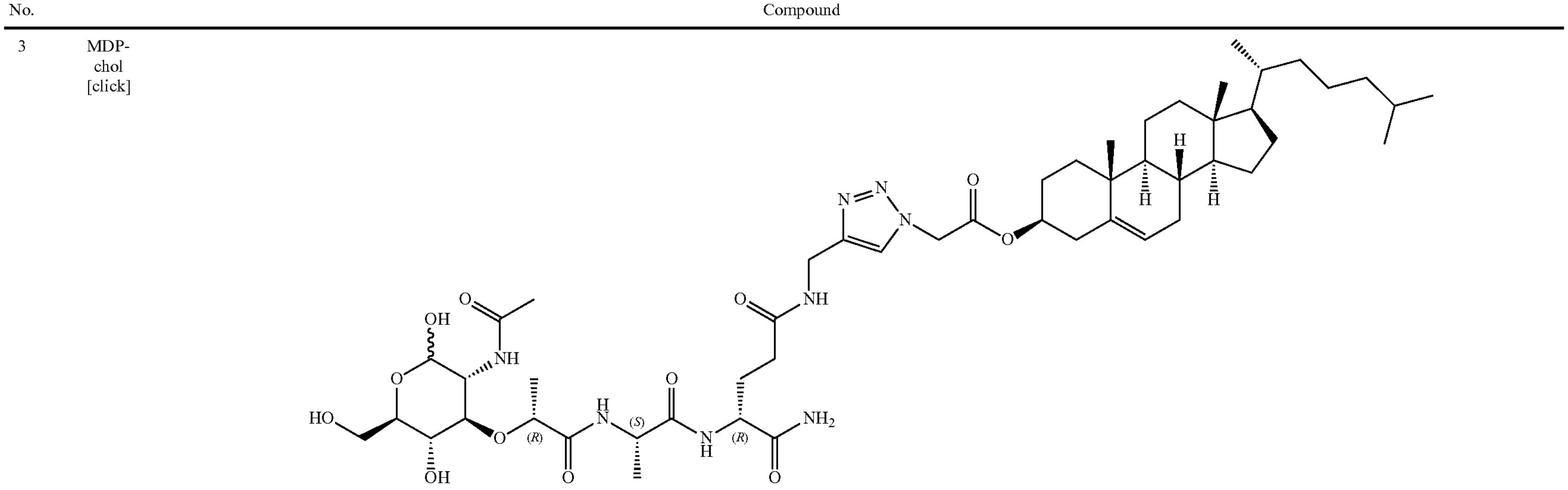 |
| 4 | MDP-DSPE$_2$ [click] | 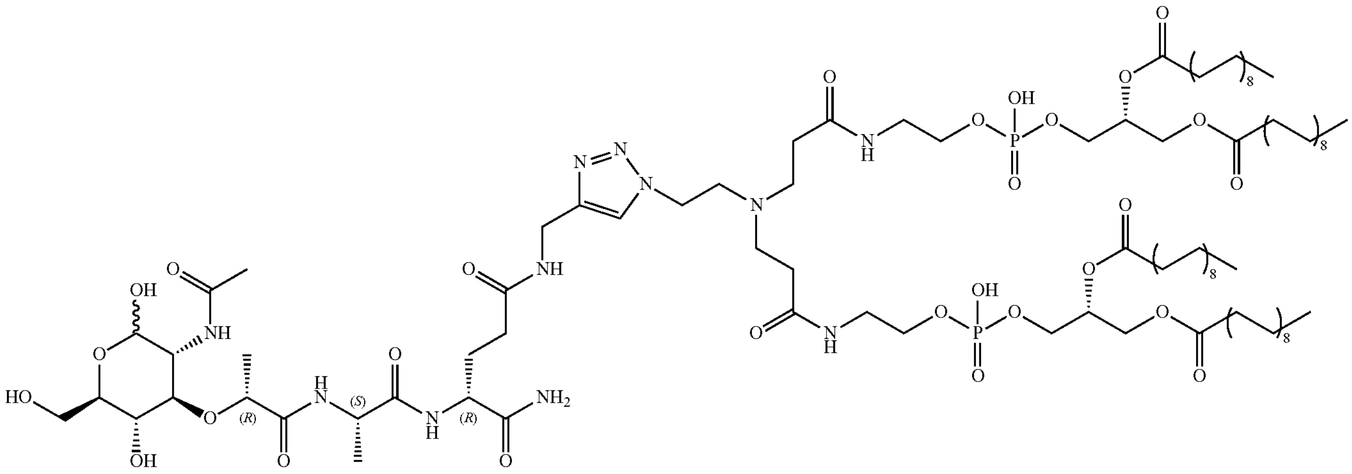 |

TABLE 1-continued
| Compounds | | |
|---|---|---|
| No. | | Compound |
| 5 | MDP-Chol$_2$ [click] | 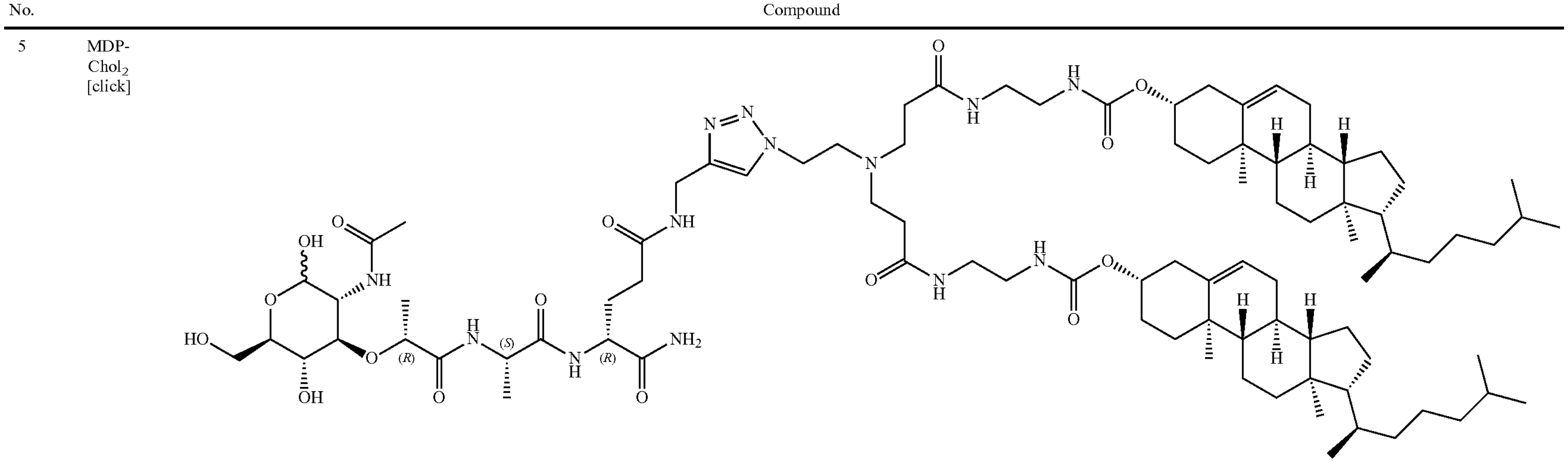 |
| 6 | MDP-DSG [click] | 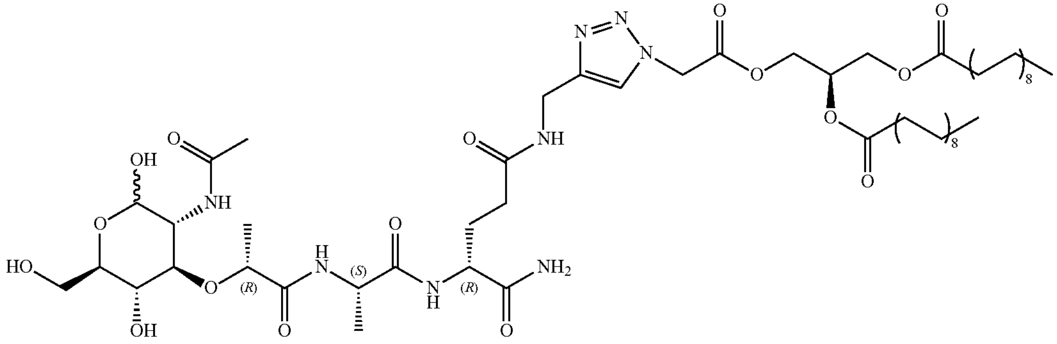 |

TABLE 1-continued
| Compounds | | |
|---|---|---|
| No. | | Compound |
| 7 | MDP (Bn)- DSPE [click] | 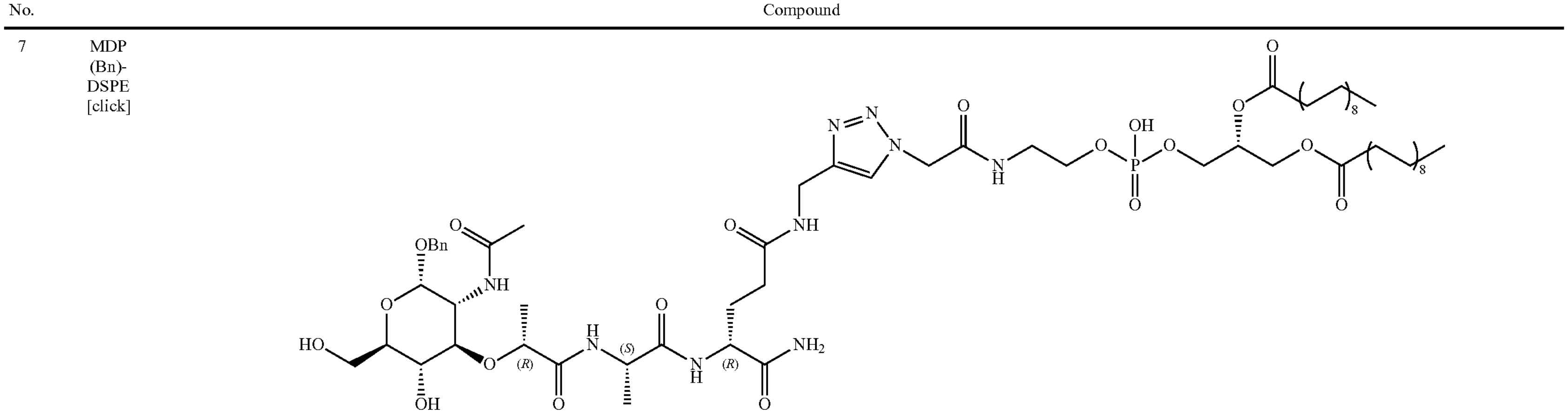 |
| 8 | MDP (Bn)- chol [click] | 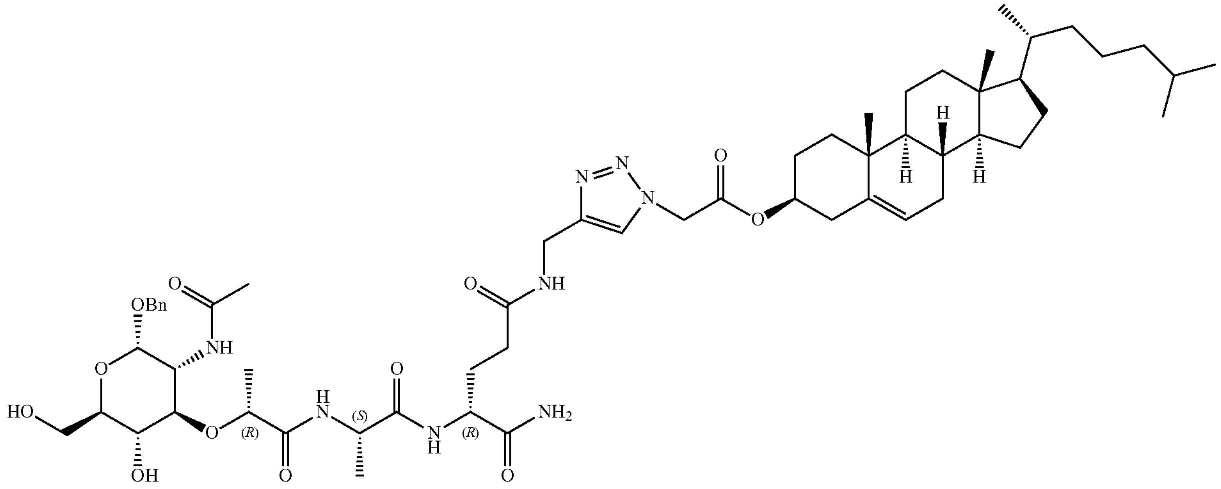 |

TABLE 1-continued
| No. | Compounds | Compound |
| --- | --- | --- |
| 9 | MTP-b-C18 [invclick] | 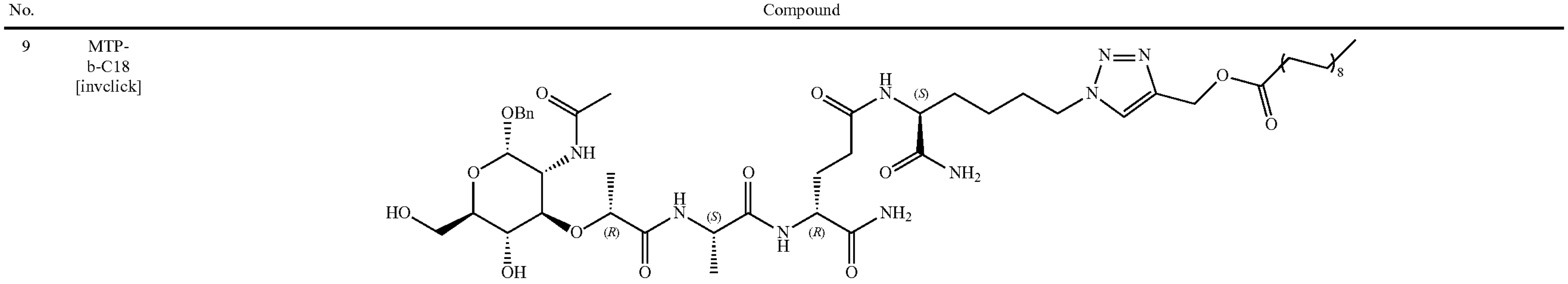 |
| 10 | MTP-b-C18 | 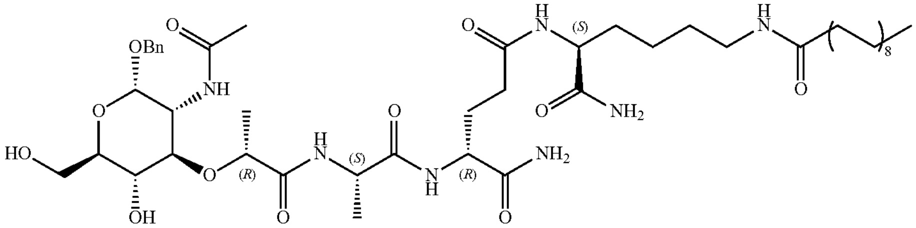 |
| 11 | MDP-C18 | 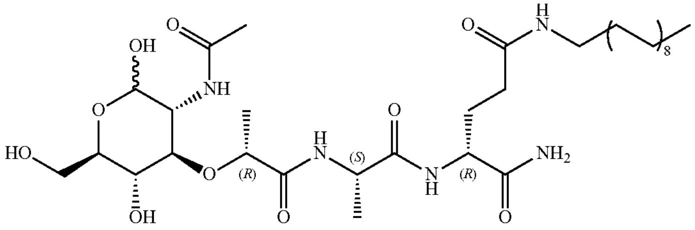 |
| 12 | MDP-DSPE | 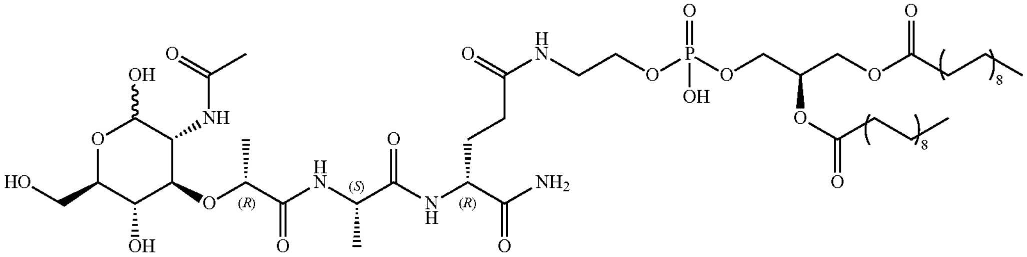 |

TABLE 1-continued
| No. | Compounds Compound | |
|---|---|---|
| 13 | MTP-b-DSG | 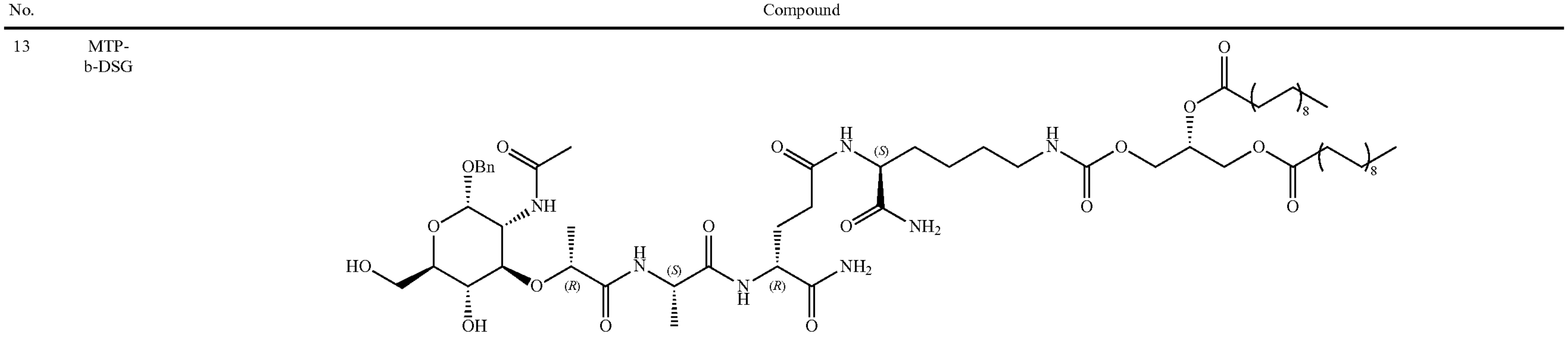 |
| 14 | MTP (Bn)-a-DPPE | 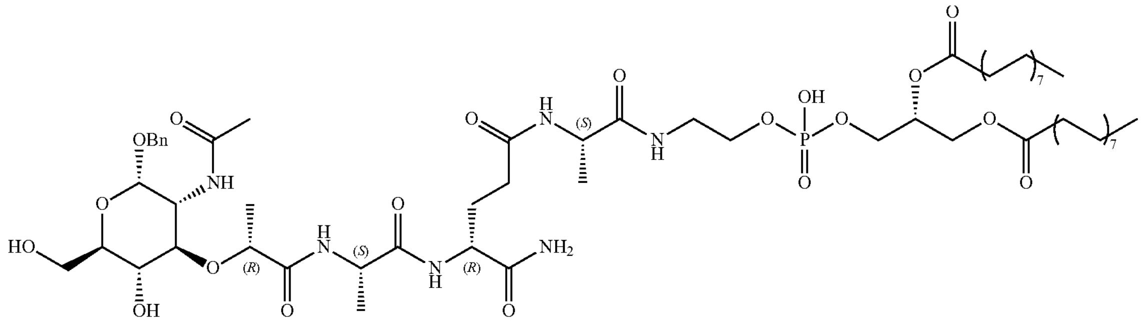 |

TABLE 1-continued
| Compounds | | |
| --- | --- | --- |
| No. | | Compound |
| 15 | MTP-a-chol | 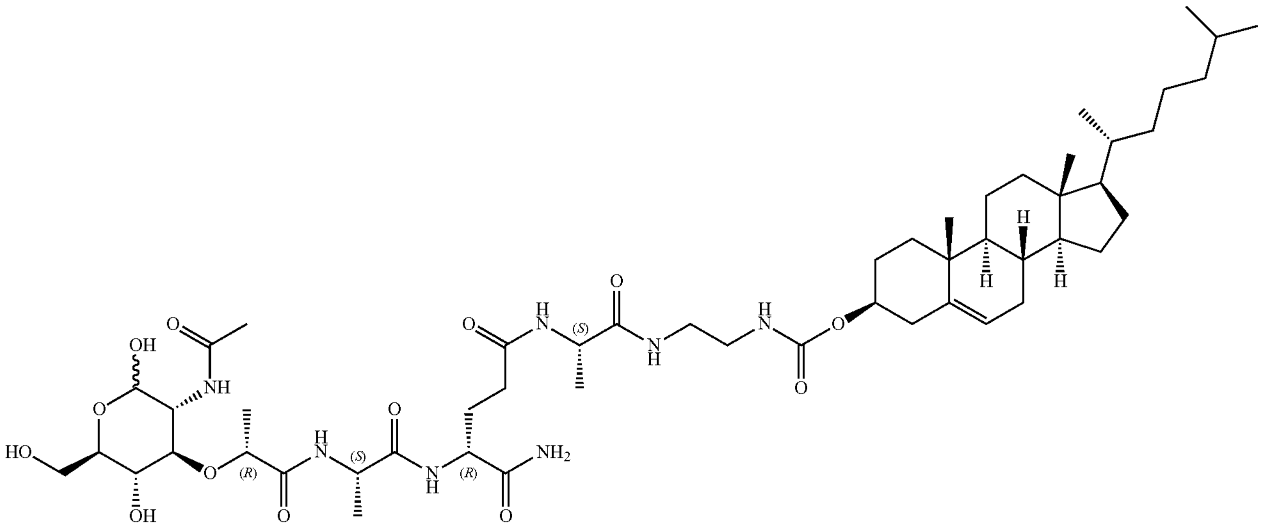 |
| 16 | MDP (Bn)-chol | 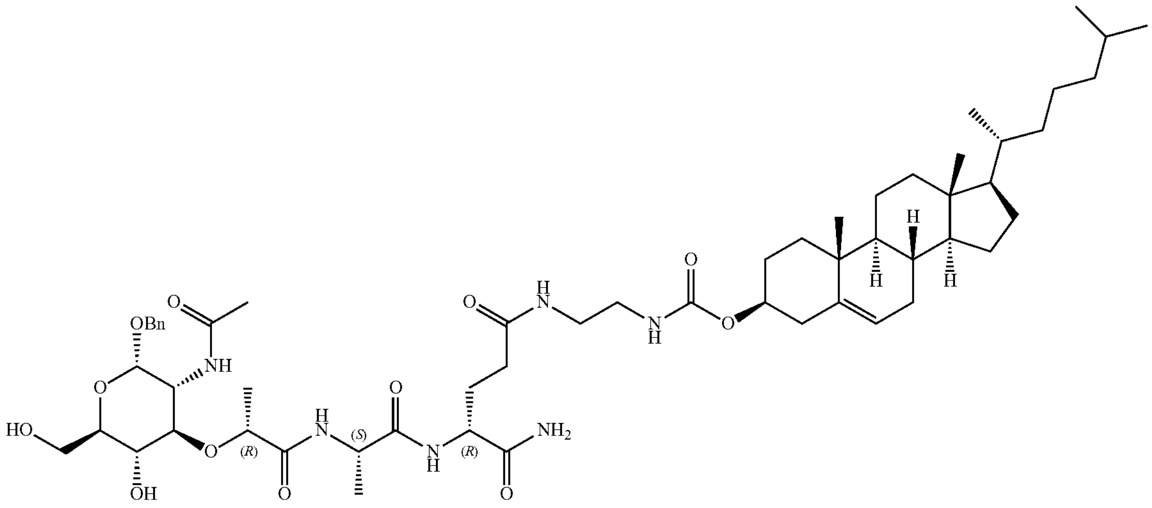 |

TABLE 1-continued
| Compounds | | |
|---|---|---|
| No. | | Compound |
| 17 | MTP-a-DSPE | 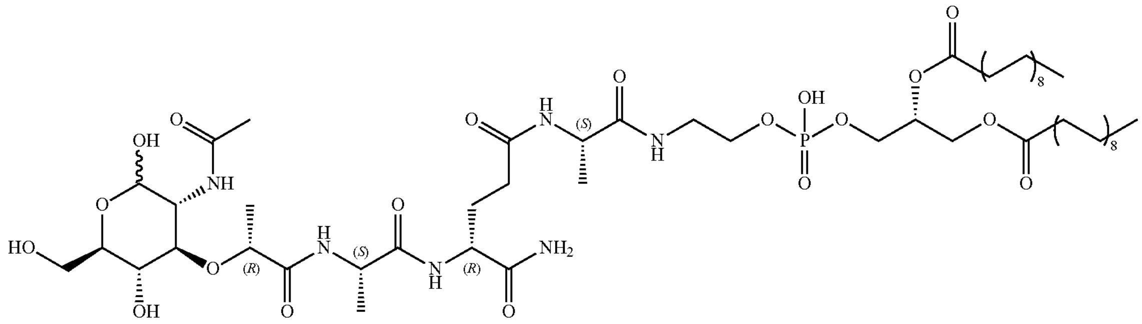 |
| 18 | MTP (Bn)-a-DSPE | 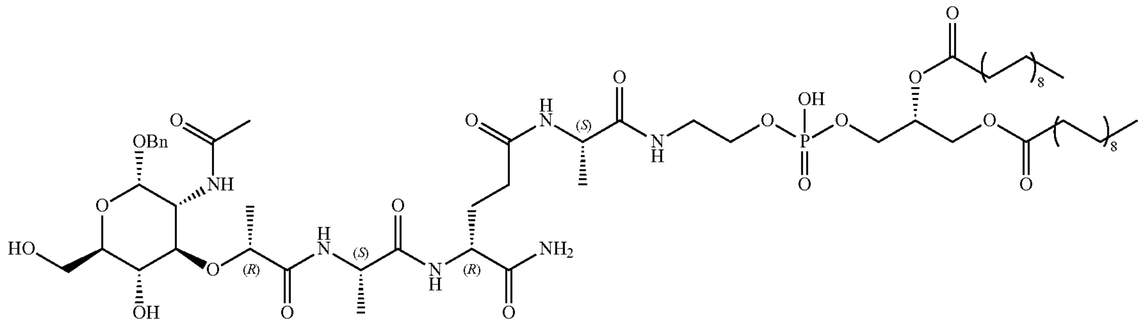 |
| 19 | MDP (Bn)-DSPE | 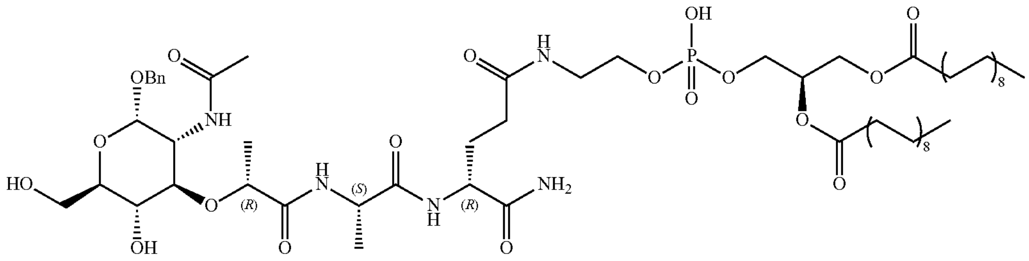 |

Muramyl tripeptide phosphatidylethanolamine; N—(N-Acetylmuramoyl)-L-alanyl-D-alpha-glutaminyl-N-[(7R)-4-hydroxy-4-oxido-10-oxo-7-[(1-oxohexadecyl)oxy]-3,5,9-trioxa-4-phosphapentacos-1-yl]-L-alaninamide (MTP-a-DPPE or Mifamurtide): Molecular weight: 1238 Dalton. CLogP=10.59 (uncharged) and 4.80 (negatively charged). Mifamurtide (CAS-number [83461-56-7]) was prepared as according to literature procedures (e.g. Brundish, D. E.; Wade, R. (1985) J Label Compd Radiopharm. 22 (1): 29-35. doi:10.1002/jlcr.2580220105). The lipophilicity of this molecule is relatively low at CLogP 4.80 in physiological circumstances.

N-Acetylmuramyl-L-Alanyl-D-Isoglutamine-6-O-Stearoyl (MDP-C18[mur]) Molecular weight: 759 Dalton. CLogP=5.39 (uncharged) and 1.39 (negatively charged). MDP-C18[mur](CAS-number [60398-08-5]) was prepared as according to literature procedures (e.g. Matsumoto K. et al. (1981) Infect Immun. 32(2):748-58). The lipophilicity of this molecule is low at CLogP 1.39 in physiological circumstances is unlikely to be sufficient to ensure its robust incorporation into HDL-derived nanoparticles.

Romurtide (CAS-number [78113-36-7]) Molecular weight: 887 Dalton. CLogP=3.90 (uncharged) and 0.61 (negatively charged) has a lipophilicity (CLogP 0.61 in physiological circumstances). The lipophilicity of this compound is low with a CLogP of the charged molecule that is close to 0.

Murabutide (CAS-number [74817-61-1]) Molecular weight: 549 Dalton. CLogP=−1.53 (uncharged) has a CLogP value that is negative. This molecule is hydrophilic given its CLogP value that is below 0.

In embodiments, compounds of the present disclosure (such as one or more compounds of formula (I), (IA), (IB), (II), (II-1), (II-2), (IIA), (IIA-1), (IIA-2) or Table 1) activate nucleotide-binding oligomerization domain-containing protein 2 (NOD2).

Anomers and Open/Closed Ring Structures

In embodiments, the molecules of the present disclosure bear an —OH substituent at the anomeric hemi-acetal carbon of the muramyl sugar group, i.e. when $R_2$=H, it is understood that both anomeric isomers alpha and beta are included in the compounds of the present disclosure.

Furthermore, in these cases where $R_2$=H, it is known in the art that such molecules (in aqueous environments) actually exist in both the closed ring isomer as well as the open ring structure. Again, it is understood that both the open and closed ring isomers are included in the compounds of the present disclosure.

Below, in non-limiting examples, the top structures show the alpha and beta anomers, and the bottom structures show the general anomeric ring-closed structure (left) and the open ring structure (right).

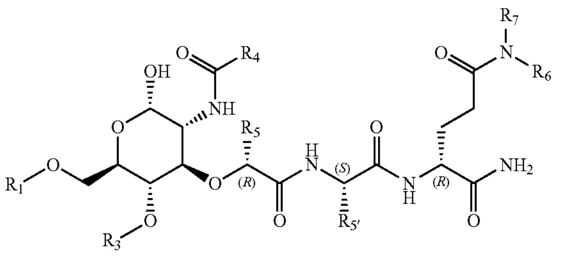

-continued

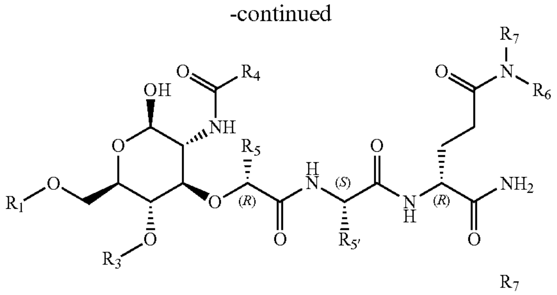

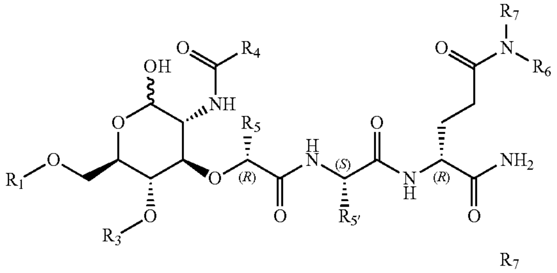

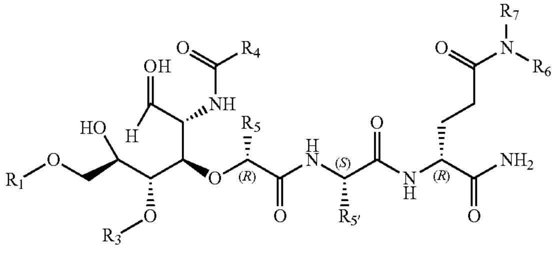

Molecular Weight

The compounds of the invention preferably have a molecular weight higher than 500 Dalton, higher than 700 Dalton, higher than 950 Dalton, or higher than 1,200 Dalton.

The compounds of the invention preferably have a molecular weight lower than 10,000 Dalton, lower than 5,000 Dalton, lower than 2,500 Dalton, or lower than 1,750 Dalton.

Hydrophobicity

The compounds of the disclosure are, in particular embodiments, hydrophobic in nature. Hydrophobiicty can be estimated by calculation of the CLogP value. This can be done in software programs such as for example Perkin Elmer's ChemDraw or ChemDraw Professional (v18). The higher the CLogP value of a compound, the more hydrophobic a compound is.

In embodiments, the compounds of the present disclosure have a CLogP value higher than about 1, higher than about 3, higher than about 5, higher than about 7, higher than about 9, or higher than about 11.

The CLogP value represents the n-octanol/water partition coefficient (Log Po/w) of a molecule, and is a calculated value as opposed to Log P values, i.e. values assessed by experimentation. Accordingly, CLogP values may deviate from Log P values. Importantly, however, CLogP values give a good comparison between the lipophilicities of molecules. CLogP values can be assessed for molecules in either their uncharged or their charged state. This is the case for molecules that have ionogenic groups, such as molecules with carboxylic acid (—COOH) or phosphate (—OP(O)OH—O—) groups. At physiological pH (about 7.4) these particular groups are deprotonated and thus become charged. Also alkyl(ated) amine groups become charged at physiological pH, in this case by protonation.

At physiological pH, the molecules of the invention have CLogP values that are lower than 20, or lower than 15, or lower than 10. Moreover, at physiological pH, the molecules of the invention have CLogP values that are higher than 3, or higher than 4, or higher than 5, or higher than 5.5.

Nanobiologic Compositions

Provided herein are nanobiologic compositions comprising a nanoparticle carrier and one or more compounds of the present disclosure (such as a compound of formula (I), (IA), (IB), (II), (II-1), (II-2), (IIA), (IIA-1), or (IIA-2) as disclosed herein or Table 1).

In embodiments, the compounds of the present disclosure can be formulated in a nanoparticle carrier, which can include, but is not limited to polyplexes, colloidal dispersion systems, such as macromolecule complexes, nanocapsules, microspheres, beads, and lipid-based systems including oil-in-water emulsions, micelles, mixed micelles, liposomes, lipoplexes, lipid nanoparticles, lipid nanocapsules, lipidoids, rapidly eliminated lipid nanoparticles (reLNPs), micro- and nano-emulsions, and the like, HDL-derived nanoparticles, polymeric nanoparticles, including poly (lactic-co-glycolic acid) (PLGA) nanoparticles such as PLGA microspheres, poly(lactide) (PLA) nanoparticles, poly(ε-caprolactone) (PCL) nanoparticles, poly(butyl cyanoacrylate) (PBCA) nanoparticles, demdrimers, hyperbranched polyglycerol (HPG) nanoparticles, PEG-polyaspartate micellar nanoparticles, cationic polymers including for example poly(L-lysine), polyethylenimine (PEI), DEAE-dextran, poly (amino esters) (PBAE) and chitosan, cyclodextrin nanoparticles, metallic nanopartides, surfactant based emulsions, virus like particles (e.g., particles that are primarily made up of viral structural proteins but that are not infectious or have low infectivity), peptide or protein-based particles such as albumin nanopartides, nanowires, gold nanoparticles, magnetic nanoparticles, core-shell nanoparticles, carbon nanotubes, nanocrystals, hyaluronidase, and combinations thereof.

In embodiments, the compounds of the present disclosure may be formulated in a nanoparticle carrier, such as those described in U.S. Pat. Nos. 5,567,434, 5,552,157, 5,565,213, 5,738,868, 5,795,587, 10,485,884, US2018/0263907, US2016/0317647, US2019/0290593, US2020/0253884, US2020/0376146, and WO2018/071549 the contents of each of which are incorporated herein by reference.

In embodiments, the nanoparticle carrier is a high-density lipoprotein (HDL)-derived nanoparticle. The high-density lipoprotein (HDL)-derived nanoparticles are envisioned as delivery vehicles that may, for example, improve the therapeutic index of small-molecule immunomodulatory compounds and/or confer innate immune cell-specific delivery. By conferring targeting specificity for innate immune cells (such as myeloid cells, myeloid progenitor cells, and hematopoietic stem cells in the bone marrow, blood and/or spleen), the therapeutic agents encapsulated or incorporated in the HDL-derived nanoparticles may be deposited in a concentrated and localized fashion. In embodiments, the high-density lipoprotein (HDL)-derived nanoparticle comprises apoA-I or a peptide mimetic of apoA-I. In embodiments, the high-density lipoprotein (HDL)-derived nanoparticle comprises apoA-I.

Human apoA-I can be isolated or prepared by any method known in the art. In embodiments, human apoA-I is isolated from human HDL. Another known method comprises the synthesis of apoA-I by recombinant protein expression, for example, in *E. coli* organisms. When expressed in bacteria the apoA-I may include an N-terminal methionine or a formyl-methionine. The presence of the methionine group can be assessed by mass spectroscopic (MS) methods that are known in the art. The position of the methionine in the protein sequence can be assessed after digestion of apoA-I with subsequent analysis of the peptide mixture with MS, as is also known in the art.

In embodiments, purifications of apoA-I, including any of its variations, may comprise any method known in the art (e.g. use of hydrophobic interaction chromatography, ion exchange columns, precipitations, etc.). Production methods may or may not comprise the use of affinity tags that enable the purification of the proteins; such tags require removal after purification to restore the human apoA-I identity.

In embodiments, the high-density lipoprotein (HDL)-derived nanoparticle comprises ApoA-1 Milano.

Suitable apoA-I mimetic polypeptides may have the sequence shown in Table 2 (SEQ ID NOS: 256 to 263, and 342 to 346) or in SEQ ID NOS: 1 to 341.

TABLE 2

ApoA-I mimetics

| SEQ ID NO | Amino Acid Sequence |
|---|---|
| 256 | DWLKAFYDKVAEKLKEAF (18A) |
| 257 | Ac-DWLKAFYDKVAEKLKEAF-$NH_2$ (2F) |
| 260 | Ac-DWFKAFYDKVAEKFKEAF-$NH_2$ (4F) |
| 258 | Ac-DWFKAFYDKVAEKLKEAF-$NH_2$ ($3^{F3}$) |
| 259 | Ac-DWLKAFYDKVAEKFKEAF-$NH_2$ ($3F^{14}$) |
| 261 | Ac-DWLKAFYDKVFEKFKEFF-$NH_2$ (5F) |
| 262 | Ac-DWLKAFYDKFFEKFKEFF-$NH_2$ (6F) |
| 263 | Ac-DWFKAFYDKFFEKFKEFF-$NH_2$ (7F) |
| 342 | Ac-FWLKAFYDKVAEKLKEAF-$NH_2$ (3F-1) |
| 343 | AC-DFLKAFYDKVAEKLKEAF-$NH_2$ (3F-2) |
| 344 | Ac-DWFRAFYDKVAEKFREAF-$NH_2$ $(4F\text{-}R)^{q}$ |
| 345 | Ac-DWFKAFYDRVAERFKEAF-$NH_2$ $(4F\text{-}R')^{q}$ |
| 346 | Ac-DWLXAFYDXVAEXLXEAF-$NH_2$ (2F') |

In embodiments, the apoA-I mimetic is DWLKAFYDK-VAEKLKEAF (SEQ ID NO. 256). In embodiments, the apoA-I mimetic is Ac-DWLKAFYDKVAEKLKEAF-$NH_2$ (SEQ ID NO. 257). In embodiments, the apoA-I mimetic is Ac-DWFKAFYDKVAEKFKEAF-$NH_2$ (SEQ ID NO. 260).

In embodiments, apoA-I mimetics are optionally acetylated on the N-terminus, or optionally amidated on the C-terminus. In embodiments, the apoA-I mimetics are acetylated on the N-terminus. In embodiments, the apoA-I mimetics are amidated on the C-terminus. In embodiments, the apoA-I mimetics are acetylated on the N-terminus and amidated on the C-terminus. In embodiments, the HDL-derived nanoparticles of the present disclosure comprise one or more phospholipids. All phospholipids ranging in chain length from $C_4$ to $C_{30}$, saturated or unsaturated, cis or trans, unsubstituted or substituted with 1-6 side chains, and with or without the addition of lysolipids are contemplated for use in the nanoparticles described herein. Additionally, other synthetic variants and variants with other phospholipid headgroups are also contemplated.

In embodiments, the HDL-derived nanoparticle comprises a phospholipid. In embodiments, the HDL-derived nanoparticle comprises a phospholipid and a lysolipid.

Non-limiting examples of the phospholipids that may be used in the present composition include phosphatidylcholines (PC), phosphatidylglycerols (PG), phosphatidylserines (PS), phosphatidylethanolamines (PE). In embodiments phosphatidic acid/esters (PA(may be used.

In embodiments, the phospholipid or lysolipid is one or more of the following: DDPC CAS-3436-44-0 1,2-Didecanoyl-sn-glycero-3-phosphocholine, DEPA-NA CAS-80724-31-8 1,2-Dierucoy 1-sn-glycero-3-phosphate (Sodium Salt), DEPC CAS-56649-39-9. 1,2-Dierucoyl-sn-glycero-3-phosphocholine, DEPE CAS-988-07-2 1,2-Dierucoyl-sn-glycero-3-phosphoethanolamine, DEPG-NA 1,2-Dierucoyl-sn-glycero-3-phospho-rac-(l-glycerol) (Sodium Salt), DLOPC CAS-998-06-1 1,2-Dilinoleoyl-sn-glycero-3-phosphocholine, DLPA-NA 1,2-Dilauroyl-sn-glycero-3-phosphate (Sodium Salt), DLPC CAS-18194-25-7 1,2-Dilauroyl-sn-glycero-3-phosphocholine, DLPE 1,2-Dilauroyl-sn-glycero-3-phosphoethanolamine, DLPG-NA 1,2-Dilauroyl-sn-glycero-3-phospho-rac-(l-glycerol) (Sodium Salt), DLPG-NH4 1,2-Dilauroyl-sn-glycero-3-phospho-rac-(l-glycerol) (Ammonium Salt), DLPS-NA 1,2-Dilauroyl-sn-glycero-3-phosphoserine (Sodium Salt), DMPA-NA CAS-80724-3 1,2-Dimyristoyl-sn-glycero-3-phosphate (Sodium Salt), DMPC CAS-18194-24-6 1,2-Dimyristoyl-sn-glycero-3-phosphocholine, DMPE CAS-988-07-2 1,2-Dimyristoyl-sn-glycero-3-phosphoethanolamine, DMPG-NA CAS-67232-80-8 1,2-Dimyristoyl-sn-glycero-3-phospho-rac-(l-glycerol) (Sodium Salt), DMPG-NH4 1,2-Dimyristoyl-sn-glycero-3-phospho-rac-(l-glycerol) (Ammonium Salt), DMPG-NH4/NA 1,2-Dimyristoyl-sn-glycero-3-phospho-rac-(lglycerol) (Sodium/Ammonium Salt), DMPS-NA 1,2-Dimyristoyl-sn-glycero-3-phosphoserine (Sodium Salt), DOPA-NA 1,2-Dioleoyl-sn-glycero-3-phosphate (Sodium Salt), DOPC CAS-4235-95-4 1,2-Dioleoyl-sn-glycero-3-phosphocholine, DOPE CAS-4004-5-1 1,2-Dioleoyl-sn-glycero-3-phosphoethanolamine, DOPG-NA CAS-62700-69-0 1,2-Dioleoyl-sn-glycero-3-phospho-rac-(l-glycerol)(Sodium Salt), DOPS-NA CAS-70614-14-1 1,2-Dioleoyl-sn-glycero-3-phosphoserine (Sodium Salt), DPPA-NA CAS-71065-87-7 1,2-Dipalmitoyl-sn-glycero-3-phosphate (Sodium Salt), DPPC CAS-63-89-8 1,2-Dipalmitoyl-sn-glycero-3-phosphocholine, DPPE CAS-923-61-5 1,2-Dipalmitoyl-sn-glycero-3-phosphoethanolamine, DPPG-NA CAS-67232-81-9 1,2-Dipalmitoyl-sn-glycero-3-phospho-rac-(l-glycerol) (Sodium Salt), DPPG-NH4 CAS-73548-70-6 1,2-Dipalmitoylsn-glycero-3-phospho-rac-(l-glycerol) (Ammonium Salt), DPPS-NA 1,2-Dipalmitoyl-sn-glycero-3-phosphoserine (Sodium Salt), DSPA-NA CAS-108321-18-2 1,2-Distearoyl-snglycero-3-phosphate (Sodium Salt), DSPC CAS-816-94-4 1,2-Distearoyl-sn-glycero-3-phosphocholine, DSPE CAS-1069-79-0 1,2-Distearoyl-sn-glycero-3-phosphoethanolamine, DSPG-NA CAS-67232-82-0 1,2-Distearoyl-sn-glycero-3-phospho-rac-(l-glycerol) (Sodium Salt), DSPG-NH4 CAS-108347-80-4 1,2-Distearoyl-sn-glycero-3-phospho-rac-(1-glycerol) (Ammonium Salt), DSPS-NA 1,2-Distearoyl-sn-glycero-3-phosphoserine (Sodium Salt), EPC Egg-PC, HEPC Hydrogenated Egg PC, HSPC Hydrogenated Soy PC, LYSOPC MYRISTIC CAS-18194-24-6 1-Myristoyl-sn-glycero-3-phosphocholine, LYSOPC PALMITIC CAS-17364-16-8 1-Palmitoyl-sn-glycero-3-phosphocholine, LYSOPC STEARIC CAS-19420-57-6 1-Stearoyl-sn-glycero-3-phosphocholine, Milk Sphingomyelin, MPPC 1-Myristoyl-2-palmitoyl-sn-glycero 3-phosphocholine, MSPC 1-Myristoyl-2-stearoyl-sn-glycero-3-phosphocholine, PMPC 1-Palmitoyl-2-myristoyl-sn-glycero-3-phosphocholine, POPC CAS-26853-31-6 1-Palmitoyl-2-oleoyl-sn-glycero-3-phosphocholine, POPE 1-Palmitoyl-2-oleoyl-sn-glycero-3-phosphoethanolamine, POPG-NA CAS-81490-05-31-Palmitoyl-2-oleoyl-sn-glycero-3[Phospho-rac-(l-glycerol)] (Sodium Salt), PSPC 1-Palmitoyl-2-stearoyl-sn-glycero-3-phosphocholine, SMPC 1-Stearoyl-2-myristoyl-snglycero-3-phosphocholine, SOPC 1-Stearoyl-2-oleoyl-sn-glycero-3-phosphocholine, SPPC1-S tearoy 1-2-palmitoy 1-sn-glycero-3-phosphocholine. In some preferred embodiments, specific non-limiting examples of phospholipids include: dimyristoylphosphatidylcholine (DMPC), soy lecithin, dipalmitoylphosphatidylcholine (DPPC), distearoylphosphatidylcholine (DSPC), dilaurylolyphosphatidylcholine (DLPC), dioleoylphosphatidylcholine (DOPC), dilaurylolylphosphatidylglycerol (DLPG), dimyristoylphosphatidylglycerol (DMPG), dipalmitoylphosphatidylglycerol (DPPG), distearoylphosphatidylglycerol (DSPG), dioleoylphosphatidylglycerol (DOPG), dimyristoyl phosphatidic acid (DMPA), dimyristoyl phosphatidic acid (DMPA), dipalmitoyl phosphatidic acid (DPPA), dipalmitoyl phosphatidic acid (DPPA), dimyristoyl phosphatidylethanolamine (DMPE), dipalmitoyl phosphatidylethanolamine (DPPE), dimyristoyl phosphatidylserine (DMPS), dipalmitoyl phosphatidylserine (DPPS), dipalmitoyl sphingomyelin (DPSP), distearoyl sphingomyelin (DSSP), and mixtures thereof.

In embodiments, the phospholipid is 1,2-dimyristoyl-sn-glycero-3-phosphatidylcholine (DMPC), and the lysolipid is 1-myristoyl-2-hydroxy-sn-glycero-phosphocholine (MHPC).

In embodiments, the phospholipid is 1-palmitoyl-2-oleoyl-sn-glycero-3-phosphocholine (POPC), and the lysolipid is1-palmitoyl-2-hydroxy-sn-glycero-3-phosphocholine (PHPC).

In embodiments, when the present composition comprises (or consists essentially of, or consists of) two or more types of lipids (such as a phospholipid, or a lysolipid), the weight ratio of two types of phospholipids ranges from about 1:10 to about 10:1, including about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, to about 10:1, including all values and ranges therebetween.

In embodiments, the HDL-derived nanoparticles comprise DMPC, and MHPC, and the weight ratio of DMPC to MHPC may range from about 1:10 to about 10:1, from about 2:1 to about 4:1, from about 1:1 to about 5:1, from about 2:1 to about 5:1, from about 6:1 to about 10:1, from about 7:1 to about 10:1, from about 8:1 to about 10:1, from about 7:1 to about 9:1, or from about 8:1 to about 9:1. The weight ratio of DMPC to MHPC may be about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1, including all values and ranges therebetween.

In embodiments, the HDL-derived nanoparticles comprise POPC and PHPC, and the weight ratio of POPC to PHPC may range from about 1:10 to about 10:1, from about 2:1 to about 4:1, from about 1:1 to about 5:1, from about 2:1 to about 5:1, from about 6:1 to about 10:1, from about 7:1 to about 10:1, from about 8:1 to about 10:1, from about 7:1 to about 9:1, or from about 8:1 to about 9:1. The weight ratio of POPC to PHPC may be about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, or about 10:1.

In embodiments, the phospholipids in nanoparticles of the present disclosure comprise (or consists essentially of, or consists of) a mixture of a two-chain diacyl-phospholipid and a single chain acyl-phospholipid/lysolipid.

In embodiments, the high-density lipoprotein (HDL)-derived nanoparticle comprises apoA-I or a peptide mimetic of apoA-I, and a phospholipid. In embodiments, the high-density lipoprotein (HDL)-derived nanoparticle comprises apoA-I or a peptide mimetic of apoA-I, a phospholipid, and a compound of Formula (I), (II), (II-1), (II-2), (II-A), (IIA-1) or (IIA-2).

In embodiments, the high-density lipoprotein (HDL)-derived nanoparticle comprises i) apoA-I or a peptide mimetic of apoA-I; ii) a phospholipid; iii) a lysolipid, and iv) cholesterol. In embodiments, the high-density lipoprotein (HDL)-derived nanoparticle comprises i) apoA-I or a peptide mimetic of apoA-I; ii) a phospholipid; iii) a lysolipid, iv) cholesterol and a compound of Formula (I), (II), (II-1), (II-2), (II-A), (IIA-1) or (IIA-2).

In embodiments, the high-density lipoprotein (HDL)-derived nanoparticle comprises i) apoA-I or a peptide mimetic of apoA-I; ii) a phospholipid; and iii) cholesterol. In embodiments, the high-density lipoprotein (HDL)-derived nanoparticle comprises i) apoA-I or a peptide mimetic of apoA-I; ii) a phospholipid; iii) cholesterol, and a compound of Formula (I), (II), (II-1), (II-2), (II-A), (IIA-1) or (IIA-2).

In embodiments, the high-density lipoprotein (HDL)-derived nanoparticle comprises i) apoA-I or a peptide mimetic of apoA-I; ii) a phospholipid; iii) a lysolipid, iv) a hydrophobic matrix core and v) cholesterol. In embodiments, the high-density lipoprotein (HDL)-derived nanoparticle comprises i) apoA-I or a peptide mimetic of apoA-I; ii) a phospholipid; iii) a lysolipid, iv) a hydrophobic matrix core v) cholesterol and a compound of Formula (I), (II), (II-1), (II-2), (II-A), (IIA-1) or (IIA-2).

In embodiments, the high-density lipoprotein (HDL)-derived nanoparticle comprises i) apoA-I or a peptide mimetic of apoA-I; ii) a phospholipid; iii) a lysolipid, iv) a triglyceride v) cholesterol, and a compound of Formula (I), (II), (II-1), (II-2), (II-A), (IIA-1) or (IIA-2).

In embodiments, the structure and properties of the HDL-derived nanoparticles (e.g., particle size, rigidity, viscosity, loading, etc.) can be modified by incorporating a hydrophobic matrix. As used herein, hydrophobic matrix refers to a core or filler or structural modifier of the nanobiologic. Non-limiting examples of suitable hydrophobic matrix molecules include, triglycerides, fatty acid esters, hydrophobic polymers, sterol esters, or combinations thereof.

For example, the inclusion of one or more triglycerides and/or one or more polymers in the nanoparticles disclosed herein, may facilitate modulation of nanoparticle size (e.g., from about 10 nm to over 100 nm) and shape (from discoisal to spherical). In turn, the size, rigidity, and viscosity of the HDL-derived nanoparticle may also affect loading and biodistribution. In a non-limiting example, a HDL-derived nanoparticle comprising phospholipids and apoA-I may have a diameter of about 10 nm to about 50 nm, and adding a hydrophobic matrix molecule (such as triglycerides), swells the HDL-derived nanoparticle from a minimum of about 10 nm to at least about 30 nm. Adding more triglycerides can further increase the diameter of the HDL-derived nanoparticle to at least 50 nm, at least 75 nm, at least 100 nm, at least 150 nm, at least 200 nm, at least 300 nm, and up to 400 nm, including all values and ranges therebetween.

Any suitable synthetic or natural fatty acid or fatty acid ester, known in the art are contemplated for use in the HDL-derived nanoparticles of the present disclosure. Non-limiting examples of fatty acids of use include: arachidonic acid, oleic acid, arachidic acid, lauric acid, sad, capric acid, myristic acid, Palmic acid, stearic acid, linoleic acid, linolenic acid, dicaprate, three decanoins, glycerin mono-fatty acid ester, Dilaurin, 1-Sunsoft 767, laurocapram (1-dodecyl-aza-cycloheptane-2-ketone), acylcarnitines, acyl group choline or $C_1$-$C_{10}$arrcostab (such as isopropyl myristate IPM), monoglyceride, diglyceride or its pharmaceutically acceptable salt.

Any suitable synthetic or natural triglycerides, known in the art are contemplated for use in the HDL-derived nanoparticles of the present disclosure. Non-limiting examples of triglycerides of use include: tricaprylin, tristearin, triolein, tripalmitin, 1,2-dipalmitoolein, 1,3-dipalmitoolein, 1-palmito-3-stearo-2-olein, 1-palmito-2-stearo-3-olein, 2-palmito-1-stearo-3-olein, trilinolein, 1,2-dipalmitolinolein, 1-palmito-dilinolein, 1-stearo-dilinolein, 1,2-diacetopalmitin, 1,2-distearo-olein, 1,3-distearo-olein, trimyristin, trilaurin and combinations thereof. Suitable triglycerides may be added to the present compositions in neat form.

Additionally, or alternatively, oils and/or processed oils containing suitable triglycerides may be added to the compositions. Non-limiting examples of oils include coconut oil, corn germ oil, olive oil, palm seed oil, cottonseed oil, palm oil, rapeseed oil, sunflower oil, whale oil, soybean oil, peanut oil, linseed oil, tall oil, and combinations thereof.

The hydrophobic polymer or polymers may be selected from the group of polymers approved for human use (i.e. biocompatible and FDA-approved). Such polymers include, for example, but are not limited to the following polymers, derivatives of such polymers, co-polymers, block co-polymers, branched polymers, and polymer blends: polyalkenedicarboxlates, polyanhydrides, poly(aspartic acid), polyamides, polybutylenesuccinates (PBS), polybutylenesuccinates-co-adipate (PBSA), poly(ε-caprolactone) (PCL), polycarbonates including poly-alkylene carbonates (PC), polyesters including aliphatic polyesters and polyester-amides, polyethylenesuccinates (PES), polyglycolides (PGA), polyimines and polyalkyleneimines (Pl, PAI), polylactides (PLA (polylactic acid), PLLA, PDLLA), polylactic-co-glycolic acid (PLGA), poly(l-lysine), polymethacrylates, polypeptides, polyorthoesters, poly-p-dioxanones (PPDO), (hydrophobic) modifiedpolysaccharides, polysiloxanes and poly-alkyl-siloxanes, polyureas, polyurethanes, and polyvinyl alcohols, and biodegradable polyalkyl-cyanoacrylate.

In embodiments of the HDL-derived nanoparticle of the present disclosure, the addition of cholesterol to the nanoparticle carrier stabilizes the composition and improves entrapment efficiency. Typically, the HDL-derived nanoparticle comprises from about 1 mol % to about 100 mol % of cholesterol relative to phospholipid (e.g., relative to DMPC), including about 1% mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, about 21 mol %, about 22 mol %, about 23 mol %, about 24 mol %, about 25 mol %, about 26 mol %, about 27 mol %, about 28 mol %, about 29 mol %, about 30 mol %, about 35 mol %, about 40 mol %, about 45 mol %, about 50 mol %, about 55 mol %, about 60 mol %, about 65 mol %, about 70 mol %, about 75 mol %, about 80 mol %, about 85 mol %, about 90 mol %, about 95 mol %, to about 100 mol % (i.e. 1:1 mol/mol mixture of cholesterol and phospholipd (e.g. DMPC) including all ranges and values therebetween. In embodiments, the HDL-derived nanoparticle comprises from about 1 mol % to about 30 mol % cholesterol. In embodiments, the HDL-derived nanoparticle comprises from about 15 mol % to about 25 mol % cholesterol, relative to phospholipid. In embodiments, the HDL-derived nanoparticle comprises from about 20 mol % cholesterol, relative to phospholipid. In embodiments, the HDL-derived nanoparticle comprises from about 10 mol % to about 35 mol % cholesterol, relative to phospholipid. In embodiments, the HDL-derived nanoparticle comprises from about 15 mol % to about 30 mol % cholesterol, relative to phospholipid. In embodiments, the HDL-derived nanoparticle comprises from about 15 mol % to about 25 mol % cholesterol, relative to phospholipid. In embodiments, the HDL-derived nanoparticle comprises from about 28 mol % to about 23 mol % cholesterol, relative to phospholipid. In embodiments, the HDL-derived nanoparticle comprises from about 20 mol % to about 27 mol % cholesterol, relative to phospholipid.

In embodiments, the HDL-derived nanoparticle is cholesterol free. In embodiments, the molar ratio of cholesterol: phospholipid, in the HDL-derived nanoparticle is about 0:1, about 0.025:1, about 0.05:1, about 0.075:1, about 0.1:1, about 0.125:1, about 0.15:1, about 0.175:1, about 0.2:1, about 0.225:1, about 0.25:1, about 0.275:1, about 0.3:1, about 0.325:1, about 0.35:1, about 0.375:1, about 0.4:1, about 0.425:1, about 0.45:1, about 0.475:1 or about 0.5:1, including all values therebetween. In embodiments, the molar ratio of cholesterol:phospholipids ranges from about 0:1 to about 0.5:1, including about 0:1, about 0.025:1, about 0.05:1, about 0.075:1, about 0.1:1, about 0.125:1, about 0.15:1, about 0.175:1, about 0.2:1, about 0.225:1, about 0.25:1, about 0.275:1, about 0.3:1, about 0.325:1, about 0.35:1, about 0.375:1, about 0.4:1, about 0.425:1, about 0.45:1, about 0.475:1 to about 0.5:1, including all ranges therebetween. In embodiments, the molar ratio of cholesterol:phospholipids ranges from about 0.05:1 to about 0.25:1. In embodiments, the molar ratio of cholesterol is about 0.2:1.

In embodiments, the HDL-derived nanoparticle comprises one or more phospholipids and cholesterol in a molar ratio in the range of about 1:0.05 to about 1:0.25. In embodiments, the HDL-derived nanoparticle comprises one or more phospholipids and cholesterol in a molar ratio of about 1:0.2.

In embodiments, the weight percentage of cholesterol ranges from about 0% (w/w) to about 15% (w/w) of the nanoparticle, lipid, or composition, including from about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), about 10% (w/w), about 10.5% (w/w), about 11% (w/w/), about 11.5% (w/w), about 12% (w/w), about 12.5% (w/w), about 13% (w/w), about 13.5% (w/w), about 14% (w/w), about 14.5% (w/w), to about 15% (w/w). In embodiments, the weight percentage of cholesterol ranges from about 0% (w/w) to about 15%, (w/w) of the nanoparticle, lipid, or composition, including from about 1% (w/w), about 1.5% (w/w), about 2% (w/w), about 2.5% (w/w), about 3% (w/w), about 3.5% (w/w), about 4% (w/w), about 4.5% (w/w), about 5% (w/w), about 5.5% (w/w), about 6% (w/w), about 6.5% (w/w), about 7% (w/w), about 7.5% (w/w), about 8% (w/w), about 8.5% (w/w), about 9% (w/w), about 9.5% (w/w), about 10% (w/w), about 10.5% (w/w), about 11% (w/w/), about 11.5% (w/w), about 12% (w/w), about 12.5% (w/w), about 13% (w/w), about 13.5% (w/w), about 14% (w/w), about 14.5% (w/w), to about 15% (w/w). In embodiments, the weight percentage is the weight percentage of cholesterol relative to phospholipids. In embodiments, the weight percentage of cholesterol ranges from about 1 to 10% cholesterol (w/w %) of the composition. the weight percentage of cholesterol ranges from about 2 to 8% cholesterol (w/w %) of the composition. In embodiments, the weight percentage of cholesterol ranges from about 3.5 to 7.5% cholesterol (w/w %) of the composition. In embodiments, the weight percentage of cholesterol ranges from about 5 to 10% cholesterol (w/w %) of the composition. In embodiments, the weight percentage of cholesterol is about 3.6 (w/w %) of the composition. In embodiments, the weight percentage of cholesterol is about 7.2 (w/w %) of the composition. In embodiments, the weight percentage of cholesterol is about 5.9 (w/w %) of the composition.

In embodiments, the size and circulating time of the nanoparticles can be modulated, for example, by controlling the ratio of lipids-to-APOA1 and the ratio of lipids to polymer or lipids to triglyceride.

In embodiments, the HDL-derived nanoparticle comprises from about a 5:1 to 1000:1 ratio (e.g., on a molar basis) of phospholipids:apoA-I or a mimetic of apoA-I, including about 5:1, about 10:1, about 20:1, about 30:1, about 40:1, about 50:1, about 60:1, about 70:1, about 80:1, about 90:1, about 100:1, about 110:1, about 120:1, about 130:1, about 140:1, about 150:1, about 160:1, about 170:1, about 180:1, about 190:1, about 200:1, about 210:1, about 220:1 about 230:1, about 240:1, about 250:1, about 260:1, about 270:1, about 280:1, about 290:1, about 300:1, about 310:1, about 320:1, about 330:1, about 340:1, about 350:1, about 360:1, about 370:1, about 380:1, about 390:1, about 400:1, about 410:1, about 420:1, about 430:1, about 440:1, about 450:1, about 460:1, about 470:1, about 480:1, about 490:1, about 500:1, about 510:1, about 520:1, about 530:1, about 540:1, about 550:1, about 560:1, about 570:1, about 580:1, about 590:1, about 600:1, about 610:1, about 620:1, about 630:1, about 640:1, about 650:1, about 660:1, about 670:1, about 680:1, about 690:1, about 700:1, about 710:1, about 720:1 about 730:1, about 740:1, about 750:1, about 760:1, about 770:1, about 780:1, about 790:1, about 800:1, about 810:1, about 820:1, about 830:1, about 840:1, about 850:1, about 860:1, about 870:1, about 880:1, about 890:1, about 900:1, about 910:1, about 920:1, about 930:1, about 940:1, about 950:1, about 960:1, about 970:1, about 980:1, about 990:1, to about 1000:1, including all subranges and values therebetween. In embodiments, the HDL-derived nanoparticle comprises from about a 10:1 to 1000:1 ratio (e.g., on a molar basis) of phospholipids:apoA-I or a mimetic of apoA-I. In embodiments, the HDL-derived the nanoparticle comprises from about a 70:1 to 125:1 ratio (e.g., on a molar basis) of phospholipids:apoA-I. In embodiments, the HDL-derived the nanoparticle comprises from about a 5:1 to 10:1 ratio (e.g., on a molar basis) of mimetic of apoA-I.

In embodiments, the HDL-derived nanoparticle comprises from about a 2:1 to 3:1 ratio by weight of phospholipids:apoA-I or a mimetic of apoA-I.

In embodiments, the HDL-derived nanoparticle comprises from about, or at least about 0.1 mol % to about 100 mol % of a compound of Formula I relative to phospholipid (e.g., DMPC), including about, or at least about 0.1 mol %, about or at least about 0.5 mol %, about or at least about 0.75 mol %, about, or at least about 1% mol %, about, or at least about 2 mol %, about, or at least about 3 mol %, about, or at least about 4 mol %, about, or at least about 5 mol %, about, or at least about 6 mol %, about, or at least about 7 mol %, about, or at least about 8 mol %, about, or at least about 9 mol %, about, or at least about 10 mol %, about, or at least about 11 mol %, about, or at least about 12 mol %, about, or at least about 13 mol %, about, or at least about 14 mol %, about, or at least about 15 mol %, about, or at least about 16 mol %, about, or at least about 17 mol %, about, or at least about 18 mol %, about, or at least about 19 mol %, about, or at least about 20 mol %, about, or at least about 21 mol %, about, or at least about 22 mol %, about, or at least about 23 mol %, about, or at least about 24 mol %, about, or at least about 25 mol %, about, or at least about 26 mol %, about, or at least about 27 mol %, about, or at least about 28 mol %, about, or at least about 29 mol %, to about, at least about 30 mol %, about or at least about or at least about 35 mol %, about or at least about 40 mol %, about or at least about 45 mol %, about or at least about 50 mol %, about or at least about 55 mol %, about or at least about 60 mol %, about or at least about 65 mol %, about or at least about 70 mol %, about or at least about 75 mol %, about or at least about 80 mol %, about or at least about 85 mol %, about or at least about 90 mol %, about or at least about 95 mol %, to about or at least about 100 mol % (1:1 mol/mol mixture of compound and phospholipd (e.g. DMPC)), including all ranges and values therebetween. In embodiments, the HDL-derived nanoparticle comprises from about 10 mol % to about 30 mol % of a compound of Formula I relative to phospholipid. In embodiments, the HDL-derived nanoparticle comprises from about 12 mol % to about 25 mol % compound, relative to phospholipid.

In embodiments, the nanoparticle size ranges from about 5 nm to about 500 nm in diameter, including about 5 nm, about 10 nm, about 15 num, about 20 nm, about 25 num, about 30 nm, about 35 nm, about 40 nm, about 50 nm, about 55 nm, about 60 nm, about 65 nm, about 70 nm, about 75 nm, about 80 nm, about 85 nm, about 90 nm, about 95 nm, to about 100 nm, about 110 nm, about 120 nm, about 130 nm, about 140 nm, about 150 nm about 160 nm, about 170 nm, about 180 nm, about 190 nm, about 200 nm, about 210 nm, about 220 nm, about 230 nm, about 240 nm, about 250 run, about 260 nm, about 270 nm, about 280 nm, about 290 nm, about 300 nm, about 310 nm, about 320 nm, about 330 nm, about 340 nm, about 350 nm, about 360 nm, about 370 nm, about 380 nm, about 390 nm, about 400 nm, about 410 nm, about 420 nm, about 430 nm, about 440 nm, about 450 nm, about 460 nm, about 470 nm, about 480 nm, about 490 nm, to about 500 nm, including all ranges and values therebetween. In embodiments, the nanoparticle size is less than about 50 nm. In embodiments, the nanoparticle size is about 50 nm to about 100 nm, or about 5 nm to about 30 nm. In embodiments, the nanoparticle sizes are measured by dynamic light scattering (DLS). In embodiments, to target immune cells in tissue with limited access to circulation, nanoparticles having long blood half-lives and small size (<50 nm) may be used. In embodiments, to target immune cells in well-perfused tissues, nanoparticles having short blood half-lives and large size (about 100 nm) may be used. These tissues include spleen, liver, kidney, lungs, and bone marrow.

In embodiments, the HDL-derived nanoparticle is discoidal in shape. In embodiments, the HDL-derived nanoparticle is spherical in shape. In embodiments the HDL-derived nanoparticle morphology is visualized by transmission electron microscopy (TEM).

In embodiments, the length of the HDL-derived nanoparticle is about 5 to about 100 nm in length, including about 5 nm, about 10 nm, about 15 nm, about 20 nm, about 25 nm, about 30 nm, about 35 nm, about 40 nm, about 50 nm, about 55 nm, about 60 nm, about 65 nm, about 70 nm, about 75 nm, about 80 nm, about 85 nm, about 90 nm, about 95 nm, to about 100 nm in length, including all ranges and values therebetween. In embodiments, the HDL-derived nanoparticle is about 10 nm to 80 nm in length. In embodiments, the HDL-derived nanoparticle is about 15 nm to 50 nm in length. In embodiments, the HDL-derived nanoparticle is longer than about 10 nm, or longer than about 15 nm. In embodiments, the HDL-derived nanoparticle has a thicknesses of about 1 nm to 10 nm, including about 1 nm, about 2 nm, about 3 nm, about 4 nm, about 5 nm, about 6 nm, about 7 nm, about 8 nm, about 9 nm, to about 10 nm, including all ranges and values therebetween. In embodiments, the thicknesses of the HDL-particles are about 1 to 10 nm, or 2 to 7 nm, or 3 to 6 nm. In embodiments, the dimensions (e.g., length and thickness) are recorded by cryo-TEM. In embodiments, the HDL-particles have a worm-like morphology by cryo-TEM.

In embodiments, the HDL-derived nanoparticle is discoidal in shape with a diameter between about 5 nm to about 50 nm (e.g., as measured by dynamic light scattering (DLS)), including about 5 nm, about 10 nm, about 15 nm, about 20 nm, about 25 nm, about 30 nm, about 40 nm, to about 50 nm, including all subranges and values therebetween. In embodiments, the nanodisc is about 5 nm to about 30 nm in diameter.

In embodiments, the HDL-derived nanoparticle is spherical in shape with a diameter between about 10 nm to about 400 nm in diameter (e.g., as measured by dynamic light scattering (DLS)), including about 10 nm, about 15 nm, about 20 nm, about 30 nm, about 40 nm, about 50 nm, about 60 nm, about 70 nm, about 80 nm, about 100 nm, about 110 nm, about 120 nm, about 130 nm, about 140 nm, about 150 nm, about 160 nm, about 170 nm, about 180 nm, about 190 nm, about 200 nm, about 210 un, about 220 nm, about 230 un, about 240 nm, about 250 nm, about 260 nm, about 270 nm, about 280 un, about 290 nm, about 300 nm, about 310 nm, about 330 nm, about 340 nm, about 350 nm, about 360 nm, about 370 nm, about 380 nm, about 390 nm, to about 400 nm in diameter, including all values and ranges therebetween. In embodiments, the nanosphere is between about 15 nm to about 250 nm in diameter. In embodiments, the nanosphere is between about 30 nm, about 100 nm in diameter.

Stability of the HDL-derived nanoparticle can be assessed by performing DLS measurements. In embodiments, the HDL-derived nanoparticle is stable for at least about 1 week, or at least about 2 weeks, or at least about 5 weeks e.g., by DLS.

In embodiments, the nanobiologic composition promotes a hyper-responsive innate immune response in the patient in need thereof. In embodiments, the hyper-responsive innate immune response is promoted for at least about 7 to about 30 days. In embodiments, the hyper-responsive innate immune response is promoted for at least 30 to 100 days. In embodiments, the hyper-responsive innate immune response is promoted for more than 100 days and up to 3 years. In embodiments, the nanobiologic composition is administered once and wherein the hyper-responsive innate immune response is promoted for at least 30 days. In embodiments, the nanobiologic composition is administered at least once per day in each day of a multiple-dosing regimen, and wherein the hyper-responsive innate immune response is promoted for at least 30 days.

Production methods can prepare uniform size HDL-derived nanoparticles, or a non-uniform sized mixture of HDL-derived nanoparticles, either by not filtering, or by preparing a range of different sized HDL-derived nanoparticles and re-combining them in a post-production step. The larger the size of the HDL-derived nanoparticles, the more drug can be incorporated. However, larger sizes e.g. >120 nm, can limit, prevent or slow diffusion of the HDL-derived nanoparticles into the tissues of the patient being treated. Smaller HDL-derived nanoparticles do not hold as much drug per particle, but are able to access the bone marrow, blood, or spleen, or other localized tissue affected by trained immunity, e.g. myeloid cells, myeloid progenitor cells, and hematopoietic stem cells in the bone marrow, blood and/or spleen, and so forth (biodistribution).

Using a non-uniform mixture of nanoparticles sizes in a single administration or regimen can produce an immediate reduction in innate immune hyper-responsiveness, and simultaneously produce a durable, long-term reduction in innate immune hyper-responsiveness that can last days, weeks, months, and years, wherein the nanobiologic has reversed, modified, or reregulated the metabolic, epigenetic, and inflammasome pathways of the hematopoietic stem cells (HSC), the common myeloid progenitors (CMP), and the myeloid cells such as monocytes, macrophages and other short-lived circulating cells.

In embodiments, the maximum loading capacity of the HDL-derived nanoparticle can be determined dividing the volume of the interior of the HDL-derived nanoparticle by the volume of a drug-load spheroid.

Particle: assume a 100 nm spherical particle having 2.2 nm-3.0 nm phospholipid wall, yielding a 94 nm diameter interior with volume (L)@4/3n(r)3.

Drug: assume STIMULATOR at 12×12×35 Angstrom or as a cylinder 1.2×1.2×3.5 nm, where multiple drug molecule cylinders, e.g. seven or nine, etc. could assume a 3.5 nm diameter spheroid having a radius of 1.75 nm Vol(small) @4/3n(r)3.

Maximum Loading Capacity (calc): –487 k 3.5 nm spheroids within a 100 nm particle.

Formulations

When employed as pharmaceuticals, the compounds and HDL-derived nanoparticles of the present disclosure are typically administered in the form of a pharmaceutical composition. Such compositions can be prepared in a manner well known in the pharmaceutical art and comprise at least one active compound. In embodiments, the pharmaceutical composition comprises a nanobiologic composition of the present disclosure, and a pharmaceutically acceptable carrier.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, intraocular, transdermal, subcutaneous, intravenous, intramuscular, intraperitoneal, intradermal, directly into cerebrospinal fluid, intratracheal, and intranasal.

Depending on the intended route of delivery, the compounds of this invention are preferably formulated as either injectable or oral compositions or as salves, as lotions or as patches all for transdermal administration. In embodiments, the composition is administered intraveneously or intraarterially.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, a compound as described herein is usually a minor component (from about 0.1 to about 50% by weight or preferably from about I to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

Nanoparticles described herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, $17^{th}$ edition, 1985, Mack Publishing Company, Easton, Pennsylvania, which is incorporated herein by reference.

For injection, nanoparticles described herein can be provided in an injection grade saline solution, in the form of an injectable liposome solution, slow-release polymer system or the like.

Nanoparticles described herein can also be administered in sustained release forms or from sustained release drug delivery systems. A description of representative sustained release materials can be found in Remington's Pharmaceutical Sciences.

Methods

Provided herein are methods of treating a subject susceptible to or afflicated with immune-related diseases and conditions, including, for example, immunoparalysis in sepsis and infections, cell proliferation disorders (such as cancer), and other diseases and conditions caused by defective trained immunity.

In embodiments, the present disclosure provides methods for treating a cell-proliferation disorder, comprising administering to a subject in need thereof a therapeutically effective amount of a nanobiologic composition comprising a high-density lipoprotein (HDL)-derived nanoparticle comprising a compound of the present disclosure (such as a compound of Formula I). In embodiments, the compounds, compositions provided herein are useful for treating cancer by inducing trained immunity.

In embodiments, the cell proliferation disorder is cancer. In embodiments, the cancer is one or more of the following cancers: advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scelroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapyinsensitive prostate cancer, papillary thyroid carcinoma, follicular thyroid carcinoma, medullary thyroid carcinoma, and leiomyoma. In embodiments, the cancer is selected from the group consisting of bladder cancer, cancer of the blood vessels, bone cancer, brain cancer, breast cancer, cervical cancer, chest cancer, colon cancer, endometrial cancer, esophageal cancer, eye cancer, head cancer, kidney cancer, liver cancer, cancer of the lymph nodes, lung cancer, mouth cancer, neck cancer, ovarian cancer, pancreatic cancer, prostate cancer, rectal cancer, colorectal cancer, skin cancer, stomach cancer, testicular cancer, throat cancer, thyroid cancer, urothelial cancers, and uterine cancer. In embodiments, the cancer is selected from the group consisting of breast cancer, prostate cancer, melanoma, colorectal cancer, lung cancer, pancreatic cancer, and glioblastoma. In embodiments, the cancer is metastatic. In embodiments, the cancer is refractory or resistance to chemotherapy or radiation; in particular, refractory to thalidomide.

In embodiments, the cancer is selected from the group consisting of bladder cancer, cancer of the blood vessels, bone cancer, brain cancer, breast cancer, cervical cancer, chest cancer, colon cancer, endometrial cancer, esophageal cancer, eye cancer, head cancer, kidney cancer, liver cancer, cancer of the lymph nodes, lung cancer, mouth cancer, neck cancer, ovarian cancer, pancreatic cancer, prostate cancer, rectal cancer, colorectal cancer, skin cancer, stomach cancer, testicular cancer, throat cancer, thyroid cancer, urothelial cancers, and uterine cancer.

In embodiments, the cancer is selected from the group consisting of breast cancer, prostate cancer, melanoma, colorectal cancer, lung cancer, pancreatic cancer, and glioblastoma.

In embodiments, the present disclosure provides methods for treating sepsis comprising administering to a subject in need thereof a therapeutically effective amount of a nanobiologic composition of the present disclosure. In embodiments, the patient has sepsis associated with a bacterial, viral or fungal infection of the lungs, abdomen, kidney, or bloodstream.

The compounds of the present disclosure and their carriers disclosed herein may be used to augment immune responses. Accordingly, disclosed herein are methods of inducing immune responses comprising administering an immunogenic composition to a subject, wherein the composition comprises (i) at least one antigen and (ii) a compound disclosed herein, optionally in a nanoparticle carrier, such as a HDL-derived nanoparticle or liposome.

The antigens are typically from pathogens, though neoantigens from subjects having cancer may also be used. Illustrative pathogen antigens may be from a virus, a bacteria, a parasite or a yeast. In aspects, the antigen may be a secreted from a pathogen; for example, an exotoxin or an endotoxin.

Exemplary viruses include Adenovirus, Adeno-associated virus (AAV), Chikungunya, Dengue, Influenza, Ebola, Epstein-Barr, Hanta, Hepatitis (e.g., Hepatitis A, B, C, D, E), CMV, HPV (e.g., one or more of HPV1-18), Coronavirus, (e.g., SARS, MERS, COVID-19), Polio, Rabies, Zika. Exemplary bacteria include *Vibrio cholerae, E. coli, Salmonella* spp., *N. gonorrheae, N., meningitidis, Streptococcus pyogenes, Mycobacterium tuberculosis, Legionella pneumophila, Brucella bortus*, and *Listeria monocytogenes.*

The antigen may be, for example, a polypeptide, including a glycosylated peptide, or a carbohydrate. In aspects, the immunogenic composition may contain a nucleic acid that encodes an antigen, typically polypeptide that is transcribed and/or translated from the nucleic acid. The nucleic acid may be a DNA or an RNA, or a derivative of DNA or of RNA. Common derivatives of RNA include covalent modification to the molecule to enhance stability and/or expression. In aspects, the nucleic acid encoding the polypeptide may be within a plasmid or a viral vector, such as adenoviral vectors, adeno-associated virus vectors, baculoviral vectors, lentiviral vectors, and the like.

In aspects, the administration may be preventative; for example, to vaccinate the subject prior to exposure to the pathogen. In other aspects, the administration may be a treatment; for example, inducing an immune response against a tumor carrying neo-antigens in a subject suffering from cancer. In embodiments, the nanobiologic composition is administered in a treatment regimen comprising two or more doses to the patient to generate an accumulation of drug in myeloid cells, myeloid progenitor cells, and hematopoietic stem cells in the bone marrow, blood and/or spleen.

In embodiments, the nanobiologic composition is administered intravenously or intra-arterially.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Oral dose levels range from about 0.01 to about 20 mg/kg of the compound of the invention, including all ranges and values there between. For example, dose levels range from about 0.1 to about 10 mg/kg or from about 1 to about 5 mg/kg.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa.

One of skill in the art would choose an appropriate delivery models based on a variety of parameters, including the organ or tissue site in a patient with a disease or condition that is most severely affected by the disease or condition.

The compounds of this invention can be administered as the sole active agent or they can be administered in combination with one or more additional pharmaceutical agents, including other compounds that demonstrate the same or a similar therapeutic activity and are determined to safe and efficacious for such combined administration. In embodiments, the additional pharmaceutical agent is an inhibitor of a checkpoint protein. In embodiments, the methods provided herein further comprise co-administering a cancer drug as a combination therapy with the nanobiologic composition.

A compound or composition described herein can be provided in a kit. In some embodiment the kit includes (a) a compound described herein, or a composition that includes a compound described herein (wherein, e.g., the compound can be an NOD2 modulator described herein), and, optionally (b) informational material. The informational material can be descriptive, instructional, marketing or other material that relates to the methods described herein and/or the use of a compound or composition described herein for the methods described herein. In embodiments, the informational material can include information about production of the compound. In embodiments, the informational material relates to methods for administering the compound. In embodiments, the informational material can include instructions to administer a compound or composition described herein in a suitable manner to perform the methods described herein, e.g., in a suitable dose, dosage form, or mode of administration (e.g., a dose, dosage form, or mode of administration described herein). In embodiments, the informational material can include instructions to administer a compound described herein to a suitable subject, e.g., a human, e.g., a human having or at risk for a disorder described herein.

The kit can include one or more containers for the composition containing a compound or composition described herein. In embodiments, the kit contains separate containers, dividers or compartments for the composition and informational material. For example, the composition can be contained in a bottle, vial, or syringe, and the informational material can be contained in a plastic sleeve or packet. In embodiments, the separate elements of the kit are contained within a single, undivided container. For example, the composition is contained in a bottle, vial or syringe that has attached thereto the informational material in the form of a label. In embodiments, the kit includes a plurality (e.g., a pack) of individual containers, each containing one or more unit dosage forms (e.g., a dosage form described herein) of a compound or composition described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

Also provided herein is a process for manufacturing a nanobiologic composition of the present disclosure, the process comprising:

a) forming a lipid film comprising: i) a compound of the present disclosure; ii) one or more phospholipids; optionally iii) a hydrophobic matrix comprising one or more triglycerides, fatty acid esters, hydrophobic polymers, or sterol esters, or a combination thereof; and optionally iv) cholesterol; under conditions effective to form the lipid film; and
b) dissolving the lipid film in a solvent to form a lipid solution; and contacting the lipid solution with apoA-I or a peptide mimetic of apoA-I under conditions effective to form a HDL-derived nanoparticle comprising a compound of the present disclosure.

In embodiments, provided herein is a nanobiologic composition prepared according to the methods disclosed herein.

EXAMPLES

The therapeutic agents described herein and nanoparticles comprising same may be prepared from known or commercially available starting materials and reagents by one skilled in the art of organic synthesis.

Materials and Methods

All chemicals were purchased from commercial sources and used without further purification unless specified. N-methylmorpholine was redistilled, collecting the fraction from 110° C. to 112° C. Cholesterol azidoacetate was synthesized according known procedures (RSC Adv. 2015, 5, 12094), as was 1-azidooctadecane. Dry solvents were obtained with an MBRAUN Solvent Purification System (MB-SPS). Toluene was dried over 4 Å molecular sieves before use. Glassware used for reactions carried out under argon atmosphere was dried with a heat gun prior to use. Thin-layer chromatography (TLC) was performed using 60-F254 silica gel plates from Merck and visualized by UV light at 254 nm, permanganate staining and/or cerium molybdate (CeMo) staining. Normal and reversed-phase automated column chromatography was conducted on a Biotage Isolera One or Grace Reveleris X2 Flash Chromatography System using Biotage Sfar Silica, Buchi FlashPure ID Silica or BUchi FlashPure ID C18 columns. Elution gradients are specified in column volumes (CVs). Non-stabilized THE was used for the water/THF gradients.

NMR spectra were recorded on Bruker 400 MHz Ultrashield spectrometer (400 MHz for 1H NMR). Deuterated solvents used are indicated in each case. Chemical shifts (6) are expressed in ppm and are referred to the residual peak of the solvent. Peak multiplicity is abbreviated as s: singlet; d: doublet; t: triplet; dt: doublet of triplets; ddt: doublet of doublets of triplets; td: triplet of doublets; tt: triplet of triplets; q: quartet; ABq: AB quartet; dq: doublet of quartets; qd: quartet of doublets; sept: septet; m: multiplet; bs: broad singlet. Matrix assisted laser desorption/ionization time-of-flight (MALDI-TOF) mass spectra were obtained on a PerSeptive Biosystems Voyager DE-PRO spectrometer using α-cyano-4-hydroxycinnamic acid (CHCA) or trans-2-

[3-(4-tert-butylphenyl)-2-methyl-2-propenylidene]-malononitrile (DCTB) as matrix. Gas chromatography-mass spectrometry (GC-MS) measurements were conducted on a Shimadzu GC-17A gas chromatograph with a Shimadzu AOC-20i auto injector, Shimadzu GCMS-QP5000 gas chromatograph mass spectrometer and Phenomenex Zebron ZB-35 column (l=30 meters, ID=0.25 mm, film thickness=0.25 μm). High-pressure liquid chromatography mass spectrometry (HPLC-ESI-MS) experiments using a water/acetonitrile gradient were performed a Shimadzu setup with 2× LC-20 AD pumps, DGU-20A3 degasser, SIL-20AC autosampler, SPD-M20A PDA and ThermoScientific LCQ fleet MS. Column: Phenomenex Kinetex 5 um EVO C18 100 Å LC (50×2.1 mm). Gradient: water/MeCN (+0.1% formic acid) from 5 to 100% MeCN, 0.300 mL/min. Electrospray ionization (ESI) was used to create the charges for MS-detection. HPLC-MS and HPLC-ELSD experiments with a water/THF or water/MeOH gradient were performed on a Shimadzu Nexera-i LC-2040C 3D Plus with Shimadzu LCMS-8045. Column: Alltech Alltima C18 (150×3.2 mm; 5 um; no. 88383). Gradient: water/THF (+0.1% TFA) or water/MeOH (+0.1% TFA), 0.400 mL/min. This HPLC setup was also used in combination with ELSD (evaporative light scattering detection).

Alternatively, HPLC-MS(SIM) and HPLC-ELSD were performed on a Phenomenex Kinetex 5 micrometer EVO C18 100 Å LC-column (50×2.1 mm) employing a gradient from A to B eluent, where A=20 mM $NH_4HCO_2$ in $H_2O$ with 0.1 v/v % formic acid, and B=2-propanol/MeCN/$H_2O$ 85:15:5, also with 20 mM $NH_4HCO_2$ and 0.1 v/v % formic acid.

Abbreviations

HPLC=high performance liquid chromatography; ELSD=evaporative light scattering detection; ESI-MS=electrospray ionization mass spectrometry; SIM=selected ion mode; NMR=nuclear magnetic resonance.

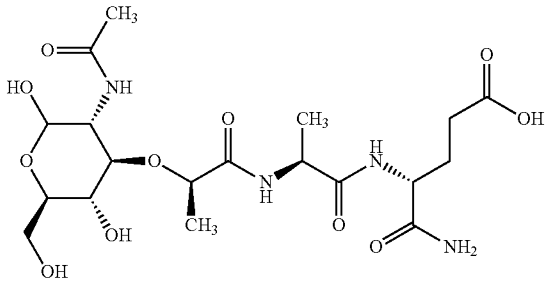

MDP - [53678-77-6]

MDP=Muramyl dipeptide muramyl (or N-Acetylmuramyl-L-alanyl-D-isoglutamine) CAS [53678-77-6]. Was either prepared according to standard peptide synthesis or bought from commercial sources.

NHS=N-hydroxy succinimide; DiC or DIC=N,N'-diisopropylcarbodiimide; EDC=N-(3-dimethylaminopropyl)-N'-ethylcarbodiimide (used hydrochloride); PyBOP=(benzotriazol-1-yloxytripyrrolidinophosphonium hexafluorophosphate); SPPS=solid phase peptide synthesis.

TEA=triethyl-amine; THF=tetrahydrofuran; MeOH=methanol; DMF=dimethylformamide; FA=formic acid; TFA=trifluoro-acetic acid.

Building Blocks

DSPE-azidoacetate (DSPE-CO—$CH_2$—$N_3$)

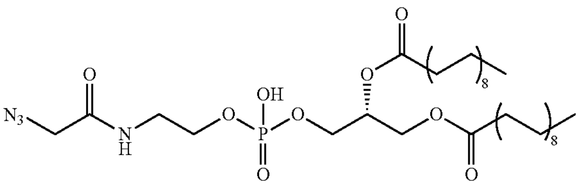

(2R)-3-(((2-Aminoethoxy)(hydroxy)phosphoryl)oxy)propane-1,2-diyl distearate (260 mg, 0.35 mmol), 2,3,5,6-tetrafluorophenyl 2-azidoacetate (prepared according to D. J. Vugts et al., Bioconjugate Chem. 2011, 22, 2072-2081; 87 mg, 0.35 mmol, 1 eq) and N,N-diisopropylethylamine (184 μL, 1.1 mmol, 3 eq) were combined in chloroform (2 mL). The mixture was stirred at 50° C. for 1 h during which the white suspension cleared. Chloroform (200 mL) was added and the organic layer was gently washed twice with I M HCl (100 mL). After drying with MgSO4, filtration and removal of the solvent in vacuo, the compound was purified with column chromatography (flash $SiO_2$) using an elution gradient of 5% to 40% MeOH in chloroform. This yielded pure DSPE-azidoacetate (244 mg, 0.29 mmol, 84%) as a white solid. $^1$H-NMR (400 MHz, $CDCl_3$/$CD_3OD$ 9:1): δ=5.23 (dt, J=9.0, 4.6 Hz, 1H), 4.35 (dd, J=12.0, 3.7 Hz, 1H), 4.22-3.99 (m, 5H), 3.95 (s, 2H), 3.53 (t, J=5.1 Hz, 2H), 2.33 (q, J=7.6 Hz, 4H), 1.61 (td, J=7.4, 4.2 Hz, 4H), 1.48-1.16 (m, 56H), 0.88 (t, J=6.7 Hz, 6H). $^{13}$C-NMR (101 MHz, $CDCl_3$): δ=173.7, 173.4, 168.3, 69.7, 69.6, 66.1, 66.0, 65.2, 62.1, 52.5, 40.01, 39.95, 34.3, 34.2, 34.1, 32.1, 29.9, 29.80, 29.7, 29.62, 29.59, 29.50, 29.47, 29.46, 29.4, 29.30, 29.26, 25.00, 24.97, 24.9, 22.8, 14.2. $^{31}$P-NMR (162 MHz, $CDCl_3$): δ=−0.48. MALDI-TOF MS: m/z Calc. for $C_{43}H_{83}N_4O_9P$ 830.59; Obs. $[M+Na]^+$ 853.62, $[M-H+2Na]^+$ 875.58.

MDP-propargyl

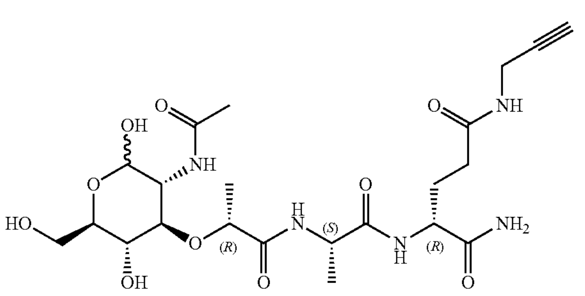

A 50 mL round-bottomed flask was filled with MDP (0.113 g, 0.23 mmol, 1.00 eq). The material was dissolved in dry DMF (~1.5 mL, 0.15 M) and the flask purged with argon.

EDC.HCl (0.066 g, 0.34 mmol, 1.50 eq) and N,N-diisopropylethylamine (0.050 g, 0.068 mL, 0.39 mmol, 1.70 eq) and 4-(N,N-dimethylamino)pyridine (0.0028 g, 0.023 mmol, 0.10 eq) were added, and the resulting clear solution stirred at RT for 5 min. Next, prop-2-yn-1-amine (0.018 g, 0.021 mL, 0.32 mmol, 1.40 eq) was added syringe. Stirring was continued at RT. After 21 h reaction time, LC-MS (water/MeOH) confirmed full conversion of the MDP starting material. The reaction mixture was concentrated in vacuo, giving crude product as a yellow glass. The material was purified twice by automated column chromatography (reversed-phase (C18); product:C18-silica 1:100; detection: 200-400 nm), eluting with water/MeOH 90/10-82/18. Pure fractions were lyophilized, giving pure product as a white solid (0.050 g, 41%).

$^1$H NMR (400 MHz, MeOD) δ 5.16 (d, J=3.4 Hz, 1H), 4.42-4.23 (m, 3H), 3.95 (t, J=2.3 Hz, 2H), 3.94-3.57 (m, 5H), 3.52-3.39 (m Hz, 1H), 2.58 (t, J=2.6 Hz, 1H), 2.33-2.26 (m, 2H), 2.25-2.13 (m, 1H), 2.00-1.85 (m, 4H), 1.45-1.33 ppm (m, 6H). $^{13}$C NMR (100 MHz, MeOD) δ 175.26, 174.83, 173.89, 173.06, 172.08, 91.01, 79.15, 78.92, 76.68, 71.86, 70.83, 70.21, 63.35, 61.22, 54.13, 52.66, 49.48, 31.54, 28.11, 27.10, 23.85, 21.46, 18.31, 16.21 ppm. HPLC-MS (water/MeCN): t (product)=0.76 and 1.02 min. Found: m/z=512.08 $[M-H_2O+H]^+$; 552.33 $[M+Na]^+$ (pos. mode); 325.17 $[M\text{-muramyl}]^-$ (neg. mode).

MDP(Bn)

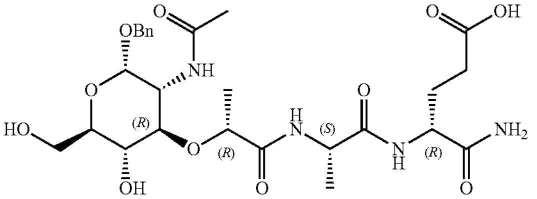

MDP(Bn) was synthesized using standard SPPS methods in an 100 mL glass reactor vessel with glass frit filter bottom. Sufficient agitation of the reaction mixture was ensured by applying a constant argon flow through the glass frit filter, whilst excess reagent and washing solutions were removed by vacuum filtration. The crude MDP(Bn) was purified twice by automated column chromatography (reversed-phase (C18); product:C18-silica 1:200; detection: 200-400 nm), eluting with water/MeCN+0.1% formic acid 90/10-82/18. Pure fractions were lyophilized, giving pure product as a fluffy, white material (0.309 g, 67%).

$^1$H NMR (400 MHz, DMF-d7) δ 8.18 (d, J=8.6 Hz, 1H), 8.15 (d, J=8.6 Hz, 1H), 7.75 (d, J=6.5 Hz, 1H), 7.53-7.28 (m, 6H), 7.11-7.03 (m, 1H), 4.86 (d, J=3.5 Hz, 1H), 4.76 (d, J=12.3 Hz, 1H), 4.72-4.56 (m, 1H), 4.51 (d, J=12.3 Hz, 1H), 4.47-4.32 (m, 3H), 4.01 (ddd, J=10.7, 8.4, 3.5 Hz, 1H), 3.83 (dd, J=11.6, 2.2 Hz, 1H), 3.78-3.61 (m, 3H), 3.60-3.40 (m, 1H), 2.39 (t, J=7.8 Hz, 2H), 2.24-2.12 (m, 1H), 1.97-1.83 (m, 4H), 1.40 (d, J=7.0 Hz, 3H), 1.34 ppm (d, J=6.7 Hz, 3H). $^{13}$C NMR (100 MHz, DMF-d7) 8 174.30, 173.74, 173.60, 172.82, 170.19, 138.47, 128.58, 127.93, 127.79, 97.05, 80.16, 77.36, 73.94, 70.66, 68.61, 61.76, 53.64, 52.59, 49.41, 35.63, 30.57, 30.47, 27.78, 22.65, 19.05, 18.04 ppm. HPLC-MS (water/MeCN): t(product)=3.11 min. Found: m/z=583.08 $[M+H]^+$.

MDP(Bn)-propargyl

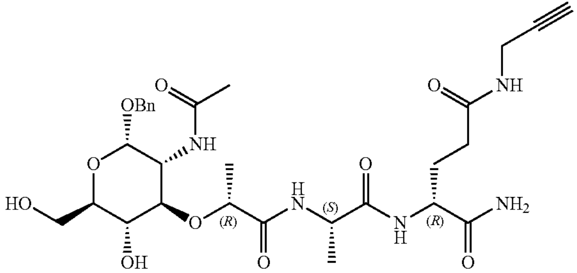

A 5 mL round-bottomed flask was charged with MDP(Bn) (0.110 g, 0.19 mmol, 1.00 eq) under argon atmosphere. The material was dissolved in dry DMF (0.5 mL). PyBOP (0.127 g, 0.25 mmol, 1.30 eq) and N,N-diisopropylethylamine (0.049 g, 0.066 mL, 0.38 mmol, 2.00 eq) were added, resulting in a clear, colorless solution. The mixture was stirred for 5 minutes at RT. Next, prop-2-yn-1-amine (0.021 g, 0.024 mL, 0.38 mmol, 2.00 eq) was added and the resulting light yellow mixture stirred at RT. After 2 h reaction time, the reaction mixture was concentrated in vacuo, giving crude product as a beige, sticky solid. The material was purified by automated column chromatography (reversed-phase (C18); product:C18-silica 1:100; detection: 200-400 nm), eluting with water/MeCN 90/10-80/20. Pure fractions were lyophilized, giving pure product as a white solid (0.096 g, 82%).

$^1$H NMR (400 MHz, DMF-d7) δ 8.25 (t, J=5.5 Hz, 1H), 8.20-8.15 (m, 2H), 7.75 (d, J=6.6 Hz, 1H), 7.51-7.28 (m, 6H), 7.08-7.03 (m, 1H), 5.47 (d, J=6.3 Hz, 1H), 4.86 (d, J=3.5 Hz, 1H), 4.76 (d, J=12.3 Hz, 1H), 4.63 (t, J=6.0 Hz, 1H), 4.51 (d, J=12.4 Hz, 1H), 4.47-4.27 (m, 3H), 4.05-3.95 (m, 3H), 3.83 (ddd, J=11.5, 5.7, 2.2 Hz, 1H), 3.75-3.61 (m, 3H), 3.54-3.46 (m, 1H), 3.04 (t, J=2.5 Hz, 1H), 2.32-2.26 (m, 2H), 2.21-2.11 (m, 1H), 1.95-1.83 (m, 4H), 1.39 (d, J=7.0 Hz, 3H), 1.34 ppm (d, J=6.8 Hz, 3H). $^{13}$C NMR (100 MHz, DMF-d7) δ 173.79, 173.59, 172.74, 171.93, 170.19, 138.47, 128.58, 127.93, 127.80, 97.05, 81.35, 80.16, 77.36, 73.94, 72.14, 70.63, 68.62, 61.76, 53.65, 52.94, 49.38, 35.63, 32.21, 30.47, 28.31, 28.25, 22.66, 19.01, 18.06 ppm. HPLC-MS (water/MeCN): t (product)=3.35 min. Found: m/z=620.17 $[M+H]^+$.

MTP-b on Resin

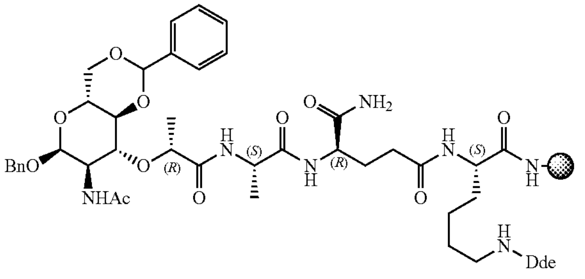

MTP-b on-resin was synthesized using standard SPPS methods in an 100 mL glass reactor vessel with glass frit filter bottom. Sufficient agitation of the reaction mixture was ensured by applying a constant argon flow through the glass frit filter, whilst excess reagent and washing solutions were removed by vacuum filtration. After performing the final post-coupling wash, the resin was washed again with DCM (2×20 mL) and dried in an argon flow. The material was stored at −20° C. A sample was cleaved from the resin using TFA/TIPS/water 95/2.5/2.5 (0.1 mL, 10 min) and checked with HPLC-MS (water/MeCN). HPLC-MS (water/MeCN): t (product)=3.65 min. Found: m/z=874.42 $[M+H]^+$ (pos. mode); m/z=918.08 $[M+HCOO]^-$ (neg. mode).

MTP-b-N3

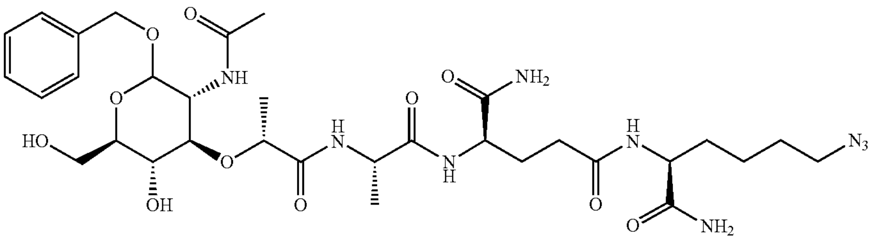 [SMILES: CC(=O)N[C@H]1C(OCc2ccccc2)O[C@H](CO)[C@@H](O)[C@@H]1O[C@H](C)C(=O)N[C@@H](C)C(=O)N[C@H](CCC(=O)N[C@@H](CCCCN=[N+]=[N-])C(N)=O)C(N)=O]

A 20 mL PE syringe with PE frit was charged with on-resin MTP-b (429 mg, approx. 0.15 mmol MTP-b) and the resin was swollen in DMF (12 mL) for 30 min. The resin was treated twice with 2% hydrazine hydrate solution in DMF (12 mL) for 15 min. After filtration the resin was washed with DMF (4×12 mL) for 1 min. A solution of $CuSO_4 \cdot 5H_2O$ (0.6 mg, 2.4 μmol, 1.5 mol %), imidazole-1-sulfonyl azide HCl-salt (170 mg, 0.77 mmol, 5 eq) and N,N-diisopropylethylamine (0.34 mL, 1.9 mmol, 12 eq) in DMF (12 mL) was added to the resin and the beads were agitated at room temperature for 24 h (slight overpressure was relieved every now and then). After filtration the resin was washed with DMF (5×12 mL) for 1 min and dichloromethane (4×10 mL) for 1 min. The resin was then subjected to cleavage in TFA/TIPS/$H_2O$ 95:2.5:2.5 (4 mL) for 2 h. After filtration the resin was washed with TFA (4 mL) for 5 min. The combined TFA filtrates were concentrated in vacuo (keeping the temperature as low as possible to avoid TFA-ester formation). Automated column chromatography (reversed-phase (C18); detection: λ=200 nm), using an elution gradient of 5% to 60% MeCN in $H_2O$ (both containing 0.1% TFA) yielded impure compound. This was further purified with RP-HPLC using an elution gradient of 26% to 35% MeCN in $H_2O$ (both containing 0.1% TFA) yielding pure product (37.5 mg, 51 μmol, 34%) as a white fluffy solid after lyophilization. $^1$H-NMR (400 MHz, DMF-d7/$D_2O$ 9:1): δ=8.45 (t, J=9.1 Hz, 2H), 8.26 (d, J=7.9 Hz, 1H), 7.99 (d, J=6.5 Hz, 1H), 7.81 (d, J=2.8 Hz, 2H), 7.64-7.45 (m, 5H), 7.31 (d, J=17.2 Hz, 2H), 5.82 (d, J=6.3 Hz, 1H), 5.03 (d, J=3.5 Hz, 1H), 4.93 (d, J=12.4 Hz, 1H), 4.68 (d, J=12.4 Hz, 1H), 4.63-4.46 (m, 4H), 4.19 (dd, J=10.7, 3.6 Hz, 1H), 4.00 (dd, J=6.8, 6.3 Hz, 1H), 3.92-3.79 (m, 3H), 3.66 (t, J=9.0 Hz, 1H), 3.52 (t, J=6.8 Hz, 2H), 2.53 (t, J=7.5 Hz, 2H), 2.37 (dtd, J=16.5, 7.9, 4.3 Hz, 1H), 2.10 (s, 3H), 2.09-1.93 (m, 2H), 1.88-1.55 (m, 5H), 1.58 (d, J=7.1 Hz, 3H), 1.52 (d, J=6.7 Hz, 3H). $^{13}$C-NMR (100 MHz, DMF-d7/$D_2O$ 9:1): δ=174.9, 174.24, 174.17, 174.00, 173.93, 173.14, 173.06, 172.9, 172.8, 170.90, 170.8, 138.2, 128.6, 127.9, 127.8, 96.8, 80.0, 77.3, 73.7, 70.3, 68.6, 61.5, 53.6, 53.5, 53.2, 53.13, 53.10, 52.7, 52.6, 51.2, 49.4, 49.3, 32.1, 31.7, 28.5, 28.2, 23.2, 22.53, 22.48, 18.9, 17.80, 17.76. ESI-MS: m/z Calc. for $C_{32}H_{49}N_9O_{11}$ 735.36; Obs. $[M+H]^+$ 736.25, $[M+Na]^+$ 758.42.

DSG 4-nitrophenylcarbonate

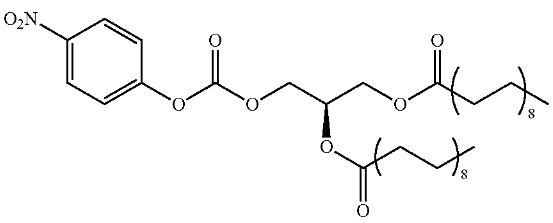

A 25 mL round-bottom flask was filled with a solution of commercially available [(2S)-3-hydroxy-2-octadecanoyloxypropyl]octadecanoate (0.601 g, 0.96 mmol, 1.00 eq) in chloroform (6.5 mL, ~0.15 M). Pyridine (0.122 g, 0.125 mL, 1.54 mmol, 1.60 eq) was added and the resulting clear solution cooled in icewater. Next, solid 4-nitrophenyl chloroformate (0.252 g, 1.25 mmol, 1.30 eq) was added in small portions. The light yellow reaction mixture was stirred at RT overnight. Full conversion of the alcohol was confirmed by $^1$H NMR ($CDCl_3$). Subsequently, the reaction mixture was precipitated in MeOH (100 mL) and collected by filtration through glass filter. The material was washed with MeOH (30 mL total) and $Et_2O$ (10 mL total) and dried in a vacuum oven 30° C. Product (0.713 g, 94%) was obtained as a white solid.

$^1$H NMR (400 MHz, $CDCl_3$) δ 8.29 (d, J=9.1 Hz, 2H), 7.39 (d, J=9.1 Hz, 2H), 5.38 (p, J=5.2 Hz, 1H), 4.50 (dd, J=11.7, 3.9 Hz, 1H), 4.41-4.32 (m, 2H), 4.22 (dd, J=12.0, 5.6 Hz, 1H), 2.35 (dt, J=9.8, 7.5 Hz, 4H), 1.68-1.58 (m, 4H), 1.37-1.17 (m, 56H), 0.88 ppm (t, J=6.7 Hz, 6H). $^3$C NMR (101 MHz, $CDCl_3$) δ 173.24, 172.92, 155.35, 152.29, 145.56, 125.36, 121.76, 68.33, 66.97, 61.63, 34.16, 34.03, 31.93, 29.71, 29.68, 29.64, 29.49, 29.37, 29.29, 29.13, 29.07, 24.87, 22.70, 14.12 ppm.

2,3,5,6-Tetrafluorophenyl stearate

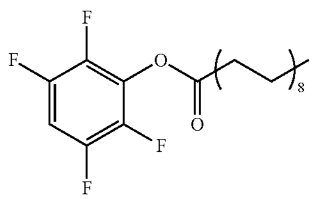

Trietylamine (2.8 mL, 5 eq.) was added slowly to a solution of stearoyl chloride (1.26 g, 4.2 mmol) and tetrafluorophenol (0.72 g, 1.04 eq.) in DCM (10 mL), causing the immediate formation of a white precipitate. The heterogeneous reaction mixture was stirred for another 2 hours, diluted with 25 mL DCM and extracted with water (50 mL), 0.1 M HCl (2×50 mL), dried with MgSO4 and evaporated to dryness. The resulting solid was redissolved in 50 mL diethyl ether and extracted again with 1M $NaHCO_3$ (50 mL), 0.1 M HCl (50 mL), water (50 mL) and brine (2×50 mL). The organic phase was dried with MgSO4 (augmented with a small amount of activated carbon) and evaporated to dryness. The resulting crude material was redissolved in chloroform and flushed over a silica plug and again evaporated to dryness to afford 1.2 g (67%) of the desired compound as a white solid. $^{1}H$ NMR (400 MHz, $CDCl_3$) δ 6.98 (tt, J=9.9, 7.0 Hz, 1H), 2.66 (t, J=7.4 Hz, 2H), 1.78 (p, J=7.4 Hz, 2H), 1.26 (s, 28H), 0.88 (t, J=6.7 Hz, 3H) ppm. $^{19}F$ NMR (376 MHz, $CDCl_3$) δ −139.21 (ddd, J=24.0, 11.8, 7.8 Hz), −153.03-−153.20 (m). $^{13}C$ NMR (101 MHz, $CDCl_3$) δ 169.56, 147.23 (m), 144.74 (m), 141.94, 141.86 (m), 139.41 (m), 129.78 (m), 103.01 (t), 33.42, 31.92, 29.69, 29.65, 29.61, 29.54, 29.39, 29.36, 29.14, 28.85, 24.78, 22.68, 14.09 ppm.

Synthetic Approaches

First approach. Compounds of the invention can be prepared by using the starting reactants MDP or MDP(Bn)—vide supra. These molecules have a functional carboxylic acid group that originates from the glutamic acid (Glu) building block. The COOH-group enables conjugation to amine-functional reactants that comprise lipophilic groups. Such lipophilic groups can for example be $C_{18}$-moieties, for examples those derived from stearic acid, oleic acid, stearyl alcohol, oleyl alcohol, stearyl amine or oleyl amine; or sterol moieties, for example those derived from cholesterol. Saturated linear lipophilic moieties are preferred, as well as moieties derived from cholesterol. Particularly useful building blocks are PE-phospholipids such as DSPE ([1069-79-0]) or DOPE ([4004-05-1]); these molecules are already amine functional. Mixed acyl PE-phospholipids can also be useful (e.g. 16:0-18:1 PE or 18:0-18:1 PE or 18:0-16:0 PE). Another useful building block is cholesterol. Yet other useful building blocks are diglycerides, such as 1,2-dioctadecanoyl-sn-glycerol (18:0 DG [51063-97-9]) or 1-2-dioleoyl-sn-glycerol (18:1 DG [24529-88-2]). Mixed acyl diglycerides can also be used (e.g. 16:0-18:1 DG or 18:0-18:1 DG or 18:0-16:0 DG). PE-phospholipids as well as the diglycerides have two lipophilic chains, and such building blocks are preferably used in this approach.

This first approach is illustrated in Examples 10 to 19.

Second approach. In a particularly suitable alternative modular approach, copper-catalyzed azide-alkyne cycloadditions ("click reactions") are employed to connect the MDP (or MTP) reactant to the lipophilic reactant. Here, MDP, MDP(Bn), MTP or MTP(Bn) building blocks are used that have azide (—$N_3$) or alkyne (—C≡C—H) functionalities. Non-limiting examples of such molecules are MDP-propargyl, MDP(Bn)-propargyl or MTP-b-$N_3$—vide supra. In the copper-catalyzed click reactions, these molecules can be coupled to alkyne- or azide-functional molecules that comprise lipophilic groups. Using the click-reaction, azide- or alkyne functional intermediates are targeted that can be prepared easily and modularly and that are stable. This allows simple isolation and storage of intermediates. Furthermore, the copper-catalyzed click cycloadditions can be performed— and are best performed—in an aqueous environment (such as e.g. THF/water or tBuOH/water) or in an aqueous two-phase liquid/liquid solvent combination (such as e.g. dichloromethane/water). In these reaction media, both the hydrophilic MDP (or MTP) reactant (with or without Bn-group) and the lipophilic reactant are conveniently soluble, highly improving ease of conjugation and reaction yields. In this click-approach, the lipophilic groups comprised in the azide or alkyne reactants can be C14, C16 or C18-moieties, such as those derived from stearic acid, palmitic acid, myristic acid, oleic acid, palmitoleic acid, myristoleic acid, stearyl alcohol or amine, palmityl alcohol or amine, myristyl alcohol or amine, oleyl alcohol or amine, palmitoleyl alcohol or amine, myristoleyl alcohol or amine; or sterol moieties, for example those derived from cholesterol. Saturated linear lipophilic moieties are preferred, as well as moieties derived from cholesterol. Particularly useful building blocks are PE-phospholipids, mixed acyl PE-phospholipids, diglycerides (DG) or mixed-acyl diglycerides, with C14, C16 and/or C18 moieties in them, as well as cholesterol. Lipophilic azide or alkyne reactants that comprise two lipophilic chains or that comprise a cholesteryl group are preferred.

This second approach is illustrated in Examples 1 to 9.

Note that both approaches allow the introduction of an extra amino-acid unit attached to the glutamic acid unit of MDP or MDP(Bn). Suitable amino acid units are those derived from L-Lysine or L-Alanine. With an extra amino acid unit connected, the MDP (muramyl dipeptide) moiety is converted to an MTP (muramyl tripeptide) moiety, either with or without Bn-group. Illustrations are found in Examples 9-10, 13-15 and 17-18.

Example 1. Synthesis of MDP-C18 [Click](1)

(1)

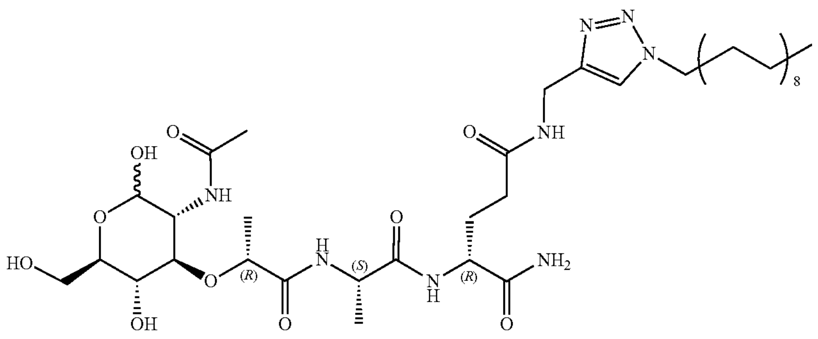

Molecular weight: 825 Dalton. CLogP=4.15.

This synthesis illustrates general conditions for Cu-click type reactions.

A 5 mL vial was charged with MDP-propargyl (0.011 g, 0.02 mmol, 1.00 eq). To this was added L-ascorbic acid (0.4 M aq. solution, 104 μL, 41.5 μmol ascorbic acid, 2.00 eq). To the resulting slightly opaque solution, a solution of 1-azidooctadecane (0.012 g, 0.04 mmol, 2.00 eq) in DCM (0.8 mL) was added, followed by aqueous copper(II) sulfate pentahydrate solution (0.2 M, 104 μL, 20.8 gmol Cu, 1.00 eq). The bi-layered reaction mixture was then stirred at 1400 rpm at RT, resulting in a light yellow/green emulsion. After 16 h, the reaction mixture was concentrated in a stream of $N_2$, giving crude product as a light brown sludge. The material was taken up in chloroform/MeOH 4:1 and impregnated on celite (90 mg, ~1:5 loading ratio). Purification was done by automated column chromatography (product:silica 1:500; detection: 200-400 nm), eluting with chloroform/MeOH/water 90/9/1-70/27/3, giving product (0.005 g, 31%) as a white solid.

$^1$H NMR (400 MHz, MeOD) δ 7.64-7.61 (m, 1H), 5.33 (d, J=3.4 Hz, 1H), 4.58-4.21 (m, 7H), 3.85-3.46 (m, 6H), 2.35-2.26 (m, 2H), 2.23-2.08 (m, 1H), 2.06-1.84 (m, 6H), 1.42-1.36 (m, 6H), 1.35-1.22 (m, 30H), 0.88 ppm (t, J=6.8 Hz, 3H). $^{13}$C NMR (100 MHz, MeOD) δ 175.75, 174.66, 174.04, 173.58, 171.91, 144.63, 122.53, 91.00, 76.01, 71.84, 71.18, 67.16, 61.98, 54.15, 52.98, 50.67, 34.78, 32.20, 32.03, 30.34, 29.80, 29.76, 29.72, 29.65, 29.52, 29.46, 29.12, 27.49, 26.60, 22.83, 22.79, 22.69, 19.34, 16.95, 16.57, 14.15 ppm. HPLC-MS (water/MeCN): t (product) =5.64 min. Found: m/z=825.33 $[M+H]^+$.

Example 2. Synthesis of MDP-DSPE [Click](2)

(2)

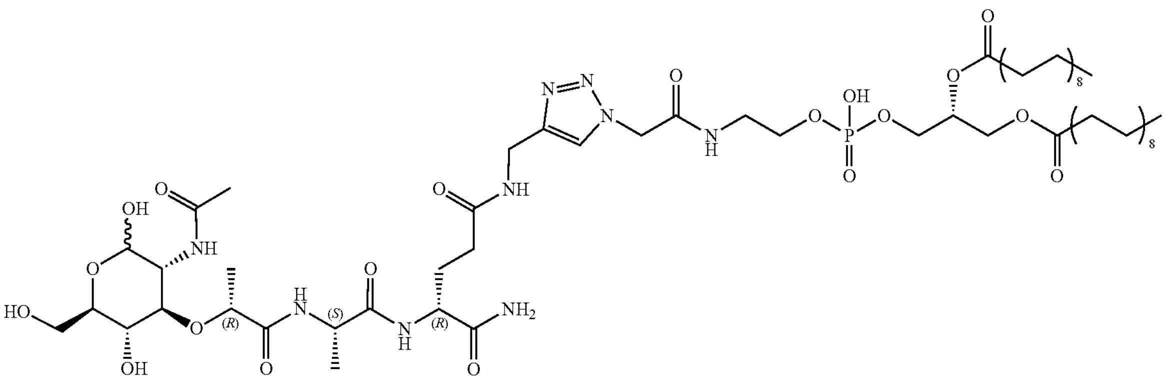

Molecular weight: 1361 Dalton. CLogP=11.56 (uncharged) and 5.78 (negatively charged).

MDP-propargyl (24.4 mg, 46 μmol) was dissolved in 0.4 M ascorbic acid (0.24 mL, 2 eq) and a solution of DSPE-azidoacetate (38.5 mg, 46 μmol, 1 eq) in dichloromethane (0.5 mL) was added. Under vigorous stirring 0.2 M $CuSO_4 \cdot 5H_2O$ (0.24 mL, 1 eq) was added and the two-phase system was vigorously stirred at room temperature for 19 h. The solvents were removed in vacuo and the greenish solid was subjected to column chromatography (flash $SiO_2$) using an elution gradient of 20% to 50% MeOH in chloroform, concluded by (45% MeOH+5% $H_2O$) in chloroform (a significant amount of compound only elutes after the addition of $H_2O$). This yielded impure product which was further purified with automated column chromatography (reversed-phase (Cis); product:$C_{18}$-silica 1:200; detection: A=210 nm), using an elution gradient of 25% to 70% THF in $H_2O$. This yielded pure product (19.5 mg, 14 mol, 31%) as a white fluffy solid after lyophilization.

$^1$H NMR (400 MHz, $CDCl_3$+MeOD) δ 7.93 (s, 1H), 5.29-5.22 (m, 2H), 5.16 (s, 2H), 4.51-4.41 (m, 4H), 4.38-4.25 (m, 2H), 4.20 (dd, J=12.1, 6.8 Hz, 1H), 4.05-3.89 (m, 4H), 3.88-3.77 (m, 2H), 3.77-3.63 (m, 6H), 3.55-3.42 (m, 3H), 2.34 (q, J=7.3 Hz, 6H), 2.22 (dddd, J=18.4, 13.5, 8.4, 5.7 Hz, 1H), 1.98 (d, J=5.7 Hz, 4H), 1.93 (s, OH), 1.62 (q, J=6.4 Hz, 5H), 1.46-1.36 (m, 6H), 1.28 (s, 61H), 0.89 (t, J=6.8 Hz, 6H). Peaks between 4.9 and 4.6 ppm are not visible due to overlap with the $H_2O$ peak. MALDI-TOF MS: m/z Calc. for $C_{65}H_{118}N_9O_{19}P$ 1359.83; Obs. $[M+Na]^+$ 1382.83, $[M-H+2Na]^+$ 1404.84. HPLC-MS ($H_2O$/THF, gradient: 65-95% THF): t (product)=2.33 min; m/z=1360.80 $[M+H]^+$ (SIM mode).

Example 3. Synthesis of MDP-chol [Click](3)

(3)

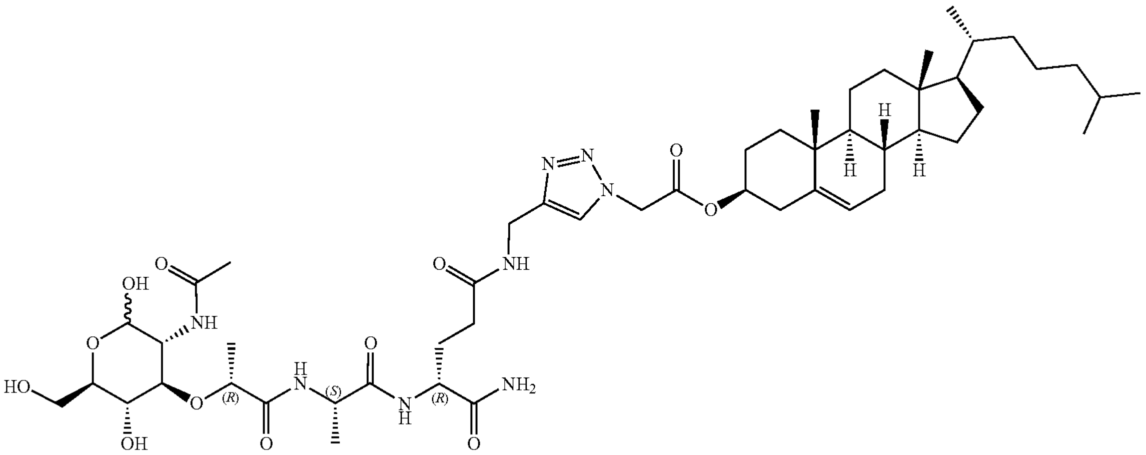

Molecular weight: 999 Dalton. CLogP=5.04.

MDP-propargyl (25 mg, 47 μmol) was dissolved in 0.4 M ascorbic acid (0.24 mL, 2 eq) and a solution of cholesterol azidoacetate (26.6 mg, 57 μmol, 1.2 eq) in dichloromethane (0.5 mL) was added. Under vigorous stirring 0.2 M $CuSO_4 \cdot 5H_2O$ (0.24 mL, 1 eq) was added and the two-phase system was vigorously stirred at room temperature for 17 h. $H_2O$/brine 1:1 (50 mL) was added and the bluish aqueous layer was extracted with chloroform/MeOH 2:1 (5×20 mL). The combined organic layers were dried using $Na_2SO_4$, filtrated and the solvent was removed in vacuo. The resulting colorless solid was purified with repeated column chromatography (flash $SiO_2$) using an elution gradient of 6% to 20% MeOH in chloroform. This yielded pure product (24.4 mg, 24 μmol, 52%) as a white fluffy solid after lyophilization from THF/$H_2O$. $^1$H-NMR (400 MHz, THF-d8/$D_2O$ 95:5): δ=7.81 (s, 1H), 5.28 (d, J=4.9 Hz, 1H), 5.16 (s, 2H), 5.10 (d, J=3.4 Hz, 1H), 4.59-4.46 (m, 1H), 4.46-4.16 (m, 5H), 3.75-3.17 (m, 6H), 2.26 (d, J=8.2 Hz, 2H), 2.20 (t, J=7.5 Hz, 2H), 2.12-1.99 (m, 1H), 1.98-1.69 (m, 8H), 1.58-1.33 (m, 5H), 1.32-1.23 (m, 7H), 1.18 (s, 5H), 1.13-0.97 (m, 4H), 0.94 (s, 3H), 0.84 (d, J=6.5 Hz, 3H), 0.77 (dd, J=6.6, 1.4 Hz, 8H), 0.61 (s, 3H). $^{13}$C-NMR (100 MHz, THF-d8/$D_2O$ 95:5): δ=175.2, 174.9, 173.7, 173.4, 171.9, 166.6, 165.1, 139.6, 122.4, 91.0, 78.7, 76.7, 75.4, 72.0, 70.2, 61.1, 56.8, 56.2, 54.0, 52.6, 50.5, 50.2, 49.5, 42.2, 39.8, 39.4, 37.7, 36.8, 36.4, 36.1, 35.8, 34.4, 31.9, 31.8, 29.6, 28.1, 27.9, 27.5, 27.4, 22.5, 22.2, 22.1, 21.9, 20.9, 18.8, 18.7, 18.2, 16.8, 13.5, 11.3. MALDI-TOF MS: m/z Calc. for $C_{51}H_{82}N_8O_{12}$ 998.60; Obs. $[M+Na]^+$ 1021.58. HPLC-MS ($H_2O$/THF, gradient: 65-95% THF): t (prod)=2.20 min; m/z=999.60 $[M+H]^+$ (SIM mode). Note: THF-d8/$D_2O$ 95:5 was found to be an optimal solvent combination for NMR characterization. Nevertheless, the spectrum suffers from overlap and is very complicated. Therefore, integration is tentative.

Example 4. Synthesis of MDP-$DSPE_2$[Click](4)
(4)
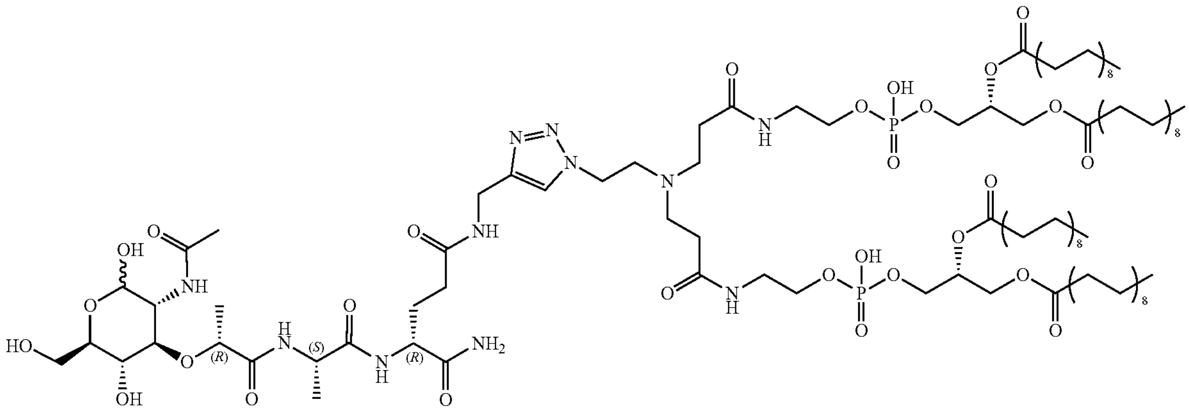
Molecular weight: 2192 Dalton.
Example 5. MDP-Chol2[Click]
(5)
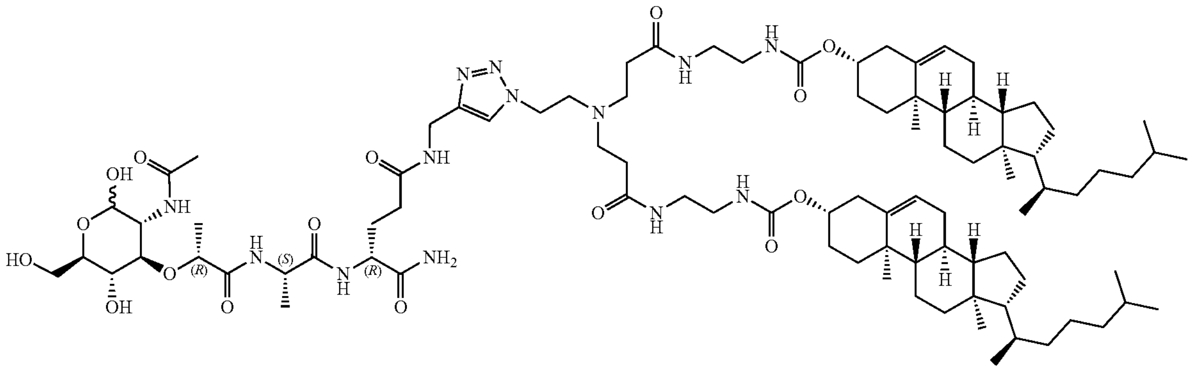
Molecular weight: 1669 Dalton. CLogP=15.31.
Example 6. MDP-DSG[Click](6)
(6)
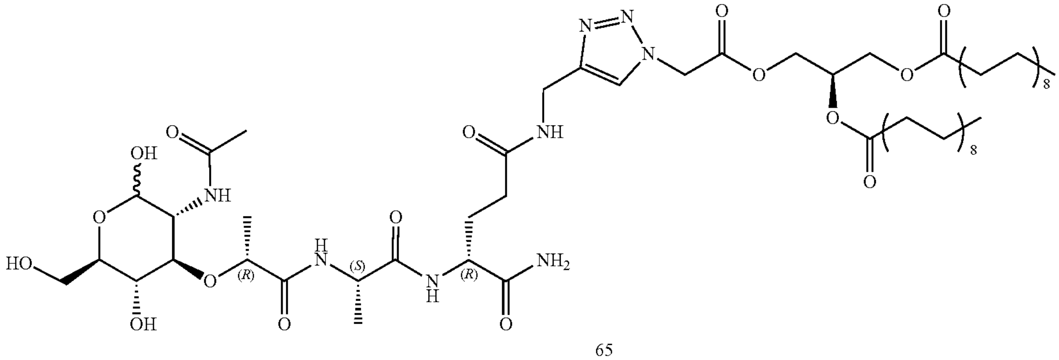
Molecular weight: 1238 Dalton. CLogP=12.45.

Example 7. MDP(Bn)-DSPE [Click](7)

(7)

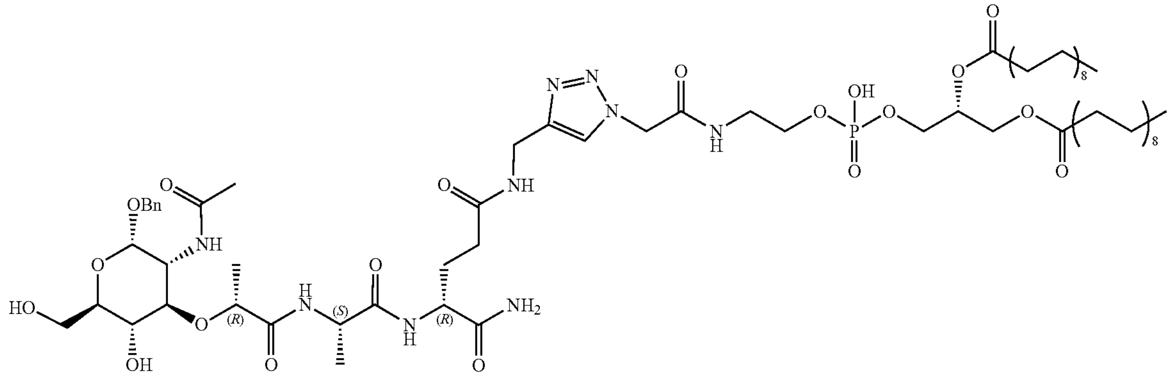

Molecular weight: 1451 Dalton. CLogP=13.85 (uncharged) and 8.06 (negatively charged).

Following the general conditions for Cu-click reactions, MDP(Bn)-propargyl (0.028 g, 0.045 mmol, 1.00 eq) and DSPE-azidoacetate (0.039 g, 0.047 mmol, 1.05 eq) were reacted overnight. During the reaction, some material precipitated out, resulting in a white suspension/emulsion. Afterwards, the reaction mixture was diluted with chloroform/MeOH 1:1. The resulting clear solution was impregnated on celite (~200 mg, 1:3 loading ratio). The impregnated crude product was first purified by automated column chromatography (reversed-phase (C18); product:C18-silica 1:200; detection: ELSD and UV 200-400 nm), eluting with water/THF 60/40-20/80. The combined product fractions were lyophilized and then purified again by automated column chromatography (normal phase (silica); product: silica 1:300; detection: ELSD), eluting with chloroform/MeOH/water 90/9/1-75/22.5/2.5. Pure fractions were concentrated in vacuo, dissolved in water/THF 70/30 and lyophilized. Thus, pure product was obtained as a white fluffy solid (0.027 g, 41%).

$^1$H NMR (400 MHz, $CDCl_3$+MeOD 1:1) δ 7.99 (d, J=8.2 Hz, 1H), 7.90 (s, 1H), 7.43-7.23 (m, 5H), 5.24 (m, 1H), 5.13 (s, 2H), 4.93 (d, J=3.5 Hz, 1H), 4.73 (d, J=12.0 Hz, 1H), 4.51 (d, J=12.0 Hz, 2H), 4.48-4.40 (m, 2H), 4.37-4.15 (m, 3H), 4.05-3.89 (m, 5H), 3.86-3.73 (m, 2H), 3.71-3.53 (m, 3H), 3.49-3.42 (m, 2H), 2.37-2.28 (m, 6H), 2.25-2.11 (m, 1H), 2.05-1.89 (m, 4H), 1.67-1.56 (m, 4H), 1.52-1.19 (m, 72H), 0.89 ppm (t, J=6.8 Hz, 611). $^{13}$C NMR (100 MHz, MeOD) δ 174.97, 174.73, 173.93, 173.66, 173.57, 173.46, 171.92, 166.34, 137.16, 128.28, 128.09, 127.84, 124.43, 96.38, 79.09, 76.52, 72.55, 70.40, 69.75, 69.28, 63.66, 63.44, 62.56, 61.14, 53.18, 52.60, 52.13, 49.45, 40.52, 34.62, 34.12, 33.96, 31.81, 31.73, 29.57, 29.53, 29.43, 29.41, 29.23, 29.21, 29.03, 29.00, 27.12, 24.82, 24.77, 22.52, 22.20, 18.70, 16.75, 13.69 ppm. MALDI-TOF: m/z calcd for $C_{72}H_{124}N_9O_{19}P+2Na^+—H^+$: 1494.85 $[M+2Na—H]^+$; found: 1494.94. HPLC-MS (water/THF, gradient: 55-95% THF): t (product)=5.09 min; m/z=1450.9 $[M+H]^+$ and 1472.9 $[M+Na]^+$ (SIM mode).

Example 8. Synthesis of MDP(Bn)-chol[Click](8)

(8)

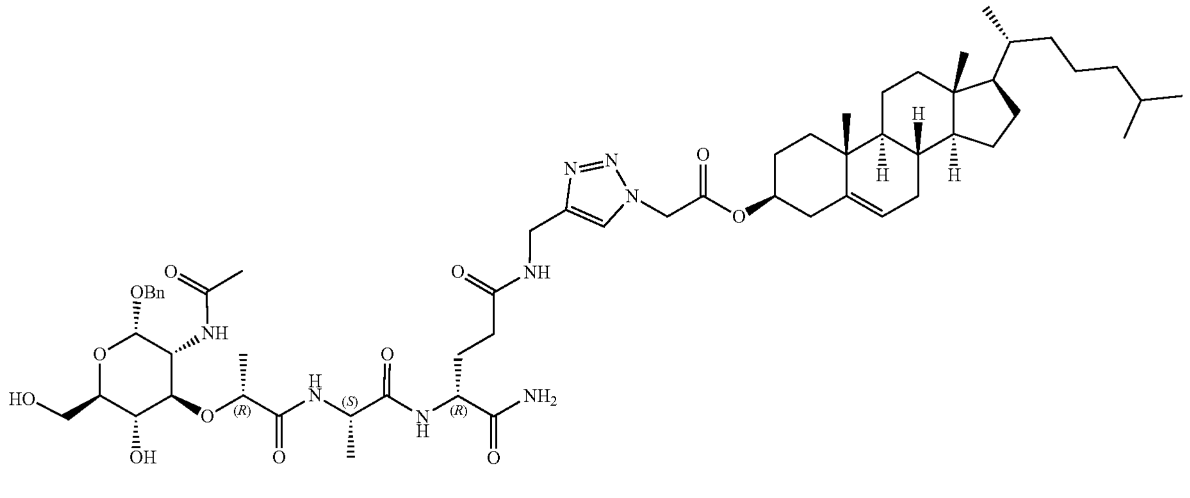

Molecular weight: 1089 Dalton. CLogP=6.83.

Following the general conditions for Cu-click reactions, MDP(Bn)-propargyl (0.030 g, 0.048 mmol, 1.00 eq) and cholesterol azidoacetate (0.025 g, 0.053 mmol, 1.10 eq) were reacted overnight, resulting in a white emulsion. The reaction mixture was then concentrated in vacuo and impregnated on celite (150 mg). The impregnated crude product was purified by automated column chromatography (reversed-phase (C18); product:C18-silica 1:200; detection: 200-400 nm), eluting with water/THF 70/30-15/85. The combined product fractions were lyophilized and then purified again by automated column chromatography (normal phase (silica); product:silica 1:350; detection: ELSD), eluting with chloroform/MeOH 96/4-86/14. Pure fractions were concentrated in vacuo, giving pure product as a white solid (0.028 g, 53%).

$^1$H NMR (400 MHz, $CDCl_3$+MeOD 1:1) δ 7.78 (s, 1H), 7.39-7.28 (m, 5H), 5.38 (d, J=5.1 Hz, 1H), 5.16 (d, J=1.6 Hz, 2H), 4.93 (d, J=3.6 Hz, 1H), 4.70 (d, J=11.8 Hz, 2H), 4.56-4.37 (m, 3H), 4.30 (dt, J=8.9, 4.4 Hz, 1H), 4.27-4.17 (m, 2H), 4.02 (dd, J=10.1, 3.6 Hz, 1H), 3.93-3.67 (m, 24H), 3.67-3.53 (m, 3H), 3.40 (d, J=3.2 Hz, OH), 2.44-2.32 (m, 2H), 2.27 (td, J=7.1, 3.7 Hz, 2H), 2.12 (dtd, J=14.9, 7.5, 4.3 Hz, 1H), 2.07-1.74 (m, 8H), 1.72-1.42 (m, 5H), 1.38 (dd, J=13.0, 7.0 Hz, 7H), 1.34-0.94 (m, 13H), 0.92 (d, J=6.4 Hz, 3H), 0.87 (dd, J=6.6, 1.8 Hz, 6H), 0.69 ppm (s, 3H). $^{13}$C NMR (100 MHz, $CDCl_3$+MeOD 1:1) δ 175.17, 174.60, 173.71, 173.62, 171.76, 166.21, 145.18, 139.13, 137.21, 128.65, 128.37, 128.25, 124.35, 123.47, 96.91, 79.14, 76.83, 76.49, 72.44, 69.79, 61.63, 56.82, 56.28, 53.17, 52.57, 51.14, 50.14, 49.78, 42.45, 39.84, 39.65, 38.01, 36.97, 36.68, 36.32, 35.93, 34.85, 32.02, 31.97, 29.81, 28.34, 28.14, 27.74, 27.58, 24.39, 23.95, 22.87, 22.80, 22.77, 22.61, 21.16, 19.34, 18.98, 18.80, 16.90, 11.94 ppm. MALDI-TOF: m/z calcd for $C_{55}H_{88}N_8O_{12}$+$Na^+$: 1111.64 $[M+Na]^+$; found: 1111.65. HPLC-MS (water/THF, gradient: 65-95% THF): t (product)=2.79 min; m/z=1089.70 $[M+H]^+$ (SIM mode).

Example 9. Synthesis of MTP-b-C18[Invclick](9)

(9)

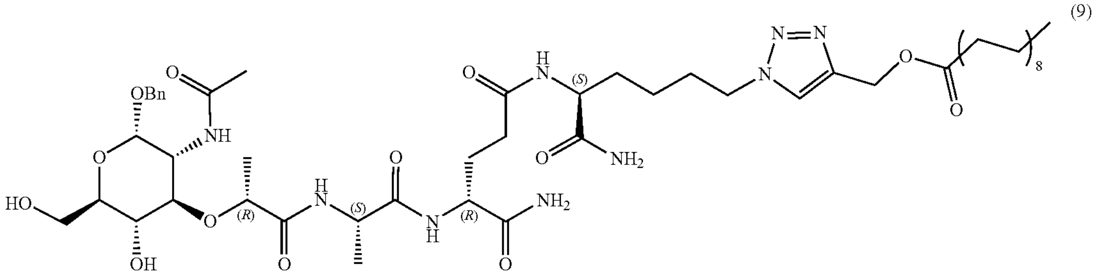

Molecular weight: 1058 Dalton. CLogP=5.68.

MTP-b-N3 (26 mg, 35 mol) and prop-2-yn-1-yl stearate (11.3 mg, 35 μmol, 1 eq) were suspended in THF (0.36 mL) and 0.4 M ascorbic acid (0.18 mL, 2 eq) was added yielding a clear solution. Prop-2-yn-1-yl stearate was prepared using known procedures. Under vigorous stirring 0.2 M $CuSO_4 \cdot 5H_2O$ (0.18 mL, 1 eq) was added and the mixture was vigorously stirred at room temperature (initially gelation occurred but gentle heating resulted in a yellow solution). After 1 h, HPLC-MS ($THF/H_2O$) indicated the absence of starting compounds and the opaque solution was lyophilized. The crude product was adsorbed onto Celite from chloroform/MeOH 2:1 and subjected to column chromatography (flash $SiO_2$) using an elution gradient of 10% to 25% MeOH in chloroform. Column chromatography was repeated using a similar gradient yielding pure product (31.5 mg, 30 mol, 84%) as a white fluffy solid after lyophilization from $THF/H_2O$. $^1$H-NMR (400 MHz, THF-d8/$D_2O$ 4:1): δ=7.92 (s, 1H), 7.31 (d, J=7.5 Hz, 2H), 7.23 (t, J=7.5 Hz, 2H), 7.15 (t, J=7.3 Hz, 1H), 5.04 (s, 2H), 4.74 (d, J=3.5 Hz, 1H), 4.63 (d, J=12.2 Hz, 1H), 4.40 (d, J=12.2 Hz, 11H), 4.31-4.15 (m, 6H), 3.96 (dd, J=10.5, 3.6 Hz, 1H), 3.66 (d, J=3.2 Hz, 2H), 3.59-3.45 (m, 3H), 2.22 (dt, J=15.3, 7.7 Hz, 4H), 2.09 (tt, J=12.9, 6.0 Hz, 1H), 1.87-1.70 (m, 6H), 1.64-1.54 (m, 1H), 1.47 (q, J=7.3 Hz, 2H), 1.32 (d, J=7.2 Hz, 3H), 1.28 (d, J=6.7 Hz, 3H), 1.18 (s, 30H), 0.78 (t, J=6.6 Hz, 3H). $^{13}$C-NMR (100 MHz, THF-d8/$D_2O$ 4:1): δ=175.5, 174.9, 174.8, 173.73, 173.66, 173.2, 171.7, 142.3, 137.8, 128.1, 128.0, 127.4, 124.3, 96.6, 80.0, 77.3, 72.8, 69.1, 68.8, 60.9, 57.2, 53.2, 53.1, 52.2, 49.7, 49.5, 33.6, 31.8, 31.5, 30.9, 29.7, 29.54, 29.50, 29.4, 29.24, 29.20, 29.0, 27.7, 22.54, 22.49, 21.9, 18.6, 16.9, 13.5. MALDI-TOF MS: m/z Calc. for $C_{53}H_{87}N_9O_{13}$ 1057.64; Obs. $[M+Na]^+$ 1080.63, $[M+K]^+$ 1096.65. HPLC-MS ($H_2O$/THF, gradient: 65-95% THF): t (prod)=2.15 min; m/z=1058.60 $[M+H]^+$ (SIM mode).

Example 10. Synthesis of MTP-b-C18 (10)

(10)

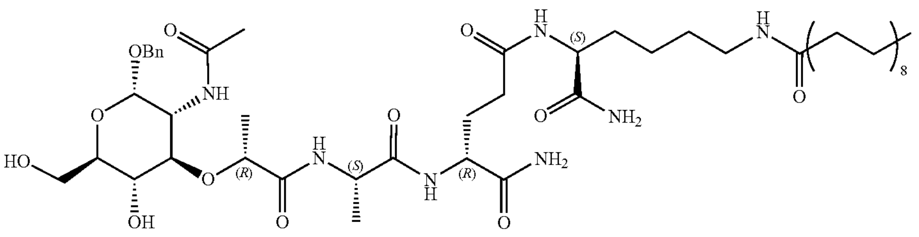

Molecular weight: 976 Dalton. CLogP=5.31

A 10 mL PE syringe with PE frit was charged with MTP-b on-resin (137 mg, approx. 0.0493 mmol MTP-b, 1.00 eq). The resin was swollen in DMF (5 mL) for 30 min. Next, the resin was treated twice with 2% hydrazine hydrate solution in DMF (10 mL) for 15 min. The hydrazine solution was removed and the resin washed with DMF (4×5 mL). Next, a solution of 2,3,5,6-tetrafluorophenyl stearate (0.064 g, 0.15 mmol, 3.00 eq) and 4-methylmorpholine (0.030 g, 0.033 mL, 0.30 mmol, 6.00 eq) in DMF/DCM (1+1 mL; ~0.075 M) was added. The beads were agitated overnight at RT. Afterwards, the supernatant was removed and the resin washed with DMF/DCM 50/50 (4×5 mL) and DCM (2×5 mL). The resin was then treated with TFA/TIPS/water 95/2.5/2.5 (200 uL) for 1 h. The filtrate was collected and the resin washed with additional cleavage cocktail. The combined filtrates were concentrated in vacuo, giving the crude product as a white solid. The material was impregnated on celite (200 mg, 1:4 loading ratio) from THF/water solution (95/5). The impregnated crude product was purified by automated column chromatography (reversed-phase (C18); product:C18-silica 1:250; detection: ELSD), eluting with water/THF 50/50-10/90. The combined product fractions were lyophilized and then purified again by automated column chromatography (normal phase (silica); product: silica 1:500; detection: ELSD), eluting with dichloromethane/MeOH 90/10-70/30. Pure fractions were concentrated in vacuo, giving the product as a white solid (0.016 g, 33%). $^1$H NMR (400 MHz, $CDCl_3$+TFA-d3) 6 7.40-7.24 (m, 5H), 4.94-4.89 (m, 1H), 4.71-4.65 (m, 1H), 4.57-4.17 (m, 6H), 4.03-3.74 (m, 4H), 3.38 (bs, 2H), 2.60-2.22 (m, 5H), 2.30 (s, 1H), 2.11-1.55 (s, 11H), 1.50-1.17 (m, 36H), 0.87 ppm (t, J=6.6 Hz, 3H). HPLC-MS (water/MeCN): t (product)=5.64 min. Found: m/z=976.33 $[M+H]^+$ (pos. mode); 1020.25 $[M+HCOO]^-$ (neg. mode).

Example 11. Synthesis of MDP-C18 (11)

(11)

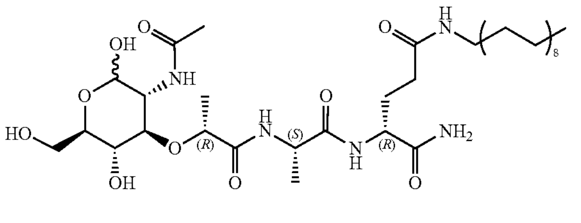

Molecular weight: 744 Dalton. CLogP=4.79.

MDP (10 mg, 20 μmol), octadecyl amine (5.2 mg, 0.95 eq.), NHS (2.4 mg, 1 eq.) and EDC-HCl (7.9 mg, 2 eq.) were stirred in DMF (0.7 mL) at 50° C. for 3 hours. The reaction mixture was subsequently allowed to cool to room temperature and stirred for another 16 hours. The resulting dispersion was heated to 40° C. to redissolve all the precipitated solids and subsequently precipitated with 5 mL ether. The collected precipitate was washed 2 more times with ether, dried and then suspended in demineralized water, collected by centrifugation, resuspended in demineralized water, and again collected by centrifugation. The resulting solid was lyophilized to remove all water to afford 13.8 mg (96%) of the desired compound as a white powder. $^1$H NMR (400 MHz, DMF-d7) 6 8.31 (d, J=7.7 Hz, minor isomer), 8.23 (d, J=8.0 Hz, major isomer), 8.12 (d, J=7.9 Hz, minor isomer), 8.09 (d, J=7.6 Hz, major isomer), 7.96 (d, J=6.6 Hz, minor isomer), 7.90 (d, J=6.5 Hz, major isomer), 7.77 (m, 1H), 7.47 (m, 1H), 7.10 (m, minor isomer), 7.01 (m, major isomer), 6.86 (d, J=6.0 Hz, minor isomer), 6.74 (dd, J=4.1, 1.2 Hz, major isomer), 5.44-5.29 (m, 1H), 5.16 (t, J=3.7 Hz, major isomer), 4.79 (t, J=6.1 Hz, minor isomer), 4.60 (dd, J=8.2, 6.0 Hz, minor isomer), 4.57-4.22 (m, 4H), 3.93-3.57 (m, 5H), 3.45 (m, 1H), 3.13 (m, 2H), 2.42-2.07 (m, 3H), 2.00-1.78 (m, 4H), 1.56-1.07 (m, 38H), 0.88 (m, 3H) ppm. $^{13}$C NMR (101 MHz, DMF-d7) 6 174.25, 174.20, 173.93, 173.89, 172.75, 172.56, 172.07, 172.02, 171.76, 170.11, 96.92, 91.66, 82.46, 79.55, 77.39, 77.00, 72.97, 71.30, 70.95, 62.05, 57.49, 54.49, 53.16, 53.03, 49.54, 39.26, 32.55, 32.05, 29.83, 29.49, 28.62, 28.41, 27.18, 22.86, 22.76, 22.73, 19.19, 17.80, 17.62, 13.93 ppm. ESI-MS: m/z 743.50 (calc.), found 744.42 ($M+H^+$), 788.33 ($M-FA^-$).

Example 12. Synthesis of MDP-DSPE (12)

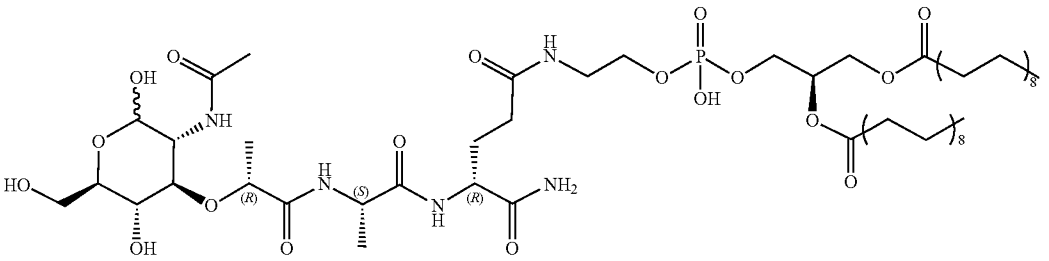

(12)

Molecular weight: 1223 Dalton. CLogP=12.96 (uncharged) and 7.18 (negatively charged).

MDP (14 mg, 29 μmol), NHS (5.6 mg, 1.7 eq.), and DIC (7.3 mg, 2 eq) were stirred in 0.9 mL DMF for 2 hours to activate the MDP. The resulting mixture was added to a dispersion of DSPE (17 mg, 0.8 eq.) in 2.7 mL tert-butanol with TEA (9 mg, 3.1 eq.) at 50° C. and stirred for 3½ hours at that temperature. The resulting mixture was evaporated to dryness and the resulting material was purified by repeated column chromatography ($SiO_2$, $CHCl_3/MeOH/H_2O$, 70/30/5, 5:4:1 and gradient 95/5/0 to 60/40/0) to afford 6 mg (21%) of the desired compound as a white fluffy material after lyophilization from water/THF. $^1H$-NMR (400 MHz, $CDCl_3/CD_3OD$ 5:) δ 5.29 (d, major isomer), 5.24 (m, 1H), 4.54 (d, minor isomer), 4.47 (m, obscured by HDO), 4.41 (dd, obscured by HDO), 4.31 (m, obscured by HDO), 4.19 (dd, 1H), 4.00-3.90 (m, mixture of isomers), 3.87-3.75 (m, mixture of isomers), 3.72 (m, 1H), 3.63 (m, 1H), 3.53-3.30 (m, obscured by $CD_3OD$), 2.37-2.26 (m, 5H), 2.25-2.10 (m, 2H), 2.10-1.92 (m, 4H), 1.61 (m, 4H), 1.50-1.15 (br.m, 62H), 0.88 (t, 6H) ppm. $^{31}P$-NMR (162 MHz, $CDCl_3/CD_3OD$ 5:1) δ 0.14 (br.m) ppm. $^{13}C$-NMR (101 MHz, $CDCl_3/CD_3OD$ 5:1) δ 174.63, 174.00, 173.27, 173.08, 172.92, 172.89, 171.34, 90.19, 75.19, 71.09, 70.18, 69.73, 69.65, 63.24, 62.76, 61.86, 60.84, 53.13, 52.04, 48.77, 48.19, 39.71, 33.48, 33.32, 31.29, 31.14, 28.91, 28.87, 28.76, 28.74, 28.57, 28.54, 28.37, 28.34, 26.44, 24.14, 24.10, 21.88, 21.78, 18.35, 15.98, 13.14 ppm. MALDI-MS: m/z 1221.77 (calc.), found 1220.82 ($M-H^-$), negative mode. HPLC-ELSD (C18, 65-95% $THF/H_2O$): single peak plus shoulder for the alpha and beta isomers.

Example 13. Synthesis of MTP-b-DSG (13)

A 20 mL PE syringe with PE frit was charged with MTP-b on-resin (0.291 g, approx. 0.11 mmol MTP-b, 1.00 eq). The resin was swollen in DMF (5 mL) for 30 min. Next, the resin was treated twice with 2% hydrazine hydrate solution in DMF (5 mL) for 15 min. The hydrazine solution was removed and the resin washed with DMF (4×5 mL). Next, a solution of DSG 4-nitrophenylcarbonate (0.249 g, 0.32 mmol, 3.00 eq) and N,N-diisopropylethylamine (0.081 g, 0.110 mL, 0.63 mmol, 6.00 eq) in chloroform (4 mL) was added. The beads were agitated overnight at RT. Afterwards, the bright yellow supernatant was removed and the resin washed with chloroform (3×5 mL), MeOH (3×5 mL) and again chloroform (2×5 mL). The resin was treated with TFA/TIPS/water 95/2.5/2.5 (5 mL) for 45 min. The supernatant was injected into ice-cold diethyl ether (100 mL) under stirring, resulting in the slow formation of a white flocculate. This cleavage and precipitation procedure was repeated twice. The solids were collected by filtration through a disposable PE filter, giving crude product as a white solid. The material was impregnated on celite (250 mg, 1:2.5 loading ratio) from chloroform/MeOH (1:2) solution. The impregnated crude product was purified by automated column chromatography (reversed-phase (C18); product:C18-silica 1:150; detection: 200-400 nm), eluting with water/THF 60/40-0/100. The combined product fractions were lyophilized and then purified again by automated column chromatography (normal phase (silica); product: silica 1:250; detection: 200-400 nm), eluting with chloroform/MeOH 95/5-60/40. Pure fractions were concentrated in vacuo, giving the product as a white solid (0.030 g, 21%).

$^1H$ NMR (400 MHz, $CDCl_3$+MeOD) δ 7.39-7.27 (m, 5H), 5.25 (p, J=5.3 Hz, 1H), 4.89 (d, J=3.5 Hz, 1H), 4.73 (d, J=11.9 Hz, 1H), 4.50 (d, J=11.9 Hz, 1H), 4.42-4.31 (m, 2H),

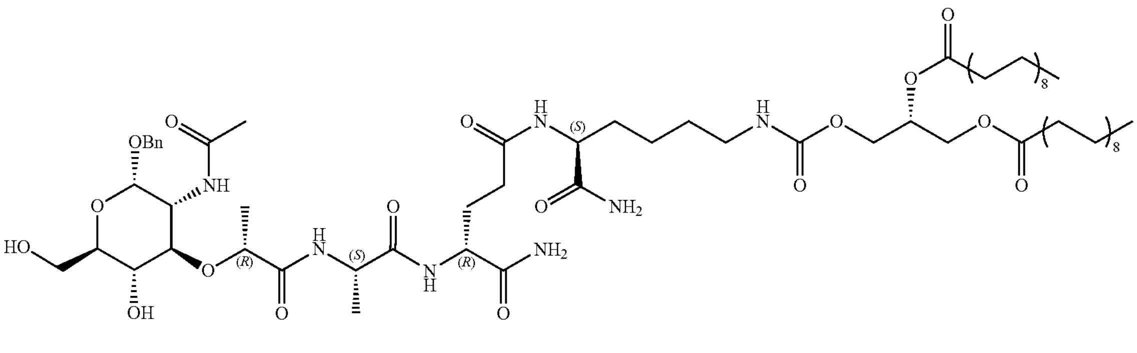

(13)

Molecular weight: 1361 Dalton. CLogP=15.05.

4.31-4.19 (m, 4H), 4.15 (dd, J=11.9, 6.2 Hz, 2H), 4.10-3.97 (m, 1H), 3.87-3.75 (m, 2H), 3.72-3.53 (m, 3H), 3.12 (t, J=6.9 Hz, 2H), 2.37-2.27 (m, 6H), 2.26-2.13 (m, 1H), 1.93 (s, 3H), 1.92-1.74 (m, 2H), 1.71-1.56 (m, 6H), 1.56-1.47 (m, 2H), 1.43 (d, 7.0 Hz, 3H), 1.40 (d, 7.0 Hz, 3H), 1.36-1.19 (s, 56H), 0.89 ppm (t, J=6.7 Hz, 6H). $^{13}$C NMR (100 MHz, $CDCl_3$+MeOD) δ 175.80, 174.79, 174.30, 173.86, 173.76, 173.44, 173.25, 171.70, 156.58, 137.07, 128.36, 128.14, 127.95, 96.52, 79.36, 76.83, 72.38, 69.48, 69.43, 69.37, 62.50, 62.29, 61.30, 53.52, 53.24, 51.71, 49.46, 40.33, 34.13, 33.97, 31.82, 31.29, 31.08, 29.58, 29.54, 29.52, 29.41, 29.39, 29.25, 29.20, 29.18, 29.09, 29.01, 28.98, 28.16, 24.80, 24.77, 22.88, 22.55, 22.35, 18.61, 16.89, 13.77 ppm. HPLC-MS (water/THF, gradient: 55-95% THF): t (product)=6.20 min. Found: m/z=1360.9 $[M+H]^+$ and 1382.9 $[M+Na]^+$ (SIM mode).

Example 14. Synthesis of MTP(Bn)-a-DPPE (14)

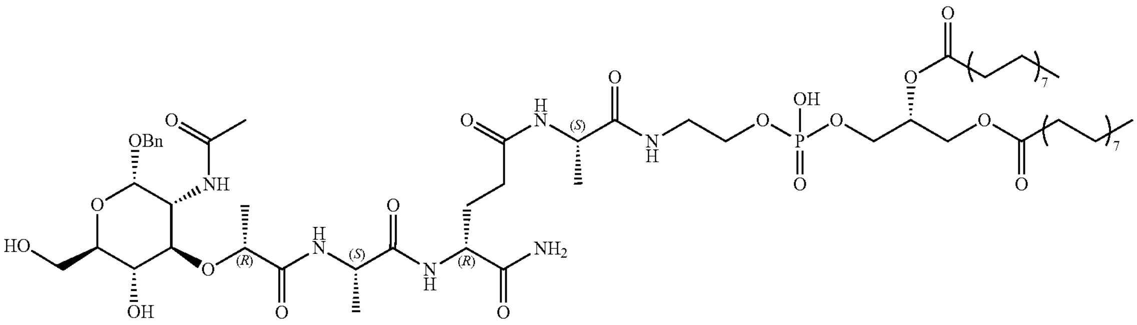

Molecular weight: 1328 Dalton. CLogP=12.88 (uncharged) and 7.09 (negatively charged)

Building Block (CBz)-Ala-DPPE

N-CBz-protected L-alanine (390 mg, 1.7 mmol) and N-hydroxysuccinimide (222 mg, 1.89 mmol, 1.1 eq) were dissolved in chloroform (6 mL), yielding an almost clear solution. N,N'-Diisopropylcarbodiimide (DIC; 0.32 mL, 2.0 mmol, 1.2 eq) was added and the mixture was stirred at r.t. for 40 min (after 1 min the solution turns hazy and after 25 min 1H-NMR shows full conversion). This solution was then added to a 60° C. solution containing 1,2-dipalmitoyl-sn-glycero-3-phosphoethanolamine (DPPE; 1.06 g, 1.5 mmol, 0.9 eq) and triethylamine (600 μL, 0.71 mmol, 2.5 eq) in chloroform (12 mL; DPPE dissolved at reflux and triethylamine was added at a lowered temperature). The resulting clear solution was stirred at 60° C. for 1 h (the solution remains clear and after 1 h $^1$H-NMR shows full conversion). Chloroform (360 mL) was added and the organic layer was gently washed with 0.1 M HCl (100 mL). The organic layer was dried using $Na_2SO_4$, filtrated and the solvent was removed in vacuo. Column chromatography (flash $SiO_2$) using an elution gradient of 2% to 30% methanol in chloroform yielded the title compound that was partly contaminated with triethylamine. The impure fractions were dissolved in chloroform and the organic layer was gently washed with 0.1 M HCl. The organic layer was dried using $Na_2SO_4$, filtrated and the solvent was removed in vacuo. This effectively removed triethylamine and the pure fractions were combined yielding pure product (1.22 g, 1.4 mmol, 91%) as a colorless waxy solid.

$^1$H-NMR (400 MHz, DMSO-d6): δ=8.06 (t, J=5.7 Hz, 1H), 7.47-7.22 (m, 6H), 5.15 (dq, J=8.3, 4.6 Hz, 1H), 5.01 (q, J=12.6 Hz, 2H), 4.28 (dd, J=12.0, 3.2 Hz, 1H), 4.11 (dd, J=12.1, 7.0 Hz, 1H), 4.06-3.92 (m, 3H), 3.82 (q, J=6.4 Hz, 2H), 3.33-3.18 (m, 2H), 2.27 (dt, J=12.8, 5.0 Hz, 4H), 1.50 (q, J=6.9 Hz, 4H), 1.32-1.16 (m, 51H), 0.85 (t, J=6.7 Hz, 6H). $^{31}$P-NMR (162 MHz, DMSO-d6): δ=−1.4.

Building Block Ala-DPPE

In a 2-neck round-bottom flask (CBz)-Ala-DPPE (308 mg, 0.34 mmol) and Pd/C (374 mg, 10% Pd, pre-wetted Degussa/Evonik type) were combined in chloroform/ethanol 1:2 (36 mL). The flask was evacuated and back-filled with Ar three times. A $H_2$-balloon was attached, the flask was evacuated and back-filled with $H_2$ three times and the mixture was stirred under a positive $H_2$ pressure for 3 h at room temperature. The solution was filtrated over Celite which was copiously washed with ethanol, chloroform/ethanol 1:1 and chloroform. The combined filtrates were evaporated to dryness, the resulting compound was dissolved in chloroform/ethanol 2:1 (90 mL) and dried using $Na_2SO_4$. The solution was filtrated over Celite which was copiously washed with chloroform/ethanol 2:1. The filtrate was evaporated to dryness yielding the product (224 mg, 0.29 mmol, 86%) as a slightly yellowish waxy solid, which contained trace amounts of Pd.

$^1$H-NMR (400 MHz, DMSO-d6): δ=8.60 (br, 1H), 8.08 (br, 2H), 5.15 (br, 1H), 4.28 (d, J=13.2 Hz, 1H), 4.12 (dd, J=6.9 Hz, 1H), 4.00 (m, 2H), 3.88 (m, 2H), 3.80 (br, 1H), 3.09 (br, 1H), 2.35-2.23 (m, 4H), 1.50 (br, 4H), 1.41-1.14 (m, 51H), 0.85 (t, J=6.6 Hz, 6H). $^{31}$P-NMR (DMSO-d6): δ=−1.4.

MTP(Bn)-a-DPPE (14)

MDP(Bn) (20.0 mg, 34 μmol) and Ala-DPPE (26.2 mg, 34 μmol, 1.0 eq) were combined in DMAc (0.3 mL) and N,N-diisopropylethylamine (24 μL, 0.14 mmol, 4 eq) and PyBOP (22 mg, 41 μmol, 1.2 eq) were added consecutively. The resulting suspension was stirred at 50° C. for 1 h, after which the mixture had almost cleared. The volatiles were removed in vacuo (oil pump, 45° C.) and the mixture was flushed once with chloroform. Column chromatography (flash $SiO_2$) using an elution gradient of 15% to 40% methanol in chloroform was followed by automated column chromatography (reversed-phase C18; product:C18-silica 1:200; detection: λ=200-220 nm), using an elution gradient of 30% to 80% THF in $H_2O$. This yielded product 14 (8.0 mg, 6 μmol, 18%) as a white fluffy solid after lyophilization. HPLC-MS: t[product]=3.92 min.; m/z=1327.80 $[M+H]^+$ (SIM mode). HPLC-ELSD: t[prod]=3.48 min; 99.2% relative peak area.

Example 15. MTP-a-chol

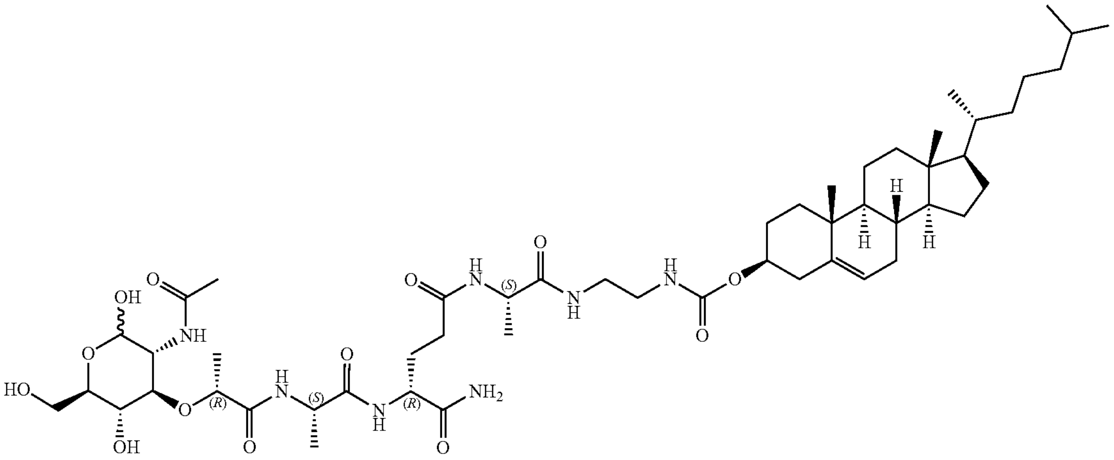

Molecular weight: 1018 Dalton. CLogP=5.64.

N-(2-aminoethyl)-cholesterol carbamate building block.

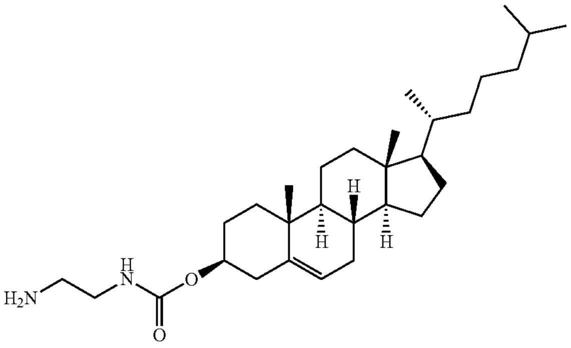

A solution of cholesterol chloroformate (0.95 g, 2.1 mmol) in 20 mL DCM was slowly added to a solution of ethylenediamine (2 mL, 14 eq.) in 30 mL DCM in about 2 hours.

The reaction was allowed to proceed for another 30 minutes, after which the reaction mixture was evaporated to dryness. The resulting white material was purified via column chromatography ($SiO_2$, $CHCl_3$/MeOH/formic acid 78:20:2), yielding 720 mg (72%) of the desired compound as a white solid.

$^{1}H$ NMR (400 MHz, $CDCl_3$) δ 5.46-5.27 (m, 1H), 4.99 (br. s, 1H), 4.50 (br.m, 1H), 3.22 (q, J=5.6 Hz, 2H), 2.82 (t, J=5.9 Hz, 2H), 2.43-2.19 (m, 2H), 2.06-1.75 (m, 5H), 1.64-0.80 (m, 35H), 0.68 (s, 3H) ppm. $^{13}C$ NMR (101 MHz, $CDCl_3$) δ 156.41, 139.83, 122.47, 74.31, 56.68, 56.13, 50.00, 43.63, 42.30, 41.79, 39.73, 39.51, 38.57, 36.99, 36.56, 36.18, 35.79, 31.90, 31.87, 28.22, 28.17, 28.00, 24.28, 23.82, 22.81, 22.55, 21.03, 19.33, 18.71, 11.85. MALDI: m/z=472.40 (calc.), found: 495.39 (M+Na+). A prominent peak is observed at m/z=369.37, which is attributed to a 3,4-eliminated product formed in MALDI (not observed in NMR).

This building block can be coupled to N-Boc-L-Alanine (CAS [15761-38-3]) via amidation; next the Boc-group can be deprotected; finally, the formed amine functional molecule can be coupled to MDP to arrive at MTP-a-chol.

Example 16. MDP(Bn)-chol
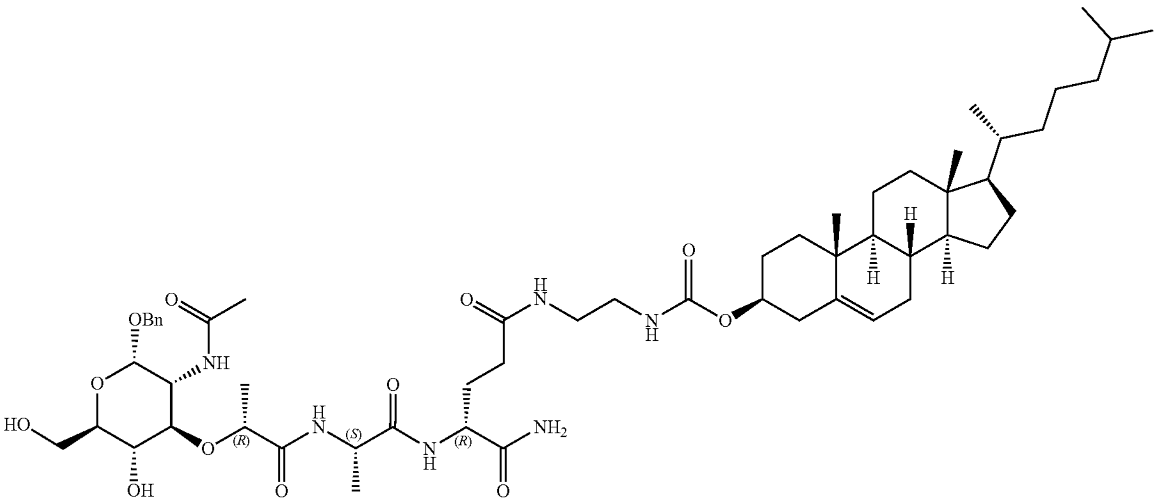
Molecular weight: 1037 Dalton. CLogP=7.69.
The N-(2-aminoethyl)-cholesterol carbamate building block (see Example 15) can be coupled to MDP(Bn) via amidation, arriving at molecule MDP(Bn)-chol.
Example 17 (MTP-a-DSPE), Example 18 (MTP (Bn)-a-DSPE) and Example 19 (MDP(Bn)-DSPE)
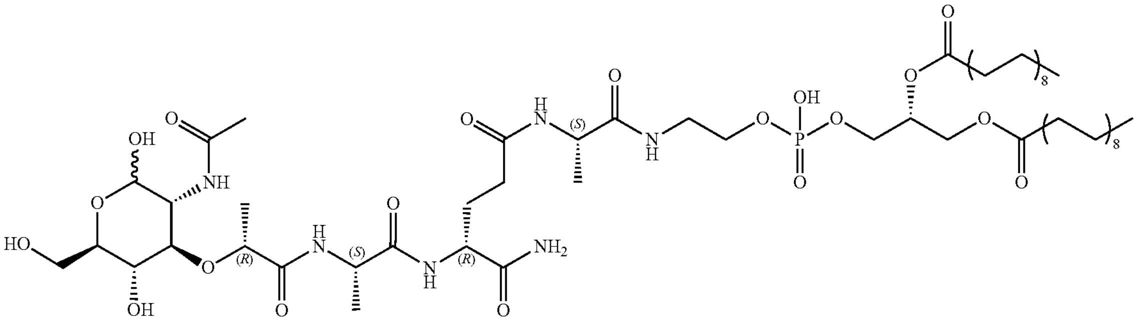
MTP-a-DSPE
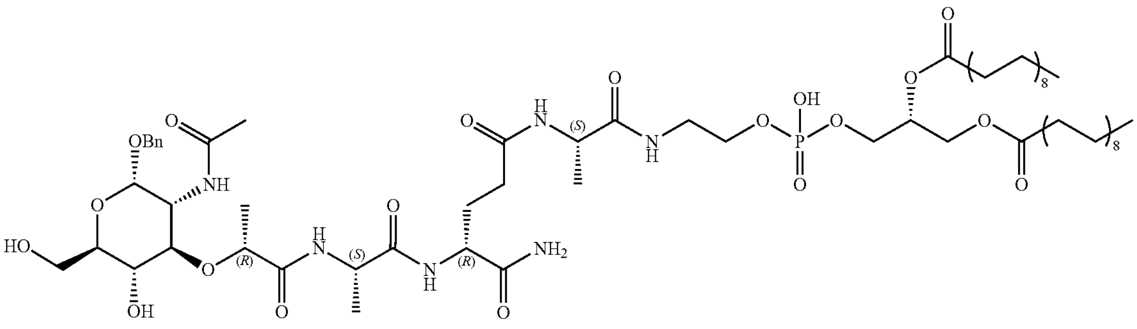
MTP(Bn)-a-DSPE -continued

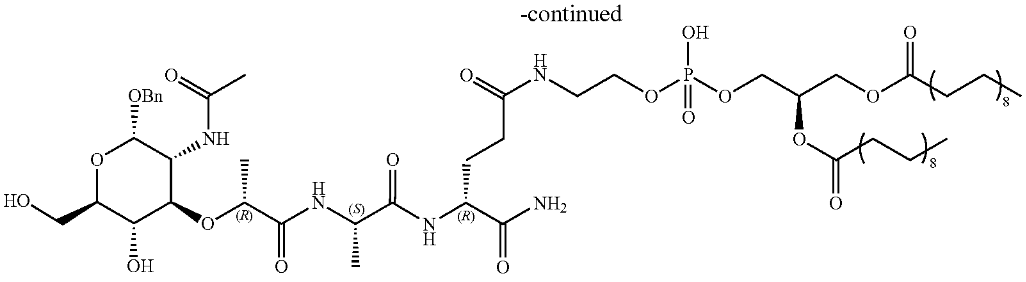

MDP(Bn)-DSPE

MTP-a-DSPE: MW is 1294 Dalton. CLogP=12.70 and 6.92 (uncharged and charged).

MTP(Bn)-a-DSPE: MW is 1384 Dalton. CLogP=14.99 and 9.21 (uncharged and charged).

MDP(Bn)-DSPE: MW is 1313 Dalton. CLogP=15.25 and 9.46 (uncharged and charged).

1,2-Distearoyl-sn-glycero-3-phosphoethanolamine (DSPE; CAS [1069-79-0]) can be connected to N-Boc-L-Alanine (CAS [15761-38-3]) via amidation; next the Boc-group can be deprotected; finally, the formed amine functional molecule can be either coupled to MDP, to arrive at MTP-a-DSPE, or to MDP(Bn), to arrive at MTP(Bn)-a-DSPE.

Alternatively, DSPE can be coupled to MDP(Bn) via amidation, arriving at molecule MDP(Bn)-DSPE.

Example 20: Lipophilicity Studies

The C log P values of the exemplary compounds of the disclosure were assessed, using Perkin Elmer ChemDraw Professional, version 18.0.0231 (4029) software. The results show values from about 4.15 to 18.28. At the physiological pH of about 7.4 (i.e. COOH and $PO_3H$ groups become charged), 2 molecules of the invention have CLogP values between 4 and 5, three have values between 10 and 20, and the rest of the molecules have values between 5 and 10.

Experimentally, one can also compare lipophilicities of molecules by performing HPLC using the same elution gradient. Molecules that have higher affinities with the hydrophobic C18-material of the column are more lipophilic and as a result have a higher retention time. The below Table shows that the Example molecules of the invention (Entries 1-4) have higher retention times as compared to the Comparative Example molecules (Entries 5 and 6), and are thus more lipophilic.

Methods: HPLC-MS(SIM) and HPLC-ELSD were performed on a Phenomenex Kinetex 5 micrometer EVO C18 100 Å LC-column (50×2.1 mm) employing the same gradient from A to B eluent, where A=20 mM $NH_4HCO_2$ in $H_2O$ with 0.1 v/v % formic acid, and B=2-propanol/MeCN/$H_2O$ 85:15:5, also with 20 mM $NH_4HCO_2$ and 0.1 v/v % formic acid.

TABLE 3

HPLC-MS or HPLC-ELSD retention times of molecules with C16, C18 and/or benzyl lipophilic units.

| Entry | Example | Lipophilic unit(s) | CLogP (uncharged) (-) | CLogP (at pH = 7.4) (-) | HPLC-MS t (min) | HPLC-ELSD t (min) |
|---|---|---|---|---|---|---|
| 1 | 2 | C18 (2×) | 11.56 | 5.78 | 4.46 | 4.58 |
| 2 | 7 | C18 (2×)/Bn | 13.85 | 8.06 | 5.16 | 5.16 |
| 3 | 13 | C18 (2×)/Bn | 15.05 | 15.05 | n.d. | 5.49 |
| 4 | 14 | C16 (2×)/Bn | 12.88 | 7.09 | 3.61 | 3.5 |
| 5 | Comp-1 | C16 (2×) | 10.59 | 4.8 | 2.85 | 3.04 |
| 6 | Comp-2 | C18 | 5.39 | 1.39 | 0.95 | n.d. |

n.d. = not determined;
cmpd-1 = mifamurtide;
cmpd-2 = MDP-C18[mur]

Example 21. Aqueous Solubility Studies

Compounds of the disclosure were tested for their solubility in PBS-buffer and in water; applying low concentrations.

First, compounds were weighed in a vial and PBS buffer (137, 2.7, 10 and 1.8 mM in NaCl, KCl, $Na_2HPO_4$, $KH_2PO_4$, respectively; pH=7.4) was added, such that the concentration would become 0.2 mg/mL in case full dissolution would take place. The sample was shaken, left to stand for an hour, shaken again, and then the appearance of the solution at room temperature (RT) was checked. Next, the sample was warmed for 1 minute in a water bath of 37° C., and the appearance of the solution was checked again. In the below table the results are compiled.

None of the tested compounds spontaneously dissolve in PBS, not at room temperature and not at 37° C. In contrast, the tested Comparative Example compounds dissolve spontaneously under these conditions. Further treatment of the sample solutions with a heat gun did not give dissolution for entries 4, 5 and 6, while entries 2 and 3 gave hazy solutions after cooling down to RT.

TABLE 4

Solubility tests on solutions in PBS, at RT and at 37° C.

| Entry | Example | CLogP at pH = 7.4 | Appearance at RT | Appearance at 37° C. |
|---|---|---|---|---|
| 1 | Ex-2 | 5.78 | hazy | hazy |
| 2 | Ex-3 | 5.04 | suspension | hazy |
| 3 | Ex-7 | 8.06 | suspension | hazy |
| 4 | Ex-8 | 6.83 | suspension | suspension |
| 5 | Ex-11 | 4.79 | suspension | suspension |

TABLE 4-continued

| Solubility tests on solutions in PBS, at RT and at 37° C. | | | | |
|---|---|---|---|---|
| Entry | Example | CLogP at pH = 7.4 | Appearance at RT | Appearance at 37° C. |
| 6 | Ex-13 | 15.05 | suspension | suspension |
| 7 | Comp-1 | 4.80 | hazy | clear |
| 8 | Comp-2 | 1.39 | clear | clear |

cmpd-1 = mifamurtide;
cmpd-2 = MDP-C18[mur]

Next, compounds were weighed and dissolved in chloroform/methanol. The solutions were left to dry in a vial forming a film of the materials. The vials were put in vacuo to remove traces of organic solvent. Demineralized water was added, such that the concentration of the compounds would become 0.3 mM in case full dissolution would take place (0.3 mM corresponds to 0.3 mg/mL for a MW=1000 Dalton compound). The vial was briefly sonicated in a water bath, left to stand overnight, and once again sonicated (sonication at RT). The appearances of the solutions at RT were checked to assess solubilities. In the below table the results are compiled.

None of the tested compounds of the disclosure spontaneously dissolve in water at room temperature. In contrast, the tested Comparative Example compounds dissolve spontaneously under these conditions.

TABLE 5

| Solubility tests on solutions in water at RT | | | |
|---|---|---|---|
| Entry | Example | CLogP at pH = 7.4 | Appearance at RT |
| 1 | Ex-2 | 5.78 | Gelly/hazy/precipitate |
| 2 | Ex-3 | 5.04 | Gelly/hazy/precipitate |
| 3 | Ex-7 | 8.06 | Hazy |
| 4 | Ex-8 | 6.83 | Precipitate |
| 5 | Ex-9 | 5.68 | Precipitate |
| 6 | Ex-10 | 5.31 | Precipitate |
| 7 | Ex-11 | 4.79 | Precipitate |
| 8 | Ex-13 | 15.05 | Gel/precipitate |
| 9 | Comp-Ex-1 | 4.80 | Clear |
| 10 | Comp-Ex-2 | 1.39 | Clear |

cmpd-1 = mifamurtide;
cmpd-2 = MDP-C18[mur]

Finally, comparative Examples 1 and 2 were also tested with respect to their solubilities in PBS (0.01 M, pH=7.4) and demineralized water at a level of 1 mg/mL. The same results as indicated in the above two tables were found at this concentration.

Taken together, these results show that a series of compounds of the invention do not spontaneously dissolve in PBS or water at concentrations as low as 0.2 mg/mL (and higher). In contrast, comparative Example materials are soluble in PBS or water to give clear and transparent solutions at concentrations as high as at least 0.2 mg/mL or even 1 mg/mL.

Because the disclosed compounds have a low solubility in aqueous solution, their physico-chemical properties find particular use in producing stable HDL-derived NPs. Without being bound by theory, it is thought that the disclosed compounds provide improved anchoring into the NPs, reducing leakage, and providing products with greater stability and shelf-life.

Example 22. Degradation by Augmented Oxidation Test

The reference compounds MDP and MDP(Bn) as well as the Bn-substituted compounds from Example 7 (i.e. MDP (Bn)-DSPE[click] and Example 14 (i.e. MTP(Bn)-a-DPPE) were mixed with 12% hydrogen peroxide in water and were heated to 80° C. for 4 hours, in order to get a fast degradation of the molecules by oxidation, mimicking slower in-vivo oxidation events.

The resulting reaction mixtures were diluted with acetonitrile and water (1:1) for the MDP and MDP(Bn) test solutions, or with iPrOH, acetonitrile and water (40:7.5:52.5) with 0.1% formic acid and 20 mM ammonium formate for the MDP(Bn)-DSPE[click] and the MTP(Bn)-a-DPPE solutions. The 4 diluted samples were analyzed by HPLC-MS. For reference, the 4 starting materials were also analyzed by HPLC-MS, as well as MDP-DSPE[click] and MTP-a-DPPE, i.e. the de-benzylated reference compounds to the Bn-substituted test molecules.

For all 4 test solutions, the un-affected starting compounds were traced. In addition, multiple derivatives with masses of +14, +16, +28, +30 and +32 were found, indicating oxidations from $CH_2$ to CO moieties (+14) and from C—H to C—OH moieties (+16), and combinations of these oxidation events. The tested MDP(Bn)-DSPE[click] and the MTP(Bn)-a-DPPE compounds mainly degraded via oxidation of the Bn-group to a benzoate group (+14) followed by hydrolysis of the benzoate (−104). This was testified by the dominant presence of the de-benzylated MDP-DSPE[click] and MTP-a-DPPE compounds as degradation products: corroborating retention times in HPLC were found as well as corroborating masses in MS (−90 relative to the starting compounds).

The results indicate that the Bn-groups in the compounds of the invention have the highest propensity for in-vivo oxidative degradation. After Bn-oxidation and cleavage, the regular MDP- or MTP-group is formed, and these groups will degrade in-vivo in a similar fashion as other MDP/MTPs—that are known in the art—do.

Example 23. Nanobiologic Synthesis

Method 1—Film

The phospholipids, (pro-)drug and optional triglycerides or polymer are dissolved (typically in chloroform, ethanol or acetonitrile). This solution is then evaporated under vacuum to form a film of the components. Subsequently, a buffer solution is added to hydrate the film and generate a vesicle suspension. The phospholipids, (pro-)drug and optional triglycerides or polymer are dissolved (typically in chloroform, ethanol or acetonitrile). This solution is infused—or added drop-wise—to a mildly heated buffer solution under stirring, until complete evaporation of the organic solvents, generating a vesicle suspension.

To the vesicle suspension, generated using A or B, apolipoprotein A-I (apoA-I) (note that apoA-I can also already be in B)—use dropwise to avoid denature, is added and the resulting mixture is sonicated for 30 minutes using a tip sonicator while being thoroughly cooled using an external ice-water bath. The obtained solution containing the nanobiologics and other by products is transferred to a Sartorius Vivaspin tube with a molecular weight cut-off depending on the estimated size of the nanobiologics (typically Vivaspin tubes with cut-offs of 10.000-100.000 kDa are used). The tubes are centrifuged until ~90% of the solvent volume has passed through the filter. Subsequently, a volume of buffer, roughly equal to the volume of the remaining solution, is added and the tubes are spun again until roughly half the volume has passed through the filter. This is repeated twice after which the remaining solution is passed through a polyethersulfone 0.22 μm syringe filter, resulting in the final nanobiologic solution.

Method 2—Microfluidics

In an alternative approach, the phospholipids, (pro-)drug and optional triglycerides, cholesterol, steryl esters, or polymer are dissolved (typically in ethanol or acetonitrile) and loaded into a syringe. Additionally, a solution of apolipoprotein A-I (apoA-I) in phosphate buffered saline is loaded into a second syringe. Using microfluidics pumps, the content of both syringes is mixed using a microvortex platform. The obtained solution containing the nanobiologics and other by products is transferred to a Sartorius Vivaspin tube with a molecular weight cut-off depending on the estimate size of the particles (typically Vivaspin tubes with cut-offs of 10.000-100.000 kDa are used). The tubes are centrifuged until ~90% of the solvent volume has passed through the filter. Subsequently, a volume of phosphate buffered saline roughly equal to the volume of the remaining solution is added and the tubes are spun again until roughly half the volume has passed through the filter. This is repeated twice after which the remaining solution is passed through a polyethersulfone 0.22 μm syringe filter, resulting in the final nanobiologic solution.

Method 3—Microfluidizer

In another method according to the invention, microfluidizer technology is used to prepare the nanoscale assembly and the final nanobiologic composition. Microfluidizers are devices for preparing small particle size materials operating on the submerged jet principle. In operating a microfluidizer to obtain nanoparticulates, a premix flow is forced by a high pressure pump through a so-called interaction chamber consisting of a system of channels in a ceramic block which split the premix into two streams. Precisely controlled shear, turbulent and cavitational forces are generated within the interaction chamber during microfluidization. The two streams are recombined at high velocity to produce shear. The so-obtained product can be recycled into the microfluidizer to obtain smaller and smaller particles. Advantages of microfluidization over conventional milling processes include substantial reduction of contamination of the final product, and the ease of production scaleup.

Formulation 1

The below Table provides details on the preparation of HDL-derived nanoparticle formulations. First, DMPC, cholesterol and the compound of the invention were dissolved in the given molar ratios in ethanol (entries A, B and D) or in ethanol/DMSO 4/1 (entries C, E and F), while protein apoA-1 was separately dissolved in PBS buffer (pH=7.5). In these formulations, the amount of applied apoA-I was related to the amount of DMPC, by weight. The organic solution was mixed with the PBS buffer solution by bringing them together by T-junction mixing.

Purification of the resulting solutions was performed by TFF (tangential flow fractionation), thereby getting rid of the organic solvents and dissolving the nanoparticles in PBS. Concentration of the NP solutions was performed by spin-filter centrifugation. Finally, the HDL-derived nanoparticle solutions were filtered over 0.2 micrometer Acrodisk PES filters.

The final HDL-derived nanoparticle solutions had typical recoveries of the used compounds (Examples 2, 3, 7, 8 and 13), of DMPC and of cholesterol that exceeded 80%. Recoveries were determined by HPLC (for the compounds), and using assays that are known in the art (for DMPC and cholesterol). Concentrations of the final HDL-derived nanoparticle solutions were about 2 to 4 mg/mL in compound.

TABLE 6

Formulation compositions of HDL-derived nanoparticles

| Entry | Compound | DMPC mol % | Compound mol % | Cholesterol mol % | APO-A1 * mg-to-mg |
|---|---|---|---|---|---|
| A | None (Blank) | 90 | 0 | 10 | 1-to-2 |
| B | Example 2 | 90 | 10 | 10 | 1-to-2 |
| C | Example 3 | 90 | 10 | 10 | 1-to-2 |
| D | Example 7 | 90 | 10 | 10 | 1-to-2 |
| E | Example 8 | 90 | 10 | 10 | 1-to-2 |
| F | Example 13 | 90 | 10 | 10 | 1-to-2 |

* APO-A1 is employed in about half the amount in weight (mg) as DMPC

The stability of the nano-biologics as assessed by dynamic light scattering (DLS).

The formulations of entries A to F were characterized by DLS over a time period of 8 weeks. The nanoparticles in the Example 2, 3, 7 and 13 formulations had Z-averaged (intensity weighted mean hydrodynamic size) diameters of about 20, 30, 20 and 45 nm, respectively. The dimensions of these nanoparticles stayed constant in time, with also the dispersity in particle size (PDI) remaining constant. The unloaded particles (Entry A) were also stable in time (at about 30 nm diameter). The nanoparticles in the Example 8 formulation showed diameters that grew as of the 2-week time point to the 5-week time-point, from about 50 to about 225 nm. Dimensions stabilized as of the 5-week time point. Using other processing conditions, also this Example 8 material can most likely be formulated to stable 10 to 50 nm sized particles.

Figure 2:
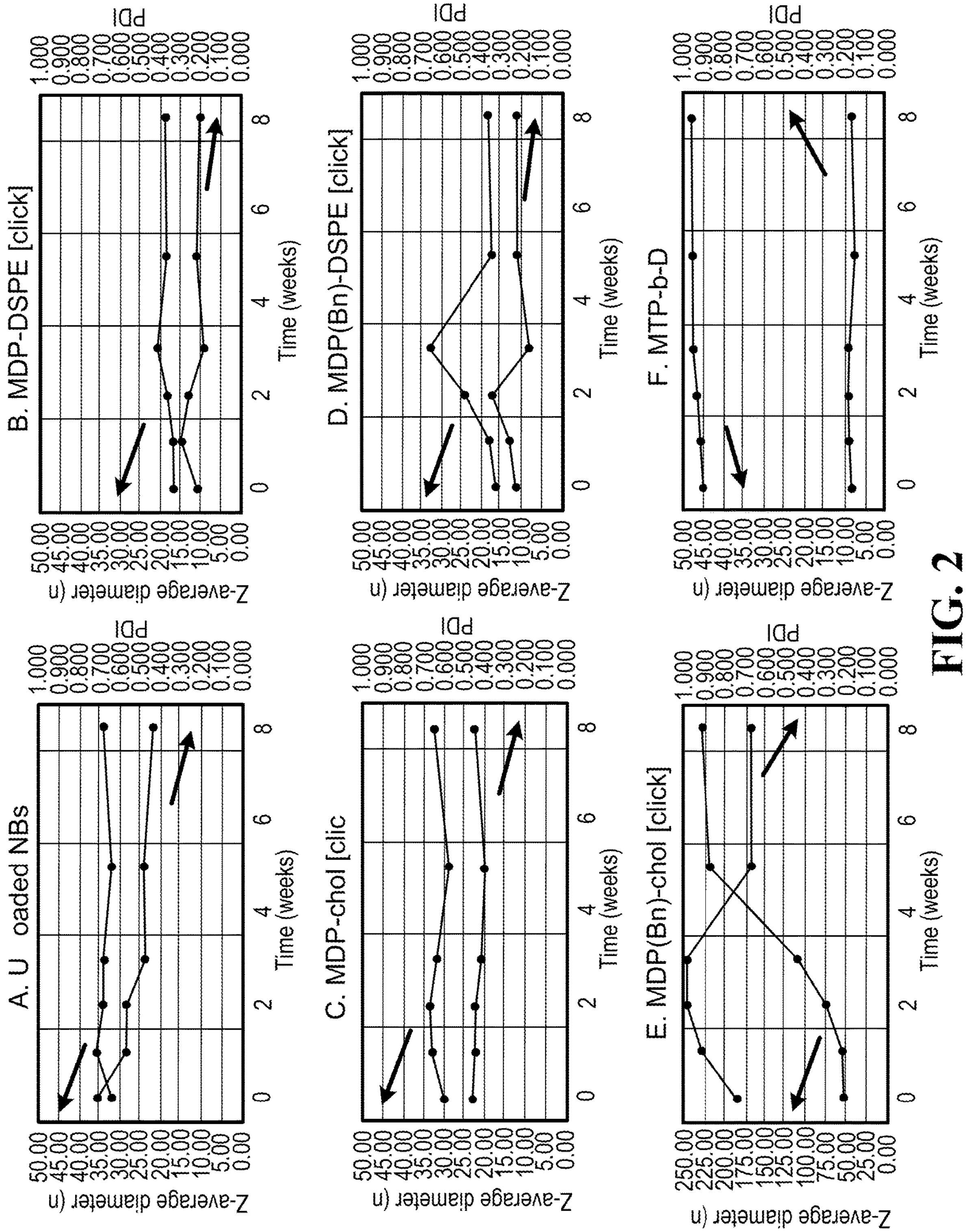
FIG. 2 DLS-determined Z-averaged diameters and PDI-values for nanoparticles in formulations A to F in formulation 1 of Example 23.

DLS-determined Z-averaged diameters and PDI-values for nanoparticles in formulations A to F are shown in FIG. 2.

Tip sonication formulation A: DSPC ([816-94-4]; 2.7 mg), cholesterol (0.26 mg) and the compound (0.46 mg) were dissolved in a glass vial with chloroform/methanol (9:1). The solvents were removed by an argon gas flow and the resulting film was dried in vacuo for >1 h. A solution of apoA-I PBS (6 mL) was added to the vial, which was subsequently bath sonicated for 5 minutes, incubated at 37° C. for 20 minutes, and then tip-sonicated for 10 minutes. The resulting dispersion was centrifuged to remove larger aggregates. The supernatant was transferred to a Vivapin 20 ultrafiltration unit (cutoff 10 kDa) and spun down to a volume of approximately 1 mL. The resulting dispersion was diluted with PBS and spun down to 1 mL, and this procedure was repeated twice. Finally, the volume was diluted to 2 mL using PBS to afford the desired nanoparticle solution.

Tip sonication formulation B: DMPC (2.7 mg), cholesterol (0.30 mg) and the compound (0.57 mg) were dissolved in a glass vial with chloroform/methanol (9:1). The solvents were removed by an argon gas flow and the resulting film was dried in vacuo for >1 h. A solution of peptide-2F (an apoA-I mimetic 18-mer; sequence 257 in Table 2) in PBS (6 mL) was added to the vial, which was subsequently bath sonicated for 5 minutes, incubated at 37° C. for 20 minutes, and then tip-sonicated for 5 minutes. The resulting dispersion was centrifuged to remove larger aggregates. The supernatant was transferred to a Vivapin 20 ultrafiltration unit (cutoff 10 kDa) and spun down to approximately 1 mL. The resulting dispersion was diluted with PBS and spun down to 1 mL, and this procedure was repeated twice. Finally, the volume was diluted to 2 mL using PBS to afford the desired nanoparticle solution.

T-junction formulation C: DMPC, cholesterol and the compound were dissolved in ethanol, while apoA-1 was dissolved in PBS buffer (pH=7.5). The organic solution was mixed with the buffer solution applying T-junction mixing. Purification of the resulting solutions was performed by TFF (tangential flow filtration), thereby getting rid of the organic solvents. Samples were concentrated by spin-filtration. The final HDL-derived nanoparticle solutions had typical recoveries for compound, DMPC and cholesterol that exceeded 75%. Concentrations of the final HDL-derived nanoparticle solutions were about 2 to 4 mg/mL in the compound.

TABLE 7

Formulations of HDL-derived nanoparticle

| Entry | PC-type mol % | Compound mol % | Cholesterol mol % | apoA-I or 2F * mg-to-mg | DLS # nm (error) |
|---|---|---|---|---|---|
| A | DSPC 100 | Example 2 10 | 20 | apoA-I 2-to-5 * | 51 (19) |
| B | DMPC 100 | Example 7 10 | 20 | 2F 2-to-5 * | 12.9 (0.7) |
| C | DMPC 80 | Example 2 20 | 20 | apoA-I 1-to-1 ** | 16.4 (4.2) |

* apoA-I or the 2F-peptide are employed in mg-to-mg phosphocholine PC);
** apoA-I is employed in mg-to-mg compound;
# number averaged diameter.

*apoA-I or the 2F-peptide are employed in mg-to-mg phosphocholine PC); **apoA-I is employed in mg-to-mg compound; #number averaged diameter.

The above examples highlight, that DSPC can be used instead of DMPC (POPC can also be employed e.g.), that peptidomimetics instead of apoA-I can be used, and that high levels of compounds of the disclosure can be incorporated. Furthermore, tip-sonication can be used as processing technique, instead of e.g. T-junction mixing or micro-fluidic mixing.

APOLIPOPROTEIN A-I (apoA-I) ISOLATION Human apoA-I was isolated from human HDL concentrates (Bioresource Technology) following a previously described procedure (Zamanian-Daryoush et al., 2013). Briefly, a potassium bromide solution (density: 1.20 g/mL) was layered on top of the concentrate and purified HDL was obtained by ultracentrifugation. The purified fraction was added to a chloroform/methanol solution for delipidation. The resulting milky solution was filtered and the apoA-I precipitate was allowed to dry overnight. The protein was renatured in 6 M guanidine hydrochloride, and the resulting solution dialyzed against PBS. Finally, the apoA-I PBS solution was filtered through a 0.22 μm filter and the protein's identity and purity were established by gel electrophoresis and size exclusion chromatography.

Example 24. Cryo-TEM Measurements on HDL-Derived Nanoparticle Formulations

The molecule compounds of Example 2 and Example 7, respectively, i.e. MDP-DSPE[click] and MDP(Bn)-DSPE [click] were formulated together with 1,2-dimyristoyl-sn-glycero-3-phosphocholine (DMPC; (CAS [18194-24-6]) and APO-A1, and with varying amounts of cholesterol, to create HDL-derived nanoparticle formulations. The following table shows the employed relative molar amounts of the DMPC, compound and cholesterol components. APO-A1 was used in twice the amount (in mg) as the compound of the invention (in mg). The dynamic scattering data (DLS) of the processed formulation are also given: the recorded diameter and its error in brackets are based on the number-averaged DLS data. The DLS-recorded polydispersity in the dimensions of the particles is also given.

TABLE 8

Formulations for Cryo-TEM measurements

| Entry | Compound | DMPC mol % | Compound mol % | Cholesterol mol % | APO-A1* mg-to-mg | DLS nm (error) | DLS PDI |
|---|---|---|---|---|---|---|---|
| A | Example 2 | 90 | 10 | 0 | 2-to-1 | 10.1 (2.1) | 0.42 |
| B | Example 7 | 90 | 10 | 0 | 2-to-1 | 9.9 (1.8) | 0.57 |
| C | Example 2 | 90 | 10 | 10 | 2-to-1 | 11.9 (3.0) | 0.32 |
| D | Example 7 | 90 | 10 | 10 | 2-to-1 | 11.4 (2.1) | 0.42 |
| E | Example 2 | 90 | 10 | 20 | 2-to-1 | 22.2 (6.1) | 0.18 |
| F | Example 7 | 90 | 10 | 20 | 2-to-1 | 31.0 (6.0) | 0.48 |

*APO-A1 is employed in twice the amount in weight (mg) as the compound

Formulation: DMPC, cholesterol and the compound were dissolved in ethanol (entries A, C and E) or in ethanol/DMSO (entries B, D, F), while apoA-1 was dissolved in PBS buffer (pH=7.5). The organic solution was mixed with the buffer solution applying T-junction mixing. Purification of the resulting solutions was performed by TFF (tangential flow filtration), thereby getting rid of the organic solvents. Samples were concentrated by spin-filtration. The final HDL-derived nanoparticle solutions had typical recoveries of the used compounds (Example 2 and 7), DMPC and cholesterol that exceeded 75%. Recoveries were determined by HPLC (for the compounds), and using assays that are known in the art (for DMPC and cholesterol). Concentrations of the final HDL-derived nanoparticle solutions were about 2 to 4 mg/mL in the compound (Example 2 or 7).

FIG. 1 shows the recorded Cryo-TEM pictures for the HDL-derived nanoparticle of entries A to F. The 50 nm bar applies to all 6 pictures. When 0% cholesterol is used, spherical disc-like particles are dominantly observed (A and B; sizes about 5 to 10 nm). Applying 10% of cholesterol mostly shows slightly extended discs (C and D; lengths about 5 to 25 nm and thicknesses about 5 nm). Using 20% cholesterol shows clearly extended worm-like particles. The lengths of these worm-like particles is about 20 to about 50 nm and the thicknesses are about 5 nm (picture C). In picture F, the lengths of the worms are about 50 to 100 nm; again, the thicknesses are about 5 nm. In F one also observes that the worm-like particles aggregate to larger stacks.

The results highlight that the HDL-derived nanoparticle particle dimensions can be steered using the cholesterol content of the formulation (compare C with E, and D with F), but also with the lipophilicity of the compound and/or the substitution of the $R_2$ position in Formula (I) of the compounds of the invention (clear: compare E with F; less clear: in D the particles seem to be a bit more extended than in C).

Method: Just before processing the samples, 200-mesh lacey carbon supported copper grids (Electron Microscopy Sciences) were surface plasma treated for 40 seconds using a Cressington 208 carbon coater. Next, 3 μL of the HDL-derived nanoparticle sample solutions was transferred to the grids. A thin film of sample solution was then vitrified on the grid by plunge vitrification in liquid ethane, using an automated vitrification robot (FEI Vitrobot Mark IV). Processed films were stored until measurement took place. Cryo-TEM imaging of the prepared films was carried out on a Cryo-TITAN microscope (Thermo Fisher) equipped with a field emission gun (FEG), a post-column Gatan imaging filter (model 2002), and a post-GIF 2 k×2 k Gatan CCD camera (model 794).

Example 25: In Vitro NOD2 Activation Assay

The stimulation of human NOD2 (hNOD2) by compounds disclosed herein was studied by monitoring activation of NF-κB in HEK-Blue™ hNOD2 cells (Invitrogen). 50,000 HEK-Blue™ hNOD2 cells were seeded in HEK-Blue™ Detection Medium in flat-bottom tissue culture plates. Concentration ranges of the test article (compounds diluted from DMSO-solutions (17.8 mmol/L), first with demineralized water and then with PBS to the desired concentrations) were added to the cells in the tissue culture plates. Cells were incubated overnight at 37° C. and 5% $CO_2$. The following day, supernatants were collected in an ELISA plate and the OD was measured at 620 nm using a spectrophotometer.

Figure 3:
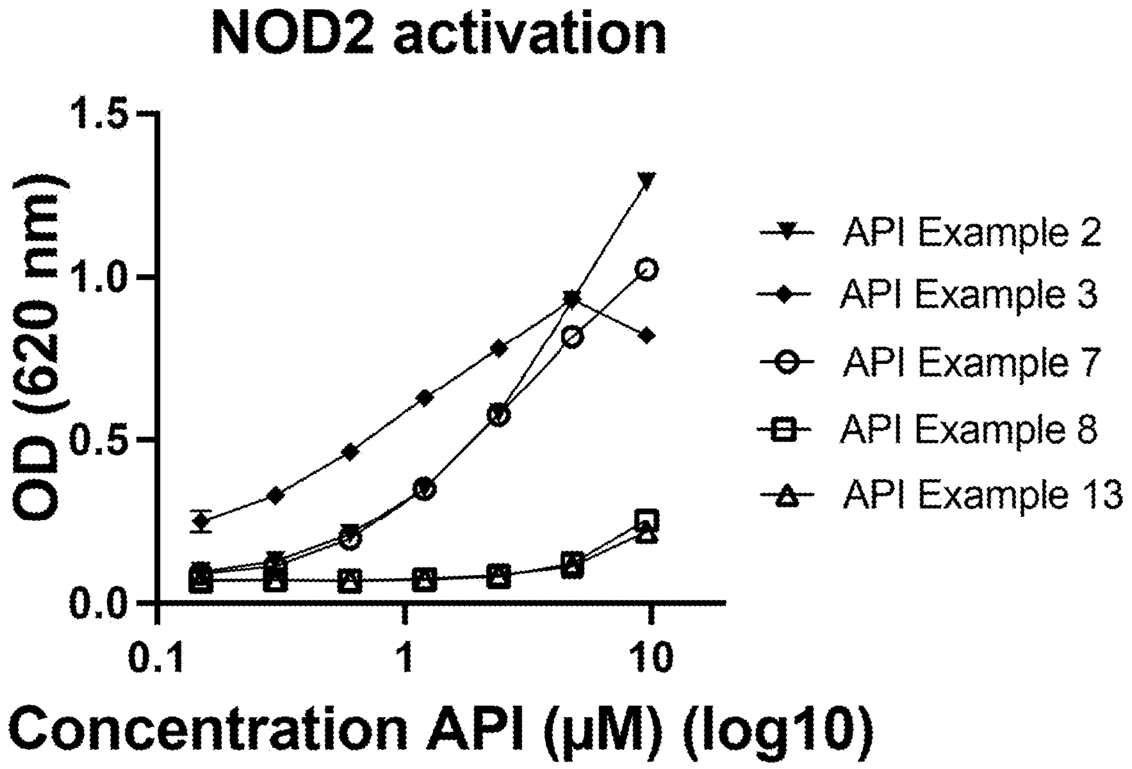
FIG. 3 is a graph showing OD values as a function of test article concentration in the NOD2 activation assay described in Example 25.
Figure 4A:
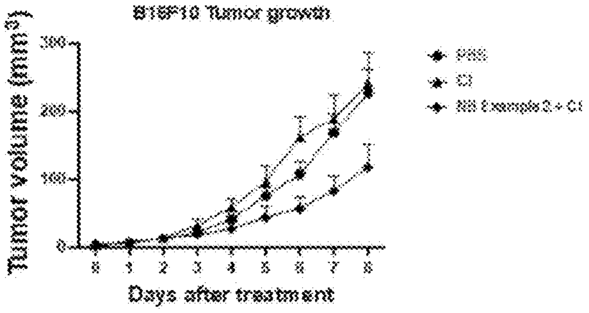
FIG. 4A, FIG. 4B, FIG. 4C, FIG. 4D, and FIG. 4E depict tumor growth curves for the study described in Example 26.
Figure 4B:
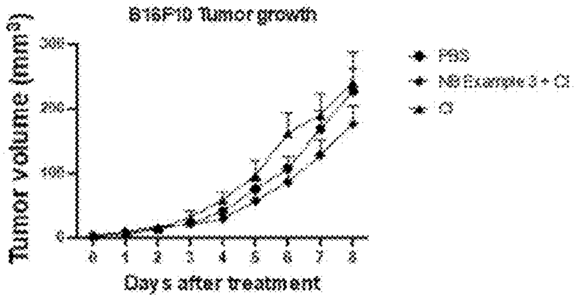
Figure 4C:
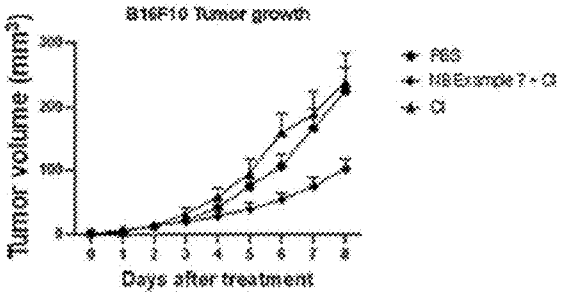
Figure 4D:
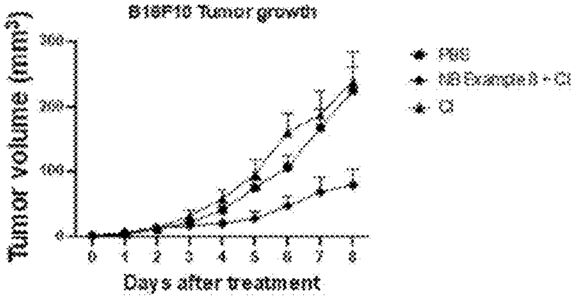
Figure 4E:
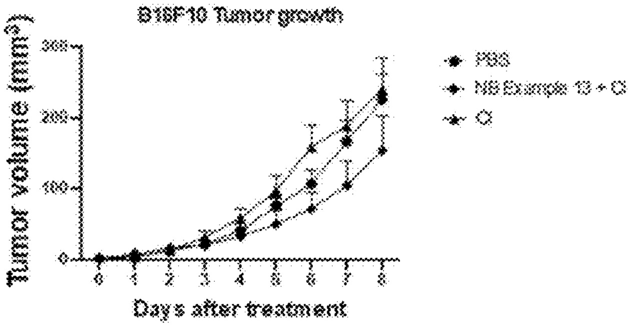

The signal in this assay is based on NOD2 stimulation with a ligand which subsequently activates NF—KCB and AP-1, resulting in the production of SEAP. Levels of SEAP were then determined with HEK-Blue™ Detection medium (Invitrogen). The hydrolysis of the substrate in the medium by SEAP produces a purple/blue color that was then measured with an Absorbance microplate reader. OD values are mapped based on test article concentration and are depicted in FIG. 3. Assay performance was validated with muramyl dipeptide (CAS number [53678-77-6]).

All tested compounds of the invention (APIs) are capable of activating NOD2. Potency for Example 2, 3 and 7 compounds is comparable. Example 8 and 13 compounds are also able to activate NOD2, but seemingly to a lesser extent than the Example 2, 3 and 7 compounds.

Example 26: Combination Activity of (i) HDL-Derived Nanoparticles and (ii) Immune Checkpoint Inhibition in the B16F10 Mouse Model Formulations In-Vivo Study 1.

The formulations for these in-vivo studies were prepared by T-junctions mixing, followed by tangential flow filtration (TFF). Processing and purification procedures were applied as those highlighted in the formulations for the Cryo-TEM measurements (Table 8).

Compounds used were those of Example 2, 3, 7, 8 and 13 (i.e. these Example materials are collectively named APIs in these descriptions of the in-vivo studies). For the 5 administered formulations, the following relative ratio of components have been used.

| Entry | Compound | DMPC Mol % | Compound Mol % | Cholesterol Mol % | apoA-1* mg-to-mg |
|---|---|---|---|---|---|
| 1 | Example 2 | 90 | 10 | 10 | 2-to-1 |
| 2 | Example 3 | 90 | 10 | 10 | 2-to-1 |
| 3 | Example 7 | 90 | 10 | 10 | 2-to-1 |
| 4 | Example 8 | 90 | 10 | 10 | 1-to-1 |
| 5 | Example 13 | 90 | 10 | 10 | 1-to-1 |

*relative to the compound

Protocol and Results

The panel of Example APIs was formulated to HDL-derived nanoparticles (or nanobiologics, NBs) that were screened for their anti-tumor activity in combination with immune checkpoint inhibitors in the B16F10 syngeneic mouse tumor model. To this end, B16F10 murine melanoma cells were cultured in Dulbecco's modified Eagle's medium (DMEM)(Gibco) supplemented with 10% FBS (Gibco) and 1% penicillin/streptomycine (P/S). At the day of injection, cells were harvested and resuspended at $1\times10^6$ viable cells/mL in PBS with 0.5% FBS. During counting the cells were checked for viability using Trypan Blue Solution, 0.4% (Gibco). At the start of the experiment $1\times10^5$ B16F10 tumor cells in 100 μL PBS supplemented with 0.5% fetal bovine serum (FBS) were injected subcutaneously in the flank of 7-week-old female C57BL/6 mice (The Jackson Laboratory).

Seven days after tumor inoculation, mice were randomized in groups with similar average group size (n=10). Average tumor size of groups was 3.26 $mm^3$. After randomization mice were ear notched and weighed. Subsequently doses were calculated and aliquoted. Aliquoted doses were stored until use at 4° C.

The study consisted of the following: a PBS control group, an immune checkpoint inhibitors group (CI) and 6 treatment groups. The immune checkpoint inhibitors treated mice received an intraperitoneal injection on day 2, 4 and 8, using doses of 200 pg anti-CTLA-4 (clone, 9H10, BioXcell) and/or 200 μg anti-PD-1 (clone, RMP1-14, BioXcell). Treatment groups consisted of NBs prepared from the Example 2 compound, NBs from Example 3, NBs from Example 7, NBs from Example 8, NBs from Example 13 combined with the immune checkpoint inhibitors therapy (CI) as described above. Dosing for treatment groups was about 9 mg MDP/kg (or about 27 mg/kg of the respective APIs contained in the NBs) in question on day 0, 2 and 4.

Tumor growth curves are depicted in FIG. 4A-E and in each graph the same PBS and CI groups have been mapped to allow for comparison between graphs.

PBS treated animals or animals that were treated with immune checkpoint inhibitors alone did not show tumor growth inhibition. The groups of animals treated with combination therapy all showed tumor growth inhibition and it was most pronounced for those groups in which NBs of Example 2 (FIG. 4A), NBs of Example 7 (FIG. 4C) or NBs of Example 8 (FIG. 4D) was part of the combination therapy.

Note that the above results on the combination therapy were obtained with an applied formulation that contained 10 mol % cholesterol relative to the applied 90 mol % DMPC (see the above Table), and thus these particles had dimensions of approximately 5 to maximally 10 nm (see the Cryo-TEM panels C and D in FIG. 1).

Example 27: Single Agent Activity of Nanobiologics in B16F10 Mouse Model

The formulations for these in-vivo studies were prepared by T-junctions mixing, followed by tangential flow filtration (TFF). Processing and purification procedures were applied as those highlighted in the formulations for the Cryo-TEM measurements (Table 8). The below table shows the employed relative ratios of components to prepare the HDL-derived nanoparticles.

| Entry | Compound | DMPC Mol % | Compound Mol % | Cholesterol Mol % | apoA-1* mg-to-mg | DLS # (nm) | DLS # PDI (–) |
|---|---|---|---|---|---|---|---|
| 1 | Example 2 | 90 | 10 | 10 | 2-to-1 | 11.9 (3.0) | 0.32 |
| 2 | Example 7 | 90 | 10 | 10 | 2-to-1 | 11.4 (2.1) | 0.42 |
| 3 | Example 2 | 90 | 10 | 20 | 2-to-1 | 22.2 (6.1) | 0.18 |
| 4 | Example 2 | 80 | 20 | 20 | 1-to-1 | 16.4 (4.2) | 0.21 |
| 5 | Example 7 | 80 | 20 | 20 | 1-to-1 | 24.4 (4.4) | 0.47 |

*relative to the compound;
# number averaged diameters.

Protocol and Results

Two APIs (the Example 2 and Example 7 compounds) were used to generate a set of different HDL-derived nanoparticle formulations (or nanobiologic formulations; nanobiologics; NBs) to determine their potencies. The resulting nanobiologics were screened for their single agent antitumor activity in the B16F10 syngeneic mouse tumor model. To this end B16F10 murine melanoma cells were cultured in Dulbecco's modified Eagle's medium (DMEM)(Gibco) supplemented with 10% FBS (Gibco) and 1% penicillin/streptomycine (P/S). The day of injection cells were harvested and resuspended at $1\times10^6$ viable cells/mL in PBS with 0.5% FBS. During counting cells were checked for viability using a Cell Counter and Analyzer (Casy). At the start of the experiment $1\times10^5$ B16F10 tumor cells in 100 μL PBS supplemented with 0.5% fetal bovine serum (FBS) were injected subcutaneously in the flank of 7-week-old female C57BL/6J mice (Charles River).

Seven days after tumor inoculation, mice were randomized in groups with similar average group size. Groups consisted of 8-10 mice. Average tumor size of groups was 6.33 $mm^3$. After randomization mice were tattooed with a number on the tail. Subsequently doses were calculated and aliquoted. Aliquoted doses were stored until use at 4° C.

Figure 5A:
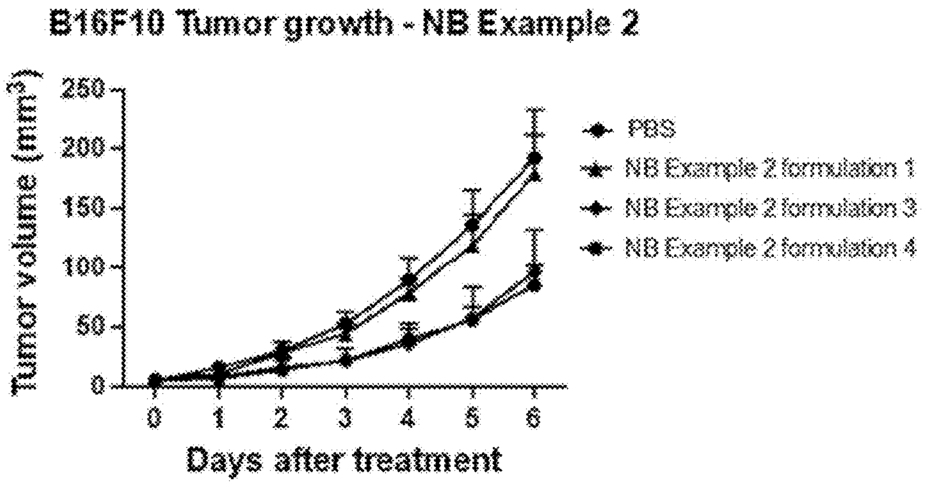
FIG. 5A, FIG. 5B, and FIG. 5C depict tumor growth curves for the study described in Example 27.
Figure 5B:
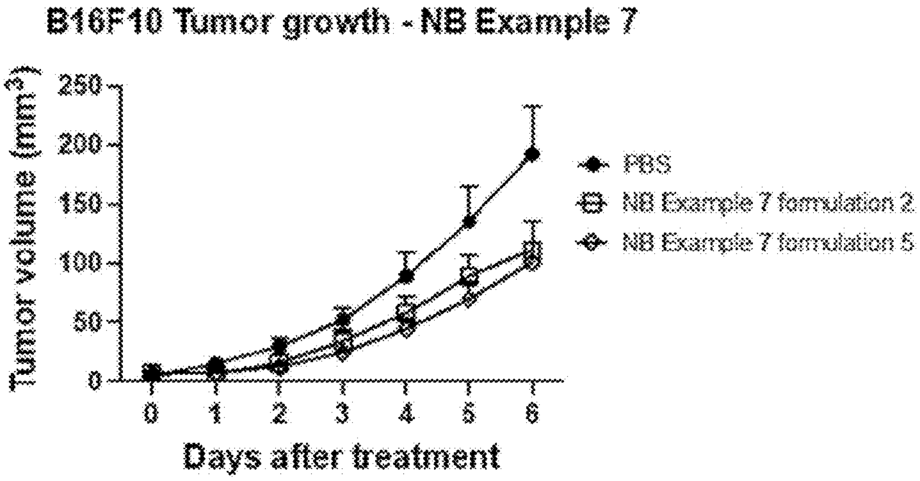
Figure 5C:
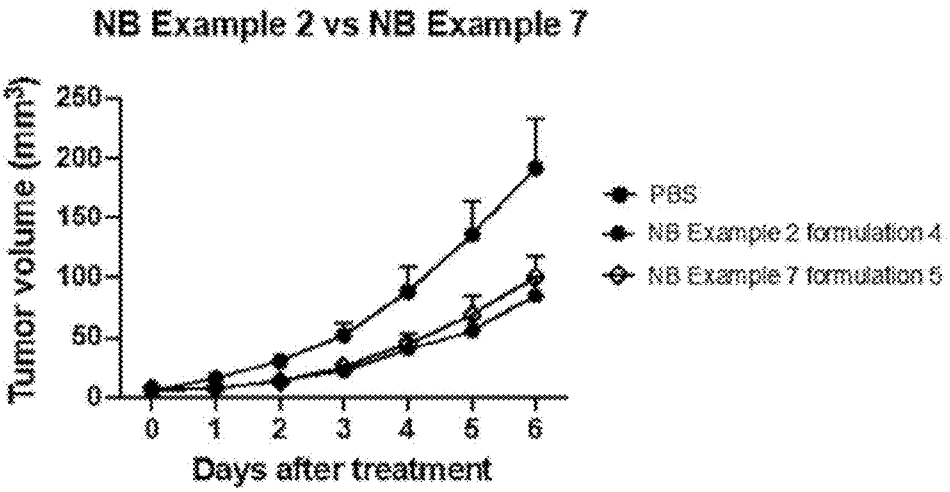

The study consisted of the following: a PBS control group and 5 treatment groups: NBs of Example 2 (formulation Entries 1, 3 and 4) and NBs of Example 7 (formulation Entries 2 and 5). Dosing for treatment groups was about 3 mg MDP/kg (or about 9 mg/kg of the respective APIs contained in the NBs) in question on day 0, 2 and 4. Tumor size was measured at set times during the course of the study. Tumor growth curves are depicted in FIG. 5A-C and in each graph the same PBS group is mapped to allow for comparison between graphs. Apart from the NBs of Example 2 (formulation Entry 1), all nanobiologics clearly showed a reduction in the tumor growth in comparison with the PBS control group. For both Example 2 (FIG. 5A) and Example 7 (FIG. 5B) the nanobiologics formulations with 20 mol % cholesterol performed best. FIG. 5C shows that NBs of Example 2 slightly outperform NBs of Example 7 (using the formulations of Entries 4 and 5, respectively).

Note that in Figure FIG. 5A, the Example-2 formulation containing 10 mol % cholesterol (Entry 1 in the above Table) showed a minor single agent activity (compare to PBS). Surprisingly, and in comparison, the Example-2 formulations with 20 mol % cholesterol (Entries 3 and 4 in the above Table) show extraordinarily enhanced tumor suppressions. For the Example-7 formulations, this can also be seen (FIG. 5B). Apparently, the dimensions of the formed particles play a decisive role in the activity of the prepared HDL-derived nanoparticles: the 10% cholesterol formulations give spherical or only slightly stretched disk-like particles with 5 to 10 nm dimensions, while the 20% cholesterol formulations give elongated worm-like particles about 15 to 50 nm in length, and about 5 nm in thickness (compare panels C and E in FIG. 1; cryo-TEM data).

The disclosed HDL-derived nanoparticles have certain dimensions, and these features find particular use in producing stable and potent HDL-derived NPs. Without being bound by theory, it is thought that the disclosed HDL-derived nanoparticles provide improved (multivalent) presentation of the MDP (or MDP(Bn) or MTP or MTP(Bn)) moieties to cells, dramatically improving their potency.

Embodiments

1. A compound of formula (I):

(I)

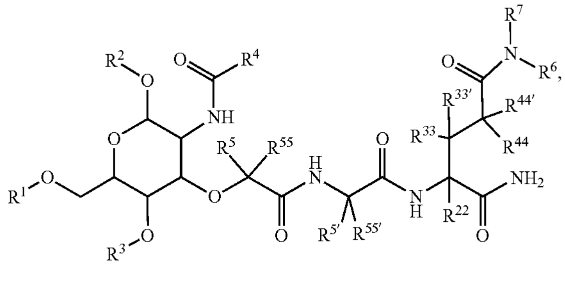

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^{5'}$ are each independently —H, or alkyl;

$R^7$ is a $C_{9-30}$ fatty acid chain, —Y—N($R^{5'}$)—C(O)—O-alkylene-C(H)($OR^8$)-alkylene-$OR^9$, —C($R^{10}$)(C(O)$NH_2$)-alkylene-N($R^{11}$)—C(O)—$C_{16-30}$ fatty acid chain, —($CR^{10}R^{10}$)$_2$—O—P(O)(OH)—O-alkylene-C($R^{10}$)($OR^Z$)-alkylene-$OR^Z$, or —Y-triazolyl-L;

$R^Z$ is a $C_{8-30}$ fatty acid or —C(O)—$C_{16-30}$ fatty acid chain;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W)$_2$, and -alkylene-N-(alkylene-C(O)—W)$_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^{10}$, $R^{22}$, $R^{33}$, $R^{33'}$, $R^4$, $R^{4'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of halo, alkoxy, haloalkoxy, cyano, hydroxyl, —N($R^C$)($R^D$), —C(O)N($R^C$)($R^D$), —N($R^C$)C(O)$R^B$, —OC(O)$NR^CR^D$, —NRCC(O)$OR^B$, —OC(O)$R^B$, —C(O)$OR^B$, —C(O)$R^B$, —$CO_2$H, —$NO_2$, —SH, S(O)$_X R^B$ (wherein X is 0, 1, or 2), aryl, arylalkyl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)$OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro;

wherein, when $R^7$ is $C_{9-30}$ fatty acid chain, $R^2$ is —H.

2. The compound of embodiment 1, wherein the compound of formula (I) is a compound of formula (IA):

(IA)

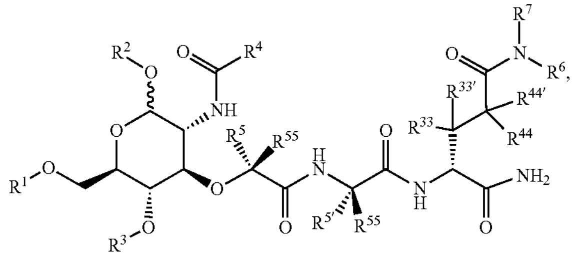

or a pharmaceutically acceptable salt thereof.

3. The compound of embodiment 1 or 2, wherein $R^2$ is —H or benzyl.

4. The compound of any one of embodiments 1-3, wherein $R^2$ is —H.

5. The compound of any one of embodiments 1-4, wherein $R^{10}$, $R^{22}$, $R^{33}$, $R^{33}$, $R^{44}$, $R^{44'}$, $R^{55}$, and $R^{55'}$ are each —H.

6. The compound of any one of embodiments 1-5, wherein $R^4$ is alkyl.

7. The compound of any one of embodiments 1-6, wherein $R^4$ is methyl.

8. The compound of any one of embodiments 1-7, wherein $R^3$ and $R^6$ are both —H.

9. The compound of any one of embodiments 1-8, wherein Y is alkylene optionally substituted with —C(O)N($R^C$)($R^D$).

10. The compound of embodiment 9, wherein Y is —$CH_2$—or

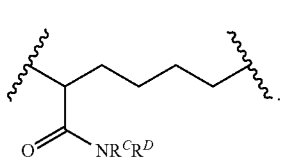

11. The compound of embodiment 10, wherein Y is —$CH_2$—.

12. The compound of any one of embodiments 1-11, wherein $R^7$ is —Y-triazolyl-L;

13. The compound of any one of embodiments 1-12, wherein the compound of formula (I) is a compound of formula (II):

(II)

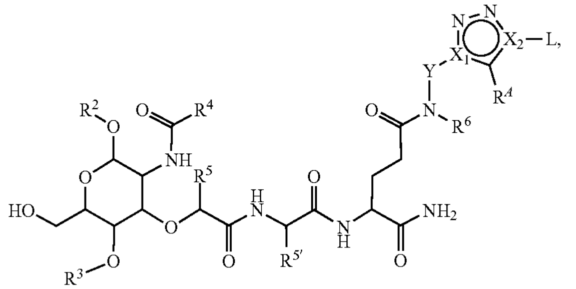

or a pharmaceutically acceptable salt thereof, wherein:

$X_1$ is —N— and $X_2$ is —C—; or $X_1$ is —C— and $X_2$ is —N—.

14. The compound of embodiment 13, wherein the compound of formula (I) is a compound of formula (IIA):

(IIA)

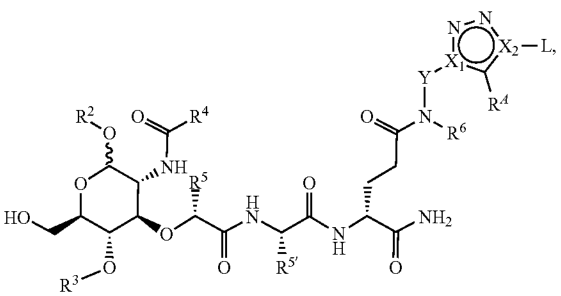

or a pharmaceutically acceptable salt thereof.

15. The compound of embodiment 13 or 14, wherein Y is $C_{1-6}$alkylene.

16. The compound of any one of embodiments 13-15, wherein $R^A$ is —H.

17. The compound of any one of embodiments 1-16, wherein L is selected from the group consisting of $C_{8-30}$ fatty acid chain, $—CH_2—C(O)—W$, $—CH_2—O—C(O)—W$, $—CH_2CH_2—N—CH_2CH_2—C(O)—NR^{11}—CH_2CH_2—NR^{11}—C(O)—W)_2$, and $—CH_2CH_2—N—(CH_2CH_2—C(O)—W)_2$.

18. The compound of embodiment 17, wherein L is a $C_{12-18}$ fatty acid chain.

19. The compound of embodiment 17, wherein L is $—CH_2(CH_2CH_2)_8—CH_3$.

20. The compound of any one of embodiments 1-19, wherein W is a $C_{8-30}$ fatty acid chain.

21. The compound of any one of embodiments 1-19, wherein W is a $C_{12-18}$ fatty acid chain.

22. The compound of any one of embodiments 1-19, wherein W is:

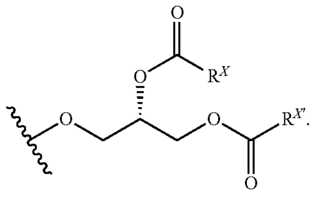

23. The compound of embodiment 22, wherein $R^X$ and $R^{X'}$ is each independently a $—C_{8-30}$ fatty acid chain 24. The compound of embodiment 22 or 23, wherein $R^X$ and $R^{X'}$ is each independently a $C_{12-18}$fatty acid chain.

25. The compound of embodiment 24, wherein $R^X$ and $R^{X'}$ are both $—(CH_2CH_2)_8—CH_3$.

26. The compound of any one of embodiments 1-19, wherein W is cholesterol:

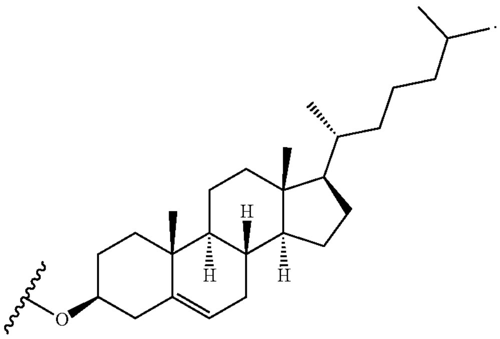

(cholesterol)

27. The compound of any one of embodiments 1-19, wherein W is a phospholipid selected from the group consisting of: a phosphatidylcholine (PC), a phosphatidylglycerol (PG), a phosphatidylserine (PS), a phosphatidylethanolamine (PE), a phosphatidic acid (PA), and a lysophosphatidylcholine.

28. The compound of embodiment 27, wherein W is a phospholipid having the structure:

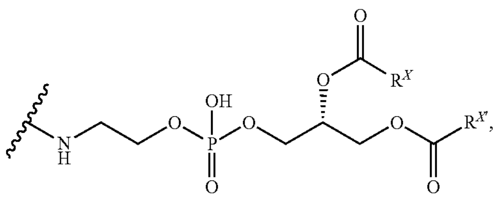

or a pharmaceutically acceptable salt thereof;

wherein $R^X$ and $R^{X'}$ are each independently a $C_{8-30}$ fatty acid chain.

29. The compound of embodiment 28, wherein $R^X$ and $R^{X'}$ are each independently a $C_{12-18}$ fatty acid.

30. The compound of embodiment 28 or 29, wherein the fatty acid is saturated.

31. The compound of embodiment 28, wherein $R^X$ and $R^{X'}$ are both $—(CH_2CH_2)_8—CH_3$.

32. The compound of embodiment any one of embodiments 1-11, wherein $R^7$ is $—C(H)(C(O)NH_2)—C_5$alkylene-$N(R^{11})—C(O)—C_{17-30}$ fatty acid.

33. The compound of any one of embodiments 1-11, wherein $R^7$ is $—CH_2CH_2—O—P(O)(OH)—O—CH_2—C(H)(OR^Z)—CH_2—OR^Z$ 34. The compound of any one of embodiments 1-33 selected from the group consisting of:

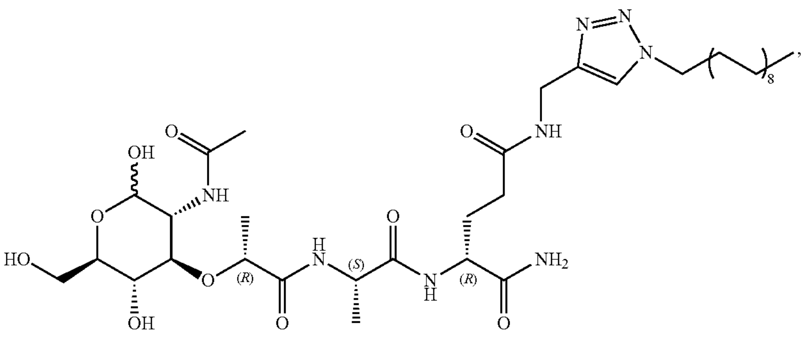
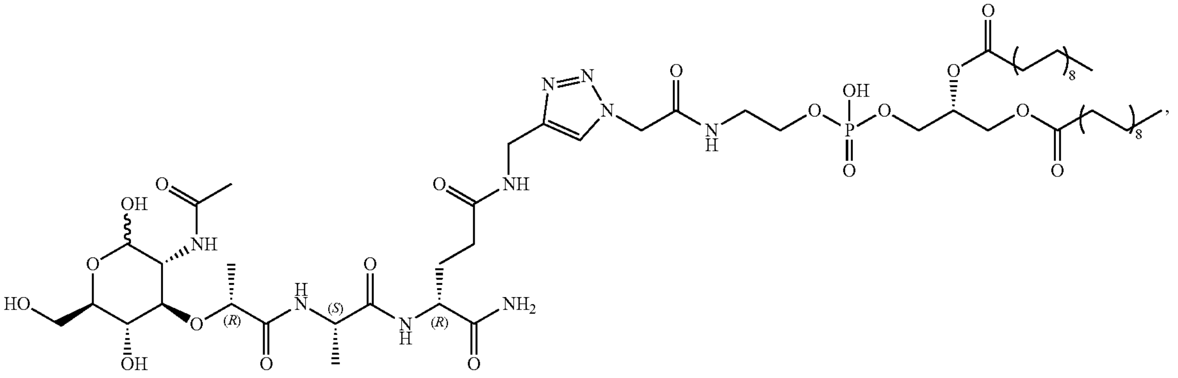
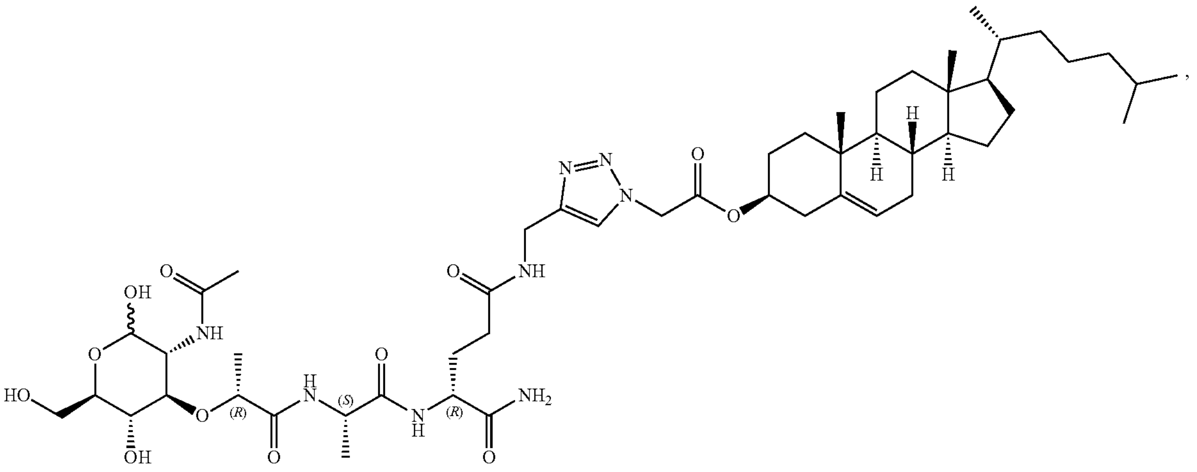
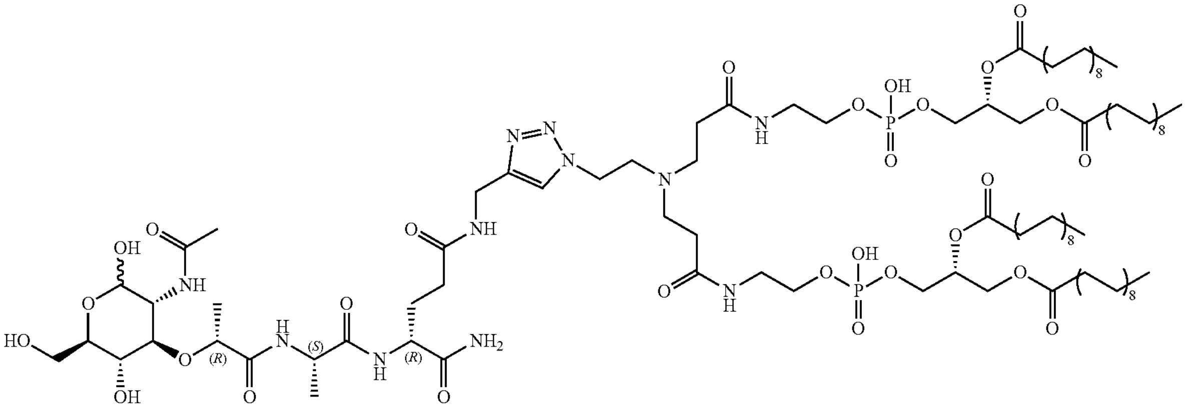

-continued
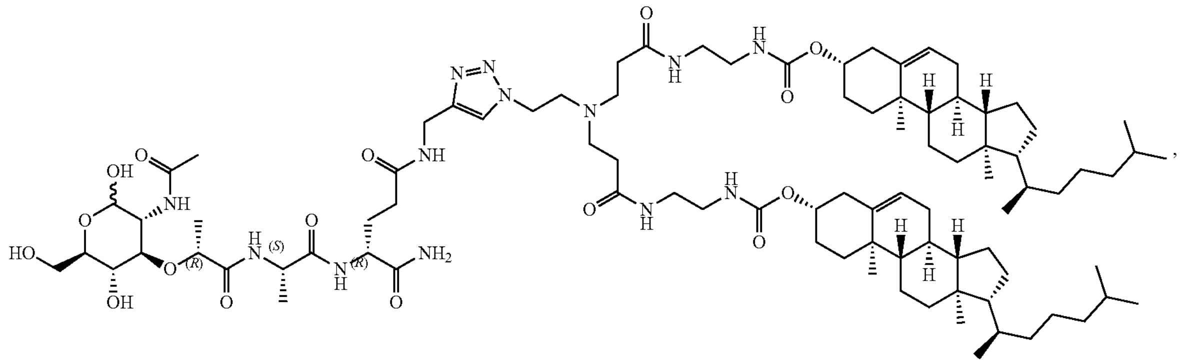
,
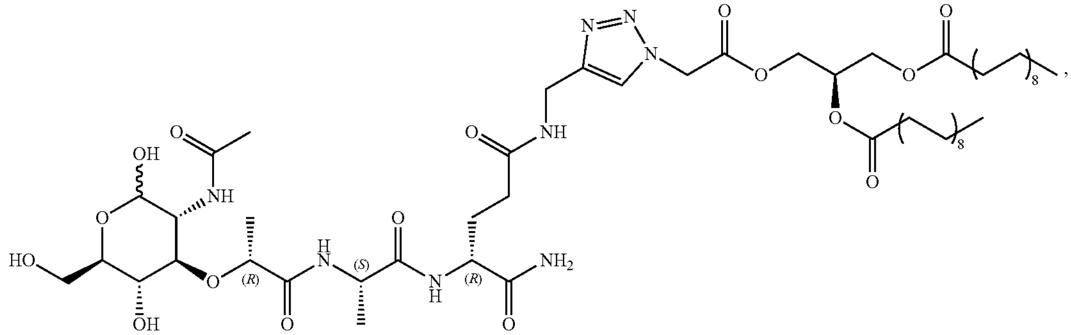
,
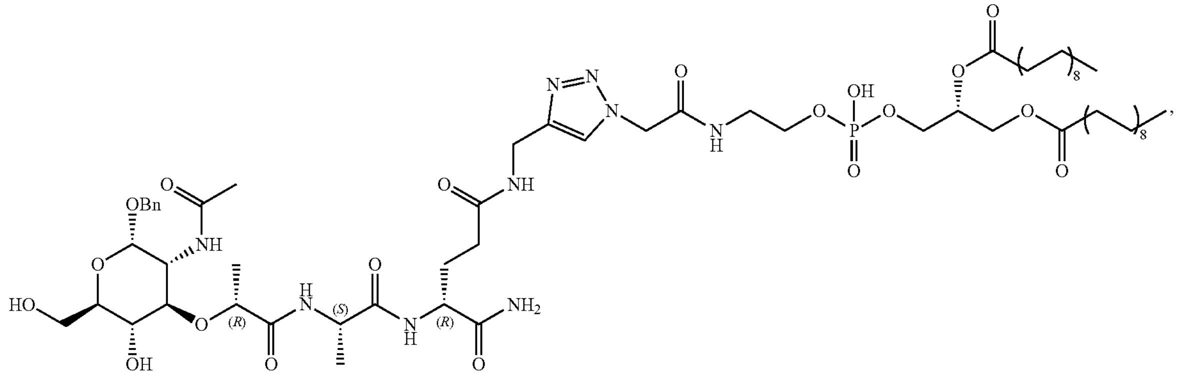
,
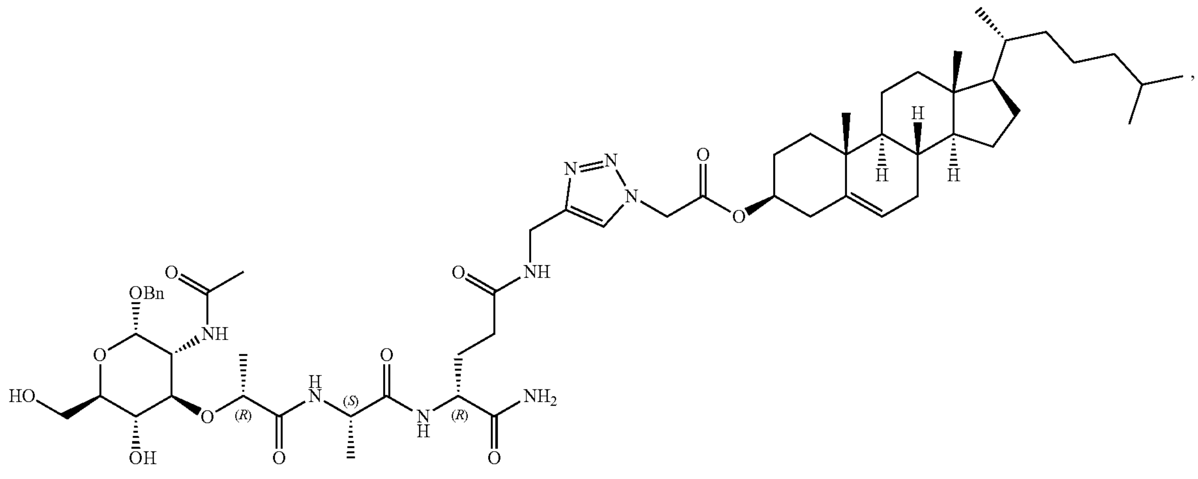
,

-continued
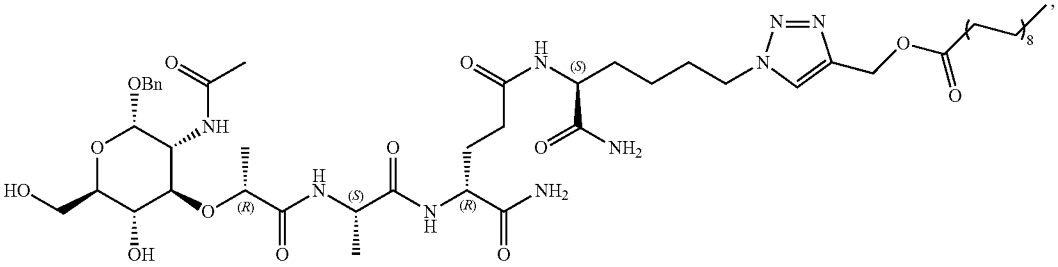
,
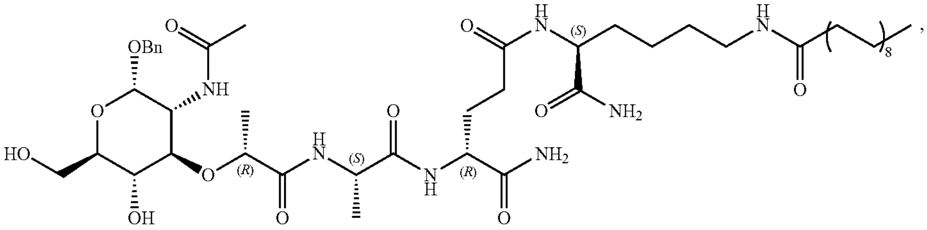
,
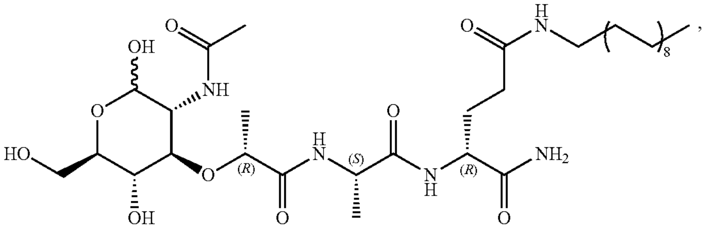
,
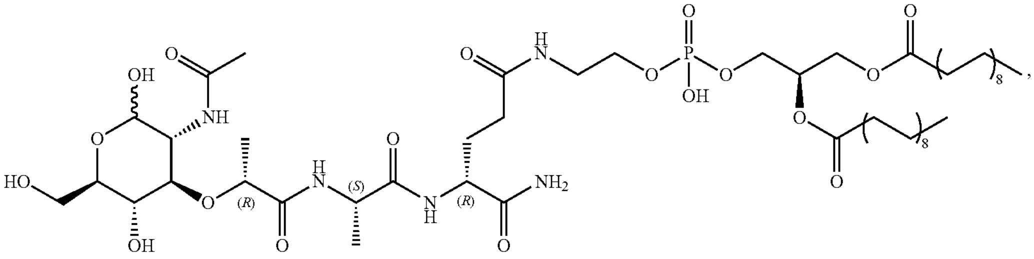
, and
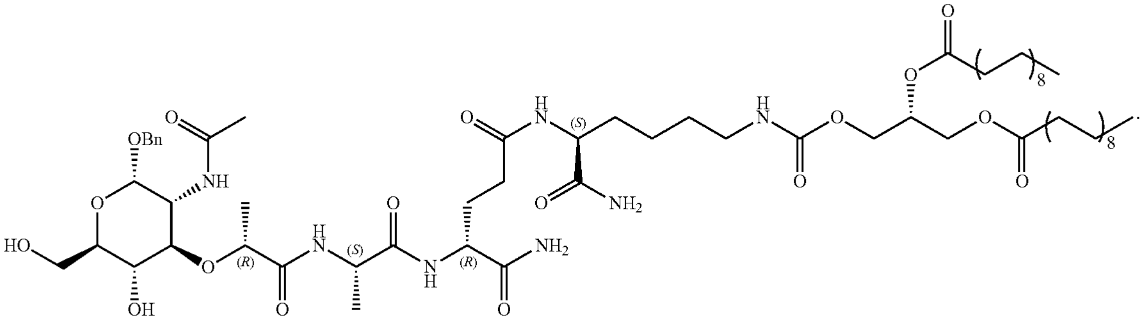
.

35. A nanobiologic composition comprising a high-density lipoprotein (HDL)-derived nanoparticle, wherein the nanoparticle comprises a compound of formula (I):

(I)

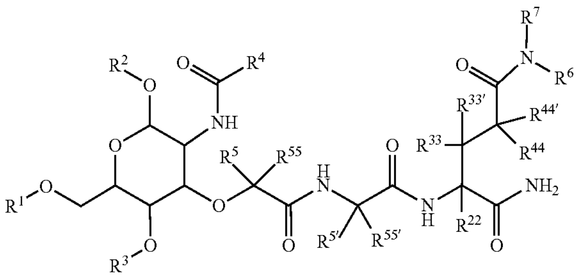

or a pharmaceutically acceptable salt thereof, wherein:

$R^1$ is —H or —C(O)—$R^X$;

$R^2$ and $R^3$ are each independently selected from the group consisting of —H, alkyl, alkylene-aryl, —C(O)-alkyl, and —C(O)-aryl;

$R^4$, $R^5$, and $R^{5'}$ are each alkyl;

$R^6$ and $R^1$ are each independently —H, or alkyl;

$R^7$ is a fatty acid chain, —Y—N($R^6$)—C(O)—O-alkylene-C(H)(ORs)-alkylene-$OR^9$, —Y—N($R^6$)—C(O)—$R^X$, —Y—O—P(O)(OH)—O-alkylene-C(H)($OR^8$)-alkylene-$OR^9$, or —Y— triazolyl-L;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—$W)_2$, and -alkylene-N-(alkylene-C(O)—$W)_2$;

W is a fatty acid chain, —O-alkylene-C(H)($OR^8$)-alkylene-$OR^9$, a phospholipid, or a sterol;

$R^8$ and $R^9$ are each independently $R^X$ or —C(O)—$R^X$;

$R^{10}$, $R^{22}$, $R^{33}$, $R^{33'}$, $R^{44}$, $R^{44'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of halo, alkoxy, haloalkoxy, cyano, hydroxyl, —N($R^C$)($R^D$), —C(O)N($R^C$)($R^D$), —N($R^C$)C(O)R, —OC(O)$NR^CR^D$, —NRCC(O)$OR^B$, —OC(O)$R^B$, —C(O)$OR^B$, —C(O)$R^B$, —$CO_2$H, —$NO_2$, —SH, $S(O)_XR^B$ (wherein X is 0, 1, or 2), aryl, heteroaryl, heteroarylalkyl, cycloalkyl, heterocycloalkyl, and $R^B$;

$R^C$ and $R^D$ are independently selected for each occurrence from the group consisting of hydrogen, alkyl, haloalkyl —C(O)$R^B$, and —C(O)$OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro.

36. A nanobiologic composition, comprising a high-density lipoprotein (HDL)-derived nanoparticle, wherein the nanoparticle comprises a compound of any one of embodiments 1-34.

37. The nanobiologic composition of embodiment 35 or 36, wherein the HDL-derived nanoparticle comprises one or more phospholipids.

38. The nanobiologic composition of embodiment 37, wherein the phospholipid is independently selected from the group consisting of a phosphatidylcholine, a phosphatidylethanolamine, a phosphatidylinositol, a phosphatidylserine, a sphingomyelin or other ceramide, a phospholipid-containing oil, a phosphatidylglycerol, a phosphatidic acid, a lysophosphatidylcholine, and combinations thereof.

39. The nanobiologic composition of embodiment 35 or 36, comprising a phospholipid selected from the group consisting of 1,2-dimyristoyl-sn-glycero-3-phosphatidylcholine (DMPC) and 1-palmitoyl-2-oleoyl-sn-glycero-3-phosphocholine (POPC), and a lysolipid selected from the group consisting of 1-myristoyl-2-hydroxy-sn-glycero-phosphocholine (MHPC), and 1-palmitoyl-2-hydroxy-sn-glycero-3-phosphocholine (PHPC).

40. The nanobiologic composition of any one of embodiments 35-39, wherein the HDL-derived nanoparticle comprises apoA-I or a peptide mimetic of apoA-I.

41. The nanobiologic composition of any one of embodiments 35-40, wherein the HDL-derived nanoparticle further comprises one or more triglycerides, fatty acid esters, hydrophobic polymers, sterol esters, or combinations thereof.

42. The nanobiologic composition of any one of embodiments 35-41, wherein the HDL-derived nanoparticle further comprises cholesterol.

43. The nanobiologic composition of embodiment 42, wherein the HDL-derived nanoparticle comprises one or more phospholipids and cholesterol in a molar ratio in the range of about 1:0.05 to about 1:0.25.

44. The nanobiologic composition of embodiment 43, wherein the HDL-derived nanoparticle comprises one or more phospholipids and cholesterol in a molar ratio of about 1:0.2.

45. The nanobiologic composition of any one of embodiments 1-44, wherein the HDL-derived nanoparticle is a nanodisc or nanosphere.

46. The nanobiologic composition of embodiment 45, wherein the nanodisc or nanosphere is about 8 nm to about 400 nm in diameter.

47. A pharmaceutical composition comprising a compound of any one of embodiments 1-34 or a pharmaceutically acceptable salt thereof, and a pharmaceutically acceptable carrier.

48. A method for treating a cell-proliferation disorder in a patient in need thereof, comprising administering to the patient a therapeutically effective amount of the nanobiologic composition of any one of embodiments 35-46.

49. The method of embodiment 48, wherein the cell-proliferation disorder is cancer.

50. The method of embodiment 49, wherein the cancer is selected from the group consisting of bladder cancer, cancer of the blood vessels, bone cancer, brain cancer, breast cancer, cervical cancer, chest cancer, colon cancer, endometrial cancer, esophageal cancer, eye cancer, head cancer, kidney cancer, liver cancer, cancer of the lymph nodes, lung cancer, mouth cancer, neck cancer, ovarian cancer, pancreatic cancer, prostate cancer, rectal cancer, colorectal cancer, skin cancer, stomach cancer, testicular cancer, throat cancer, thyroid cancer, urothelial cancers, and uterine cancer.

51. The method of embodiment 49, wherein the cancer is selected from the group consisting of breast cancer, prostate cancer, melanoma, colorectal cancer, lung cancer, pancreatic cancer, and glioblastoma.

52. The method of any one of embodiments 48-51, wherein the method further comprises co-administering a cancer drug as a combination therapy with the nanobiologic composition.

53. A method for treating sepsis in a patient in need thereof, comprising administering to the patient a therapeutically effective amount of the nanobiologic composition of any one of embodiments 35-46.

54. The method of embodiment 53, wherein the patient has sepsis associated with a bacterial, viral or fungal infection of the lungs, abdomen, kidney, or bloodstream.

55. The method of any one of embodiments 48-54, wherein the nanobiologic composition promotes a hyper-responsive innate immune response in the patient in need thereof.

56. The method of embodiment 55, wherein the hyper-responsive innate immune response is promoted for at least about 7 to about 30 days.

57. The method of embodiment 55, wherein the hyper-responsive innate immune response is promoted for at least 30 to 100 days.

58. The method of embodiment 55, wherein the hyper-responsive innate immune response is promoted for more than 100 days and up to 3 years.

59. The method of embodiment 55, wherein the nanobiologic composition is administered once and wherein the hyper-responsive innate immune response is promoted for at least 30 days.

60. The method of embodiment 55, wherein the nanobiologic composition is administered at least once per day in each day of a multiple-dosing regimen, and wherein the hyper-responsive innate immune response is promoted for at least 30 days.

61. The method of any one of embodiments 48-58, wherein the nanobiologic composition is administered in a treatment regimen comprising two or more doses to the patient to generate an accumulation of drug in myeloid cells, myeloid progenitor cells, and hematopoietic stem cells in the bone marrow, blood and/or spleen.

62. The method of any one of embodiments 48-61, wherein the nanobiologic composition is administered intravenously or intra-arterially.

63. A method for activating a NOD2 receptor in a subject in need thereof, comprising administering to the subject an effective amount of the nanobiologic composition of any one of embodiments 35-46.

64. A process for manufacturing a nanobiologic composition of any one of embodiments 35-46, the process comprising:

a) forming a lipid film comprising: i) a compound of any one of embodiments 1-34; ii) one or more phospholipids; optionally iii) a hydrophobic matrix comprising one or more triglycerides, fatty acid esters, hydrophobic polymers, or sterol esters, or a combination thereof; and optionally iv) cholesterol; under conditions effective to form the lipid film; and b) dissolving the lipid film in a solvent to form a lipid solution; and contacting the lipid solution with apoA-I or a peptide mimetic of apoA-I under conditions effective to form a HDL-derived nanoparticle comprising a compound of any one of embodiments 1-34.

65. A nanobiologic composition prepared according to embodiment 64.

66. A kit comprising a nanobiologic composition of any one of embodiments 35-46.

67. The method of embodiment 52 wherein the cancer drug is a checkpoint inhibitor.

68. The method of embodiment 67 wherein the checkpoint inhibitor is selected from an anti-PD-1 antibody, an anti-CTLA-4 antibody, and combinations thereof.

The invention claimed is:

1. A method for treating a cell-proliferation disorder in a patient in need thereof, comprising administering to the patient a therapeutically effective amount of a nanobiologic composition comprising a high-density lipoprotein (HDL)-derived nanoparticle, wherein the nanoparticle comprises a compound of formula (I):

(I)

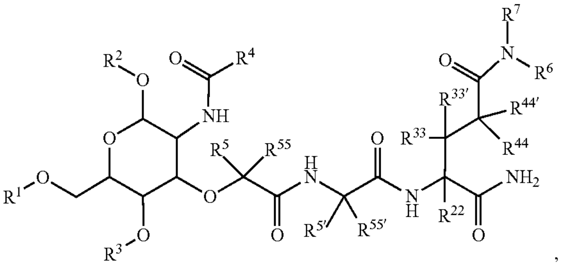

or a pharmaceutically acceptable salt thereof, wherein:

$R^1$ is —H or —C(O)—$R^X$;

$R^2$ and $R^3$ are each independently selected from the group consisting of —H, alkyl, aryl, alkylene-aryl, —C(O)-alkyl, and —C(O)-aryl;

$R^4$, $R^5$, and $R^{5'}$ are each alkyl;

$R^6$ and $R^{11}$ are each independently —H or alkyl;

$R^7$ is —Y-triazolyl-L;

Y is alkylene;

L is selected from the group consisting of a fatty acid chain, -alkylene-C(O)—W, -alkylene-O—C(O)—W, -alkylene-N-(alkylene-C(O)—$NR^{11}$-alkylene-$NR^{11}$—C(O)—W$)_2$, and -alkylene-N-(alkylene-C(O)—W$)_2$;

W is a fatty acid chain, —O-alkylene-C(H)($OR^8$)-alkylene-$OR^9$, a phospholipid, or a sterol;

$R^1$ and $R^9$ are each independently $R^X$ or —C(O)—$R^X$;

$R^{22}$, $R^{33}$, $R^{33'}$, $R^{44}$, $R^{44'}$, $R^{55}$, and $R^{55'}$ are each independently H or $R^A$;

$R^X$ is a fatty acid chain;

wherein each aforementioned alkyl, alkylene, alkylene-aryl, aryl, and triazolyl is optionally substituted with one or more $R^A$, wherein $R^A$ is independently selected for each occurrence from the group consisting of hydrogen, halo, alkoxy, haloalkoxy, cyano, hydroxyl, —$N(R^C)(R^D)$, —$C(O)N(R^C)(R^D)$, —$N(R^C)C(O)R^B$, —$OC(O)NR^CR^D$, —$NR^CC(O)OR^B$, —$OC(O)R^B$, —$C(O)OR^B$, —$C(O)R^B$, —$CO_2H$, —$NO_2$, —SH, $S(O)_xR^B$, aryl, arylalkyl, heteroaryl, heteroarylalkyl, cycloalkyl, heterocycloalkyl, and $R^B$; wherein x is 0, 1, or 2;

$R^C$ and $R^D$ are independently selected for each occurrence from the group consisting of hydrogen, alkyl, haloalkyl —$C(O)R^B$, and —$C(O)OR^B$; or $R^C$ and $R^D$ are taken together with the nitrogen to which they are attached to form a heterocyclic ring optionally substituted with $R^A$; and $R^B$ is alkyl, alkenyl, or alkynyl optionally substituted with one or more fluoro.

2. The method of claim 1, wherein the compound of formula (I) is a compound of formula (IA):

(IA)

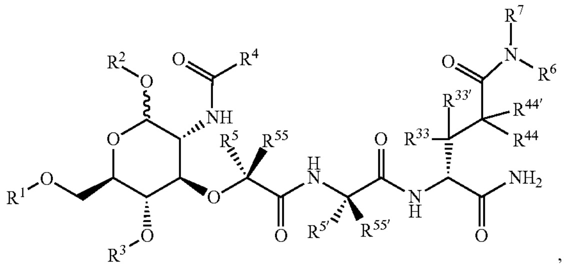

or a pharmaceutically acceptable salt thereof.

3. The method of claim 1, wherein $R^2$ is —H or benzyl.

4. The method of claim 1, wherein $R^2$ is —H.

5. The method of claim 1, wherein $R^{22}$, $R^{33}$, $R^{33'}$, $R^{44}$, $R^{44'}$, $R^{55}$, and $R^{55'}$ are each —H.

6. The method of claim 1, wherein $R^4$ is alkyl.

7. The method of claim 4, wherein $R^4$ is methyl.

8. The method of claim 1, wherein $R^3$ and $R^6$ are both —H.

9. The method of claim 1, wherein Y is —$CH_2$—.

10. The method of claim 1, wherein the compound of formula (I) is a compound of formula (II):

(II)

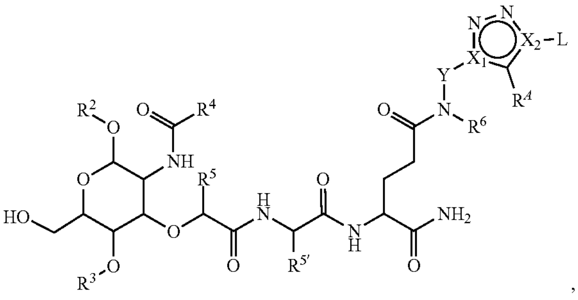

or a pharmaceutically acceptable salt thereof, wherein:

$X_1$ is —N— and $X_2$ is —C—; or $X_1$ is —C— and $X_2$ is —N—.

11. The method of claim 10, wherein the compound of formula (II) is a compound of formula (IIA):

(IIA)

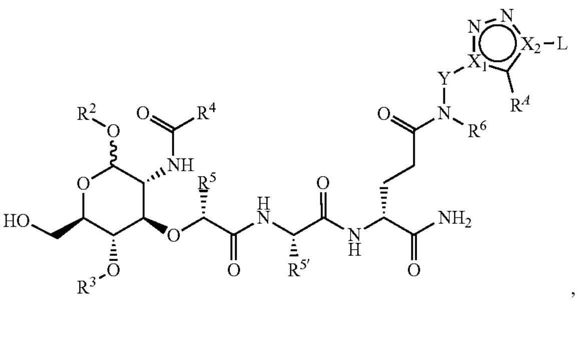

or a pharmaceutically acceptable salt thereof.

12. The method of claim 10, wherein Y is $C_{1-6}$ alkylene.

13. The method of claim 10, wherein $R^A$ is —H.

14. The method of claim 1, wherein L is $—CH_2—C(O)—W$.

15. The method of claim 1, wherein W is a $—C_{8-30}$ alkyl.

16. The method of claim 1, wherein W is:

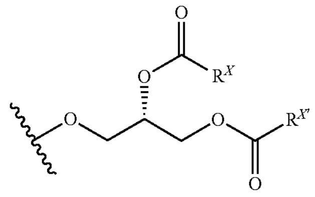

, wherein $R^X$ and $R^{X'}$ are each independently a $—C_{8-30}$ fatty acid chain.

17. The method of claim 16, wherein $R^X$ and $R^{X'}$ are each independently a $—C_{8-30}$ alkyl.

18. The method of claim 17, wherein $R^X$ and $R^{X'}$ are both $—(CH_2CH_2)_8—CH_3$.

19. The method of claim 1, wherein W is cholesterol:

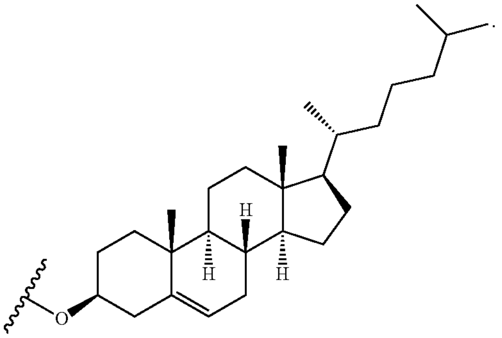

(cholesterol)

20. The method of claim 1, wherein W is a phospholipid.

21. The method of claim 20, wherein W is a phospholipid having the structure:

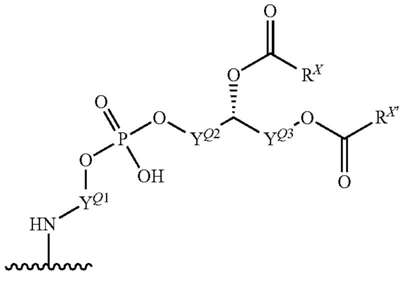

, wherein $Y^{Q1}$, $Y^{Q2}$, and $Y^{Q3}$ are each independently alkylene and $R^X$ and $R^{X'}$ are each independently a fatty acid chain having at least 15 carbons.

22. The method of claim 21, wherein $R^X$ and $R^{X'}$ are each independently a $—C_{15-20}$ alkyl or a $—C_{15-20}$ alkenyl.

23. The method of claim 20, wherein W is a phospholipid having the structure:

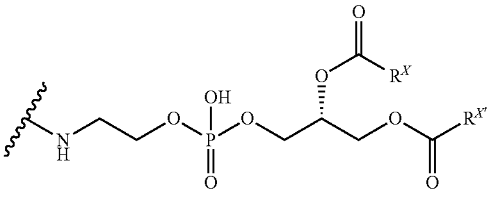

, or a pharmaceutically acceptable salt thereof;

wherein $R^X$ and $R^{X'}$ are each independently a $C_{8-30}$ fatty acid chain.

24. The method of claim 23, wherein $R^X$ and $R^{X'}$ are each independently a $C_{12-18}$ fatty acid chain.

25. The method of claim 23, wherein the fatty acid chain is saturated.

26. The method of claim 23, wherein $R^X$ and $R^{X'}$ are both $—(CH_2CH_2)_8—CH_3$.

27. The method of claim 1, wherein the compound is selected from the group consisting of:

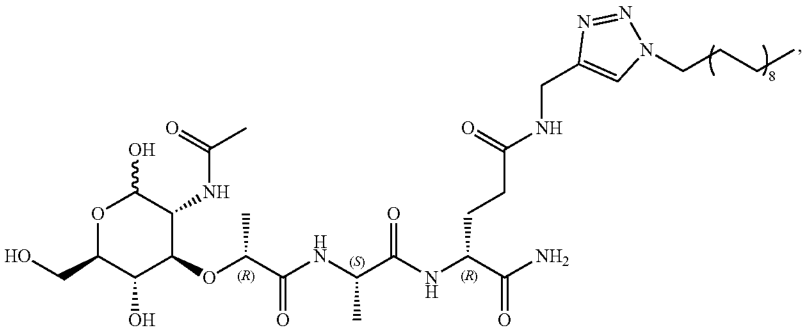

,

-continued
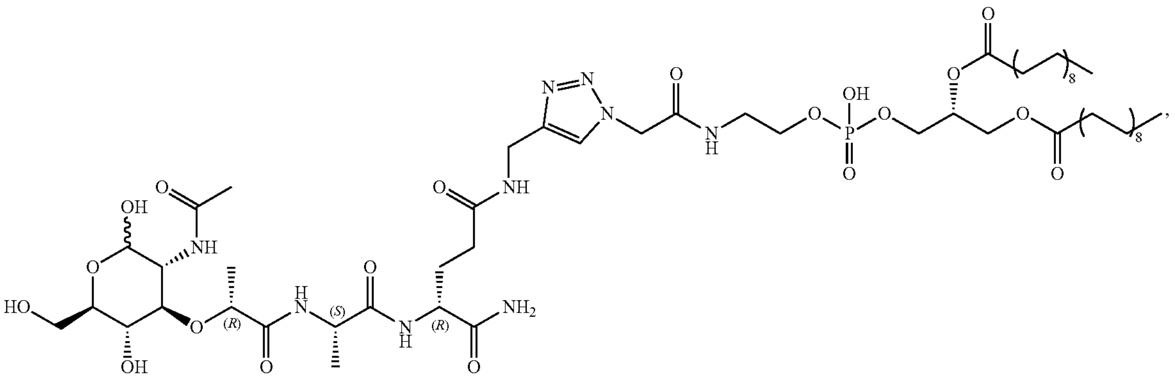
,
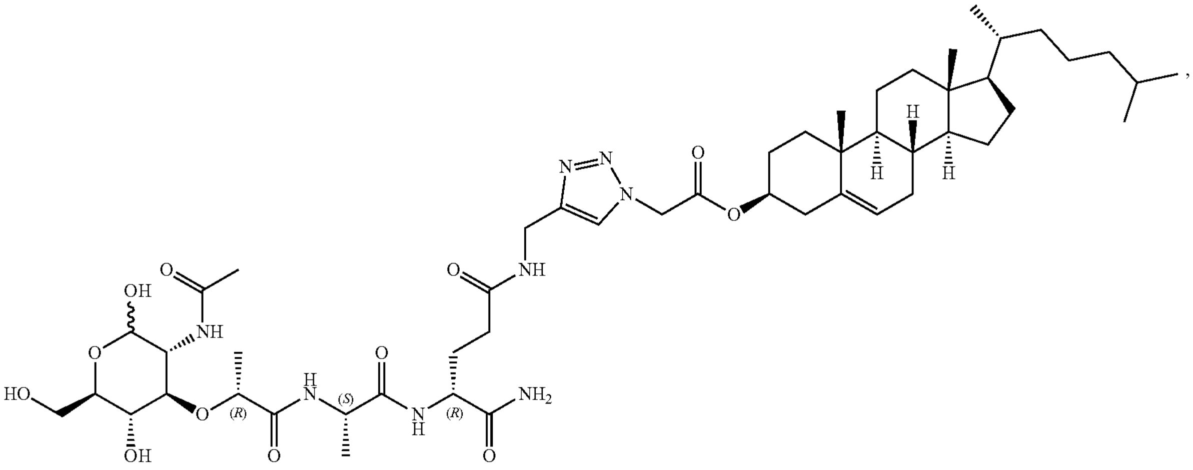
,
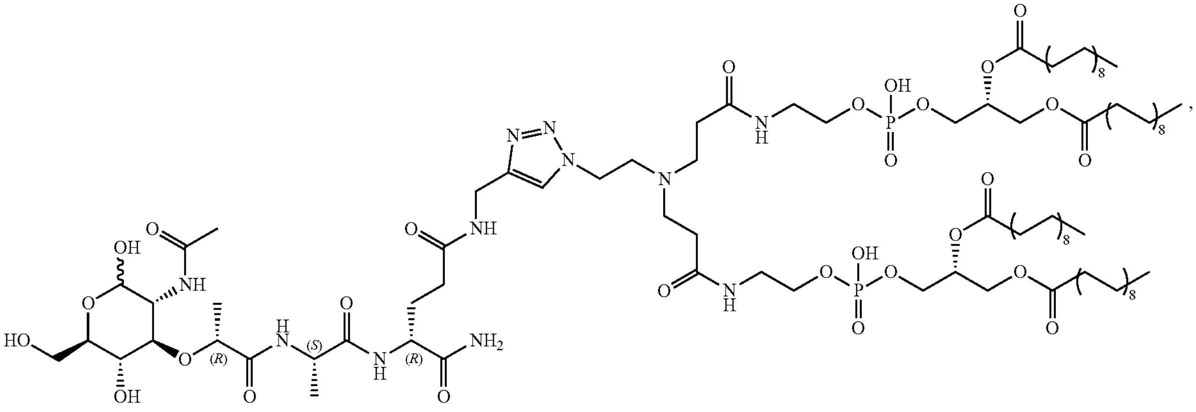
,
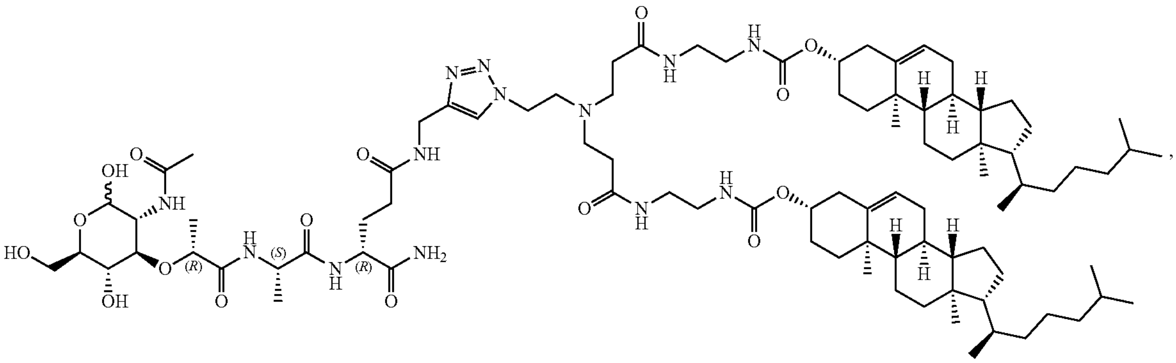
,

-continued

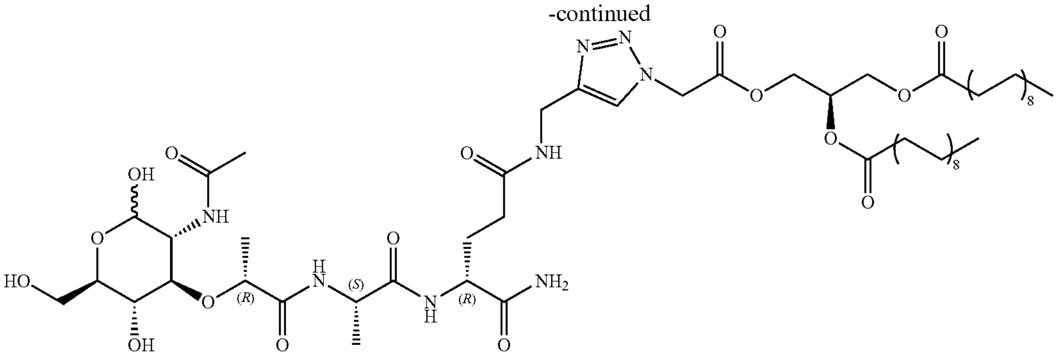

,

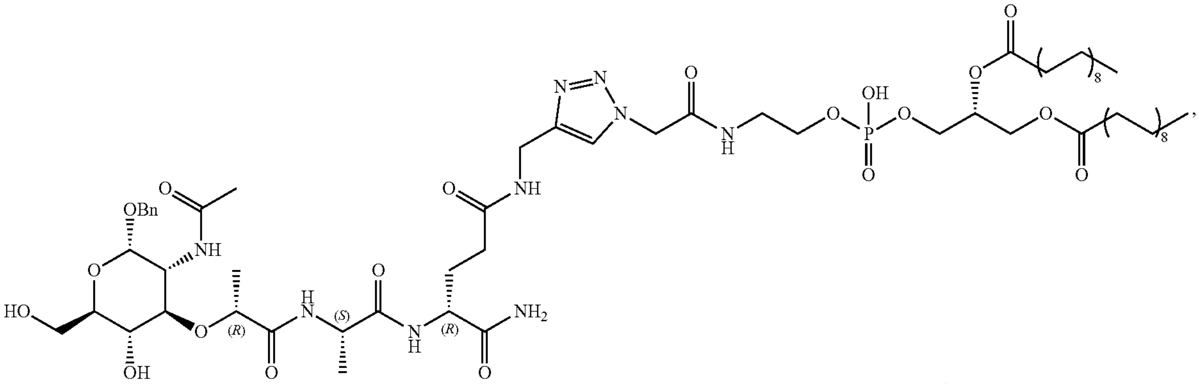

,

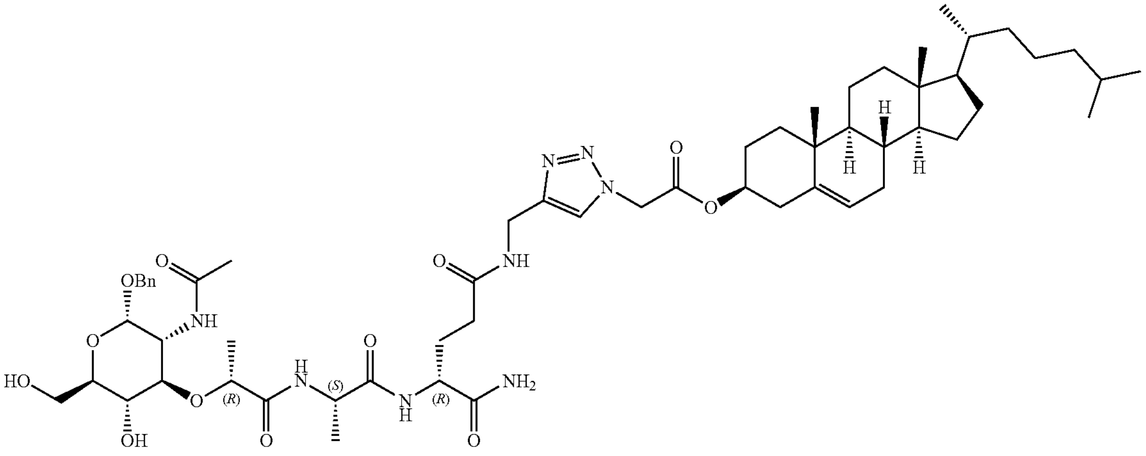

,

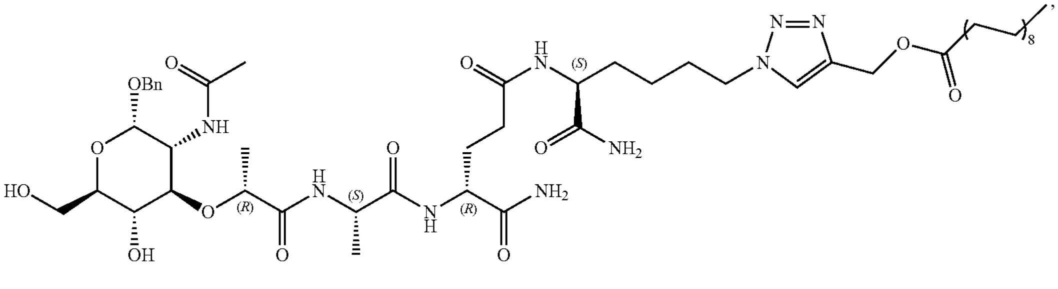

, and a pharmaceutically acceptable salt therein, wherein Bn is a benzyl group.

28. The method of claim 1, wherein the nanobiologic composition comprises a phospholipid independently selected from the group consisting of a phosphatidylcholine, a phosphatidylethanolamine, a phosphatidylinositol, a phosphatidylserine, a sphingomyelin or other ceramide, a phospholipid-containing oil, a phosphatidylglycerol, a phosphatidic acid, a lysophosphatidylcholine, and combinations thereof.

29. The method of claim 1, wherein the nanobiologic composition comprises a phospholipid selected from the group consisting of 1,2-dimyristoyl-sn-glycero-3-phosphatidylcholine (DMPC) and 1-palmitoyl-2-oleoyl-sn-glycero-3-phosphocholine (POPC), and a lysolipid selected from the group consisting of 1-myristoyl-2-hydroxy-sn-glycero-phosphocholine (MHPC), and 1-palmitovl-2-hydroxv-sn-glvcero-3-phosphocholine (PHPC).

30. The method of claim 1, wherein the HDL-derived nanoparticle comprises apoA-I or a peptide mimetic of apoA-I.

31. The method of claim 1, wherein the HDL-derived nanoparticle further comprises cholesterol.

32. The method of claim 31, wherein the HDL-derived nanoparticle comprises one or more phospholipids and cholesterol in a molar ratio in the range of about 1:0.05 to about 1:0.25.

33. The method of claim 1, wherein the cell-proliferation disorder is cancer.

34. The method of claim 33, wherein the cancer is selected from the group consisting of bladder cancer, cancer of the blood vessels, bone cancer, brain cancer, breast cancer, cervical cancer, chest cancer, colon cancer, endometrial cancer, esophageal cancer, eye cancer, head cancer, kidney cancer, liver cancer, cancer of the lymph nodes, lung cancer, mouth cancer, neck cancer, ovarian cancer, pancreatic cancer, prostate cancer, rectal cancer, colorectal cancer, skin cancer, stomach cancer, testicular cancer, throat cancer, thyroid cancer, urothelial cancer, and uterine cancer.

35. The method of claim 34, wherein the cancer is selected from the group consisting of breast cancer, prostate cancer, melanoma, colorectal cancer, lung cancer, pancreatic cancer, and glioblastoma.

36. The method of claim 1, wherein the nanobiologic composition is administered intravenously or intra-arterially.

37. The method of claim 10, wherein the compound of formula (II) is a compound of formula (II-1):

(II-1)

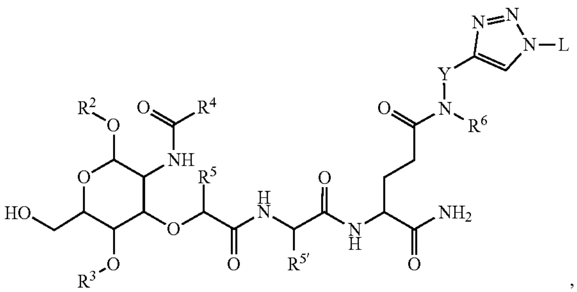

, or a pharmaceutically acceptable salt thereof.

38. The method of claim 27, wherein the compound is:

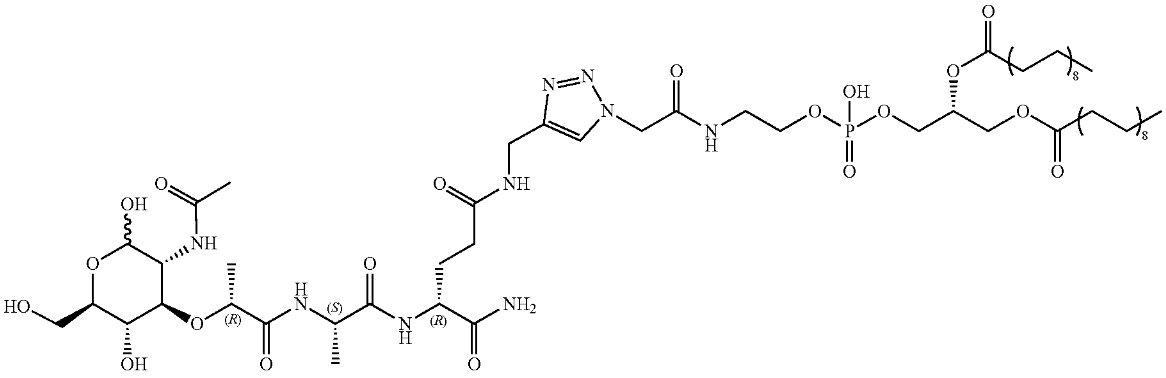

or a pharmaceutically acceptable salt thereof.

39. The method of claim 27, wherein the compound is:

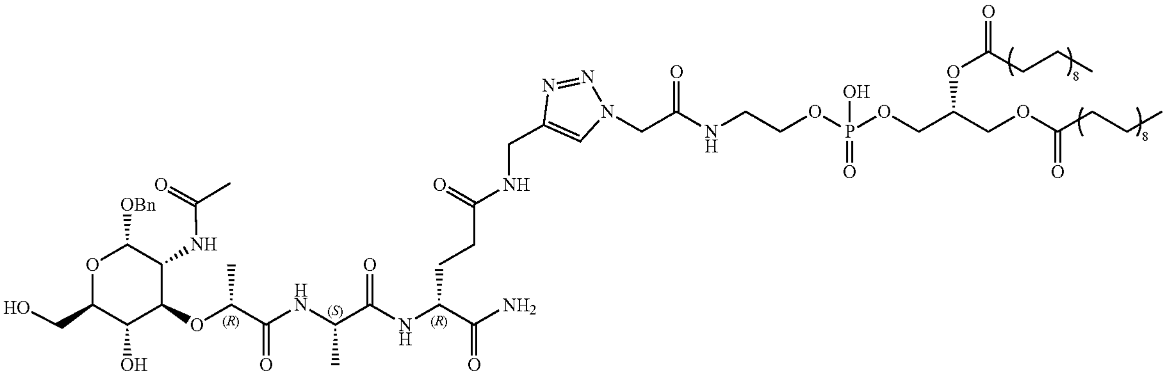

or a pharmaceutically acceptable salt thereof.

40. The method of claim 27, wherein the compound is:
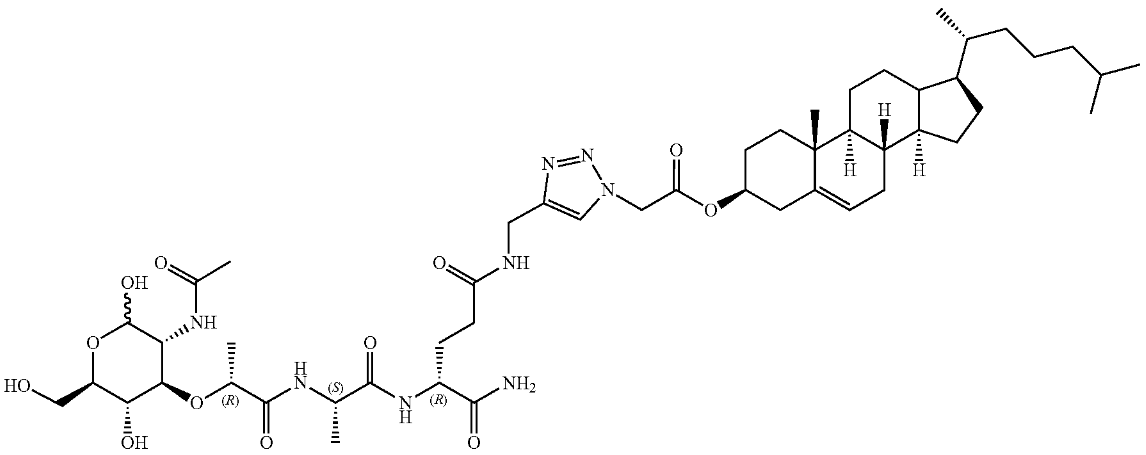
or a pharmaceutically acceptable salt thereof.
41. The method of claim 27, wherein the compound is:
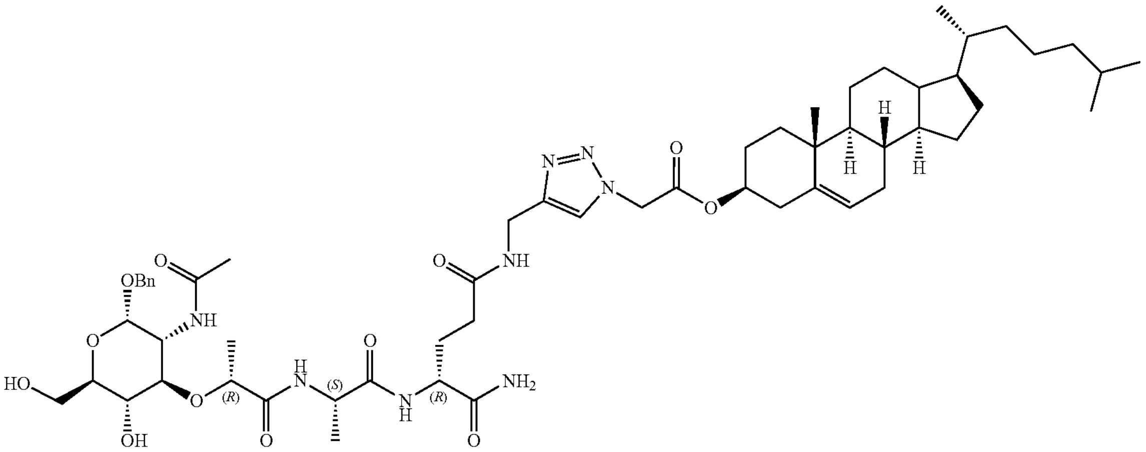
or a pharmaceutically acceptable salt thereof.
* * * * *